US011945868B2

(12) United States Patent
Chaganty et al.

(10) Patent No.: US 11,945,868 B2
(45) Date of Patent: Apr. 2, 2024

(54) ANTIBODY MOLECULES TO CD138 AND USES THEREOF

(71) Applicant: VISTERRA, INC., Waltham, MA (US)

(72) Inventors: Bharat Chaganty, Concord, MA (US); Boopathy Ramakrishnan, Braintree, MA (US); Hedy Adari-Hall, Sudbury, MA (US); Karthik Viswanathan, Acton, MA (US); James R. Myette, Waltham, MA (US); Zachary Shriver, Winchester, MA (US)

(73) Assignee: VISTERRA, INC., Waltham, MA (US)

( * ) Notice: Subject to any disclaimer, the term of this patent is extended or adjusted under 35 U.S.C. 154(b) by 14 days.

(21) Appl. No.: 16/149,854

(22) Filed: Oct. 2, 2018

(65) Prior Publication Data

US 2019/0100588 A1 Apr. 4, 2019

Related U.S. Application Data

(60) Provisional application No. 62/725,880, filed on Aug. 31, 2018, provisional application No. 62/566,936, filed on Oct. 2, 2017.

(51) Int. Cl.
*C07K 16/28* (2006.01)
*A61K 39/395* (2006.01)
*A61P 35/00* (2006.01)
*C12N 15/62* (2006.01)
*A61K 39/00* (2006.01)

(52) U.S. Cl.
CPC .... *C07K 16/2818* (2013.01); *A61K 39/39558* (2013.01); *A61P 35/00* (2018.01); *C07K 16/2896* (2013.01); *C12N 15/62* (2013.01); *A61K 2039/572* (2013.01); *C07K 2317/32* (2013.01); *C07K 2317/34* (2013.01); *C07K 2317/76* (2013.01); *C07K 2317/92* (2013.01)

(58) Field of Classification Search
CPC ............ C07K 16/2818; C07K 16/2896; C07K 2317/32; C07K 2317/34; C07K 2317/76; C07K 2317/92; A61K 39/39558; A61K 2039/572; A61K 2039/505; A61P 35/00; C12N 15/62
See application file for complete search history.

(56) References Cited

U.S. PATENT DOCUMENTS

| 4,816,567 | A | 3/1989 | Cabilly et al. |
| 5,223,409 | A | 6/1993 | Ladner et al. |
| 5,225,539 | A | 7/1993 | Winter |
| 5,585,089 | A | 12/1996 | Queen et al. |
| 5,693,762 | A | 12/1997 | Queen et al. |
| 8,840,898 | B2 | 9/2014 | Goldmakher |
| 9,221,914 | B2 | 12/2015 | Kraus et al. |
| 9,249,467 | B2 | 2/2016 | Goodison et al. |
| 9,289,509 | B2 | 3/2016 | Osterroth et al. |
| 9,387,261 | B2 | 7/2016 | Kraus et al. |
| 9,803,021 | B2 | 10/2017 | Morrison |
| 9,862,772 | B2 | 1/2018 | Radbruch et al. |
| 9,964,542 | B2 | 5/2018 | Goodison et al. |
| 10,117,932 | B2 | 11/2018 | Schulz et al. |
| 10,662,250 | B2 | 5/2020 | Dukhovlinov et al. |
| 10,975,158 | B2 | 4/2021 | Morrison |
| 2003/0215828 | A1 | 11/2003 | Mitsuhashi et al. |
| 2006/0045877 | A1 | 3/2006 | Goldmakher et al. |
| 2007/0054332 | A1* | 3/2007 | Rapraeger ............ G01N 33/574 435/7.23 |
| 2009/0169570 | A1 | 7/2009 | Daelken et al. |
| 2012/0100588 | A1 | 4/2012 | Wallage |
| 2014/0170159 | A9 | 6/2014 | Wei et al. |
| 2020/0392241 | A1 | 12/2020 | Chaganty et al. |
| 2022/0281997 | A1 | 9/2022 | Qin et al. |
| 2023/0348614 | A1 | 11/2023 | Myette et al. |

FOREIGN PATENT DOCUMENTS

| CN | 104059151 | | 9/2014 |
| EP | 125023 | A1 | 11/1984 |
| EP | 171496 | A2 | 2/1986 |
| EP | 173494 | A2 | 3/1986 |
| EP | 184187 | A2 | 6/1986 |
| EP | 0519596 | A1 | 12/1992 |
| EP | 2238168 | B1 | 10/2010 |
| EP | 2240516 | B1 | 10/2010 |
| EP | 2427216 | B1 | 3/2012 |
| EP | 2242772 | B1 | 11/2014 |
| EP | 2801584 | B1 | 11/2014 |
| EP | 2892926 | B1 | 7/2015 |
| EP | 2788030 | B1 | 6/2018 |
| GB | 2188638 | A | 10/1987 |
| WO | 8601533 | A1 | 3/1986 |
| WO | 1987002671 | A1 | 5/1987 |
| WO | 9002809 | A1 | 3/1990 |
| WO | 9100906 | A1 | 1/1991 |
| WO | 9110741 | A1 | 7/1991 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Gharbaran (Critical Reviews in Oncology/Hematology, 94: 1-17, 2015).*
Lee et al. (Immunity, 46: 690-702, Apr. 2017).*
Akl et al. "Molecular and clinical profiles of syndecan-1 in solid and hematological cancer for prognosis and precision medicine," Oncotarget. 2015; 6(30):28693-28715.

(Continued)

*Primary Examiner* — Nelson B Moseley, II
(74) *Attorney, Agent, or Firm* — K&L Gates LLP

(57) ABSTRACT

Antibody molecules that specifically bind to CD138 are disclosed. The antibody molecules can be used to treat, prevent, and/or diagnose disorders, such as multiple myeloma.

37 Claims, 25 Drawing Sheets
Specification includes a Sequence Listing.

(56) References Cited

FOREIGN PATENT DOCUMENTS

| | | |
|---|---|---|
| WO | 9117271 A1 | 11/1991 |
| WO | 9201047 A1 | 1/1992 |
| WO | 9203917 A1 | 3/1992 |
| WO | 9203918 A1 | 3/1992 |
| WO | 9209690 A2 | 6/1992 |
| WO | 9215679 A1 | 9/1992 |
| WO | 9218619 A1 | 10/1992 |
| WO | 9220791 A1 | 11/1992 |
| WO | 9301288 A1 | 1/1993 |
| WO | 9404678 A1 | 3/1994 |
| WO | 2006/099875 A1 | 9/2006 |
| WO | 2008/047242 A2 | 4/2008 |
| WO | 2009/080832 A1 | 7/2009 |
| WO | 2009080829 A1 | 7/2009 |
| WO | 2009080830 A1 | 7/2009 |
| WO | 2009080831 A1 | 7/2009 |
| WO | 2010128087 A9 | 11/2010 |
| WO | 2013/083817 A1 | 6/2013 |
| WO | 2014037519 A3 | 3/2014 |
| WO | 2014042763 A1 | 3/2014 |
| WO | 2014089354 A1 | 6/2014 |
| WO | 2017014679 A3 | 1/2017 |
| WO | 2019070726 A1 | 4/2019 |
| WO | 2019/232449 A1 | 12/2020 |
| WO | 2020/247932 A1 | 12/2020 |
| WO | 2020257289 A2 | 12/2020 |
| WO | 2020257289 A3 | 2/2021 |
| WO | 2023097254 A1 | 6/2023 |

OTHER PUBLICATIONS

Al-Otaibi et al., "Syndecan-1 (CD 138) surface expression marks cell type and differentiation in ameloblastoma, keratocystic odontogenic tumor, and dentigerous cyst," J Oral Pathol Med. 2013; 42: 186-193.
Anttonen et al., "Syndecan-1 expression has prognostic significance in head and neck carcinoma," Br J Cancer. 1999; 79: 558-564.
Barbareschi et al., "High syndecan-1 expression in breast carcinoma is related to an aggressive phenotype and to poorer prognosis," Cancer. 2003; 98(3): 474-483.
Bodoor et al., "Evaluation of BCL-6, CD10, CD138 and MUM-1 expression in diffuse large B-cell lymphoma patients: CD138 is a marker of poor prognosis," Asian Pac J Cancer Prev. 2012; 13: 3037-3046.
Cleary et al., "Antibody Distance from the Cell Membrane Regulates Antibody Effector Mechanisms," J Immunol. 2017; 198(10): 3999-4011.
Davies et al. "Distribution and clinical significance of heparan sulfate proteoglycans in ovarian cancer," Clin Cancer Res. 2004; 10: 5178-5186.
Derksen et al., "Cell surface proteoglycan syndecan-1 mediates hepatocyte growth factor binding and promotes Met signaling in multiple myeloma," Blood. 2002; 99(4): 1405-1410.
Fuki et al., "The syndecan family of proteoglycans. Novel receptors mediating internalization of atherogenic lipoproteins in vitro," J Clin Invest. 1997; 100(6):1611-1622.
Gharbaran et al., "Fibroblast growth factor-2 (FGF2) and syndecan-1 (SDC1) are potential biomarkers for putative circulating CD15+/CD30+ cells in poor outcome Hodgkin lymphoma patients," J Hematol Oncol. 2013; 6:62.
Götte et al., "An expression signature of syndecan-1 (CD138), E-cadherin and c-met is associated with factors of angiogenesis and lymphangiogenesis in ductal breast carcinoma in situ," Breast Cancer Res. 2007; 9(1):R8.
Hasengaowa et al., "Prognostic significance of syndecan-1 expression in human endometrial cancer," Ann Oncol. 2005; 16:1109-1115.
Hashimoto et al. "Association of loss of epithelial syndecan-1 with stage and local metastasis of colorectal adenocarcinomas: an immunohistochemical study of clinically annotated tumors," BMC Cancer. 2008; 8: 185.
Herbener et al., "Functional relevance of in vivo half antibody exchange of an IgG4 therapeutic antibody-drug conjugate," PLOS One (2018) vol. 13, No. 4, Article e0195823, 22 pages.
Hose et al., "Induction of angiogenesis by normal and malignant plasma cells," Blood. 2009; 114(1): 128-143.
Hu et al., "Syndecan-1-dependent suppression of PDK1/Akt/bad signaling by docosahexaenoic acid induces apoptosis in prostate cancer," Neoplasia. 2010; 12(10): 826-836.
Inki et al., "Association between syndecan-1 expression and clinical outcome in squamous cell carcinoma of the head and neck," Br J Cancer. 1994; 70: 319-323.
International Search Report and Written Opinion issued in PCT/US2018/053989, dated Feb. 11, 2019.
Jiang et al., "Transfection of chimeric anti-CD138 gene enhances natural killer cell activation and killing of multiple myeloma cells," Molecular Oncology (2014) vol. 8, No. 2, pp. 297-310.
Jilani et al., "Soluble syndecan-1 (sCD138) as a prognostic factor independent of mutation status in patients with chronic lymphocytic leukemia," Int J Lab Hematol. 2009; 31:97-105.
Joensuu et al., "Soluble syndecan-1 and serum basic fibroblast growth factor are new prognostic factors in lung cancer," Cancer Res. 2002; 62(18):5210-5217.
Khotskaya et al., "Syndecan-1 is required for robust growth, vascularization, and metastasis of myeloma tumors in vivo," J Biol Chem. 2009; 284(38): 26085-26095.
Kusumoto et al., "Clinical significance of syndecan-1 and versican expression in human epithelial ovarian cancer," Oncol Rep. 2010; 23(4): 917-25.
Kyle & Rajkumar, "Criteria for diagnosis, staging, risk stratification and response assessment of multiple myeloma," Leukemia. 2009; 23(1): 3-9.
Ledezma et al., "Altered expression patterns of syndecan-1 and -2 predict biochemical recurrence in prostate cancer," Asian J Androl. 2011; 13: 476-480.
Lendorf et al., "Syndecan-1 and syndecan-4 are independent indicators in breast carcinoma," J Histochem Cytochem. 2011; 59(6): 615-629.
Lim et al., "Syndecan-1 is a potential biomarker for triple-positive breast carcinomas in Asian women with correlation to survival," Singapore Med J. 2014; 55: 468-472.
Maeda et al., "Syndecan-1 expression by stromal fibroblasts promotes breast carcinoma growth in vivo and stimulates tumor angiogenesis," Oncogene. 2006; 25(9): 1408-1412.
Maeda et al., "Induction of syndecan-1 expression in stromal fibroblasts promotes proliferation of human breast cancer cells," Cancer Res. 2004; 64(2):612-621.
Mali et al., "Sequence of human syndecan indicates a novel gene family of integral membrane proteoglycans," J Biol Chem. 1990; 265(12): 6884-6889.
Nguyen et al., "Syndecan-1 overexpression is associated with nonluminal subtypes and poor prognosis in advanced breast cancer," Am J Clin Pathol. 2013; 140: 468-474.
Oh & Park, "Prognostic evaluation of nodal diffuse large B cell lymphoma by immunohistochemical profiles with emphasis on CD138 expression as a poor prognostic factor," J Korean Med Sci. 2006; 21: 397-405.
Orecchia et al., "A novel human anti-synecan-1 antibody inhibits vascular maturation and tumour growth in melanoma," European Journal of Cancer (2013) vol. 49, pp. 2022-2033.
Saunders et al., "Molecular cloning of syndecan, an integral membrane proteoglycan," J Cell Biol. 1989; 108(4): 1547-1556.
Seidel et al., "Serum syndecan-1: a new independent prognostic marker in multiple myeloma," Blood. 2000; 95(2): 388-392.
Shariat et al., "Prognostic value of syndecan-1 expression in patients treated with radical prostatectomy," BJU Int. 2008; 101:232-237.
Stanley et al., "Syndecan-1 expression is induced in the stroma of infiltrating breast carcinoma," Am J Clin Pathol. 1999; 112(3): 377-383.
Stepp et al., "Syndecan-1 and Its Expanding List of Contacts," Adv Wound Care (New Rochelle). 2015; 4(4):235-249.
Sun et al., "A Novel Anti-Human Syndecan-1(CD138) Monocloal Antibody 4B3: Characterization and Application," Cellular & Molecular Immunology (2007) vol. 4, No. 3, pp. 209-214.

(56) References Cited

OTHER PUBLICATIONS

Sun et al., "Peroxisome proliferator-activated receptor gamma-mediated up-regulation of syndecan-1 by n-3 fatty acids promotes apoptosis of human breast cancer cells," Cancer Res. 2008; 68(8):2912-2919.
Tassone et al., "Cytotoxic activity of the maytansinoid immunoconjugate B-B4-DM1 against CD138+ multiple myeloma cells," Blood (2004) vol. 104(12): 3688-3696.
Teng et al. "Molecular functions of syndecan-1 in disease," Matrix Biol. 2012; 31(1): 3-16.
Vassilakopoulos et al., "Serum levels of soluble syndecan-1 in Hodgkin's lymphoma," Anticancer Res. 2005; 25: 4743-4746.
Vidarsson et al., "IgG subclasses and allotypes: from structure to effector functions," Frontiers in Immunology (2014) vol. 5, Article 520, 17 pages.
Vihinen et al., "Structural organization and genomic sequence of mouse syndecan-1 gene," J Biol Chem. 1993; 268(23): 17261-17269.
Wiksten et al., "Epithelial and stromal syndecan-1 expression as predictor of outcome in patients with gastric cancer," Int J Cancer. 2001; 95(1): 1-6.
Alexander et al., "Syndecan-1 is required for Wnt-1-induced mammary tumorigenesis in mice," Nat Genet. 2000; 25(3): 329-32.
Anttonen et al., "High syndecan-1 expression is associated with favourable outcome in squamous cell lung carcinoma treated with radical surgery," Lung Cancer. 2001; 32:297-305.
Birchmeier et al., "Met, metastasis, motility and more," Nat Rev Mol Cell Biol. 2003; 4(12): 915-925.
Juuti et al., "Syndecan-1 expression-a novel prognostic marker in pancreatic cancer," Oncology. 2005; 68(2-3): 97-106.
Kim et al., "Immunohistochemical study identifying prognostic biomolecular markers in nasopharyngeal carcinoma treated by radiotherapy," Head Neck. 2011; 33:1458-1466.
Kiviniemi et al., "Altered expression of syndecan-1 in prostate cancer," Apmis. 2004; 112: 89-97.
Kumar-singh et al., "Syndecan-1 expression in malignant mesothelioma: correlation with cell differentiation, WT1 expression, and clinical outcome," J Pathol. 1998; 186:300-305.
Raab et al., "Multiple myeloma," Lancet. 2009; 374(9686): 324-39.
Roh et al., "Syndecan-1 expression in gallbladder cancer and its prognostic significance," Eur Surg Res. 2008; 41(2): 245-250.
Tsanou et al., "Clinicopathological study of the expression of syndecan-1 in invasive breast carcinomas. correlation with extracellular matrix components," J Exp Clin Cancer Res. 2004; 23(4):641-650.
Xu et al., "Syndecan-1 expression in human glioma is correlated with advanced tumor progression and poor prognosis," Mol Biol Rep. 2012; 39(9): 8979-8985.
Zellweger et al., "Tissue microarray analysis reveals prognostic significance of syndecan-1 expression in prostate cancer," Prostate. 2003; 55: 20-29.

Rudikoff et al., "Single Amino Acid Substitution Altering Antigen-Binding Specificity", Proc. Natl. Acad. Sci., vol. 79, pp. 1979-1983, Mar. 1982.
Gershoni et al., "Epitope Mapping: The First Step in Developing Epitope-Based Vaccines," Biodrugs (2007) vol. 21, No. 3, pp. 145-156.
Sun et al., "A Novel Anti-Human Syndecan-1(CD138) Monoclonal Antibody 4B3: Characterization and Application," Cellular & Molecular Immunology (2007) vol. 4, No. 3, pp. 209-214.
Yu et al., "An Immune Based, Anti-CD138 Targeting Antibody for the Treatment of Multiple Myeloma," Blood (2018) vol. 132, Supp. 1, Abstract 5617.
Dübel, Editor, "Handbook of Therapeutic Antibodies," Chapter 6, José W. Saldanha "Molecular Engineering I: Humanization," Wiley VCH (2007) pp. 119-144.
International Search Report and Written Opinion issued in PCT/US2020/038143, dated Jan. 28, 2021, 25 pages.
Yu et al., "VIS832, a novel CD138-targeting monoclonal antibody, potently induces killing of human multiple myeloma and further synergizes with IMiDs or bortezomib in vitro and in vivo," Blood Cancer Journal (2020) vol. 10, No. 110, pp. 1-13.
International Search Report and Written Opinion issued in Singapore Application No. 11202002248T, dated Nov. 5, 2021.
Diab, M. et al. "Production and characterization of monoclonal antibodies specific for canine CD138 (syndecan-1) for nuclear medicine preclinical trials on spontaneous tumours," Veterinary and Comparative Oncology vol. 15, No. 3 (2017): 932-951.
Gattei, V. et al. "Characterization of anti-CD138 monoclonal antibodies as tools for investigating the molecular polymorphism of syndecan-1 in human lymphoma cells," British Journal of Haematology vol. 104, No. 1 (1999): 152-162.
Office Action in corresponding Japanese Patent Application No. 2020-518692 dated Oct. 5, 2022.
Bendig, M. M. "Humanization of Rodent Monoclonal Antibodies by CDR Grafting," Methods: A Companion to Methods in Enzymology, vol. 8 (1995) pp. 83-93.
Colman, P. M. "Effects of amino acid sequence changes on antibody-antigen interactions," Research in Immunology vol. 145, No. 1 (1994) pp. 33-36.
Harris, R. J. et al. "Assessing genetic heterogeneity in production cell lines: detection by peptide mapping of a low level Tyr to Gln sequence variant in a recombinant antibody," Biotechnology (Nature Publishing Company) vol. 11, No. 11 (1993) pp. 1293-1297.
Johnson, G. & Wu, T. T. "The Kabat Database and a Bioinformatics Example," Methods in Molecular Biology, vol. 248: Antibody Engineering: Methods and Protocols (2004) pp. 11-25.
Paul, W. E. "Structure and Function of Immunoglobulins," Excerpt from Fundamental Immunology, 3rd Edition (Ch. 9), New York: Raven Press (1993) pp. 292-295.
International Search Report and Written Opinion in International Patent Application No. PCT/US2022/080397 dated Mar. 3, 2023.
Dübel, S. (Ed.) "Bioinformatics Tools for Antibody Engineering," Chapter 5, Handbook of Therapeutic Antibodies (2007) pp. 100-101.

* cited by examiner

Native hCD138: (Uniprot id: P18827)

```
         10         20         30         40         50         60         70         80         90        100
MRRAALWLWL CALALSLQPA LPQIVATNLP PEDQDGSGDD SDNFSGSGAG ALQDITLSQQ TPSTWKDTQL LTAIPTSPEP TGLEATAAST STLPAGEGPK
        110        120        130        140        150        160        170        180        190        200
EGEAVVLPEV EPGLTAREQE ATPRPRETTQ LPTTHLASTT TATTAQEPAT SHPHRDMQPG HHETSTPAGP SQADLHTPHT EDGGPSATER AAEDGASSQL
        210        220        230        240        250        260        270        280        290        300
PAAEGSGEQD FTFETSGENT AVVAVEPDRR NQSPVDQGAT GASQGLLDRK EVLGGVIAGG LVGLIFAVCL VGFMLYRMKK KDEGSYSLEE PKQANGGAYQ
        310
KPTKQEEFYA
```

FIG. 1

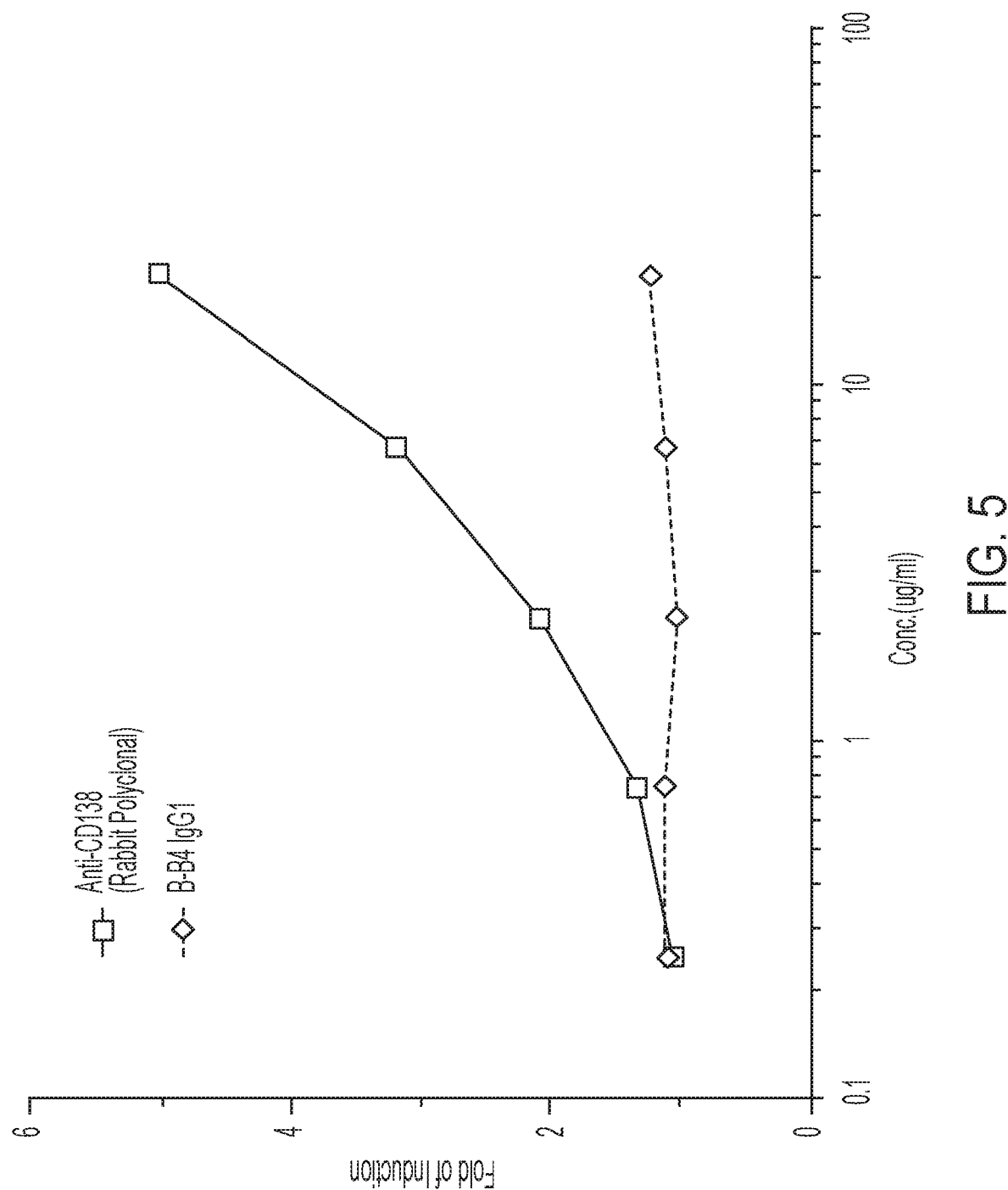

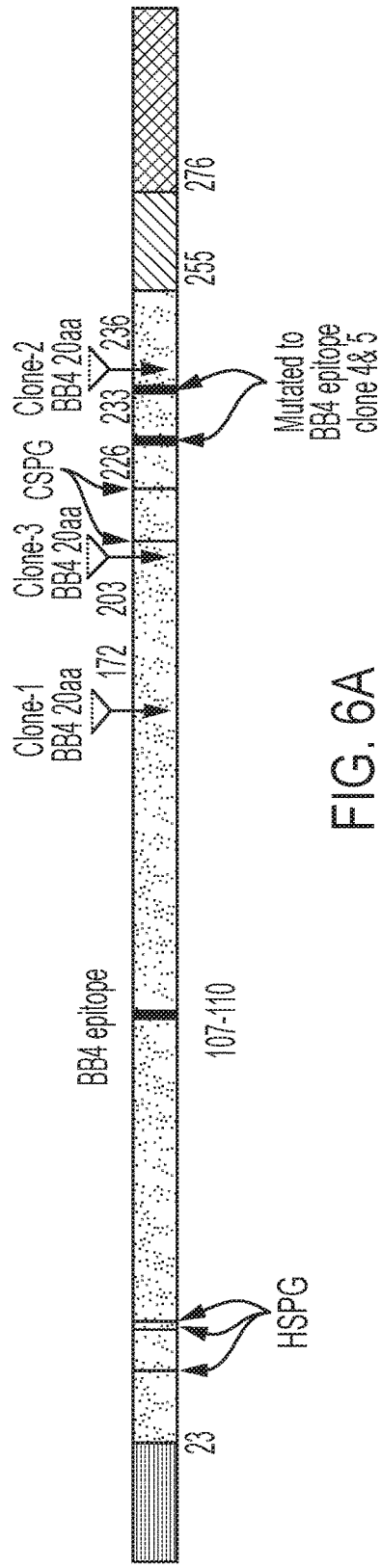

FIG. 6A

Clone 1: NativeCD138:BB4epitope between the GAGs

MRRAALWLWL CALALSLQPA LPQIVATNLP PEDQDGSGDD SDNFSGSGAG ALQDITLSQQ TPSTWKDTQL LTAIPTSPEP TGLEATAAST STLPAGEGPK
EGEAVVAAAV EPGLTAREQE ATPRPRETTQ LPTTHLASTT TATTAQEPAT SHPHRDMQPG HHETSTPAGP SQEGEAVVLPEV EPGLTAREQE ADLHTPHT
EDGGPSATER AAEDGASSQL PAAEGSGEQD FTFETSGENT AVVAVEPDRR NQSPVDQGAT GASQGLLDRK
EVLGGVIAGG LVGLIFAVCL VGFMLYRMKK KDEGSYSLEE PKQANGGAYQ KPTKQEEFYA

Clone 2: NativeCD138:BB4epitope at JMD

MRRAALWLWL CALALSLQPA LPQIVATNLP PEDQDGSGDD SDNFSGSGAG ALQDITLSQQ TPSTWKDTQL LTAIPTSPEP TGLEATAAST STLPAGEGPK
EGEAVVAAAV EPGLTAREQE ATPRPRETTQ LPTTHLASTT TATTAQEPAT SHPHRDMQPG HHETSTPAGP SQADLHTPHT EDGGPSATER AAEDGASSQL
PAAEGSGEQD FTFETSGENT AVVAVEPDRR NQSPVDEGEAVVLPEV EPGLTAREQEQGAT GASQGLLDRK EVLGGVIAGG LVGLIFAVCL VGFMLYRMKK
KDEGSYSLEE PKQANGGAYQ KPTKQEEFYA

Clone 3: NativeCD138:BB4epitope above and close to CS modification

MRRAALWLWL CALALSLQPA LPQIVATNLP PEDQDGSGDD SDNFSGSGAG ALQDITLSQQ TPSTWKDTQL LTAIPTSPEP TGLEATAAST STLPAGEGPK
EGEAVVAAAV EPGLTAREQE ATPRPRETTQ LPTTHLASTT TATTAQEPAT SHPHRDMQPG HHETSTPAGP SQADLHTPHT EDGGPSATER AAEDGASSQL
PAAEGEAVVLPEV EPGLTAREQ EGSGEQD FTFETSGENT AVVAVEPDRR NQSPVDQGAT GASQGLLDRK EVLGGVIAGG LVGLIFAVCL VGFMLYRMKK
KDEGSYSLEE PKQANGGAYQ KPTKQEEFYA

FIG. 6B

Clone 4: NativeCD138;BB4epitope below the CS
MRRAALWLWL CALALSLQPA LPQIVATNLP PEDQDGSGDD SDNFSGSGAG ALQDITLSQQ TPSTWKDTQL LTAIPTSPEP TGLEATAAST STLPAGEGPK
EGEAVAAAV EPGLTAREQE ATPRPRETTQ LPTTHLASTT TATTAQEPAT SHPHRDMQPG HHETSTPAGP SQADLHTPHT EDGGPSATER AAEDGASSQL
PAAEGSGEQD FTFETSGENT AVVAVLPEVE NQSPVDQGAT GASQGLLDRK EVLGGVIAGG LVGLIFAVCL VGFMLYRMKK KDEGSYSLEE PKQANGGAYQ
KPTKQEFYA Clone 5: NativeCD138;BB4epitope below the CS
MRRAALWLWL CALALSLQPA LPQIVATNLP PEDQDGSGDD SDNFSGSGAG ALQDITLSQQ TPSTWKDTQL LTAIPTSPEP TGLEATAAST STLPAGEGPK
EGEAVAAAV EPGLTAREQE ATPRPRETTQ LPTTHLASTT TATTAQEPAT SHPHRDMQPG HHETSTPAGP SQADLHTPHT EDGGPSATER AAEDGASSQL
PAAEGSGEQD FTFETSGENT AVAVEPDRR NQLPEVEGAT GASQGLLDRK EVLGGVIAGG LVGLIFAVCL VGFMLYRMKK KDEGSYSLEE PKQANGGAYQ
KPTKQEFYA

FIG. 6C

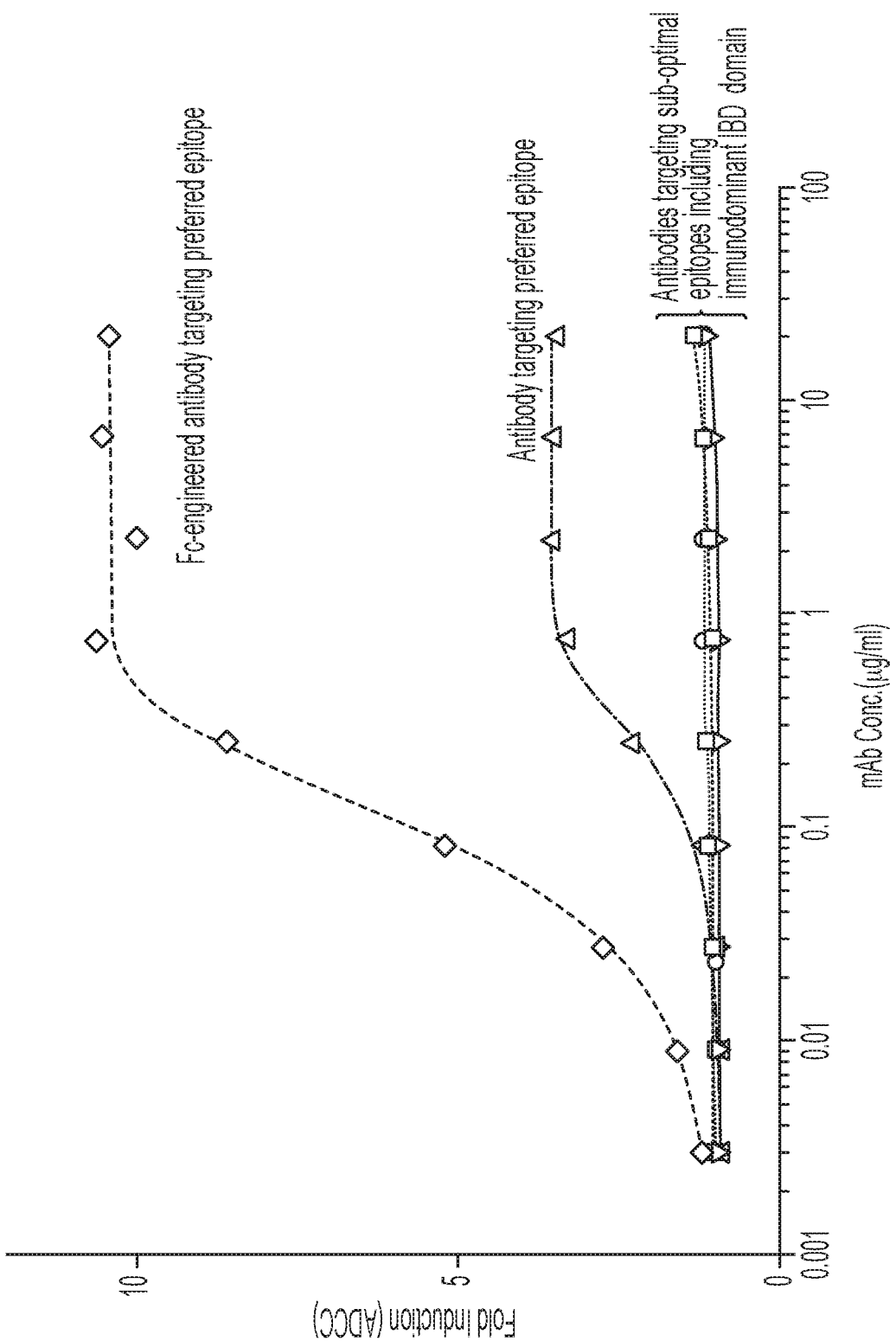

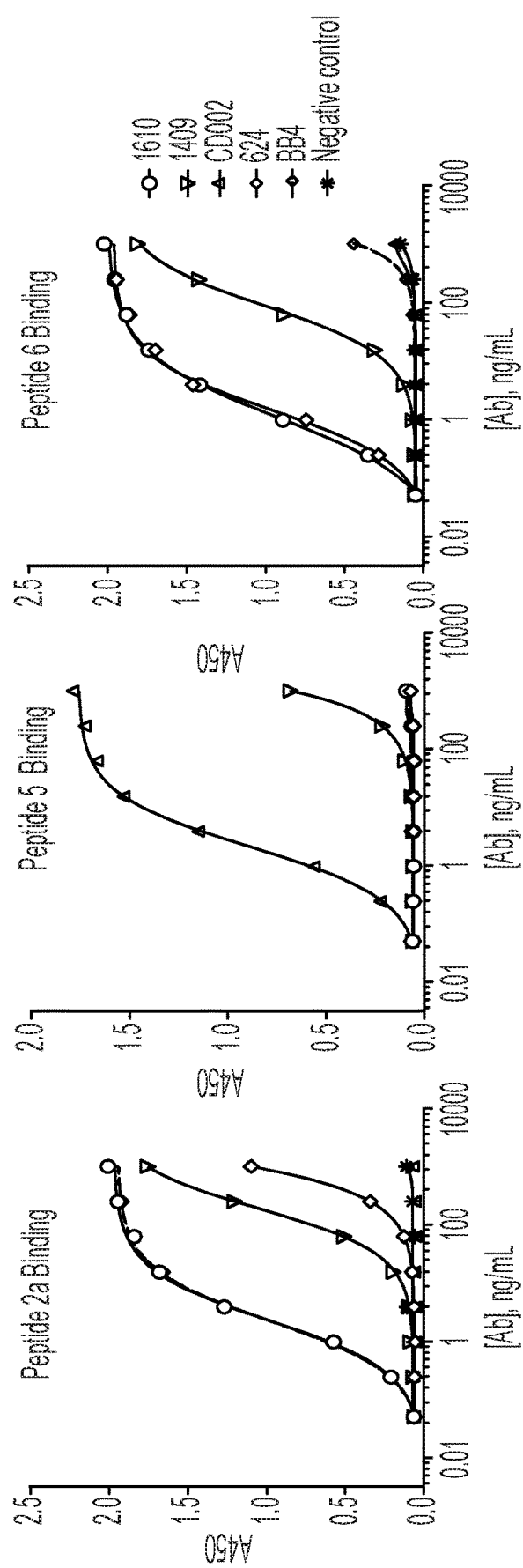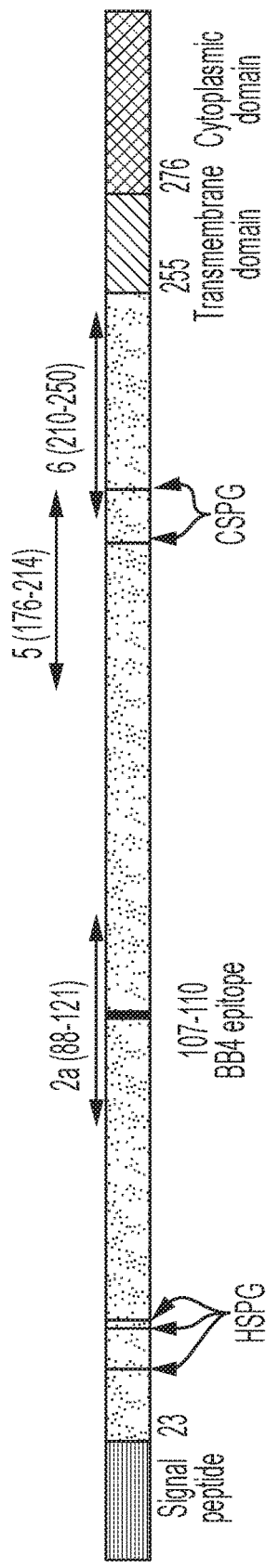
FIG. 9A  FIG. 9B  FIG. 9C  FIG. 9D

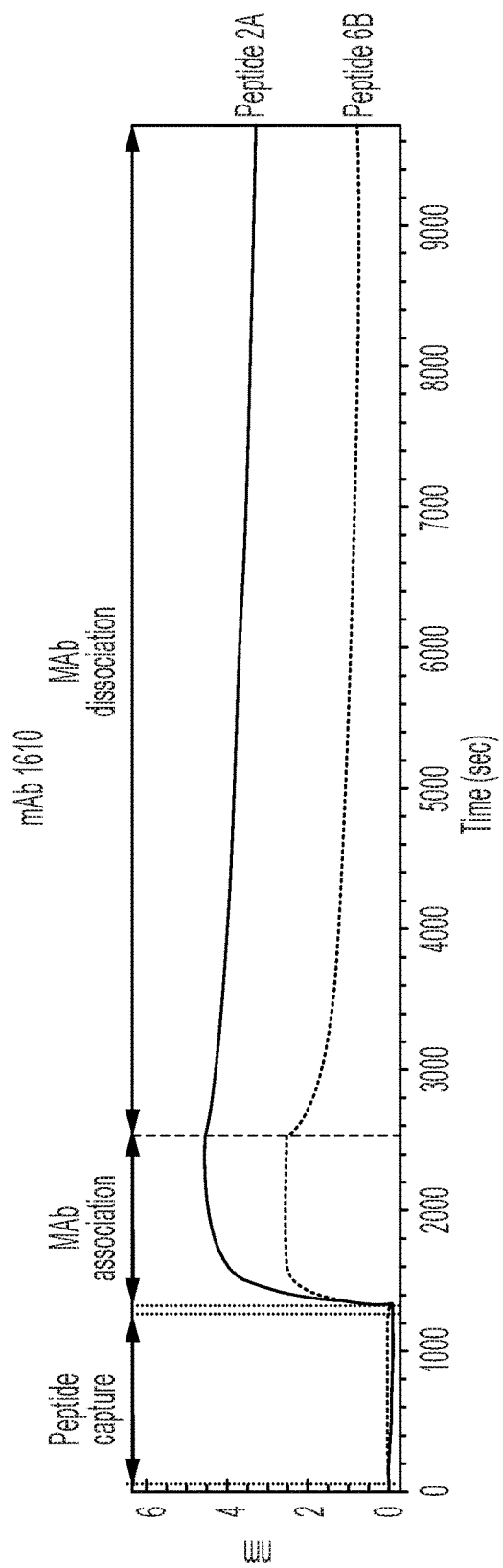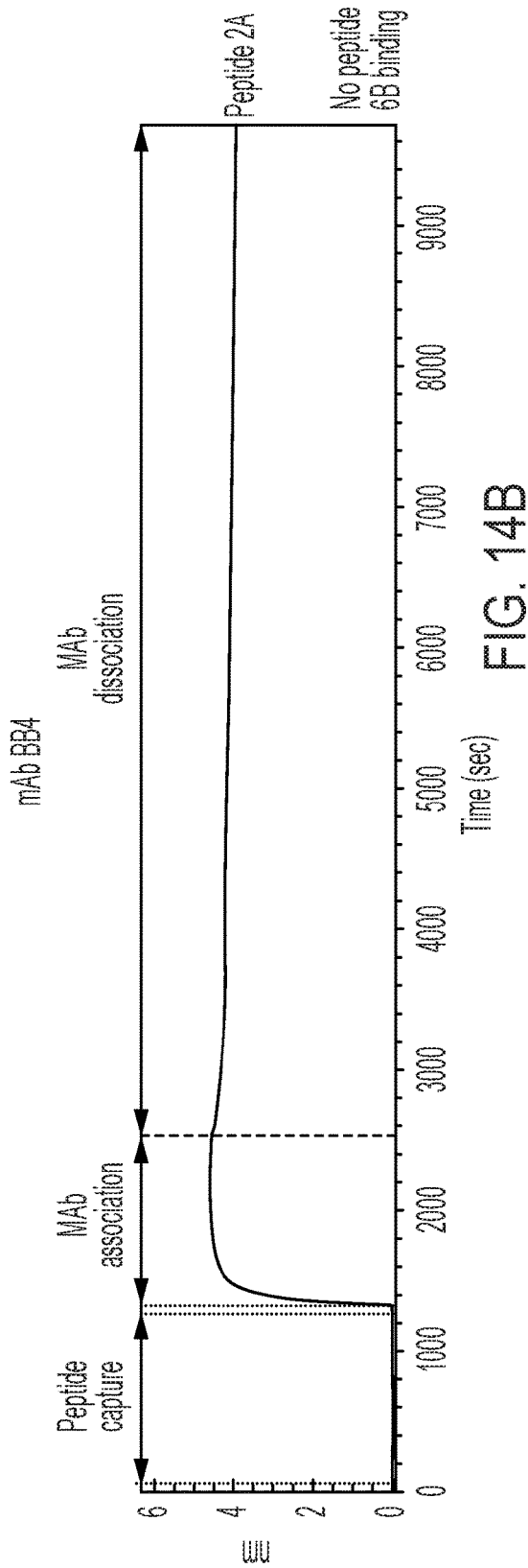

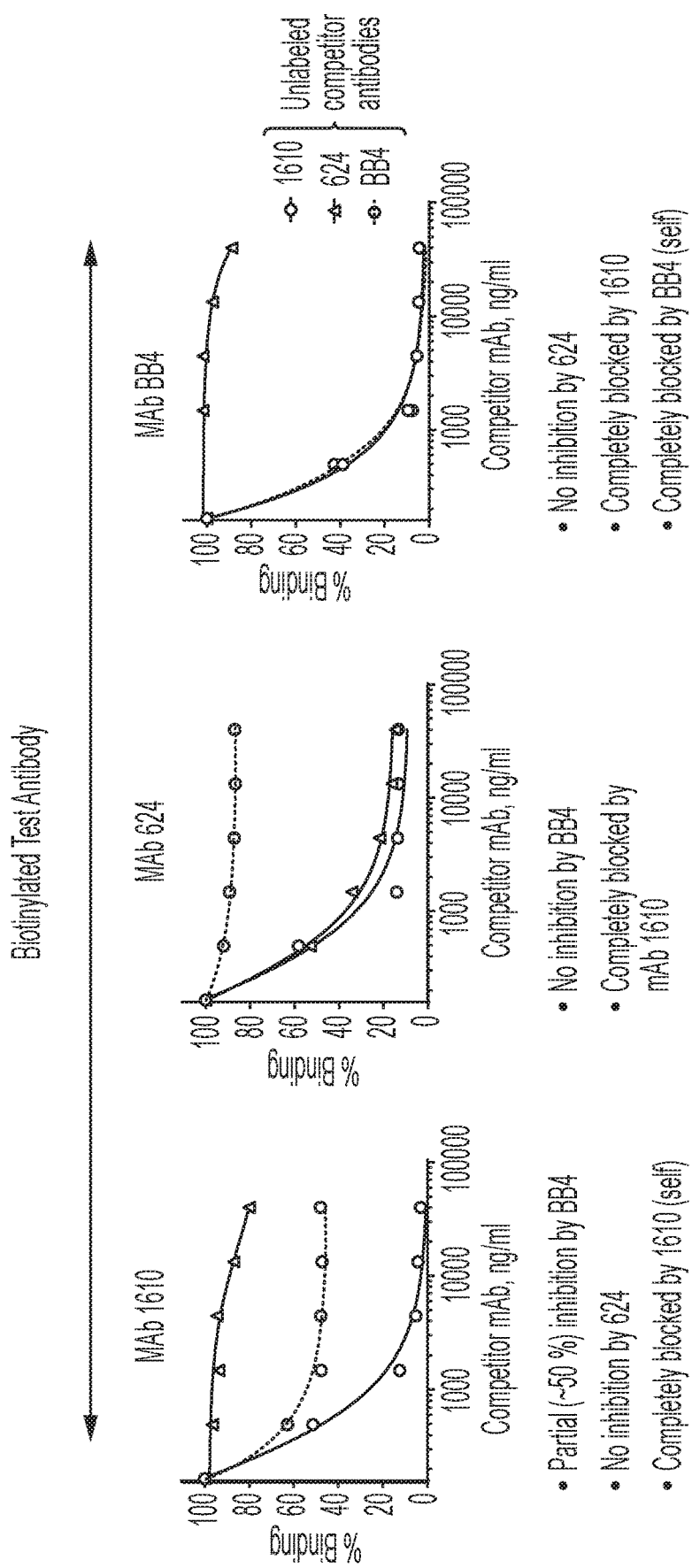

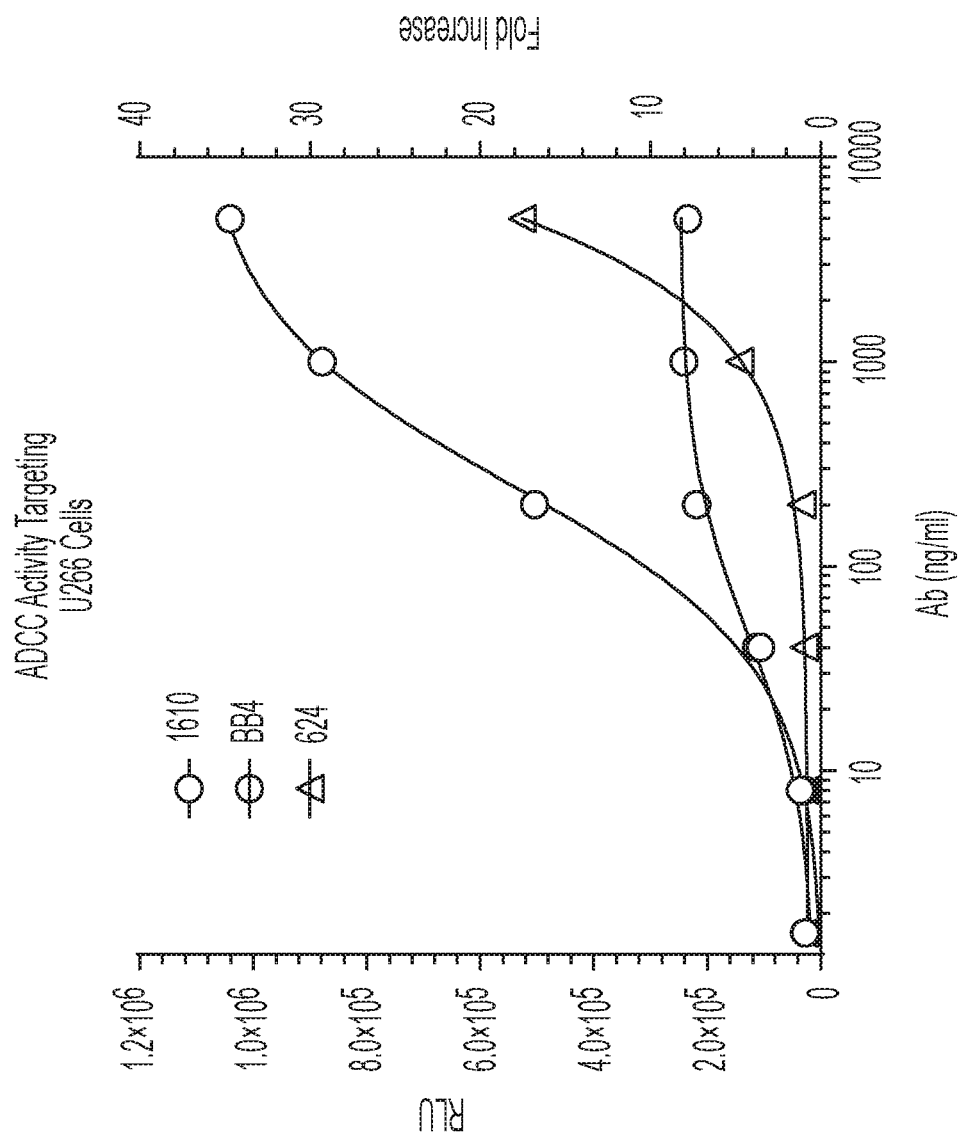

| Antibody ID | VH variant | Protein Titers |
|---|---|---|
| 1610 | wildtype | 63.1 |
| 2510 | C60Y | 103.4 |
| 2610 | N28S | 13.7 |
| 2710 | N28T | 9.6 |
| 2810 | N28S_C60Y | 70.0 |
| 2910 | N28T_C60Y | 58.7 |

FIG. 17

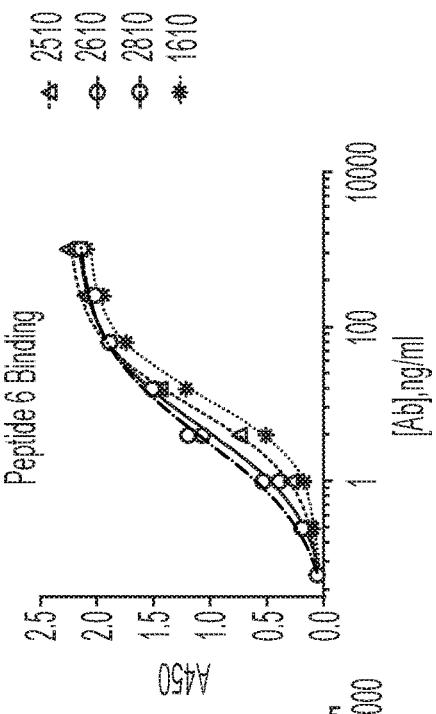
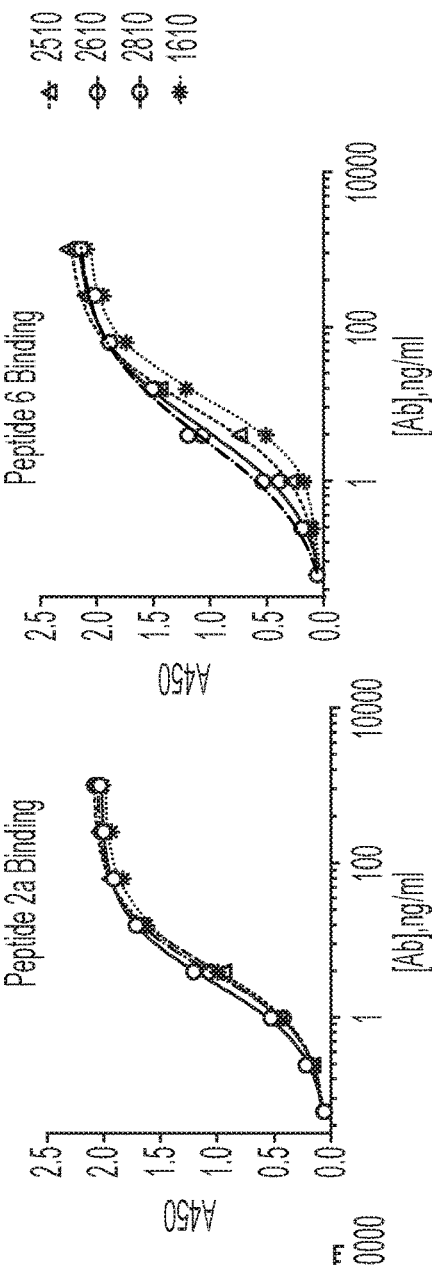
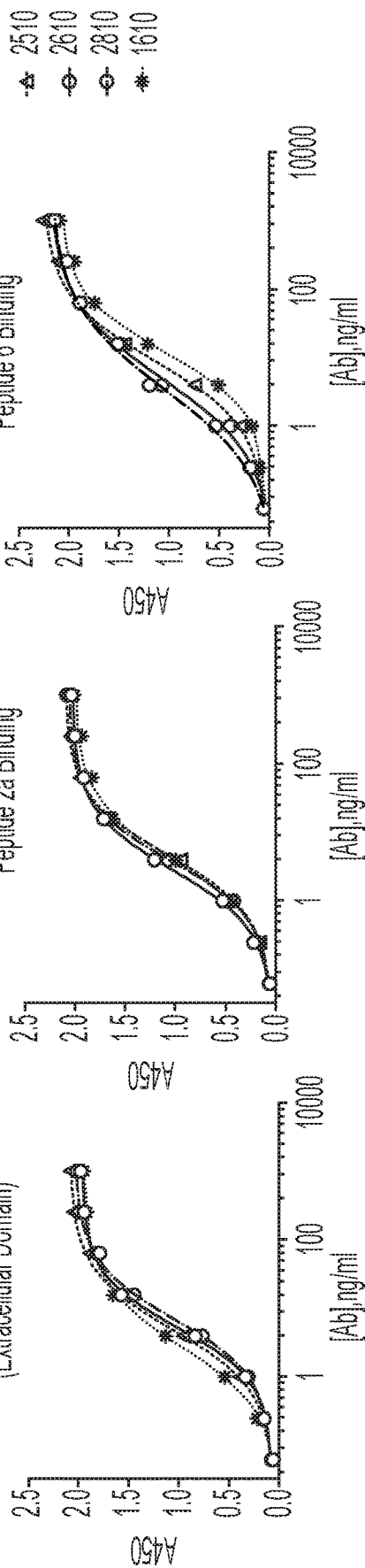
FIG. 18A
FIG. 18B
FIG. 18C
| Ab ID | Mutation | EC50 (ng/mL) | | |
|---|---|---|---|---|
| | | CD138 | Peptide 2a | Peptide 6 |
| 2510 | C60Y | 4.9 | 4.6 | 8.9 |
| 2610 | N28S | 7.0 | 3.8 | 4.9 |
| 2810 | N28S/C60Y | 5.3 | 2.8 | 3.2 |
| 1610 | WT | 2.7 | 3.9 | 12.3 |
Methods: Binding measured by ELISA
FIG. 18D (Mid region): SPEPTGLEATAASTSTLPAGEGPKEGEAVVLPEVEPGLTAREQEATPRPRETTQ Peptide 2A: ASTSTLPAGEGPKEGEAVVLPEVEPGLTAREQEA Peptide 2C: GEAVVLPEVEPGLTAREQEA Peptide 2D: GEAVVLPEVEPGLTA (Membrane Proximal): GSGEQDFTFETSGENTAVVAVEPDRRNQSPVDQGATGASQGLLDRKEVLG Peptide 6B: ENTAVVAVEPDRRNQSPVDQGATGASQGLLDRKEVLG Peptide 6E: RNQSPVDQGATGASQGLLDRKEVLG Peptide 6F: ENTAVVAVEPDRRNQ

```
6F  -ENTAVVAVEPDRRNQ----         15
2C  GEAVVLPEVEPGLTAREQEA         20
     *  .:  ****.   :
```

FIG. 22C

SEQUENCE LISTING

```
<160> NUMBER OF SEQ ID NOS: 457

<210> SEQ ID NO 1
<211> LENGTH: 310
<212> TYPE: PRT
<213> ORGANISM: Homo sapiens

<400> SEQUENCE: 1

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
    130                 135                 140

Ala Gln Glu Pro Ala Thr Ser His Pro His Arg Asp Met Gln Pro Gly
145                 150                 155                 160
```

```
His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 2
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
```

```
                195                 200                 205
Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
                260                 265                 270

Phe Met Leu Tyr Arg Met Lys Lys Asp Glu Gly Ser Tyr Ser Leu
                275                 280                 285

Glu Glu Pro Lys Gln Ala Asn Gly Gly Ala Tyr Gln Lys Pro Thr Lys
290                 295                 300

Gln Glu Glu Phe Tyr Ala
305                 310

<210> SEQ ID NO 3
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Met Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
                100                 105                 110

Gly Leu Thr Ala Arg Glu Gln Glu Ala Thr Pro Arg Pro Arg Glu Thr
            115                 120                 125

Thr Gln Leu Pro Thr Thr His Gln Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
                180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240
```

```
Gly Ala Ser Gln Gly Leu Leu Asp Arg Lys Glu Val Leu Gly Gly Val
            245                 250                 255

Ile Ala Gly Gly Leu Val Gly Leu Ile Phe Ala Val Cys Leu Val Gly
        260                 265                 270

Phe Met Leu Tyr Arg Met Lys Lys Lys Asp Glu Gly Ser Tyr Ser Leu
            275                 280                 285

Glu Glu Pro Lys Gln Ala Asn Gly Gly Ala Tyr Gln Lys Pro Thr Lys
        290                 295                 300

Gln Glu Glu Phe Tyr Ala
305                 310

<210> SEQ ID NO 4
<211> LENGTH: 933
<212> TYPE: DNA
<213> ORGANISM: Homo sapiens

<400> SEQUENCE: 4
atgaggcgcg cggcgctctg gctctggctg tgcgcgctgg cgctgagcct gcagccggcc      60
ctgccgcaaa ttgtggctac taatttgccc cctgaagatc aagatggctc tggggatgac     120
tctgacaact tctccggctc aggtgcaggt gctttgcaag atatcacctt gtcacagcag     180 acccccteca cttggaagga cacgcagctc ctgacggcta ttccacgtc tccagaaccc      240 accggcctgg aggctacagc tgcctccacc tccaccctgc cggctggaga ggggcccaag     300
gagggagagg ctgtagtcct gccagaagtg gagcctggcc tcaccgcccg ggagcaggag     360
gccacccccc gacccaggga gaccacacag ctcccgacca ctcatcaggc ctcaacgacc     420
acagccacca cggcccagga gcccgccacc tccaccccc acaggacat gcagcctggc       480 caccatgaga cctcaacccc tgcaggacca agccaagctg accttcacac tccccacaca     540
gaggatggag gtccttctgc caccgagagg gctgctgagg atggagcctc cagtcagctc     600
ccagcagcag agggctctgg ggagcaggac ttcacctttg aaacctcggg ggagaatacg     660
gctgtagtgg ccgtggagcc tgaccgccgg aaccagtccc cagtggatca gggggccacg     720
ggggcctcac agggcctcct ggacaggaaa gaggtgctgg gagggtcat tgccggaggc     780 ctcgtggggc tcatctttgc tgtgtgcctg gtgggtttca tgctgtaccg catgaagaag     840
aaggacgaag gcagctactc cttggaggag ccgaaacaag ccaacggcgg ggcctaccag     900
aagcccacca acaggagga attctatgcc tga                                   933

<210> SEQ ID NO 5
<211> LENGTH: 933
<212> TYPE: DNA
<213> ORGANISM: Homo sapiens

<400> SEQUENCE: 5
atgaggcgcg cggcgctctg gctctggctg tgcgcgctgg cgctgagcct gcagccggcc      60
ctgccgcaaa ttgtggctac taatttgccc cctgaagatc aagatggctc tggggatgac     120
tctgacaact tctccggctc aggtgcaggt gctttgcaag atatcacctt gtcacagcag     180 acccccteca cttggaagga cacgcagctc ctgacggcta ttccacgtc tccagaaccc      240 accggcctgg aggctacagc tgcctccacc tccaccctgc cggctggaga ggggcccaag     300
gagggagagg ctgtagtcct gccagaagtg gagcctggcc tcaccgcccg ggagcaggag     360
gccacccccc gacccaggga gaccacacag ctcccgacca ctcatcaggc ctcaacgacc     420
acagccacca cggcccagga gcccgccacc tccaccccc acaggacat gcagcctggc       480
```

-continued

```
caccatgaga cctcaacccc tgcaggaccc agccaagctg accttcacac tccccacaca      540
gaggatggag gtccttctgc caccgagagg gctgctgagg atggagcctc cagtcagctc      600
ccagcagcag agggctctgg ggagcaggac ttcacctttg aaacctcggg ggagaatacg      660
gctgtagtgg ccgtggagcc tgaccgccgg aaccagtccc cagtggatca gggggccacg      720
ggggcctcac agggcctcct ggacaggaaa gaggtgctgg gaggggtcat tgccggaggc      780 ctcgtgggc tcatctttgc tgtgtgcctg gtgggtttca tgctgtaccg catgaagaag       840
aaggacgaag gcagctactc cttggaggag ccgaaacaag ccaacggcgg ggcctaccag      900
aagcccacca acaggagga attctatgcc tga                                     933
```

<210> SEQ ID NO 6
<211> LENGTH: 311
<212> TYPE: PRT
<213> ORGANISM: Mus musculus

<400> SEQUENCE: 6

```
Met Arg Arg Ala Ala Leu Trp Leu Trp Leu Cys Ala Leu Ala Leu Arg
 1               5                  10                  15

Leu Gln Pro Ala Leu Pro Gln Ile Val Ala Val Asn Val Pro Pro Glu
            20                  25                  30

Asp Gln Asp Gly Ser Gly Asp Ser Asp Asn Phe Ser Gly Ser Gly
        35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Ala Pro Glu Pro Thr
65                  70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
        115                 120                 125

Thr Val Gln Leu Pro Ile Thr Gln Arg Ala Ser Thr Val Arg Val Thr
    130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Gly Thr Ser Val Ile Lys Glu Val
            180                 185                 190

Val Glu Asp Gly Thr Ala Asn Gln Leu Pro Ala Gly Glu Gly Ser Gly
        195                 200                 205

Glu Gln Asp Phe Thr Phe Glu Thr Ser Gly Glu Asn Thr Ala Val Ala
    210                 215                 220

Ala Val Glu Pro Gly Leu Arg Asn Gln Pro Val Asp Glu Gly Ala
225                 230                 235                 240

Thr Gly Ala Ser Gln Ser Leu Leu Asp Arg Lys Glu Val Leu Gly Gly
                245                 250                 255

Val Ile Ala Gly Gly Leu Val Gly Leu Ile Phe Ala Val Cys Leu Val
            260                 265                 270

Ala Phe Met Leu Tyr Arg Met Lys Lys Lys Asp Glu Gly Ser Tyr Ser
        275                 280                 285

Leu Glu Glu Pro Lys Gln Ala Asn Gly Gly Ala Tyr Gln Lys Pro Thr
```

```
                290               295               300
Lys Gln Glu Glu Phe Tyr Ala
305                 310

<210> SEQ ID NO 7
<211> LENGTH: 936
<212> TYPE: DNA
<213> ORGANISM: Mus musculus

<400> SEQUENCE: 7
atgagacgcg cggcgctctg gctctggctc tgcgcgctgg cgctgcgcct gcagcctgcc     60
ctcccgcaaa ttgtggctgt aaatgttcct cctgaagatc aggatggctc tggggatgac    120
tctgacaact tctctggctc tggcacaggt gctttgccag atactttgtc acggcagaca    180
ccttccactt ggaaggacgt gtggctgttg acagccacgc ccacagctcc agagcccacc    240
agcagcaaca ccgagactgc ttttacctct gtcctgccag ccggagagaa gcccgaggag    300
ggagagcctg tgctccatgt agaagcagag cctggcttca ctgctcggga caaggaaaag    360
gaggtcacca ccaggcccag ggagaccgtg cagctcccca tcacccaacg ggcctcaaca    420
gtcagagtca ccacagccca ggcagctgtc acatctcatc cgcacggggg catgcaacct    480
ggcctccatg agacctcggc tcccacagca cctggtcaac ctgaccatca gcctccacgt    540
gtggagggtg gcggcacttc tgtcatcaaa gaggttgtcg aggatggaac tgccaatcag    600
cttcccgcag gagagggctc tggagaacaa gacttcacct ttgaaacatc tggggagaac    660
acagctgtgg ctgccgtaga gcccggcctg cggaatcagc cccggtggga cgaaggagcc    720
acaggtgctt ctcagagcct tttggacagg aaggaagtgc tgggaggtgt cattgccgga    780
ggcctagtgg gcctcatctt tgctgtgtgc ctggtggctt tcatgctgta ccggatgaag    840
aagaaggacg aaggcagcta ctccttggag gagcccaaac aagccaatgg cggtgcctac    900
cagaaaccca ccaagcagga ggagttctac gcctga                             936

<210> SEQ ID NO 8
<211> LENGTH: 39
<212> TYPE: PRT
<213> ORGANISM: Homo sapiens

<400> SEQUENCE: 8

Gln Ile Val Ala Thr Asn Leu Pro Pro Glu Asp Gln Asp Gly Ser Gly
1               5                   10                  15

Asp Asp Ser Asp Asn Phe Ser Gly Ser Gly Ala Gly Ala Leu Gln Asp
            20                  25                  30

Ile Thr Leu Ser Gln Gln Thr
        35

<210> SEQ ID NO 9
<211> LENGTH: 45
<212> TYPE: PRT
<213> ORGANISM: Homo sapiens

<400> SEQUENCE: 9

Ala Leu Gln Asp Ile Thr Leu Ser Gln Gln Thr Pro Ser Thr Trp Lys
1               5                   10                  15

Asp Thr Gln Leu Leu Thr Ala Ile Pro Thr Ser Pro Glu Pro Thr Gly
            20                  25                  30

Leu Glu Ala Thr Ala Ala Ser Thr Ser Thr Leu Pro Ala
        35                  40                  45
```

<210> SEQ ID NO 10
<211> LENGTH: 34
<212> TYPE: PRT
<213> ORGANISM: Homo sapiens

<400> SEQUENCE: 10

Ala Ser Thr Ser Thr Leu Pro Ala Gly Glu Gly Pro Lys Glu Gly Glu
1               5                   10                  15

Ala Val Val Leu Pro Glu Val Glu Pro Gly Leu Thr Ala Arg Glu Gln
            20                  25                  30

Glu Ala

<210> SEQ ID NO 11
<211> LENGTH: 15
<212> TYPE: PRT
<213> ORGANISM: Homo sapiens

<400> SEQUENCE: 11

Ala Ser Thr Ser Thr Leu Pro Ala Gly Glu Gly Pro Lys Glu Gly
1               5                   10                  15

<210> SEQ ID NO 12
<211> LENGTH: 40
<212> TYPE: PRT
<213> ORGANISM: Homo sapiens

<400> SEQUENCE: 12

Glu Pro Gly Leu Thr Ala Arg Glu Gln Glu Ala Thr Pro Arg Pro Arg
1               5                   10                  15

Glu Thr Thr Gln Leu Pro Thr Thr His Gln Ala Ser Thr Thr Thr Ala
            20                  25                  30

Thr Thr Ala Gln Glu Pro Ala Thr
            35                  40

<210> SEQ ID NO 13
<211> LENGTH: 35
<212> TYPE: PRT
<213> ORGANISM: Homo sapiens

<400> SEQUENCE: 13

Gln Glu Pro Ala Thr Ser His Pro His Arg Asp Met Gln Pro Gly His
1               5                   10                  15

His Glu Thr Ser Thr Pro Ala Gly Pro Ser Gln Ala Asp Leu His Thr
            20                  25                  30

Pro His Thr
        35

<210> SEQ ID NO 14
<211> LENGTH: 75
<212> TYPE: PRT
<213> ORGANISM: Homo sapiens

<400> SEQUENCE: 14

His Thr Pro His Thr Glu Asp Gly Gly Pro Ser Ala Thr Glu Arg Ala
1               5                   10                  15

Ala Glu Asp Gly Ala Ser Ser Gln Leu Pro Ala Ala Glu Gly Ser Gly
            20                  25                  30

Glu Gln Asp Phe Thr Phe Glu Thr Ser Gly Glu Asn Thr Ala Val Val
            35                  40                  45

Ala Val Glu Pro Asp Arg Arg Asn Gln Ser Pro Val Asp Gln Gly Ala

```
                  50                  55                  60
Thr Gly Ala Ser Gln Gly Leu Leu Asp Arg Lys
 65                  70                  75

<210> SEQ ID NO 15
<211> LENGTH: 39
<212> TYPE: PRT
<213> ORGANISM: Homo sapiens

<400> SEQUENCE: 15

His Thr Pro His Thr Glu Asp Gly Gly Pro Ser Ala Thr Glu Arg Ala
  1               5                  10                  15

Ala Glu Asp Gly Ala Ser Ser Gln Leu Pro Ala Ala Glu Gly Ser Gly
             20                  25                  30

Glu Gln Asp Phe Thr Phe Glu
         35

<210> SEQ ID NO 16
<211> LENGTH: 41
<212> TYPE: PRT
<213> ORGANISM: Homo sapiens

<400> SEQUENCE: 16

Asp Phe Thr Phe Glu Thr Ser Gly Glu Asn Thr Ala Val Val Ala Val
  1               5                  10                  15

Glu Pro Asp Arg Arg Asn Gln Ser Pro Val Asp Gln Gly Ala Thr Gly
             20                  25                  30

Ala Ser Gln Gly Leu Leu Asp Arg Lys
         35                  40

<210> SEQ ID NO 17
<211> LENGTH: 26
<212> TYPE: PRT
<213> ORGANISM: Homo sapiens

<400> SEQUENCE: 17

Thr Ala Val Val Ala Val Glu Pro Asp Arg Arg Asn Gln Ser Pro Val
  1               5                  10                  15

Asp Gln Gly Ala Thr Gly Ala Ser Gln Gly
             20                  25

<210> SEQ ID NO 18
<211> LENGTH: 4
<212> TYPE: PRT
<213> ORGANISM: Homo sapiens

<400> SEQUENCE: 18

Asp Phe Thr Phe
  1

<210> SEQ ID NO 19
<211> LENGTH: 4
<212> TYPE: PRT
<213> ORGANISM: Homo sapiens

<400> SEQUENCE: 19

Phe Thr Phe Glu
  1

<210> SEQ ID NO 20
<211> LENGTH: 4
<212> TYPE: PRT
```

```
<213> ORGANISM: Homo sapiens

<400> SEQUENCE: 20

Thr Phe Glu Thr
1

<210> SEQ ID NO 21
<211> LENGTH: 4
<212> TYPE: PRT
<213> ORGANISM: Homo sapiens

<400> SEQUENCE: 21

Phe Glu Thr Ser
1

<210> SEQ ID NO 22
<211> LENGTH: 4
<212> TYPE: PRT
<213> ORGANISM: Homo sapiens

<400> SEQUENCE: 22

Glu Thr Ser Gly
1

<210> SEQ ID NO 23
<211> LENGTH: 4
<212> TYPE: PRT
<213> ORGANISM: Homo sapiens

<400> SEQUENCE: 23

Thr Ser Gly Glu
1

<210> SEQ ID NO 24
<211> LENGTH: 4
<212> TYPE: PRT
<213> ORGANISM: Homo sapiens

<400> SEQUENCE: 24

Ser Gly Glu Asn
1

<210> SEQ ID NO 25
<211> LENGTH: 4
<212> TYPE: PRT
<213> ORGANISM: Homo sapiens

<400> SEQUENCE: 25

Gly Glu Asn Thr
1

<210> SEQ ID NO 26
<211> LENGTH: 4
<212> TYPE: PRT
<213> ORGANISM: Homo sapiens

<400> SEQUENCE: 26

Glu Asn Thr Ala
1

<210> SEQ ID NO 27
<211> LENGTH: 4
<212> TYPE: PRT
<213> ORGANISM: Homo sapiens
```

```
<400> SEQUENCE: 27

Asn Thr Ala Val
1

<210> SEQ ID NO 28
<211> LENGTH: 4
<212> TYPE: PRT
<213> ORGANISM: Homo sapiens

<400> SEQUENCE: 28

Thr Ala Val Val
1

<210> SEQ ID NO 29
<211> LENGTH: 4
<212> TYPE: PRT
<213> ORGANISM: Homo sapiens

<400> SEQUENCE: 29

Ala Val Val Ala
1

<210> SEQ ID NO 30
<211> LENGTH: 4
<212> TYPE: PRT
<213> ORGANISM: Homo sapiens

<400> SEQUENCE: 30

Val Val Ala Val
1

<210> SEQ ID NO 31
<211> LENGTH: 4
<212> TYPE: PRT
<213> ORGANISM: Homo sapiens

<400> SEQUENCE: 31

Val Ala Val Glu
1

<210> SEQ ID NO 32
<211> LENGTH: 4
<212> TYPE: PRT
<213> ORGANISM: Homo sapiens

<400> SEQUENCE: 32

Ala Val Glu Pro
1

<210> SEQ ID NO 33
<211> LENGTH: 4
<212> TYPE: PRT
<213> ORGANISM: Homo sapiens

<400> SEQUENCE: 33

Val Glu Pro Asp
1

<210> SEQ ID NO 34
<211> LENGTH: 4
<212> TYPE: PRT
<213> ORGANISM: Homo sapiens

<400> SEQUENCE: 34
```

Glu Pro Asp Arg
1

<210> SEQ ID NO 35
<211> LENGTH: 4
<212> TYPE: PRT
<213> ORGANISM: Homo sapiens

<400> SEQUENCE: 35

Pro Asp Arg Arg
1

<210> SEQ ID NO 36
<211> LENGTH: 4
<212> TYPE: PRT
<213> ORGANISM: Homo sapiens

<400> SEQUENCE: 36

Asp Arg Arg Asn
1

<210> SEQ ID NO 37
<211> LENGTH: 4
<212> TYPE: PRT
<213> ORGANISM: Homo sapiens

<400> SEQUENCE: 37

Arg Arg Asn Gln
1

<210> SEQ ID NO 38
<211> LENGTH: 4
<212> TYPE: PRT
<213> ORGANISM: Homo sapiens

<400> SEQUENCE: 38

Arg Asn Gln Ser
1

<210> SEQ ID NO 39
<211> LENGTH: 4
<212> TYPE: PRT
<213> ORGANISM: Homo sapiens

<400> SEQUENCE: 39

Asn Gln Ser Pro
1

<210> SEQ ID NO 40
<211> LENGTH: 4
<212> TYPE: PRT
<213> ORGANISM: Homo sapiens

<400> SEQUENCE: 40

Gln Ser Pro Val
1

<210> SEQ ID NO 41
<211> LENGTH: 4
<212> TYPE: PRT
<213> ORGANISM: Homo sapiens

<400> SEQUENCE: 41

Ser Pro Val Asp
1

```
<210> SEQ ID NO 42
<211> LENGTH: 4
<212> TYPE: PRT
<213> ORGANISM: Homo sapiens

<400> SEQUENCE: 42

Pro Val Asp Gln
1

<210> SEQ ID NO 43
<211> LENGTH: 4
<212> TYPE: PRT
<213> ORGANISM: Homo sapiens

<400> SEQUENCE: 43

Val Asp Gln Gly
1

<210> SEQ ID NO 44
<211> LENGTH: 4
<212> TYPE: PRT
<213> ORGANISM: Homo sapiens

<400> SEQUENCE: 44

Asp Gln Gly Ala
1

<210> SEQ ID NO 45
<211> LENGTH: 4
<212> TYPE: PRT
<213> ORGANISM: Homo sapiens

<400> SEQUENCE: 45

Gln Gly Ala Thr
1

<210> SEQ ID NO 46
<211> LENGTH: 4
<212> TYPE: PRT
<213> ORGANISM: Homo sapiens

<400> SEQUENCE: 46

Gly Ala Thr Gly
1

<210> SEQ ID NO 47
<211> LENGTH: 4
<212> TYPE: PRT
<213> ORGANISM: Homo sapiens

<400> SEQUENCE: 47

Ala Thr Gly Ala
1

<210> SEQ ID NO 48
<211> LENGTH: 4
<212> TYPE: PRT
<213> ORGANISM: Homo sapiens

<400> SEQUENCE: 48

Thr Gly Ala Ser
1
```

```
<210> SEQ ID NO 49
<211> LENGTH: 4
<212> TYPE: PRT
<213> ORGANISM: Homo sapiens

<400> SEQUENCE: 49

Gly Ala Ser Gln
1

<210> SEQ ID NO 50
<211> LENGTH: 4
<212> TYPE: PRT
<213> ORGANISM: Homo sapiens

<400> SEQUENCE: 50

Ala Ser Gln Gly
1

<210> SEQ ID NO 51
<211> LENGTH: 4
<212> TYPE: PRT
<213> ORGANISM: Homo sapiens

<400> SEQUENCE: 51

Ser Gln Gly Leu
1

<210> SEQ ID NO 52
<211> LENGTH: 4
<212> TYPE: PRT
<213> ORGANISM: Homo sapiens

<400> SEQUENCE: 52

Gln Gly Leu Leu
1

<210> SEQ ID NO 53
<211> LENGTH: 4
<212> TYPE: PRT
<213> ORGANISM: Homo sapiens

<400> SEQUENCE: 53

Gly Leu Leu Asp
1

<210> SEQ ID NO 54
<211> LENGTH: 4
<212> TYPE: PRT
<213> ORGANISM: Homo sapiens

<400> SEQUENCE: 54

Leu Leu Asp Arg
1

<210> SEQ ID NO 55
<211> LENGTH: 4
<212> TYPE: PRT
<213> ORGANISM: Homo sapiens

<400> SEQUENCE: 55

Leu Asp Arg Lys
1

<210> SEQ ID NO 56
<211> LENGTH: 5
```

```
<212> TYPE: PRT
<213> ORGANISM: Homo sapiens

<400> SEQUENCE: 56

Asp Phe Thr Phe Glu
1               5

<210> SEQ ID NO 57
<211> LENGTH: 5
<212> TYPE: PRT
<213> ORGANISM: Homo sapiens

<400> SEQUENCE: 57

Phe Thr Phe Glu Thr
1               5

<210> SEQ ID NO 58
<211> LENGTH: 5
<212> TYPE: PRT
<213> ORGANISM: Homo sapiens

<400> SEQUENCE: 58

Thr Phe Glu Thr Ser
1               5

<210> SEQ ID NO 59
<211> LENGTH: 5
<212> TYPE: PRT
<213> ORGANISM: Homo sapiens

<400> SEQUENCE: 59

Phe Glu Thr Ser Gly
1               5

<210> SEQ ID NO 60
<211> LENGTH: 5
<212> TYPE: PRT
<213> ORGANISM: Homo sapiens

<400> SEQUENCE: 60

Glu Thr Ser Gly Glu
1               5

<210> SEQ ID NO 61
<211> LENGTH: 5
<212> TYPE: PRT
<213> ORGANISM: Homo sapiens

<400> SEQUENCE: 61

Thr Ser Gly Glu Asn
1               5

<210> SEQ ID NO 62
<211> LENGTH: 5
<212> TYPE: PRT
<213> ORGANISM: Homo sapiens

<400> SEQUENCE: 62

Ser Gly Glu Asn Thr
1               5

<210> SEQ ID NO 63
<211> LENGTH: 5
<212> TYPE: PRT
<213> ORGANISM: Homo sapiens
```

```
<400> SEQUENCE: 63

Gly Glu Asn Thr Ala
1               5

<210> SEQ ID NO 64
<211> LENGTH: 5
<212> TYPE: PRT
<213> ORGANISM: Homo sapiens

<400> SEQUENCE: 64

Glu Asn Thr Ala Val
1               5

<210> SEQ ID NO 65
<211> LENGTH: 5
<212> TYPE: PRT
<213> ORGANISM: Homo sapiens

<400> SEQUENCE: 65

Asn Thr Ala Val Val
1               5

<210> SEQ ID NO 66
<211> LENGTH: 5
<212> TYPE: PRT
<213> ORGANISM: Homo sapiens

<400> SEQUENCE: 66

Thr Ala Val Val Ala
1               5

<210> SEQ ID NO 67
<211> LENGTH: 5
<212> TYPE: PRT
<213> ORGANISM: Homo sapiens

<400> SEQUENCE: 67

Ala Val Val Ala Val
1               5

<210> SEQ ID NO 68
<211> LENGTH: 5
<212> TYPE: PRT
<213> ORGANISM: Homo sapiens

<400> SEQUENCE: 68

Val Val Ala Val Glu
1               5

<210> SEQ ID NO 69
<211> LENGTH: 5
<212> TYPE: PRT
<213> ORGANISM: Homo sapiens

<400> SEQUENCE: 69

Val Ala Val Glu Pro
1               5

<210> SEQ ID NO 70
<211> LENGTH: 5
<212> TYPE: PRT
<213> ORGANISM: Homo sapiens

<400> SEQUENCE: 70
```

Ala Val Glu Pro Asp
1               5

<210> SEQ ID NO 71
<211> LENGTH: 5
<212> TYPE: PRT
<213> ORGANISM: Homo sapiens

<400> SEQUENCE: 71

Val Glu Pro Asp Arg
1               5

<210> SEQ ID NO 72
<211> LENGTH: 5
<212> TYPE: PRT
<213> ORGANISM: Homo sapiens

<400> SEQUENCE: 72

Glu Pro Asp Arg Arg
1               5

<210> SEQ ID NO 73
<211> LENGTH: 5
<212> TYPE: PRT
<213> ORGANISM: Homo sapiens

<400> SEQUENCE: 73

Pro Asp Arg Arg Asn
1               5

<210> SEQ ID NO 74
<211> LENGTH: 5
<212> TYPE: PRT
<213> ORGANISM: Homo sapiens

<400> SEQUENCE: 74

Asp Arg Arg Asn Gln
1               5

<210> SEQ ID NO 75
<211> LENGTH: 5
<212> TYPE: PRT
<213> ORGANISM: Homo sapiens

<400> SEQUENCE: 75

Arg Arg Asn Gln Ser
1               5

<210> SEQ ID NO 76
<211> LENGTH: 5
<212> TYPE: PRT
<213> ORGANISM: Homo sapiens

<400> SEQUENCE: 76

Arg Asn Gln Ser Pro
1               5

<210> SEQ ID NO 77
<211> LENGTH: 5
<212> TYPE: PRT
<213> ORGANISM: Homo sapiens

<400> SEQUENCE: 77

Asn Gln Ser Pro Val

```
1               5

<210> SEQ ID NO 78
<211> LENGTH: 5
<212> TYPE: PRT
<213> ORGANISM: Homo sapiens

<400> SEQUENCE: 78

Gln Ser Pro Val Asp
1               5

<210> SEQ ID NO 79
<211> LENGTH: 5
<212> TYPE: PRT
<213> ORGANISM: Homo sapiens

<400> SEQUENCE: 79

Ser Pro Val Asp Gln
1               5

<210> SEQ ID NO 80
<211> LENGTH: 5
<212> TYPE: PRT
<213> ORGANISM: Homo sapiens

<400> SEQUENCE: 80

Pro Val Asp Gln Gly
1               5

<210> SEQ ID NO 81
<211> LENGTH: 5
<212> TYPE: PRT
<213> ORGANISM: Homo sapiens

<400> SEQUENCE: 81

Val Asp Gln Gly Ala
1               5

<210> SEQ ID NO 82
<211> LENGTH: 5
<212> TYPE: PRT
<213> ORGANISM: Homo sapiens

<400> SEQUENCE: 82

Asp Gln Gly Ala Thr
1               5

<210> SEQ ID NO 83
<211> LENGTH: 5
<212> TYPE: PRT
<213> ORGANISM: Homo sapiens

<400> SEQUENCE: 83

Gln Gly Ala Thr Gly
1               5

<210> SEQ ID NO 84
<211> LENGTH: 5
<212> TYPE: PRT
<213> ORGANISM: Homo sapiens

<400> SEQUENCE: 84

Gly Ala Thr Gly Ala
1               5
```

```
<210> SEQ ID NO 85
<211> LENGTH: 5
<212> TYPE: PRT
<213> ORGANISM: Homo sapiens

<400> SEQUENCE: 85

Ala Thr Gly Ala Ser
1               5

<210> SEQ ID NO 86
<211> LENGTH: 5
<212> TYPE: PRT
<213> ORGANISM: Homo sapiens

<400> SEQUENCE: 86

Thr Gly Ala Ser Gln
1               5

<210> SEQ ID NO 87
<211> LENGTH: 5
<212> TYPE: PRT
<213> ORGANISM: Homo sapiens

<400> SEQUENCE: 87

Gly Ala Ser Gln Gly
1               5

<210> SEQ ID NO 88
<211> LENGTH: 5
<212> TYPE: PRT
<213> ORGANISM: Homo sapiens

<400> SEQUENCE: 88

Ala Ser Gln Gly Leu
1               5

<210> SEQ ID NO 89
<211> LENGTH: 5
<212> TYPE: PRT
<213> ORGANISM: Homo sapiens

<400> SEQUENCE: 89

Ser Gln Gly Leu Leu
1               5

<210> SEQ ID NO 90
<211> LENGTH: 5
<212> TYPE: PRT
<213> ORGANISM: Homo sapiens

<400> SEQUENCE: 90

Gln Gly Leu Leu Asp
1               5

<210> SEQ ID NO 91
<211> LENGTH: 5
<212> TYPE: PRT
<213> ORGANISM: Homo sapiens

<400> SEQUENCE: 91

Gly Leu Leu Asp Arg
1               5

<210> SEQ ID NO 92
```

```
<211> LENGTH: 5
<212> TYPE: PRT
<213> ORGANISM: Homo sapiens

<400> SEQUENCE: 92

Leu Leu Asp Arg Lys
1               5

<210> SEQ ID NO 93
<211> LENGTH: 6
<212> TYPE: PRT
<213> ORGANISM: Homo sapiens

<400> SEQUENCE: 93

Asp Phe Thr Phe Glu Thr
1               5

<210> SEQ ID NO 94
<211> LENGTH: 6
<212> TYPE: PRT
<213> ORGANISM: Homo sapiens

<400> SEQUENCE: 94

Phe Thr Phe Glu Thr Ser
1               5

<210> SEQ ID NO 95
<211> LENGTH: 6
<212> TYPE: PRT
<213> ORGANISM: Homo sapiens

<400> SEQUENCE: 95

Thr Phe Glu Thr Ser Gly
1               5

<210> SEQ ID NO 96
<211> LENGTH: 6
<212> TYPE: PRT
<213> ORGANISM: Homo sapiens

<400> SEQUENCE: 96

Phe Glu Thr Ser Gly Glu
1               5

<210> SEQ ID NO 97
<211> LENGTH: 6
<212> TYPE: PRT
<213> ORGANISM: Homo sapiens

<400> SEQUENCE: 97

Glu Thr Ser Gly Glu Asn
1               5

<210> SEQ ID NO 98
<211> LENGTH: 6
<212> TYPE: PRT
<213> ORGANISM: Homo sapiens

<400> SEQUENCE: 98

Thr Ser Gly Glu Asn Thr
1               5

<210> SEQ ID NO 99
<211> LENGTH: 6
<212> TYPE: PRT
```

<213> ORGANISM: Homo sapiens

<400> SEQUENCE: 99

Ser Gly Glu Asn Thr Ala
1               5

<210> SEQ ID NO 100
<211> LENGTH: 6
<212> TYPE: PRT
<213> ORGANISM: Homo sapiens

<400> SEQUENCE: 100

Gly Glu Asn Thr Ala Val
1               5

<210> SEQ ID NO 101
<211> LENGTH: 6
<212> TYPE: PRT
<213> ORGANISM: Homo sapiens

<400> SEQUENCE: 101

Glu Asn Thr Ala Val Val
1               5

<210> SEQ ID NO 102
<211> LENGTH: 6
<212> TYPE: PRT
<213> ORGANISM: Homo sapiens

<400> SEQUENCE: 102

Asn Thr Ala Val Val Ala
1               5

<210> SEQ ID NO 103
<211> LENGTH: 6
<212> TYPE: PRT
<213> ORGANISM: Homo sapiens

<400> SEQUENCE: 103

Thr Ala Val Val Ala Val
1               5

<210> SEQ ID NO 104
<211> LENGTH: 6
<212> TYPE: PRT
<213> ORGANISM: Homo sapiens

<400> SEQUENCE: 104

Ala Val Val Ala Val Glu
1               5

<210> SEQ ID NO 105
<211> LENGTH: 6
<212> TYPE: PRT
<213> ORGANISM: Homo sapiens

<400> SEQUENCE: 105

Val Val Ala Val Glu Pro
1               5

<210> SEQ ID NO 106
<211> LENGTH: 6
<212> TYPE: PRT
<213> ORGANISM: Homo sapiens

```
<400> SEQUENCE: 106

Val Ala Val Glu Pro Asp
1               5

<210> SEQ ID NO 107
<211> LENGTH: 6
<212> TYPE: PRT
<213> ORGANISM: Homo sapiens

<400> SEQUENCE: 107

Ala Val Glu Pro Asp Arg
1               5

<210> SEQ ID NO 108
<211> LENGTH: 6
<212> TYPE: PRT
<213> ORGANISM: Homo sapiens

<400> SEQUENCE: 108

Val Glu Pro Asp Arg Arg
1               5

<210> SEQ ID NO 109
<211> LENGTH: 6
<212> TYPE: PRT
<213> ORGANISM: Homo sapiens

<400> SEQUENCE: 109

Glu Pro Asp Arg Arg Asn
1               5

<210> SEQ ID NO 110
<211> LENGTH: 6
<212> TYPE: PRT
<213> ORGANISM: Homo sapiens

<400> SEQUENCE: 110

Pro Asp Arg Arg Asn Gln
1               5

<210> SEQ ID NO 111
<211> LENGTH: 6
<212> TYPE: PRT
<213> ORGANISM: Homo sapiens

<400> SEQUENCE: 111

Asp Arg Arg Asn Gln Ser
1               5

<210> SEQ ID NO 112
<211> LENGTH: 6
<212> TYPE: PRT
<213> ORGANISM: Homo sapiens

<400> SEQUENCE: 112

Arg Arg Asn Gln Ser Pro
1               5

<210> SEQ ID NO 113
<211> LENGTH: 6
<212> TYPE: PRT
<213> ORGANISM: Homo sapiens

<400> SEQUENCE: 113
```

Arg Asn Gln Ser Pro Val
1               5

<210> SEQ ID NO 114
<211> LENGTH: 6
<212> TYPE: PRT
<213> ORGANISM: Homo sapiens

<400> SEQUENCE: 114

Asn Gln Ser Pro Val Asp
1               5

<210> SEQ ID NO 115
<211> LENGTH: 6
<212> TYPE: PRT
<213> ORGANISM: Homo sapiens

<400> SEQUENCE: 115

Gln Ser Pro Val Asp Gln
1               5

<210> SEQ ID NO 116
<211> LENGTH: 6
<212> TYPE: PRT
<213> ORGANISM: Homo sapiens

<400> SEQUENCE: 116

Ser Pro Val Asp Gln Gly
1               5

<210> SEQ ID NO 117
<211> LENGTH: 6
<212> TYPE: PRT
<213> ORGANISM: Homo sapiens

<400> SEQUENCE: 117

Pro Val Asp Gln Gly Ala
1               5

<210> SEQ ID NO 118
<211> LENGTH: 6
<212> TYPE: PRT
<213> ORGANISM: Homo sapiens

<400> SEQUENCE: 118

Val Asp Gln Gly Ala Thr
1               5

<210> SEQ ID NO 119
<211> LENGTH: 6
<212> TYPE: PRT
<213> ORGANISM: Homo sapiens

<400> SEQUENCE: 119

Asp Gln Gly Ala Thr Gly
1               5

<210> SEQ ID NO 120
<211> LENGTH: 6
<212> TYPE: PRT
<213> ORGANISM: Homo sapiens

<400> SEQUENCE: 120

Gln Gly Ala Thr Gly Ala
1               5

<210> SEQ ID NO 121
<211> LENGTH: 6
<212> TYPE: PRT
<213> ORGANISM: Homo sapiens

<400> SEQUENCE: 121

Gly Ala Thr Gly Ala Ser
1               5

<210> SEQ ID NO 122
<211> LENGTH: 6
<212> TYPE: PRT
<213> ORGANISM: Homo sapiens

<400> SEQUENCE: 122

Ala Thr Gly Ala Ser Gln
1               5

<210> SEQ ID NO 123
<211> LENGTH: 6
<212> TYPE: PRT
<213> ORGANISM: Homo sapiens

<400> SEQUENCE: 123

Thr Gly Ala Ser Gln Gly
1               5

<210> SEQ ID NO 124
<211> LENGTH: 6
<212> TYPE: PRT
<213> ORGANISM: Homo sapiens

<400> SEQUENCE: 124

Gly Ala Ser Gln Gly Leu
1               5

<210> SEQ ID NO 125
<211> LENGTH: 6
<212> TYPE: PRT
<213> ORGANISM: Homo sapiens

<400> SEQUENCE: 125

Ala Ser Gln Gly Leu Leu
1               5

<210> SEQ ID NO 126
<211> LENGTH: 6
<212> TYPE: PRT
<213> ORGANISM: Homo sapiens

<400> SEQUENCE: 126

Ser Gln Gly Leu Leu Asp
1               5

<210> SEQ ID NO 127
<211> LENGTH: 6
<212> TYPE: PRT
<213> ORGANISM: Homo sapiens

<400> SEQUENCE: 127

Gln Gly Leu Leu Asp Arg
1               5

```
<210> SEQ ID NO 128
<211> LENGTH: 6
<212> TYPE: PRT
<213> ORGANISM: Homo sapiens

<400> SEQUENCE: 128

Gly Leu Leu Asp Arg Lys
1               5

<210> SEQ ID NO 129
<211> LENGTH: 4
<212> TYPE: PRT
<213> ORGANISM: Homo sapiens

<400> SEQUENCE: 129

His Thr Pro His
1

<210> SEQ ID NO 130
<211> LENGTH: 4
<212> TYPE: PRT
<213> ORGANISM: Homo sapiens

<400> SEQUENCE: 130

Thr Pro His Thr
1

<210> SEQ ID NO 131
<211> LENGTH: 4
<212> TYPE: PRT
<213> ORGANISM: Homo sapiens

<400> SEQUENCE: 131

Pro His Thr Glu
1

<210> SEQ ID NO 132
<211> LENGTH: 4
<212> TYPE: PRT
<213> ORGANISM: Homo sapiens

<400> SEQUENCE: 132

His Thr Glu Asp
1

<210> SEQ ID NO 133
<211> LENGTH: 4
<212> TYPE: PRT
<213> ORGANISM: Homo sapiens

<400> SEQUENCE: 133

Thr Glu Asp Gly
1

<210> SEQ ID NO 134
<211> LENGTH: 4
<212> TYPE: PRT
<213> ORGANISM: Homo sapiens

<400> SEQUENCE: 134

Glu Asp Gly Gly
1

<210> SEQ ID NO 135
<211> LENGTH: 4
```

```
<212> TYPE: PRT
<213> ORGANISM: Homo sapiens

<400> SEQUENCE: 135

Asp Gly Gly Pro
1

<210> SEQ ID NO 136
<211> LENGTH: 4
<212> TYPE: PRT
<213> ORGANISM: Homo sapiens

<400> SEQUENCE: 136

Gly Gly Pro Ser
1

<210> SEQ ID NO 137
<211> LENGTH: 4
<212> TYPE: PRT
<213> ORGANISM: Homo sapiens

<400> SEQUENCE: 137

Gly Pro Ser Ala
1

<210> SEQ ID NO 138
<211> LENGTH: 4
<212> TYPE: PRT
<213> ORGANISM: Homo sapiens

<400> SEQUENCE: 138

Pro Ser Ala Thr
1

<210> SEQ ID NO 139
<211> LENGTH: 4
<212> TYPE: PRT
<213> ORGANISM: Homo sapiens

<400> SEQUENCE: 139

Ser Ala Thr Glu
1

<210> SEQ ID NO 140
<211> LENGTH: 4
<212> TYPE: PRT
<213> ORGANISM: Homo sapiens

<400> SEQUENCE: 140

Ala Thr Glu Arg
1

<210> SEQ ID NO 141
<211> LENGTH: 4
<212> TYPE: PRT
<213> ORGANISM: Homo sapiens

<400> SEQUENCE: 141

Thr Glu Arg Ala
1

<210> SEQ ID NO 142
<211> LENGTH: 4
<212> TYPE: PRT
<213> ORGANISM: Homo sapiens
```

<400> SEQUENCE: 142

Glu Arg Ala Ala
1

<210> SEQ ID NO 143
<211> LENGTH: 4
<212> TYPE: PRT
<213> ORGANISM: Homo sapiens

<400> SEQUENCE: 143

Arg Ala Ala Glu
1

<210> SEQ ID NO 144
<211> LENGTH: 4
<212> TYPE: PRT
<213> ORGANISM: Homo sapiens

<400> SEQUENCE: 144

Ala Ala Glu Asp
1

<210> SEQ ID NO 145
<211> LENGTH: 4
<212> TYPE: PRT
<213> ORGANISM: Homo sapiens

<400> SEQUENCE: 145

Ala Glu Asp Gly
1

<210> SEQ ID NO 146
<211> LENGTH: 4
<212> TYPE: PRT
<213> ORGANISM: Homo sapiens

<400> SEQUENCE: 146

Glu Asp Gly Ala
1

<210> SEQ ID NO 147
<211> LENGTH: 4
<212> TYPE: PRT
<213> ORGANISM: Homo sapiens

<400> SEQUENCE: 147

Asp Gly Ala Ser
1

<210> SEQ ID NO 148
<211> LENGTH: 4
<212> TYPE: PRT
<213> ORGANISM: Homo sapiens

<400> SEQUENCE: 148

Gly Ala Ser Ser
1

<210> SEQ ID NO 149
<211> LENGTH: 4
<212> TYPE: PRT
<213> ORGANISM: Homo sapiens

<400> SEQUENCE: 149

Ala Ser Ser Gln
1

<210> SEQ ID NO 150
<211> LENGTH: 4
<212> TYPE: PRT
<213> ORGANISM: Homo sapiens

<400> SEQUENCE: 150

Ser Ser Gln Leu
1

<210> SEQ ID NO 151
<211> LENGTH: 4
<212> TYPE: PRT
<213> ORGANISM: Homo sapiens

<400> SEQUENCE: 151

Ser Gln Leu Pro
1

<210> SEQ ID NO 152
<211> LENGTH: 4
<212> TYPE: PRT
<213> ORGANISM: Homo sapiens

<400> SEQUENCE: 152

Gln Leu Pro Ala
1

<210> SEQ ID NO 153
<211> LENGTH: 4
<212> TYPE: PRT
<213> ORGANISM: Homo sapiens

<400> SEQUENCE: 153

Leu Pro Ala Ala
1

<210> SEQ ID NO 154
<211> LENGTH: 4
<212> TYPE: PRT
<213> ORGANISM: Homo sapiens

<400> SEQUENCE: 154

Pro Ala Ala Glu
1

<210> SEQ ID NO 155
<211> LENGTH: 4
<212> TYPE: PRT
<213> ORGANISM: Homo sapiens

<400> SEQUENCE: 155

Ala Ala Glu Gly
1

<210> SEQ ID NO 156
<211> LENGTH: 4
<212> TYPE: PRT
<213> ORGANISM: Homo sapiens

<400> SEQUENCE: 156

Ala Glu Gly Ser

```
<210> SEQ ID NO 157
<211> LENGTH: 4
<212> TYPE: PRT
<213> ORGANISM: Homo sapiens

<400> SEQUENCE: 157

Glu Gly Ser Gly
1

<210> SEQ ID NO 158
<211> LENGTH: 4
<212> TYPE: PRT
<213> ORGANISM: Homo sapiens

<400> SEQUENCE: 158

Gly Ser Gly Glu
1

<210> SEQ ID NO 159
<211> LENGTH: 4
<212> TYPE: PRT
<213> ORGANISM: Homo sapiens

<400> SEQUENCE: 159

Ser Gly Glu Gln
1

<210> SEQ ID NO 160
<211> LENGTH: 4
<212> TYPE: PRT
<213> ORGANISM: Homo sapiens

<400> SEQUENCE: 160

Gly Glu Gln Asp
1

<210> SEQ ID NO 161
<211> LENGTH: 4
<212> TYPE: PRT
<213> ORGANISM: Homo sapiens

<400> SEQUENCE: 161

Glu Gln Asp Phe
1

<210> SEQ ID NO 162
<211> LENGTH: 4
<212> TYPE: PRT
<213> ORGANISM: Homo sapiens

<400> SEQUENCE: 162

Gln Asp Phe Thr
1

<210> SEQ ID NO 163
<211> LENGTH: 5
<212> TYPE: PRT
<213> ORGANISM: Homo sapiens

<400> SEQUENCE: 163

His Thr Pro His Thr
1               5
```

<210> SEQ ID NO 164
<211> LENGTH: 5
<212> TYPE: PRT
<213> ORGANISM: Homo sapiens

<400> SEQUENCE: 164

Thr Pro His Thr Glu
1               5

<210> SEQ ID NO 165
<211> LENGTH: 5
<212> TYPE: PRT
<213> ORGANISM: Homo sapiens

<400> SEQUENCE: 165

Pro His Thr Glu Asp
1               5

<210> SEQ ID NO 166
<211> LENGTH: 5
<212> TYPE: PRT
<213> ORGANISM: Homo sapiens

<400> SEQUENCE: 166

His Thr Glu Asp Gly
1               5

<210> SEQ ID NO 167
<211> LENGTH: 5
<212> TYPE: PRT
<213> ORGANISM: Homo sapiens

<400> SEQUENCE: 167

Thr Glu Asp Gly Gly
1               5

<210> SEQ ID NO 168
<211> LENGTH: 5
<212> TYPE: PRT
<213> ORGANISM: Homo sapiens

<400> SEQUENCE: 168

Glu Asp Gly Gly Pro
1               5

<210> SEQ ID NO 169
<211> LENGTH: 5
<212> TYPE: PRT
<213> ORGANISM: Homo sapiens

<400> SEQUENCE: 169

Asp Gly Gly Pro Ser
1               5

<210> SEQ ID NO 170
<211> LENGTH: 5
<212> TYPE: PRT
<213> ORGANISM: Homo sapiens

<400> SEQUENCE: 170

Gly Gly Pro Ser Ala
1               5

<210> SEQ ID NO 171

```
<211> LENGTH: 5
<212> TYPE: PRT
<213> ORGANISM: Homo sapiens

<400> SEQUENCE: 171

Gly Pro Ser Ala Thr
1               5

<210> SEQ ID NO 172
<211> LENGTH: 5
<212> TYPE: PRT
<213> ORGANISM: Homo sapiens

<400> SEQUENCE: 172

Pro Ser Ala Thr Glu
1               5

<210> SEQ ID NO 173
<211> LENGTH: 5
<212> TYPE: PRT
<213> ORGANISM: Homo sapiens

<400> SEQUENCE: 173

Ser Ala Thr Glu Arg
1               5

<210> SEQ ID NO 174
<211> LENGTH: 5
<212> TYPE: PRT
<213> ORGANISM: Homo sapiens

<400> SEQUENCE: 174

Ala Thr Glu Arg Ala
1               5

<210> SEQ ID NO 175
<211> LENGTH: 5
<212> TYPE: PRT
<213> ORGANISM: Homo sapiens

<400> SEQUENCE: 175

Thr Glu Arg Ala Ala
1               5

<210> SEQ ID NO 176
<211> LENGTH: 5
<212> TYPE: PRT
<213> ORGANISM: Homo sapiens

<400> SEQUENCE: 176

Glu Arg Ala Ala Glu
1               5

<210> SEQ ID NO 177
<211> LENGTH: 5
<212> TYPE: PRT
<213> ORGANISM: Homo sapiens

<400> SEQUENCE: 177

Arg Ala Ala Glu Asp
1               5

<210> SEQ ID NO 178
<211> LENGTH: 5
<212> TYPE: PRT
```

```
<213> ORGANISM: Homo sapiens

<400> SEQUENCE: 178

Ala Ala Glu Asp Gly
1               5

<210> SEQ ID NO 179
<211> LENGTH: 5
<212> TYPE: PRT
<213> ORGANISM: Homo sapiens

<400> SEQUENCE: 179

Ala Glu Asp Gly Ala
1               5

<210> SEQ ID NO 180
<211> LENGTH: 5
<212> TYPE: PRT
<213> ORGANISM: Homo sapiens

<400> SEQUENCE: 180

Glu Asp Gly Ala Ser
1               5

<210> SEQ ID NO 181
<211> LENGTH: 5
<212> TYPE: PRT
<213> ORGANISM: Homo sapiens

<400> SEQUENCE: 181

Asp Gly Ala Ser Ser
1               5

<210> SEQ ID NO 182
<211> LENGTH: 5
<212> TYPE: PRT
<213> ORGANISM: Homo sapiens

<400> SEQUENCE: 182

Gly Ala Ser Ser Gln
1               5

<210> SEQ ID NO 183
<211> LENGTH: 5
<212> TYPE: PRT
<213> ORGANISM: Homo sapiens

<400> SEQUENCE: 183

Ala Ser Ser Gln Leu
1               5

<210> SEQ ID NO 184
<211> LENGTH: 5
<212> TYPE: PRT
<213> ORGANISM: Homo sapiens

<400> SEQUENCE: 184

Ser Ser Gln Leu Pro
1               5

<210> SEQ ID NO 185
<211> LENGTH: 5
<212> TYPE: PRT
<213> ORGANISM: Homo sapiens
```

```
<400> SEQUENCE: 185

Ser Gln Leu Pro Ala
1               5

<210> SEQ ID NO 186
<211> LENGTH: 5
<212> TYPE: PRT
<213> ORGANISM: Homo sapiens

<400> SEQUENCE: 186

Gln Leu Pro Ala Ala
1               5

<210> SEQ ID NO 187
<211> LENGTH: 5
<212> TYPE: PRT
<213> ORGANISM: Homo sapiens

<400> SEQUENCE: 187

Leu Pro Ala Ala Glu
1               5

<210> SEQ ID NO 188
<211> LENGTH: 5
<212> TYPE: PRT
<213> ORGANISM: Homo sapiens

<400> SEQUENCE: 188

Pro Ala Ala Glu Gly
1               5

<210> SEQ ID NO 189
<211> LENGTH: 5
<212> TYPE: PRT
<213> ORGANISM: Homo sapiens

<400> SEQUENCE: 189

Ala Ala Glu Gly Ser
1               5

<210> SEQ ID NO 190
<211> LENGTH: 5
<212> TYPE: PRT
<213> ORGANISM: Homo sapiens

<400> SEQUENCE: 190

Ala Glu Gly Ser Gly
1               5

<210> SEQ ID NO 191
<211> LENGTH: 5
<212> TYPE: PRT
<213> ORGANISM: Homo sapiens

<400> SEQUENCE: 191

Glu Gly Ser Gly Glu
1               5

<210> SEQ ID NO 192
<211> LENGTH: 5
<212> TYPE: PRT
<213> ORGANISM: Homo sapiens

<400> SEQUENCE: 192
```

```
Gly Ser Gly Glu Gln
1               5

<210> SEQ ID NO 193
<211> LENGTH: 5
<212> TYPE: PRT
<213> ORGANISM: Homo sapiens

<400> SEQUENCE: 193

Ser Gly Glu Gln Asp
1               5

<210> SEQ ID NO 194
<211> LENGTH: 5
<212> TYPE: PRT
<213> ORGANISM: Homo sapiens

<400> SEQUENCE: 194

Gly Glu Gln Asp Phe
1               5

<210> SEQ ID NO 195
<211> LENGTH: 5
<212> TYPE: PRT
<213> ORGANISM: Homo sapiens

<400> SEQUENCE: 195

Glu Gln Asp Phe Thr
1               5

<210> SEQ ID NO 196
<211> LENGTH: 5
<212> TYPE: PRT
<213> ORGANISM: Homo sapiens

<400> SEQUENCE: 196

Gln Asp Phe Thr Phe
1               5

<210> SEQ ID NO 197
<211> LENGTH: 6
<212> TYPE: PRT
<213> ORGANISM: Homo sapiens

<400> SEQUENCE: 197

His Thr Pro His Thr Glu
1               5

<210> SEQ ID NO 198
<211> LENGTH: 6
<212> TYPE: PRT
<213> ORGANISM: Homo sapiens

<400> SEQUENCE: 198

Thr Pro His Thr Glu Asp
1               5

<210> SEQ ID NO 199
<211> LENGTH: 6
<212> TYPE: PRT
<213> ORGANISM: Homo sapiens

<400> SEQUENCE: 199

Pro His Thr Glu Asp Gly
1               5
```

```
<210> SEQ ID NO 200
<211> LENGTH: 6
<212> TYPE: PRT
<213> ORGANISM: Homo sapiens

<400> SEQUENCE: 200

His Thr Glu Asp Gly Gly
1               5

<210> SEQ ID NO 201
<211> LENGTH: 6
<212> TYPE: PRT
<213> ORGANISM: Homo sapiens

<400> SEQUENCE: 201

Thr Glu Asp Gly Gly Pro
1               5

<210> SEQ ID NO 202
<211> LENGTH: 6
<212> TYPE: PRT
<213> ORGANISM: Homo sapiens

<400> SEQUENCE: 202

Glu Asp Gly Gly Pro Ser
1               5

<210> SEQ ID NO 203
<211> LENGTH: 6
<212> TYPE: PRT
<213> ORGANISM: Homo sapiens

<400> SEQUENCE: 203

Asp Gly Gly Pro Ser Ala
1               5

<210> SEQ ID NO 204
<211> LENGTH: 6
<212> TYPE: PRT
<213> ORGANISM: Homo sapiens

<400> SEQUENCE: 204

Gly Gly Pro Ser Ala Thr
1               5

<210> SEQ ID NO 205
<211> LENGTH: 6
<212> TYPE: PRT
<213> ORGANISM: Homo sapiens

<400> SEQUENCE: 205

Gly Pro Ser Ala Thr Glu
1               5

<210> SEQ ID NO 206
<211> LENGTH: 6
<212> TYPE: PRT
<213> ORGANISM: Homo sapiens

<400> SEQUENCE: 206

Pro Ser Ala Thr Glu Arg
1               5
```

```
<210> SEQ ID NO 207
<211> LENGTH: 6
<212> TYPE: PRT
<213> ORGANISM: Homo sapiens

<400> SEQUENCE: 207

Ser Ala Thr Glu Arg Ala
1               5

<210> SEQ ID NO 208
<211> LENGTH: 6
<212> TYPE: PRT
<213> ORGANISM: Homo sapiens

<400> SEQUENCE: 208

Ala Thr Glu Arg Ala Ala
1               5

<210> SEQ ID NO 209
<211> LENGTH: 6
<212> TYPE: PRT
<213> ORGANISM: Homo sapiens

<400> SEQUENCE: 209

Thr Glu Arg Ala Ala Glu
1               5

<210> SEQ ID NO 210
<211> LENGTH: 6
<212> TYPE: PRT
<213> ORGANISM: Homo sapiens

<400> SEQUENCE: 210

Glu Arg Ala Ala Glu Asp
1               5

<210> SEQ ID NO 211
<211> LENGTH: 6
<212> TYPE: PRT
<213> ORGANISM: Homo sapiens

<400> SEQUENCE: 211

Arg Ala Ala Glu Asp Gly
1               5

<210> SEQ ID NO 212
<211> LENGTH: 6
<212> TYPE: PRT
<213> ORGANISM: Homo sapiens

<400> SEQUENCE: 212

Ala Ala Glu Asp Gly Ala
1               5

<210> SEQ ID NO 213
<211> LENGTH: 6
<212> TYPE: PRT
<213> ORGANISM: Homo sapiens

<400> SEQUENCE: 213

Ala Glu Asp Gly Ala Ser
1               5

<210> SEQ ID NO 214
<211> LENGTH: 6
```

```
<212> TYPE: PRT
<213> ORGANISM: Homo sapiens

<400> SEQUENCE: 214

Glu Asp Gly Ala Ser Ser
1               5

<210> SEQ ID NO 215
<211> LENGTH: 6
<212> TYPE: PRT
<213> ORGANISM: Homo sapiens

<400> SEQUENCE: 215

Asp Gly Ala Ser Ser Gln
1               5

<210> SEQ ID NO 216
<211> LENGTH: 6
<212> TYPE: PRT
<213> ORGANISM: Homo sapiens

<400> SEQUENCE: 216

Gly Ala Ser Ser Gln Leu
1               5

<210> SEQ ID NO 217
<211> LENGTH: 6
<212> TYPE: PRT
<213> ORGANISM: Homo sapiens

<400> SEQUENCE: 217

Ala Ser Ser Gln Leu Pro
1               5

<210> SEQ ID NO 218
<211> LENGTH: 6
<212> TYPE: PRT
<213> ORGANISM: Homo sapiens

<400> SEQUENCE: 218

Ser Ser Gln Leu Pro Ala
1               5

<210> SEQ ID NO 219
<211> LENGTH: 6
<212> TYPE: PRT
<213> ORGANISM: Homo sapiens

<400> SEQUENCE: 219

Ser Gln Leu Pro Ala Ala
1               5

<210> SEQ ID NO 220
<211> LENGTH: 6
<212> TYPE: PRT
<213> ORGANISM: Homo sapiens

<400> SEQUENCE: 220

Gln Leu Pro Ala Ala Glu
1               5

<210> SEQ ID NO 221
<211> LENGTH: 6
<212> TYPE: PRT
<213> ORGANISM: Homo sapiens
```

<400> SEQUENCE: 221

Leu Pro Ala Ala Glu Gly
1               5

<210> SEQ ID NO 222
<211> LENGTH: 6
<212> TYPE: PRT
<213> ORGANISM: Homo sapiens

<400> SEQUENCE: 222

Pro Ala Ala Glu Gly Ser
1               5

<210> SEQ ID NO 223
<211> LENGTH: 6
<212> TYPE: PRT
<213> ORGANISM: Homo sapiens

<400> SEQUENCE: 223

Ala Ala Glu Gly Ser Gly
1               5

<210> SEQ ID NO 224
<211> LENGTH: 6
<212> TYPE: PRT
<213> ORGANISM: Homo sapiens

<400> SEQUENCE: 224

Ala Glu Gly Ser Gly Glu
1               5

<210> SEQ ID NO 225
<211> LENGTH: 6
<212> TYPE: PRT
<213> ORGANISM: Homo sapiens

<400> SEQUENCE: 225

Glu Gly Ser Gly Glu Gln
1               5

<210> SEQ ID NO 226
<211> LENGTH: 6
<212> TYPE: PRT
<213> ORGANISM: Homo sapiens

<400> SEQUENCE: 226

Gly Ser Gly Glu Gln Asp
1               5

<210> SEQ ID NO 227
<211> LENGTH: 6
<212> TYPE: PRT
<213> ORGANISM: Homo sapiens

<400> SEQUENCE: 227

Ser Gly Glu Gln Asp Phe
1               5

<210> SEQ ID NO 228
<211> LENGTH: 6
<212> TYPE: PRT
<213> ORGANISM: Homo sapiens

<400> SEQUENCE: 228

Gly Glu Gln Asp Phe Thr
1               5

<210> SEQ ID NO 229
<211> LENGTH: 6
<212> TYPE: PRT
<213> ORGANISM: Homo sapiens

<400> SEQUENCE: 229

Glu Gln Asp Phe Thr Phe
1               5

<210> SEQ ID NO 230
<211> LENGTH: 6
<212> TYPE: PRT
<213> ORGANISM: Homo sapiens

<400> SEQUENCE: 230

Gln Asp Phe Thr Phe Glu
1               5

<210> SEQ ID NO 231
<211> LENGTH: 4
<212> TYPE: PRT
<213> ORGANISM: Homo sapiens

<400> SEQUENCE: 231

Ala Ser Thr Ser
1

<210> SEQ ID NO 232
<211> LENGTH: 4
<212> TYPE: PRT
<213> ORGANISM: Homo sapiens

<400> SEQUENCE: 232

Ser Thr Ser Thr
1

<210> SEQ ID NO 233
<211> LENGTH: 4
<212> TYPE: PRT
<213> ORGANISM: Homo sapiens

<400> SEQUENCE: 233

Thr Ser Thr Leu
1

<210> SEQ ID NO 234
<211> LENGTH: 4
<212> TYPE: PRT
<213> ORGANISM: Homo sapiens

<400> SEQUENCE: 234

Ser Thr Leu Pro
1

<210> SEQ ID NO 235
<211> LENGTH: 4
<212> TYPE: PRT
<213> ORGANISM: Homo sapiens

<400> SEQUENCE: 235

Thr Leu Pro Ala

<210> SEQ ID NO 236
<211> LENGTH: 4
<212> TYPE: PRT
<213> ORGANISM: Homo sapiens

<400> SEQUENCE: 236

Leu Pro Ala Gly
1

<210> SEQ ID NO 237
<211> LENGTH: 4
<212> TYPE: PRT
<213> ORGANISM: Homo sapiens

<400> SEQUENCE: 237

Pro Ala Gly Glu
1

<210> SEQ ID NO 238
<211> LENGTH: 4
<212> TYPE: PRT
<213> ORGANISM: Homo sapiens

<400> SEQUENCE: 238

Ala Gly Glu Gly
1

<210> SEQ ID NO 239
<211> LENGTH: 4
<212> TYPE: PRT
<213> ORGANISM: Homo sapiens

<400> SEQUENCE: 239

Gly Glu Gly Pro
1

<210> SEQ ID NO 240
<211> LENGTH: 4
<212> TYPE: PRT
<213> ORGANISM: Homo sapiens

<400> SEQUENCE: 240

Glu Gly Pro Lys
1

<210> SEQ ID NO 241
<211> LENGTH: 4
<212> TYPE: PRT
<213> ORGANISM: Homo sapiens

<400> SEQUENCE: 241

Gly Pro Lys Glu
1

<210> SEQ ID NO 242
<211> LENGTH: 4
<212> TYPE: PRT
<213> ORGANISM: Homo sapiens

<400> SEQUENCE: 242

Pro Lys Glu Gly
1

<210> SEQ ID NO 243
<211> LENGTH: 4
<212> TYPE: PRT
<213> ORGANISM: Homo sapiens

<400> SEQUENCE: 243

Lys Glu Gly Glu
1

<210> SEQ ID NO 244
<211> LENGTH: 4
<212> TYPE: PRT
<213> ORGANISM: Homo sapiens

<400> SEQUENCE: 244

Glu Gly Glu Ala
1

<210> SEQ ID NO 245
<211> LENGTH: 4
<212> TYPE: PRT
<213> ORGANISM: Homo sapiens

<400> SEQUENCE: 245

Gly Glu Ala Val
1

<210> SEQ ID NO 246
<211> LENGTH: 4
<212> TYPE: PRT
<213> ORGANISM: Homo sapiens

<400> SEQUENCE: 246

Glu Ala Val Val
1

<210> SEQ ID NO 247
<211> LENGTH: 4
<212> TYPE: PRT
<213> ORGANISM: Homo sapiens

<400> SEQUENCE: 247

Ala Val Val Leu
1

<210> SEQ ID NO 248
<211> LENGTH: 4
<212> TYPE: PRT
<213> ORGANISM: Homo sapiens

<400> SEQUENCE: 248

Val Val Leu Pro
1

<210> SEQ ID NO 249
<211> LENGTH: 4
<212> TYPE: PRT
<213> ORGANISM: Homo sapiens

<400> SEQUENCE: 249

Val Leu Pro Glu
1

<210> SEQ ID NO 250

```
<211> LENGTH: 4
<212> TYPE: PRT
<213> ORGANISM: Homo sapiens

<400> SEQUENCE: 250

Leu Pro Glu Val
1

<210> SEQ ID NO 251
<211> LENGTH: 4
<212> TYPE: PRT
<213> ORGANISM: Homo sapiens

<400> SEQUENCE: 251

Pro Glu Val Glu
1

<210> SEQ ID NO 252
<211> LENGTH: 4
<212> TYPE: PRT
<213> ORGANISM: Homo sapiens

<400> SEQUENCE: 252

Glu Val Glu Pro
1

<210> SEQ ID NO 253
<211> LENGTH: 4
<212> TYPE: PRT
<213> ORGANISM: Homo sapiens

<400> SEQUENCE: 253

Val Glu Pro Gly
1

<210> SEQ ID NO 254
<211> LENGTH: 4
<212> TYPE: PRT
<213> ORGANISM: Homo sapiens

<400> SEQUENCE: 254

Glu Pro Gly Leu
1

<210> SEQ ID NO 255
<211> LENGTH: 4
<212> TYPE: PRT
<213> ORGANISM: Homo sapiens

<400> SEQUENCE: 255

Pro Gly Leu Thr
1

<210> SEQ ID NO 256
<211> LENGTH: 4
<212> TYPE: PRT
<213> ORGANISM: Homo sapiens

<400> SEQUENCE: 256

Gly Leu Thr Ala
1

<210> SEQ ID NO 257
<211> LENGTH: 4
<212> TYPE: PRT
```

<213> ORGANISM: Homo sapiens

<400> SEQUENCE: 257

Leu Thr Ala Arg
1

<210> SEQ ID NO 258
<211> LENGTH: 4
<212> TYPE: PRT
<213> ORGANISM: Homo sapiens

<400> SEQUENCE: 258

Thr Ala Arg Glu
1

<210> SEQ ID NO 259
<211> LENGTH: 4
<212> TYPE: PRT
<213> ORGANISM: Homo sapiens

<400> SEQUENCE: 259

Ala Arg Glu Gln
1

<210> SEQ ID NO 260
<211> LENGTH: 4
<212> TYPE: PRT
<213> ORGANISM: Homo sapiens

<400> SEQUENCE: 260

Arg Glu Gln Glu
1

<210> SEQ ID NO 261
<211> LENGTH: 4
<212> TYPE: PRT
<213> ORGANISM: Homo sapiens

<400> SEQUENCE: 261

Glu Gln Glu Ala
1

<210> SEQ ID NO 262
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Glu Val Gln Leu Gln Gln Ser Gly Pro Glu Leu Val Lys Pro Gly Ala
1               5                   10                  15

Ser Val Lys Ile Ser Cys Glu Thr Ser Gly Phe Ser Phe Thr Ala His
            20                  25                  30

His Met His Trp Val Lys Gln Ser Pro Glu Lys Ser Leu Glu Trp Ile
        35                  40                  45

Gly Glu Ile Asp Pro Asn Thr Gly Ser Thr Thr Tyr Asn Gln Lys Phe
    50                  55                  60

Arg Ala Lys Ala Thr Leu Thr Val Asp Lys Ser Ser Asn Thr Thr Tyr
65                  70                  75                  80

Met Gln Leu Lys Ser Leu Thr Phe Glu Asp Ser Ala Val Tyr Tyr Cys
                85                  90                  95

-continued

Tyr Ser Asn Trp Phe Pro Tyr Trp Gly Gln Gly Thr Leu Val Thr Val
            100                 105                 110
Ser Ala

<210> SEQ ID NO 263
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Asp Val Val Met Thr Gln Thr Pro Leu Thr Leu Ser Ala Thr Ile Gly
1               5                   10                  15
Gln Pro Ala Ser Ile Tyr Cys Lys Ser Ser Gln Ser Leu Leu Asp Gly
            20                  25                  30
Asp Gly Lys Thr Tyr Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Trp Gln Gly
                85                  90                  95
Thr His Phe Pro Arg Thr Phe Gly Gly Gly Thr Lys Leu Glu Ile Lys
            100                 105                 110

<210> SEQ ID NO 264
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gln Val Gln Leu Gln Gln Pro Gly Ala Glu Leu Val Lys Pro Gly Ala
1               5                   10                  15
Ser Val Lys Leu Ser Cys Lys Ala Ser Gly Phe Ser Phe Ile Thr Tyr
            20                  25                  30
Trp Met Asn Trp Ile Lys Gln Arg Pro Gly Arg Gly Leu Glu Trp Ile
        35                  40                  45
Gly Arg Ile His Pro Ser Asp Ser Ala Thr Gln Tyr Asn Gln Lys Phe
    50                  55                  60
Lys Thr Lys Ala Thr Leu Thr Val Asp Lys Ser Ser Ser Thr Ala Tyr
65                  70                  75                  80
Ile Gln Leu Ser Ser Leu Thr Ser Glu Asp Ser Ala Val Tyr Tyr Cys
                85                  90                  95
Ala Arg Ser Thr Glu Gly Ala His Trp Gly Gln Gly Thr Leu Val Thr
            100                 105                 110
Val Ser Ala
        115

<210> SEQ ID NO 265
<211> LENGTH: 112
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 265

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 266
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Trp Met His Trp Val Lys Gln Arg Pro Gly Gln Gly Leu Glu Trp Ile
        35                  40                  45

Gly Glu Ile Tyr Pro Ser Ser Gly Val Thr Asn Tyr Asn Glu Arg Phe
    50                  55                  60

Lys Asn Lys Ala Thr Leu Thr Val Asp Lys Ser Ser Arg Thr Ala Tyr
65                  70                  75                  80

Met Gln Leu Ser Ser Leu Thr Ser Glu Asp Ser Ala Val Tyr Phe Cys
                85                  90                  95

Thr Pro Asn Tyr Tyr Tyr Asp Gly Leu Tyr Trp Gly Gln Gly Thr Leu
            100                 105                 110

Val Thr Val Ser Ala
        115

<210> SEQ ID NO 267
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Asp Val Val Met Thr Gln Thr Pro Leu Thr Leu Ser Val Thr Ile Gly
1               5                   10                  15

Gln Pro Ala Ser Ile Ser Cys Lys Ser Ser His Ser Leu Leu Tyr Thr
            20                  25                  30

Asn Gly Glu Thr Tyr Leu Asn Trp Leu Leu Gln Arg Pro Gly Gln Ser

```
                   35                  40                  45
Pro Lys Arg Leu Ile Tyr Leu Val Ser Asn Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Leu Gln Ser
                     85                  90                  95

Thr His Phe Pro Arg Thr Phe Gly Gly Gly Thr Lys Leu Glu Ile Lys
                    100                 105                 110

<210> SEQ ID NO 268
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gln Val Gln Leu Gln Gln Pro Gly Ala Glu Leu Val Lys Pro Gly Ala
  1                   5                  10                  15

Ser Val Lys Leu Ser Cys Lys Ala Ser Gly Phe Ser Phe Thr Arg Tyr
                     20                  25                  30

Trp Met Asn Trp Val Lys Gln Arg Pro Gly Arg Gly Leu Glu Trp Ile
                     35                  40                  45

Gly Arg Ile His Pro Ser Asp Ser Ala Ser Gln Tyr Asn Gln Lys Phe
 50                  55                  60

Lys Ser Lys Ala Thr Leu Thr Val Asp Lys Ser Ser Ser Thr Ala Tyr
 65                  70                  75                  80

Ile Gln Leu Ser Ser Leu Thr Ser Glu Asp Ser Ala Val Tyr Tyr Cys
                     85                  90                  95

Gly Arg Ser Thr Glu Gly Ala Tyr Trp Gly Gln Gly Thr Leu Val Thr
                    100                 105                 110

Val Ser Ala
         115

<210> SEQ ID NO 269
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gln Val Gln Leu Gln Gln Pro Gly Ala Glu Leu Val Lys Pro Gly Ala
  1                   5                  10                  15

Ser Val Lys Leu Ser Cys Lys Ala Ser Gly Phe Ser Phe Ile Thr Tyr
                     20                  25                  30

Trp Met Asn Trp Ile Lys Gln Arg Pro Gly Arg Gly Leu Glu Trp Ile
                     35                  40                  45

Gly Arg Ile His Pro Ser Asp Ser Ala Thr Gly Tyr Asp Gln Lys Phe
 50                  55                  60

Lys Thr Lys Ala Thr Leu Thr Val Asp Lys Ser Ser Ser Thr Ala Tyr
 65                  70                  75                  80

Ile Gln Leu Ser Ser Leu Thr Ser Glu Asp Ser Ala Val Tyr Tyr Cys
                     85                  90                  95

Ala Arg Ser Thr Glu Gly Ala His Trp Gly Pro Gly Thr Leu Val Thr
```

-continued

```
                100                 105                 110

Val Ser Ala
        115

<210> SEQ ID NO 270
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Glu Ile Gln Leu Gln Gln Ser Gly Thr Glu Leu Val Lys Pro Gly Ala
1               5                   10                  15

Ser Val Lys Ile Ser Cys Lys Thr Ser Gly Tyr Ser Phe Thr Asp Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Gly Tyr Thr Gln Asn Phe
    50                  55                  60

Glu Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Leu Tyr Tyr Cys
                85                  90                  95

Ala Arg Glu Gly His Asp Tyr Tyr Ala Met Asp Tyr Trp Gly Gln Gly
            100                 105                 110

Thr Ser Val Thr Val Ser Ala
        115

<210> SEQ ID NO 271
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Gln Val Gln Leu Gln Leu Pro Gly Ala Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile His Pro Ser Asp Ser Asp Thr Asn Tyr Asn Gln Asn Phe
    50                  55                  60

Lys Gly Lys Ala Thr Leu Ile Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Gly Phe Ser Phe Trp Gly Gln Gly Thr Leu Val Thr Val Ser
            100                 105                 110

Ala

<210> SEQ ID NO 272
<211> LENGTH: 113
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 272

Gln Val Gln Val Gln Val Pro Gly Ala Glu Leu Val Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Met Lys Arg Pro Gly Gln Gly Leu Glu Trp Ile
            35                  40                  45

Gly Arg Ile His Pro Ser Asp Ser Asp Thr Asn Tyr Asn Gln Asn Phe
        50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Thr Gly Phe Ser Phe Trp Gly Gln Gly Thr Leu Val Thr Val Ser
            100                 105                 110

Ala

<210> SEQ ID NO 273
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
                20                  25                  30

Asp Gly Lys Thr Tyr Leu Asn Trp Leu Leu Gln Arg Pro Gly Glu Ser
            35                  40                  45

Pro Lys Leu Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Thr
                85                  90                  95

Thr Ser Phe Pro Tyr Thr Phe Gly Gly Gly Thr Lys Leu Asp Ile Lys
            100                 105                 110

<210> SEQ ID NO 274
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gln Val Gln Leu Gln Gln Pro Gly Ala Glu Leu Val Lys Pro Gly Ala
1               5                   10                  15

Ser Val Lys Val Ser Cys Lys Ala Ser Gly Tyr Asn Phe Ile Asn Tyr
                20                  25                  30

Trp Met His Trp Val Lys Gln Arg Pro Gly Gln Gly Leu Glu Trp Ile
```

```
            35                  40                  45
Gly Arg Ile His Pro Ser Asp Ser Tyr Thr Asn Tyr Asn Gln Lys Phe
 50                  55                  60

Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Ser Pro Ile Ser Thr Leu Tyr Trp Gly Gln Gly Thr Thr Leu Thr
                100                 105                 110

Val Ser Ser
        115

<210> SEQ ID NO 275
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Glu Ser
            35                  40                  45

Pro Lys Leu Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Leu Gln Ala
                 85                  90                  95

Thr His Phe Pro Gln Thr Phe Gly Gly Gly Thr Lys Leu Glu Ile Lys
                100                 105                 110

<210> SEQ ID NO 276
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Gln Val Gln Leu Gln Leu Pro Gly Ala Glu Leu Val Arg Pro Gly Thr
 1               5                  10                  15

Ser Val Lys Val Ser Cys Lys Ala Ser Asp Tyr Thr Phe Thr Thr Tyr
                20                  25                  30

Trp Met His Trp Val Lys Gln Arg Pro Gly Gln Gly Leu Asp Trp Ile
            35                  40                  45

Gly Arg Ile His Pro Ser Asp Ser Asp Thr Asn Tyr Asn Gln Asn Phe
 50                  55                  60

Lys Gly Lys Ala Thr Leu Thr Val Asp Lys Ser Ser Ser Thr Ala Tyr
 65                  70                  75                  80

Met His Leu Ser Ser Leu Thr Ser Glu Asp Ser Ala Val Tyr Tyr Cys
                 85                  90                  95

Ala Thr Gly Phe Ser Phe Trp Gly Gln Gly Thr Leu Val Thr Val Ser
```

Ala

<210> SEQ ID NO 277
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Gln Val Gln Val Gln Leu Pro Gly Ala Glu Leu Val Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Lys Arg Pro Gly Gln Gly Leu Glu Trp Ile
            35                  40                  45

Gly Arg Ile His Pro Ser Asp Ser Asp Thr Asn Tyr Asn Gln Asn Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Val Tyr Tyr Cys
                85                  90                  95

Ala Thr Gly Phe Ser Phe Trp Gly Gln Gly Thr Leu Ile Thr Val Ser
                100                 105                 110

Ala

<210> SEQ ID NO 278
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
                20                  25                  30

Asp Gly Lys Thr Tyr Leu Asn Trp Leu Leu Gln Arg Pro Gly Glu Ser
            35                  40                  45

Pro Glu Leu Leu Ile Tyr Leu Val Ser Lys Met Asp Ser Gly Val Pro
    50                  55                  60

Asp Arg Phe His Gly His Gly Ser Gly Thr Ala Phe Thr Met Lys Ile
65                  70                  75                  80

Ser Arg Met Gly Gly Gly Gly Leu Gly Asn Tyr Tyr Cys Leu Pro Arg
                85                  90                  95

Thr Ser Phe Pro Tyr Thr Phe Gly Gly Gly Thr Lys Leu Glu Ile Lys
                100                 105                 110

<210> SEQ ID NO 279
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Gln Val Gln Leu Gln Leu Pro Gly Ala Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile His Pro Ser Asp Ser Asp Thr Asn Tyr Asn Gln Asn Phe
    50                  55                  60

Lys Gly Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Thr Gly Phe Ser Phe Trp Gly Gln Gly Thr Leu Val Thr Val Ser
            100                 105                 110

Ala

<210> SEQ ID NO 280
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Asp Val Val Met Thr Pro Thr Ser Leu His Leu Val Thr Ile Gly
1               5                   10                  15

Gln Pro Gly Phe Leu Phe Cys Lys Ser Ser Gln Asn Leu Leu Tyr Asn
            20                  25                  30

Glu Gly Lys Thr Tyr Leu Lys Trp Leu Leu Pro Glu Pro Gly Ala Phe
        35                  40                  45

Ser Lys Val Leu Ile Tyr Leu Val Phe Lys Met Gly Phe Gly Val Pro
    50                  55                  60

Asp Arg Phe His Gly His Gly Ser Gly Thr Asp Phe Pro Met Lys Ile
65                  70                  75                  80

Ser Arg Met Gly Gly Gly Leu Gly Gly Tyr Leu Cys Leu Pro Ser
                85                  90                  95

Thr Pro Phe Pro Tyr Thr Phe Gly Gly Thr Lys Leu Glu Ile Lys
            100                 105                 110

<210> SEQ ID NO 281
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gln Ile His Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Tyr
            20                  25                  30

Gly Met Ser Trp Val Lys Gln Ala Pro Gly Lys Ala Leu Lys Trp Met
        35                  40                  45

Gly Trp Ile Asn Thr Tyr Ser Gly Val Pro Thr Tyr Ala Asp Asp Phe
    50                  55                  60

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Thr Arg Glu Gly Ser Thr Met Val Thr Arg Tyr Tyr Phe Asp Tyr Trp
            100                 105                 110

Gly Gln Gly Thr Thr Leu Thr Val Ser Ser
        115                 120
```

<210> SEQ ID NO 282
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
             20                  25                  30

Asn Gly Asn Thr Tyr Leu Tyr Trp Phe Leu Gln Arg Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr His Cys Met Gln His
                 85                  90                  95

Leu Glu Ser Pro Tyr Thr Phe Gly Gly Gly Thr Lys Leu Glu Ile Lys
            100                 105                 110
```

<210> SEQ ID NO 283
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

```
Gln Val Gln Leu Gln Leu Pro Gly Ala Glu Leu Val Lys Pro Gly Ala
 1               5                  10                  15

Ser Val Lys Val Ser Cys Lys Ala Ser Ala Tyr Thr Phe Thr Ser Tyr
             20                  25                  30

Trp Met His Trp Val Lys Gln Arg Pro Gly Gln Gly Leu Glu Trp Ile
         35                  40                  45

Gly Arg Ile His Pro Ser Asp Ser Asp Thr Asn Tyr Asn Gln Asn Phe
     50                  55                  60

Lys Gly Lys Ala Thr Leu Thr Val Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Thr Gly Phe Ser Phe Trp Gly Gln Gly Thr Leu Val Thr Val Ser
            100                 105                 110

Ala
```

```
<210> SEQ ID NO 284
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Arg Pro
                85                  90                  95

Thr Phe Gly Gly Gly Thr Lys Leu Glu Ile Lys
            100                 105

<210> SEQ ID NO 285
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Gly Ser Thr Met Val Thr Arg Tyr Tyr Phe Asp Tyr Trp
            100                 105                 110

Gly Gln Gly Thr Thr Leu Thr Val Ser Ser
        115                 120

<210> SEQ ID NO 286
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Asp Ile Val Met Thr Gln Ala Ala Pro Ser Val Pro Val Thr Pro Gly
```

```
                1               5                  10                 15
Glu Ser Val Ser Ile Ser Cys Arg Ser Ser Lys Ser Leu Leu His Ser
                    20                 25                 30

Asn Gly Asn Thr Tyr Leu Tyr Trp Phe Leu Gln Arg Pro Gly Gln Ser
            35                  40                 45

Pro Gln Val Leu Ile Tyr Arg Met Ser Asn Leu Ala Ser Gly Val Pro
    50                  55                 60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Ser Pro Tyr Thr Phe Gly Gly Gly Thr Lys Leu Glu Ile Lys
                100                 105                 110
```

<210> SEQ ID NO 287
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 287

```
Gln Ile Gln Leu Val Gln Ser Gly Pro Glu Leu Lys Lys Pro Gly Glu
1               5                  10                 15

Thr Val Lys Ile Ser Cys Lys Ala Ser Gly Tyr Thr Phe Thr Thr Tyr
                20                 25                 30

Gly Met Ser Trp Val Lys Gln Ala Pro Gly Lys Gly Leu Lys Trp Met
            35                  40                 45

Gly Trp Ile Asn Thr Tyr Ser Gly Val Pro Thr Tyr Ala Asp Asp Phe
    50                  55                 60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Phe Phe Cys
                85                  90                  95

Ala Arg Glu Gly Ser Thr Met Val Thr Arg Tyr Tyr Phe Asp Tyr Trp
                100                 105                 110

Gly Gln Gly Thr Thr Leu Thr Val Ser Ser
            115                 120
```

<210> SEQ ID NO 288
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

```
Asp Ile Val Met Thr Gln Ala Ala Pro Ser Val Pro Thr Pro Gly
1               5                  10                 15

Glu Ser Val Ser Ile Ser Cys Arg Ser Ser Lys Ser Leu Leu His Ser
                20                 25                 30

Asn Gly Asn Thr Tyr Leu Tyr Trp Phe Leu Gln Arg Pro Gly Gln Ser
            35                  40                 45

Pro Gln Leu Leu Ile Tyr Arg Met Ser Asn Leu Ala Ser Gly Val Pro
    50                  55                 60

Asp Arg Phe Ser Gly Ser Gly Ser Gly Thr Ala Phe Thr Leu Arg Ile
```

```
65                  70                  75                  80

Ser Arg Val Glu Ala Glu Asp Val Gly Val Tyr Tyr Cys Met Gln His
                85                  90                  95

Leu Glu Tyr Pro Ser Thr Phe Gly Gly Gly Thr Lys Leu Glu Ile Lys
                100                 105                 110
```

<210> SEQ ID NO 289
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

```
Gln Val Gln Val Gln Leu Pro Gly Ala Glu Leu Val Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Lys Arg Pro Gly Gln Gly Leu Glu Trp Ile
            35                  40                  45

Gly Arg Ile His Pro Ser Asp Ser Asp Thr Asn Tyr Asn Gln Asn Phe
        50                  55                  60

Lys Gly Lys Ala Thr Leu Thr Val Asp Lys Ser Ser Ser Thr Ala Tyr
65                  70                  75                  80

Met Gln Leu Thr Ser Leu Thr Ser Glu Asp Phe Ala Val Tyr Tyr Cys
                85                  90                  95

Ser Thr Gly Phe Ser Phe Trp Gly Gln Gly Thr Leu Val Thr Val Ser
                100                 105                 110

Ala
```

<210> SEQ ID NO 290
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
                20                  25                  30

Asp Gly Lys Thr Tyr Leu Asn Trp Leu Leu Gln Arg Pro Gly Glu Ser
            35                  40                  45

Pro Lys Leu Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Thr
                85                  90                  95

Thr Tyr Phe Pro Tyr Thr Phe Gly Gly Gly Thr Lys Leu Glu Ile Lys
                100                 105                 110
```

<210> SEQ ID NO 291
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Val Gln Leu His Gln Pro Gly Thr Ser Leu Val Lys Pro Gly Ala
1               5                   10                  15

Ser Val Lys Leu Ser Cys Lys Ala Ser Gly Tyr Asn Phe Ser Ser Tyr
                20                  25                  30

Tyr Met His Trp Val Lys Gln Arg Pro Gly Gln Gly Leu Glu Trp Ile
            35                  40                  45

Gly Thr Ile His Pro Ser Asp Ser Thr Asn Cys Asn Gln Lys Phe
        50                  55                  60

Lys Gly Lys Ala Thr Leu Thr Val Asp Lys Ser Ser Arg Thr Ala Tyr
65                  70                  75                  80

Met Gln Leu Asn Ser Leu Thr Phe Glu Asp Ser Ala Val Tyr Tyr Cys
                85                  90                  95

Ala Asn Phe Val Tyr Trp Gly Gln Gly Thr Ser Val Thr Val Ser Ser
            100                 105                 110

<210> SEQ ID NO 292
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Asp Ile Val Ile Thr Gln Asp Glu Leu Ser Asn Pro Val Thr Ser Gly
1               5                   10                  15

Asp Ser Val Ser Ile Ser Cys Arg Ser Ser Lys Ser Leu Leu Tyr Lys
                20                  25                  30

Asp Gly Lys Thr Tyr Leu Asn Trp Phe Leu Gln Arg Pro Gly Gln Ser
            35                  40                  45

Pro Gln Leu Leu Ile Tyr Val Val Ser Thr Arg Ala Ser Gly Val Ser
        50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Tyr Thr Phe Gly Gly Gly Thr Lys Leu Glu Ile Lys
            100                 105                 110

<210> SEQ ID NO 293
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Val Gln Leu His Gln Pro Gly Thr Ser Leu Val Lys Pro Gly Ala
1               5                   10                  15

Ser Val Lys Leu Ser Cys Lys Ala Ser Gly Tyr Asn Phe Ser Ser Tyr
                20                  25                  30

Tyr Met His Trp Val Lys Gln Arg Pro Gly Gln Gly Leu Glu Trp Ile
            35                  40                  45

Gly Thr Ile His Pro Ser Asp Ser Thr Thr Asn Tyr Asn Gln Lys Phe
        50                  55                  60

Lys Gly Lys Ala Thr Leu Thr Val Asp Lys Ser Ser Arg Thr Ala Tyr
 65                  70                  75                  80

Met Gln Leu Asn Ser Leu Thr Phe Glu Asp Ser Ala Val Tyr Tyr Cys
                 85                  90                  95

Ala Asn Phe Val Tyr Trp Gly Gln Gly Thr Ser Val Thr Val Ser Ser
                100                 105                 110

<210> SEQ ID NO 294
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gln Val Gln Leu His Gln Pro Gly Thr Ser Leu Val Lys Pro Gly Ala
 1               5                  10                  15

Ser Val Lys Leu Ser Cys Lys Ala Ser Gly Tyr Ser Phe Ser Ser Tyr
                20                  25                  30

Tyr Met His Trp Val Lys Gln Arg Pro Gly Gln Gly Leu Glu Trp Ile
             35                  40                  45

Gly Thr Ile His Pro Ser Asp Ser Thr Thr Asn Cys Asn Gln Lys Phe
        50                  55                  60

Lys Gly Lys Ala Thr Leu Thr Val Asp Lys Ser Ser Arg Thr Ala Tyr
 65                  70                  75                  80

Met Gln Leu Asn Ser Leu Thr Phe Glu Asp Ser Ala Val Tyr Tyr Cys
                 85                  90                  95

Ala Asn Phe Val Tyr Trp Gly Gln Gly Thr Ser Val Thr Val Ser Ser
                100                 105                 110

<210> SEQ ID NO 295
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gln Val Gln Leu His Gln Pro Gly Thr Ser Leu Val Lys Pro Gly Ala
 1               5                  10                  15

Ser Val Lys Leu Ser Cys Lys Ala Ser Gly Tyr Thr Phe Ser Ser Tyr
                20                  25                  30

Tyr Met His Trp Val Lys Gln Arg Pro Gly Gln Gly Leu Glu Trp Ile
             35                  40                  45

Gly Thr Ile His Pro Ser Asp Ser Thr Thr Asn Cys Asn Gln Lys Phe
        50                  55                  60

Lys Gly Lys Ala Thr Leu Thr Val Asp Lys Ser Ser Arg Thr Ala Tyr
 65                  70                  75                  80

Met Gln Leu Asn Ser Leu Thr Phe Glu Asp Ser Ala Val Tyr Tyr Cys
                 85                  90                  95

Ala Asn Phe Val Tyr Trp Gly Gln Gly Thr Ser Val Thr Val Ser Ser
                100                 105                 110

<210> SEQ ID NO 296
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Val Gln Leu His Gln Pro Gly Thr Ser Leu Val Lys Pro Gly Ala
1               5                   10                  15

Ser Val Lys Leu Ser Cys Lys Ala Ser Gly Tyr Ser Phe Ser Ser Tyr
            20                  25                  30

Tyr Met His Trp Val Lys Gln Arg Pro Gly Gln Gly Leu Glu Trp Ile
        35                  40                  45

Gly Thr Ile His Pro Ser Asp Ser Thr Asn Tyr Asn Gln Lys Phe
    50                  55                  60

Lys Gly Lys Ala Thr Leu Thr Val Asp Lys Ser Ser Arg Thr Ala Tyr
65                  70                  75                  80

Met Gln Leu Asn Ser Leu Thr Phe Glu Asp Ser Ala Val Tyr Tyr Cys
                85                  90                  95

Ala Asn Phe Val Tyr Trp Gly Gln Gly Thr Ser Val Thr Val Ser Ser
            100                 105                 110

<210> SEQ ID NO 297
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gln Val Gln Leu His Gln Pro Gly Thr Ser Leu Val Lys Pro Gly Ala
1               5                   10                  15

Ser Val Lys Leu Ser Cys Lys Ala Ser Gly Tyr Thr Phe Ser Ser Tyr
            20                  25                  30

Tyr Met His Trp Val Lys Gln Arg Pro Gly Gln Gly Leu Glu Trp Ile
        35                  40                  45

Gly Thr Ile His Pro Ser Asp Ser Thr Asn Tyr Asn Gln Lys Phe
    50                  55                  60

Lys Gly Lys Ala Thr Leu Thr Val Asp Lys Ser Ser Arg Thr Ala Tyr
65                  70                  75                  80

Met Gln Leu Asn Ser Leu Thr Phe Glu Asp Ser Ala Val Tyr Tyr Cys
                85                  90                  95

Ala Asn Phe Val Tyr Trp Gly Gln Gly Thr Ser Val Thr Val Ser Ser
            100                 105                 110

<210> SEQ ID NO 298
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
```

-continued

```
                35                  40                  45
Ala Arg Ile Arg Ser Lys Ser Ser Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Arg Glu Leu Arg Leu Arg Tyr Ala Met Asp Tyr Trp Gly
            100                 105                 110

Gln Gly Thr Ser Val Thr Val Ser Ser
            115                 120

<210> SEQ ID NO 299
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Ile Leu Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Tyr Thr
             20                  25                  30

Asn Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Leu Gln Ser
                 85                  90                  95

Thr His Phe Pro Leu Thr Phe Gly Ala Gly Thr Lys Leu Glu Leu Lys
            100                 105                 110

<210> SEQ ID NO 300
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Phe Ser Phe Thr Ala His
 1               5

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Pro Asn Thr Gly Ser
 1               5

<210> SEQ ID NO 302
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asn Trp Phe Pro Tyr
1               5

<210> SEQ ID NO 303
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Lys Ser Ser Gln Ser Leu Leu Asp Gly Asp Gly Lys Thr Tyr Leu Asn
1               5                   10                  15

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu Val Ser Lys Leu Asp Ser
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Trp Gln Gly Thr His Phe Pro Arg Thr
1               5

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gly Phe Ser Phe Ile Thr Tyr
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307
```

His Pro Ser Asp Ser Ala
1               5

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Thr Glu Gly Ala His
1               5

<210> SEQ ID NO 309
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Lys Ser Ser Gln Ser Leu Leu His Ser Asp Gly Lys Thr Tyr Leu Asn
1               5                   10                  15

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Gln Gly Thr His Phe Pro Gln Thr
1               5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Tyr Thr Phe Thr Ser Phe
1               5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Tyr Pro Ser Ser Gly Val
1               5

<210> SEQ ID NO 313
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 313

Asn Tyr Tyr Tyr Asp Gly Leu Tyr
1               5

<210> SEQ ID NO 314
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Lys Ser Ser His Ser Leu Leu Tyr Thr Asn Gly Glu Thr Tyr Leu Asn
1               5                   10                  15

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Leu Val Ser Asn Leu Asp Ser
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Leu Gln Ser Thr His Phe Pro Arg Thr
1               5

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Phe Ser Phe Thr Arg Tyr
1               5

<210> SEQ ID NO 318
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ser Thr Glu Gly Ala Tyr
1               5
```

```
<210> SEQ ID NO 319
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Tyr Ser Phe Thr Asp Tyr
1               5

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asn Pro Tyr Tyr Gly Ser
1               5

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Glu Gly His Asp Tyr Tyr Ala Met Asp Tyr
1               5                   10

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Tyr Thr Phe Thr Ser Tyr
1               5

<210> SEQ ID NO 323
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

His Pro Ser Asp Ser Asp
1               5

<210> SEQ ID NO 324
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324
```

```
Gly Phe Ser Phe
1

<210> SEQ ID NO 325
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Lys Ser Ser Gln Ser Leu Leu Tyr Ser Asp Gly Lys Thr Tyr Leu Asn
1               5                   10                  15

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Leu Gln Thr Thr Ser Phe Pro Tyr Thr
1               5

<210> SEQ ID NO 327
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gly Tyr Asn Phe Ile Asn Tyr
1               5

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

His Pro Ser Asp Ser Tyr
1               5

<210> SEQ ID NO 329
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Pro Ile Ser Thr Leu Tyr
1               5

<210> SEQ ID NO 330
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 330

Lys Ser Ser Gln Ser Leu Leu Asp Ser Asp Gly Lys Thr Tyr Leu Asn
1               5                   10                  15

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Leu Gln Ala Thr His Phe Pro Gln Thr
1               5

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Tyr Thr Phe Thr Thr Tyr
1               5

<210> SEQ ID NO 333
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Leu Val Ser Lys Met Asp Ser
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Leu Pro Arg Thr Ser Phe Pro Tyr Thr
1               5

<210> SEQ ID NO 335
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Lys Ser Ser Gln Asn Leu Leu Tyr Asn Glu Gly Lys Thr Tyr Leu Lys
1               5                   10                  15
```

<210> SEQ ID NO 336
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Leu Val Phe Lys Met Gly Phe
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Leu Pro Ser Thr Pro Phe Pro Tyr Thr
1               5

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Tyr Thr Phe Thr Thr Tyr
1               5

<210> SEQ ID NO 339
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asn Thr Tyr Ser Gly Val
1               5

<210> SEQ ID NO 340
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Glu Gly Ser Thr Met Val Thr Arg Tyr Tyr Phe Asp Tyr
1               5                   10

<210> SEQ ID NO 341
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 341

Arg Ser Ser Lys Ser Leu Leu His Ser Asn Gly Asn Thr Tyr Leu Tyr
1               5                   10                  15

<210> SEQ ID NO 342
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Arg Met Ser Asn Leu Ala Ser
1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Met Gln His Leu Glu Ser Pro Tyr Thr
1               5

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ala Tyr Thr Phe Thr Ser Tyr
1               5

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Lys Ala Ser Gln Asp Val Ser Thr Thr Val Ala
1               5                   10

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ser Ala Ser Tyr Arg Tyr Thr
1               5

<210> SEQ ID NO 347
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 347

Gln Gln His Tyr Ser Thr Arg Pro Thr
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Met Gln His Leu Glu Tyr Pro Ser Thr
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Leu Gln Thr Thr Tyr Phe Pro Tyr Thr
1               5

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Tyr Asn Phe Ser Ser Tyr
1               5

<210> SEQ ID NO 351
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

His Pro Ser Asp Ser Thr
1               5

<210> SEQ ID NO 352
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ser Ser Lys Ser Leu Leu Tyr Lys Asp Gly Lys Thr Tyr Leu Asn
1               5                   10                  15
```

```
<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Val Val Ser Thr Arg Ala Ser
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Gln Leu Val Glu Tyr Pro Tyr Thr
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Gly Tyr Ser Phe Ser Ser Tyr
1               5

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gly Tyr Thr Phe Ser Ser Tyr
1               5

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Phe Thr Phe Asn Thr Tyr
1               5

<210> SEQ ID NO 358
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 358

Arg Ser Lys Ser Ser Asn Tyr Ala
1               5

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Glu Leu Arg Leu Arg Tyr Ala Met Asp Tyr
1               5                   10

<210> SEQ ID NO 360
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Lys Ser Ser Gln Ser Leu Leu Tyr Thr Asn Gly Lys Thr Tyr Leu Asn
1               5                   10                  15

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Leu Gln Ser Thr His Phe Pro Leu Thr
1               5

<210> SEQ ID NO 362
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ala His His Met His
1               5

<210> SEQ ID NO 363
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Glu Ile Asp Pro Asn Thr Gly Ser Thr Thr Tyr Asn Gln Lys Phe Arg
1               5                   10                  15

Ala

-continued

```
<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Thr Tyr Trp Met Asn
1               5

<210> SEQ ID NO 365
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Arg Ile His Pro Ser Asp Ser Ala Thr Gln Tyr Asn Gln Lys Phe Lys
1               5                   10                  15

Thr

<210> SEQ ID NO 366
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ser Phe Trp Met His
1               5

<210> SEQ ID NO 367
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Glu Ile Tyr Pro Ser Ser Gly Val Thr Asn Tyr Asn Glu Arg Phe Lys
1               5                   10                  15

Asn

<210> SEQ ID NO 368
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Arg Tyr Trp Met Asn
1               5

<210> SEQ ID NO 369
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 369

Arg Ile His Pro Ser Asp Ser Ala Ser Gln Tyr Asn Gln Lys Phe Lys
1               5                   10                  15
Ser

<210> SEQ ID NO 370
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Arg Ile His Pro Ser Asp Ser Ala Thr Gln Tyr Asp Gln Lys Phe Lys
1               5                   10                  15
Thr

<210> SEQ ID NO 371
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Asp Tyr Asn Met Asn
1               5

<210> SEQ ID NO 372
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Asn Ile Asn Pro Tyr Tyr Gly Ser Thr Gly Tyr Thr Gln Asn Phe Glu
1               5                   10                  15
Gly

<210> SEQ ID NO 373
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ser Tyr Trp Met His
1               5

<210> SEQ ID NO 374
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 374

Arg Ile His Pro Ser Asp Ser Asp Thr Asn Tyr Asn Gln Asn Phe Lys
1               5                   10                  15

Gly

<210> SEQ ID NO 375
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Asn Tyr Trp Met His
1               5

<210> SEQ ID NO 376
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Arg Ile His Pro Ser Asp Ser Tyr Thr Asn Tyr Asn Gln Lys Phe Lys
1               5                   10                  15

Gly

<210> SEQ ID NO 377
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Thr Tyr Trp Met His
1               5

<210> SEQ ID NO 378
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Thr Tyr Gly Met Ser
1               5

<210> SEQ ID NO 379
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Trp Ile Asn Thr Tyr Ser Gly Val Pro Thr Tyr Ala Asp Asp Phe Lys
1               5                   10                  15
```

Gly

<210> SEQ ID NO 380
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ser Tyr Tyr Met His
1               5

<210> SEQ ID NO 381
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Thr Ile His Pro Ser Asp Ser Thr Thr Asn Cys Asn Gln Lys Phe Lys
1               5                   10                  15

Gly

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Thr Ile His Pro Ser Asp Ser Thr Thr Asn Tyr Asn Gln Lys Phe Lys
1               5                   10                  15

Gly

<210> SEQ ID NO 383
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Thr Tyr Ala Met His
1               5

<210> SEQ ID NO 384
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Arg Ile Arg Ser Lys Ser Ser Asn Tyr Ala Thr Tyr Tyr Ala Asp Ser
1               5                   10                  15

Val Lys Asp

```
<210> SEQ ID NO 385
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 385
gaagtacagt tgcagcaatc tgggcctgag ctggtgaagc ccggtgcttc cgtgaaaatt      60
tcctgcgaaa cttcaggatt ctcatttact gcacatcata tgcactgggt aaaacaatct    120
ccagagaaat cactcgaatg gataggcgag attgatccaa ataccgggtc caccacatac    180
aatcagaaat ttcgcgctaa ggccaccctg actgtcgata aaagttctaa cactacatac    240
atgcagctta aatcccttac attcgaagac agtgcagtgt actactgtta ctctaactgg    300
tttccatatt ggggacaggg aacactggta accgtttccg ct                        342

<210> SEQ ID NO 386
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 386
gacgtagtta tgactcagac accacttaca ctctctgcta ctatcggaca accagcctca      60
atctattgca agtcctcaca atctttgctt gatggcgacg ggaagaccta tctcaattgg    120
cttctccaac gacctgggca aagccccaag agactcatat atctcgtttc caagctggac    180
agtggggtgc cagatagatt tactgggtca ggtagtggta ctgactttac tttgaaaata    240
tcaagagtag aggctgagga cctcggagtc tattactgct ggcaaggaac ccatttcccc    300
cgcaccttcg gaggagggac aaaattggaa ataaaa                               336

<210> SEQ ID NO 387
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387
caagtgcaac ttcagcaacc cggcgccgag cttgtgaagc ctggtgcctc cgttaaactt      60
tcttgcaagg catccggttt ctcattcatt acctactgga tgaactggat caaacaaaga    120
cctggacgtg gtctggagtg gattgggcgg attcacccct cagactccgc aacccaatac    180
aatcagaaat tcaaaacaaa ggccaccttg accgttgata aaagcagttc taccgcttat    240
attcaactgt cctctctgac ctcagaagac tccgcagtgt attactgcgc tcgctctact    300
gagggtgccc attggggtca gggaacattg gtgactgtta gtgct                     345

<210> SEQ ID NO 388
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 388
```

```
gatgttgtta tgacccaaac tcccctgaca ctttctgtaa caataggtca gcctgcctct    60
atctcatgca agtcctcaca gagtctgctg cactctgatg ggaagactta tttgaactgg   120
ttgctccagc gccccggaca gtctcctaaa cgcctgattt atttggtgag caagttggac   180
agtggcgtac cagaccgatt caccggatct ggctccggga cagactttac tttgaaaata   240
agtcgtgtcg aggctgagga tcttggcgtg tactactgct ggcagggggac acacttcccc   300 cagacctttg gaggtggaac taagctcgaa atcaaa                             336
```

<210> SEQ ID NO 389
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 389

```
aagtacagct tcagcagcca ggagcagaac ttgttaagcc cggtgcttct gtgaagctgt    60
cctgtaaagc tagtggttac acttttcacta gcttttggat gcactgggtg aaacagaggc   120
caggacaagg cttggagtgg attggagaga tataccctag cagcggtgtg accaactaca   180
atgaaagatt taagaataaa gccacccctga cagttgataa atcctcacgg acagcataca   240
tgcaactctc atctctgaca tccgaggaca gcgccgtcta ttttttgtacc ccaaactatt   300 actacgacgg cttgtactgg gggcagggga ctttggtcac agtgtccgct              350
```

<210> SEQ ID NO 390
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 390

```
gatgtggtaa tgactcaaac accacttaca ctcagtgtaa ctatcggcca acctgccagc    60
atctcctgca aatccagtca tagcttgttg tataccaatg gcgagaccta tctcaactgg   120
cttctccaga ggccaggaca gtctcccaaa agacttatat atttggtgtc taacttggac   180
tctggtgtgc ccgatagatt ttcagggtct gggtctggca ccgatttac attgaaaata   240 tccagggtgg aagccgaaga ccttggaata tactactgtc tccaatcaac ccatttttcct   300 cgcacattcg gcggcggcac taaactcgaa ataaag                             336
```

<210> SEQ ID NO 391
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 391

```
caggtacagc tccagcaacc aggggcagag ttggtaaagc ccggagccag tgtcaagctc    60
tcatgcaagg cttccggctt cagtttcacc agatactgga tgaattgggt taaacagcgc   120
ccaggacgag ggcttgaatg gataggtagg attcatccct cagactcagc aagtcagtac   180
aatcagaagt ttaagtccaa agcaacactg acagtagaca aaagcagcag cacagcttac   240
attcagttga gtagcttgac atcagaggat agcgcagttt attattgtgg ccgtagtaca   300
```

```
gaagggcctt attggggca aggaacactt gtcacagtga gtgca              345
```

<210> SEQ ID NO 392
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392

```
caagttcaat tgcagcagcc tggtgctgag ctggtgaagc caggtgcaag tgttaaactt    60
tcatgcaagg caagcggatt ctccttcatc acttattgga tgaattggat caaacaacgt   120
cctgggcggg gcctggagtg gattggtcgc atacacccat ctgactccgc tacccaatat   180
gaccagaaat tcaaaaccaa agcaaccctc actgtggata aaagcagcag caccgcatac   240
atacaactca gctccctcac ttccgaggac tctgccgttt actattgcgc acgaagcact   300
gaaggggctc attggggtcc aggaacattg gtaacagtca gcgca                  345
```

<210> SEQ ID NO 393
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 393

```
gaaatacagc ttcagcagtc aggcactgaa ctggtgaaac ccggtgcttc agtgaagatt    60
tcctgtaaga ccagtggtta cagtttcact gattacaaca tgaactgggt gaaacaatcc   120
cacggaaaaa gtctcgaatg gataggtaat ataaaccctt attacggaag caccggctac   180
actcagaatt ttgaaggtaa ggctactttg accgtggata aatcttctag tacagcatat   240
atgcagctta actcacttac ttctgaggac agcgccttgt actactgcgc tcgtgaaggg   300
catgactact acgctatgga ctactgggt caaggcacat ctgtcacagt cagctca      357
```

<210> SEQ ID NO 394
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394

```
caggtccaac ttcagctgcc cggagctgaa ctggtaaaac ccggtgcttc cgttaaggtg    60
tcttgcaaag catcaggcta cacatttact agctactgga tgcactgggt aaagcaacgt   120
ccaggtcagg gccttgaatg gatcggtcgt atacatcctt cagactcaga taccaattac   180
aatcaaaact ttaagggtaa agctactttg attgtcgata gtctcttctc aactgcatac   240
atgcagttgt cttctcttac atccgaggac agtgcagtgt attactgcgc tacaggtttc   300
tcttttttggg gacagggaac cctcgtaacc gtgagtgcc                        339
```

<210> SEQ ID NO 395
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 395

```
caggtacaag tgcaggtgcc aggagctgag ttggtcaagc caggcgctag tgtgaaagtc    60
tcatgtaagg ccagcggcta tactttcact agttactgga tgcactggat gaagaagaga   120
cccggacagg ggctcgaatg gatagggcga atccacccat ctgacagcga tacaaattac   180
aaccagaact ttaaaggaaa ggcaacactt acagttgata agtctagcag cacagcatac   240
atgcagctta gttcactcac atcagaagat tccgctgtct attttgtgc tactggtttc    300 agcttttggg gtcagggaac tctcgtaact gtgtccgca                          339
```

<210> SEQ ID NO 396
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 396

```
gatgtcgtta tgacccagac tccattgact ctgtctgtca ccataggaca acccgcatct    60
atctcctgca aatcatcaca gagcttgctg tattctgacg gaaagacata tttgaactgg   120
ctgctccaac ggcctgggga gtcccctaaa ctccttatct atctcgtttc taaacttgac   180
agtggcgtcc ctgatcgttt taccggctcc gggtctggca ctgattttac actcaagatc   240
agccgggtgg aagcagagga tttgggtgtc tactattgtc ttcagaccac ttccttccca   300
tataccttcg gcggcggaac taaattggaa atcaaa                             336
```

<210> SEQ ID NO 397
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 397

```
caagtccagt tgcagcagcc cggtgctgag cttgtcaaac ccggcgcctc agttaaagtc    60
tcatgcaagg cttctggcta taactttata aattactgga tgcactgggt caaacagcga   120
ccaggacagg gcctcgaatg gattggtaga atacacccat cagatagtta cactaattac   180
aatcagaagt ttaaaggtaa ggcaacactg actgtggaca aaagcagctc aactgcctac   240
atgcagctca gttctctcac ctccgaggat agtgctgtgt actattgtgc cagtcccata   300
tccactcttt attgggggca gggcaccacc ttgaccgtat cctca                   345
```

<210> SEQ ID NO 398
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 398

```
gatgtcgtga tgactcaaac tccattgact ctgagcgtca ctattgggca acctgctagt    60
atatcatgca gtcctctcca gtctctgttg gactccgacg ggaagactta tctcaactgg   120
ttgctgcaac gtcctggtga gagccccaag ctccttatat acctggtatc aaaactggat   180
tctggggttc cagaccgttt cactgggagc gggagcggca cagactttac cctcaagatt   240
```
tcacgggtag aagctgaaga cctgggagtg tattactgcc ttcaagccac acatttcct      300 caaacatttg ggggtggtac taagctggaa attaag                               336

<210> SEQ ID NO 399
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 399
caagttcagt tgcagcttcc tggagctgag ttggttcggc caggtacatc agttaaagta     60
agctgcaaag caagcgacta caccttcacc acatattgga tgcactgggt caaacagcgg    120
cctggacagg ggctggactg gatcgggagg atacatccta gcgattctga tactaactac    180
aatcagaatt tcaaaggtaa agccacactc actgtggaca aatcctcttc aaccgcttac    240
atgcacttgt catccttgac atccgaggac tcagcagttt attactgcgc taccggtttc    300
agcttttggg gacagggtac tttggtgaca gtgagcgcc                           339

<210> SEQ ID NO 400
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 400
caggttcaag tgcaactccc tggtgccgaa cttgtgaagc ccggagccag tgtgaaggtt     60
agctgtaagg cctctgggta cacatttact tcctactgga tgcactgggt aaaaaagcgg    120
ccaggacagg gactcgaatg gataggacgt attcacccct tccgactctga cacaaactac    180 aaccaaaact tcaaaggtaa agccactctc accgtagaca aatcatcatc aaccgcatac    240
atgctcctct catccctgac atcagaagac agtgctgttt attattgcgc tacagggttt    300
agttttgggg ccaaggaac cttgattacc gtgtccgca                            339

<210> SEQ ID NO 401
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401
gacgtggtga tgactcagac acctctgacc ctgtctgtaa ccattggcca gccagccagt     60
attagttgta aatcatctca aagtctcctc tactcagacg gcaagaccta tttgaactgg    120
ttgctccagc ggccaggcga atcacccgag ctgctcattt acttggtctc caagatggat    180
tccggtgtgc cagatagatt tcatggtcac ggaagtggga cagccttcac aatgaagatt    240
tcccggatgg gcggcggtgg attgggaaac tattactgtc tccctcgtac ctccttccct    300
tacactttcg gtggtgggac aaaactcgag ataaaa                              336

<210> SEQ ID NO 402
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402
caagtgcagt tgcagctccc cggtgccgaa ctcgtaaaac ccggcgcaag cgtgaaagtt    60
tcctgtaagg catccggcta tacattcaca tcatattgga tgcattgggt caaacagcgt   120
cctgggcagg gtcttgaatg gattgggcgg atacatccat ctgacagtga taccaactac   180
aatcaaaatt ttaaagggaa ggccaccctc acagttgaca agtctagtaa tacagcctac   240
atgcagcttt ctagcctgac tagcgaggat tctgctgttt actactgtgc aaccggattc   300 agttttggg gacaaggaac tttggtgaca gtatccgcc                            339

<210> SEQ ID NO 403
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 403
gacgtggtga tgaccccaac atcacttcat tgcttgtta ctatagggca acccggcttt     60
ttgttctgta aaagttcaca gaatctcctc tacaatgaag gaaaacata cttgaagtgg    120 cttttgcctg agccaggtgc tttctccaag gtacttatat accttgtctt caagatggga   180
tttggggttc ctgatcgctt ccacggccac ggatctggca ccgacttccc tatgaaaata   240
agccgaatgg gaggggcgg ccttgggggc tacctttgcc ttccctctac ccctttcct    300 tataccttcg gcggggtac taaacttgaa ataaaa                              336

<210> SEQ ID NO 404
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404
cagatccact tggtacagtc tggacctgag ctgaagaagc ctggagagac agtcaggatc    60
tcctgcaagg cttctgggta taccttcaca acctatggaa tgagctgggt gaagcaggct   120
ccaggaaagg ctttaaagtg gatgggctgg ataaacacct actctggagt gccaacatat   180
gctgatgact tcaagggacg gtttgccttc tctttggaaa cctctgccag cactgcctat   240
ttgcagatca acaacctcaa aaatgaggac acggctacat atttctgtac aagagaggga   300
tctactatgg ttacgaggta ctactttgac tactggggcc aaggcaccac tctcacagtc   360
tcctca                                                              366

<210> SEQ ID NO 405
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
gacattgtta tgacccaagc cgccccaagc gtaccagtta ctcctggcga gagtgtctcc    60

```
attagttgtc ggtcttcaaa aagtttgctc cactccaatg ggaatactta cctttattgg      120
ttccttcagc gtcctggtca atctccacag ctgctgattt atcgaatgag taacctggcc      180
tcaggagtcc ctgatcgctt cagtggttca gggtccggta ctgcctttac acttaggatc      240
tccagggtag aagccgagga tgtaggcgtc taccattgta tgcaacatct cgaatcaccc      300
tatactttcg gtggaggtac aaaactcgaa ataaaa                                336
```

<210> SEQ ID NO 406
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 406

```
caagtacaac tgcaactccc aggcgccgag ttggttaaac ctggcgcttc agtgaaggta      60
tcctgcaaag catctgccta cactttcaca tcttactgga tgcactgggt aaaacagcga     120
ccagggcagg gacttgaatg gattggacgc attcatcctt ccgatagcga cactaactat     180
aaccaaaatt ttaaggggaa ggccaccttg actgtggata aatctagcaa cacagcctac     240
atgcaactca gttcactgac ttctgaggat tctgccgttt attattgtgc cacaggcttc     300
tccttctggg ggcaaggaac cttggtgacc gtgtcagct                             339
```

<210> SEQ ID NO 407
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 407

```
gacatagtaa tgactcaaag ccacaaattc atgtccacca gtgttggtga ccgcgtatca      60
atcacttgca aggccagtca ggacgtatcc acaacagttg catggtatca gcaaaagcca     120
ggacaatcac ccaaacttct gatttacagt gccagttatc gatacactgg ggttcccgac     180
agattcacag gatcaggcag cggaactgat tttaccttca ccattagctc agtgcaagcc     240
gaagatctgg ccgtgtatta ttgtcaacag cactatagta ccaggcccac cttcggcggg     300
ggaactaaat tggaaataaa g                                                321
```

<210> SEQ ID NO 408
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 408

```
cagatccagt tggtacagtc tggacctgag ctgaagaagc ctggagagac agtcaagatc      60
tcctgcaagg cttctgggta taccttcaca acctatggaa tgagctgggt gaaacaggct     120
ccaggaaagg gtttaaagtg gatgggctgg ataaacacct actctggagt gccaacatat     180
gctgatgact tcaagggacg gtttgccttc tctttggaaa cctctgccag cactgcctat     240
ttgcagatca acaacctcaa aaatgaggac acggctacat atttctgtgc aagagaggga     300
tctactatgg ttacgaggta ctactttgac tactgggggcc aaggcaccac tctcacagtc     360
```

-continued

```
tcctca                                                              366
```

<210> SEQ ID NO 409
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409

```
gatattgtga tgacccaagc tgcccctcc gtccccgtca cacccggtga gtccgtgtct      60
ataagctgtc gtagttccaa gagcttgctt cactcaaatg gcaatacata cctttattgg    120
ttcctgcaac gccccggcca gagcccacag gtgttgattt atcgtatgtc aaacctggcc    180
tccggcgttc ccgacaggtt ttccggcagt ggaagcggga ccgcatttac actgcgaata    240
tctcgtgttg aggcagaaga cgttggagtc tattactgta tgcaacacct cgaaagccca    300
tacactttcg gcggtgggac taagctggaa attaaa                              336
```

<210> SEQ ID NO 410
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 410

```
cagatccagt tggttcagtc tggacctgag ctgaagaagc ctggagagac agtcaagatc     60
tcctgcaagg cttctgggta taccttcaca acctatggaa tgagctgggt gaaacaggct    120
ccaggaaagg gtttaaagtg gatgggctgg ataaacacct actctggagt gccaacatat    180
gctgatgact tcaagggacg gtttgccttc tctttggaaa cctctgccag cactgcctat    240
ttgcagatca acaacctcaa aaatgaggac acggctacgt ttttctgtgc aagagaggga    300
tctactatgg ttacgaggta ctactttgac tactggggcc aaggcaccac tctcacagtc    360
tcctca                                                              366
```

<210> SEQ ID NO 411
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411

```
gatattgtca tgacccaggc agccccagt gtccccgtga ctcctggaga aagtgttagt      60
attagctgtc gatcaagtaa atcacttctt catagtaacg gaaatactta cttgtattgg    120
ttcctccaaa ggccaggcca gtctccacag ttgctcatct atcgcatgag taatcttgct    180
tcaggtgtgc ctgatcgctt cagtggcagt ggatcaggta ctgctttcac actccgtata    240
agtagggtgg aagccgagga tgtcggtgtc tactattgta tgcagcacct ggagtatccc    300
tcaacatttg gtgggggac aaaactggag attaag                              336
```

<210> SEQ ID NO 412
<211> LENGTH: 339
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 412

```
caagtccagg tgcaactgcc tggcgccgaa cttgtgaaac ccggagcctc cgttaaggtc    60
tcctgcaagg ctagtggcta tacctttaca tcttattgga tgcactgggt gaaaaaacgc   120
ccagggcagg gcctcgaatg gatcggccgc atccacccat ctgatagcga cactaactat   180
aaccagaact ttaaaggcaa ggctactctg accgttgata aaagcagttc cactgcctac   240
atgcaactga catcccttac cagtgaggat ttcgccgtgt actactgctc cacagggttc   300
tccttctggg gccaggggac ccttgttacc gtgtccgca                          339
```

<210> SEQ ID NO 413
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 413

```
gatgtcgtta tgacccagac tccattgact ctgtctgtca ccataggaca acccgcatct    60
atctcctgca aatcatcaca gagcttgctg tattctgacg gaaagacata tttgaactgg   120
ctgctccaac ggcctgggga gtcccctaaa ctccttatct atctcgtttc taaacttgac   180
agtggcgtcc ctgatcgttt taccggctcc gggtctggca ctgattttac actcaagatc   240
agccgggtgg aagcagagga tttgggtgtc tactattgtc ttcagaccac ttacttccca   300
tataccttcg gcggcggaac taaattggaa atcaaa                             336
```

<210> SEQ ID NO 414
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 414

```
caagttcagt tgcaccaacc tggtacaagc ctcgttaagc ccggtgcgag tgtcaaactt    60
agctgcaaag catctggtta caatttttcc agtattaca tgcactgggt taaacagcgg    120
cccggccaag gactggagtg gatcggaacc atccacccct cagactcaac tacgaactgc   180
aatcagaagt tcaaggggaa ggccacgctt accgtggaca gtcaagtag gactgcttac   240
atgcaactca atagcttgac attcgaggat tccgcggtct attattgtgc gaatttcgtc   300
tattggggac aaggtaccag cgtgacggtc tccagc                             336
```

<210> SEQ ID NO 415
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 415

```
gacattgtta ttacgcaaga cgagctgtca aaccctgtta cgagtggtga ttctgtatcc    60
atatcctgtc gctcctcaaa aagtctgttg tacaaggatg gaaaaactta tctgaactgg   120
tttctgcaac ggccaggcca atctcctcaa ttgcttatat acgtcgtttc aacgagagcc   180
```

```
tcaggagtgt ctgacagatt ttccggctcc ggctctggga ccgattttac tctcgaaatc    240
agccgggtta aggccgaaga cgttggtgtg tattattgcc aacagctcgt agagtaccca    300
tatacattcg gcgggggcac aaaactcgaa ataaag                              336
```

<210> SEQ ID NO 416
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416

```
caagttcagt tgcaccaacc tggtacaagc ctcgttaagc ccggtgcgag tgtcaaactt    60
agctgcaaag catctggtta caatttttcc agttattaca tgcactgggt taaacagcgg    120
cccggccaag gactggagtg gatcggaacc atccacccct cagactcaac tacgaactac    180
aatcagaagt tcaaggggaa ggccacgctt accgtggaca agtcaagtag gactgcttac    240
atgcaactca atagcttgac attcgaggat tccgcggtct attattgtgc gaatttcgtc    300
tattggggac aaggtaccag cgtgacggtc tccagc                              336
```

<210> SEQ ID NO 417
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417

```
caagttcagt tgcaccaacc tggtacaagc ctcgttaagc ccggtgcgag tgtcaaactt    60
agctgcaaag catctggtta cagcttttcc agttattaca tgcactgggt taaacagcgg    120
cccggccaag gactggagtg gatcggaacc atccacccct cagactcaac tacgaactgc    180
aatcagaagt tcaaggggaa ggccacgctt accgtggaca agtcaagtag gactgcttac    240
atgcaactca atagcttgac attcgaggat tccgcggtct attattgtgc gaatttcgtc    300
tattggggac aaggtaccag cgtgacggtc tccagc                              336
```

<210> SEQ ID NO 418
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 418

```
caagttcagt tgcaccaacc tggtacaagc ctcgttaagc ccggtgcgag tgtcaaactt    60
agctgcaaag catctggtta caccttttcc agttattaca tgcactgggt taaacagcgg    120
cccggccaag gactggagtg gatcggaacc atccacccct cagactcaac tacgaactgc    180
aatcagaagt tcaaggggaa ggccacgctt accgtggaca agtcaagtag gactgcttac    240
atgcaactca atagcttgac attcgaggat tccgcggtct attattgtgc gaatttcgtc    300
tattggggac aaggtaccag cgtgacggtc tccagc                              336
```

<210> SEQ ID NO 419
<211> LENGTH: 336

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419
caagttcagt tgcaccaacc tggtacaagc ctcgttaagc ccggtgcgag tgtcaaactt      60
agctgcaaag catctggtta cagcttttcc agttattaca tgcactgggt taaacagcgg     120
cccggccaag gactggagtg gatcggaacc atccacccct cagactcaac tacgaactac    180
aatcagaagt tcaaggggaa ggccacgctt accgtggaca agtcaagtag gactgcttac    240
atgcaactca atagcttgac attcgaggat ccgcggtct attattgtgc gaatttcgtc     300
tattggggac aaggtaccag cgtgacggtc tccagc                              336

<210> SEQ ID NO 420
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 420
caagttcagt tgcaccaacc tggtacaagc ctcgttaagc ccggtgcgag tgtcaaactt      60
agctgcaaag catctggtta caccttttcc agttattaca tgcactgggt taaacagcgg     120
cccggccaag gactggagtg gatcggaacc atccacccct cagactcaac tacgaactac    180
aatcagaagt tcaaggggaa ggccacgctt accgtggaca agtcaagtag gactgcttac    240
atgcaactca atagcttgac attcgaggat ccgcggtct attattgtgc gaatttcgtc     300
tattggggac aaggtaccag cgtgacggtc tccagc                              336

<210> SEQ ID NO 421
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 421
gaagttcaat tggttgagtc aggggggcggt cttgttcaac ctaaaggctc cctcaagttg     60
tcctgtgcag cctctggatt tacgtttaac acttatgcta tgcactgggt tcggcaagca    120
ccggggaaag ggctcgagtg ggtggcccgc attagatcaa aatcatccaa ctatgccacc    180
tactatgccg attccgtgaa ggacagattc acaatatcac gcgatgatag ccaaagtatg    240
ctctatttgc aaatgaataa tcttaaaacc gaagacacag ctatgtatta ttgtgtcaga    300
gagttgagac ttaggtatgc tatggattac tggggccaag gtacttcagt gaccgtttca    360
tcc                                                                  363

<210> SEQ ID NO 422
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422

```
gatatactga tgacccaaac tccactgact ctgtctgtca ccatcggtca gcccgcatca      60
atcagttgta atctagtca gtccctgctg tatactaacg gaaagactta tctgaattgg     120
cttttgcaac ggcccggtca atcacccaaa aggcttatat acctggtaag caagttggac     180
agtggagttc cggatcgctt cagtggctct ggtagtggga cagattttac gctcaaaatt     240
agtagggtgg aggccgagga tcttggcgtc tattattgcc tccaatctac gcactttcca     300
ctcacgtttg gggccggaac caaactcgaa cttaaa                               336
```

<210> SEQ ID NO 423
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser
        115                 120

<210> SEQ ID NO 424
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys
            100                 105

<210> SEQ ID NO 425
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Gly Tyr Thr Phe Ser Asn Tyr
1               5

<210> SEQ ID NO 426
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Leu Pro Gly Thr Gly Arg
1               5

<210> SEQ ID NO 427
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Arg Asp Tyr Tyr Gly Asn Phe Tyr Tyr Ala Met Asp Tyr
1               5                   10

<210> SEQ ID NO 428
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ser Ala Ser Gln Gly Ile Asn Asn Tyr Leu Asn
1               5                   10

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Tyr Thr Ser Thr Leu Gln Ser
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 430

Gln Gln Tyr Ser Lys Leu Pro Arg Thr
1               5

<210> SEQ ID NO 431
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Asn Tyr Trp Ile Glu
1               5

<210> SEQ ID NO 432
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Glu Ile Leu Pro Gly Thr Gly Arg Thr Ile Tyr Asn Glu Lys Phe Lys
1               5                   10                  15

Gly

<210> SEQ ID NO 433
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433
caggttcagt tgcagcagtc tggttccgaa ttgatgatgc aggagcttc cgtgaagata      60 agctgtaagg ccacaggtta cactttcagt aactattgga tagaatgggt aaagcaaaga   120
cctggtcacg gtttggaatg gatcggggag atactgcctg gtaccggcag aactatctac   180
aacgagaaat ttaagggtaa agccactttt acagcagaca tatccagtaa tacagttcaa   240
atgcagctgt catcactcac cagtgaagat agcgccgtgt attactgcgc caggcgcgat   300
tattacggca acttttatta tgctatggat tactggggcc aaggtacttc tgtaactgta   360
agctcc                                                              366

<210> SEQ ID NO 434
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 434
gatatacaga tgacgcagtc tacttcttcc ctctctgcgt cccttggcga ccgggtcaca      60
ataagctgtt ctgcttccca gggtataaat aactacctga attggtatca gcaaaaaccg   120
gatgggacgg tcgaactcct gatatattac acatctacac ttcagtctgg tgtcccctct   180
cgcttttcag gttccggttc cggcactgat tatagcctta caattagcaa cctcgaaccg   240

```
gaggacatcg aacatatta ttgccagcaa tatagtaaac tgcccaggac gtttggcggt    300
ggcaccaagt tggaaatcaa a                                             321
```

<210> SEQ ID NO 435
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gln or His
<220> FEATURE:
<221> NAME/KEY: MOD_RES
<222> LOCATION: (8)..(8)
<223> OTHER INFORMATION: Asp, His or Tyr
<220> FEATURE:
<221> NAME/KEY: MOD_RES
<222> LOCATION: (9)..(9)
<223> OTHER INFORMATION: Gly, Ser or Thr
<220> FEATURE:
<221> NAME/KEY: MOD_RES
<222> LOCATION: (10)..(10)
<223> OTHER INFORMATION: Asp or Asn
<220> FEATURE:
<221> NAME/KEY: MOD_RES
<222> LOCATION: (12)..(12)
<223> OTHER INFORMATION: Lys or Glu

<400> SEQUENCE: 435

Lys Ser Ser Xaa Ser Leu Leu Xaa Xaa Xaa Gly Xaa Thr Tyr Leu Asn
1               5                   10                  15

<210> SEQ ID NO 436
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Asn

<400> SEQUENCE: 436

Leu Val Ser Xaa Leu Asp Ser
1               5

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or Leu
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (8)..(8)
<223> OTHER INFORMATION: Arg or Gln

<400> SEQUENCE: 437

```
Xaa Gln Xaa Thr His Phe Pro Xaa Thr
1               5
```

<210> SEQ ID NO 438
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn, Ser or Thr

<400> SEQUENCE: 438

```
Gly Tyr Xaa Phe Ser Ser Tyr
1               5
```

<210> SEQ ID NO 439
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Cys or Tyr

<400> SEQUENCE: 439

```
Thr Ile His Pro Ser Asp Ser Thr Thr Asn Xaa Asn Gln Lys Phe Lys
1               5                   10                  15

Gly
```

<210> SEQ ID NO 440
<211> LENGTH: 37
<212> TYPE: PRT
<213> ORGANISM: Homo sapiens

<400> SEQUENCE: 440

```
Glu Asn Thr Ala Val Val Ala Val Glu Pro Asp Arg Arg Asn Gln Ser
1               5                   10                  15

Pro Val Asp Gln Gly Ala Thr Gly Ala Ser Gln Gly Leu Leu Asp Arg
                20                  25                  30

Lys Glu Val Leu Gly
            35
```

<210> SEQ ID NO 441
<211> LENGTH: 25
<212> TYPE: PRT
<213> ORGANISM: Homo sapiens

<400> SEQUENCE: 441

```
Thr Ala Val Val Ala Val Glu Pro Asp Arg Arg Asn Gln Ser Pro Val
1               5                   10                  15

Asp Gln Gly Ala Thr Gly Ala Ser Gln
            20                  25
```

<210> SEQ ID NO 442
<211> LENGTH: 24
<212> TYPE: PRT
<213> ORGANISM: Homo sapiens

<400> SEQUENCE: 442

```
Glu Asn Thr Ala Val Ala Val Glu Pro Asp Arg Arg Asn Gln Ser
1               5                   10                  15

Pro Val Asp Gln Gly Ala Thr Gly
            20
```

<210> SEQ ID NO 443
<211> LENGTH: 15
<212> TYPE: PRT
<213> ORGANISM: Homo sapiens

<400> SEQUENCE: 443

```
Glu Asn Thr Ala Val Ala Val Glu Pro Asp Arg Arg Asn Gln
1               5                   10                  15
```

<210> SEQ ID NO 444
<211> LENGTH: 25
<212> TYPE: PRT
<213> ORGANISM: Homo sapiens

<400> SEQUENCE: 444

```
Arg Asn Gln Ser Pro Val Asp Gln Gly Ala Thr Gly Ala Ser Gln Gly
1               5                   10                  15

Leu Leu Asp Arg Lys Glu Val Leu Gly
            20                  25
```

<210> SEQ ID NO 445
<211> LENGTH: 15
<212> TYPE: PRT
<213> ORGANISM: Homo sapiens

<400> SEQUENCE: 445

```
Gly Glu Ala Val Val Leu Pro Glu Val Glu Pro Gly Leu Thr Ala
1               5                   10                  15
```

<210> SEQ ID NO 446
<211> LENGTH: 330
<212> TYPE: PRT
<213> ORGANISM: Homo sapiens

<400> SEQUENCE: 446

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 447
<211> LENGTH: 326
<212> TYPE: PRT
<213> ORGANISM: Homo sapiens

<400> SEQUENCE: 447

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
                100                 105                 110
Pro Val Ala Gly Pro Ser Val Phe Leu Phe Pro Pro Lys Pro Lys Asp
                115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
                180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 448
<211> LENGTH: 9
<212> TYPE: PRT
<213> ORGANISM: Homo sapiens

<400> SEQUENCE: 448

Gly Leu Val Gly Leu Ile Phe Ala Val
1               5

<210> SEQ ID NO 449
<211> LENGTH: 20
<212> TYPE: PRT
<213> ORGANISM: Homo sapiens

<400> SEQUENCE: 449

Gly Glu Ala Val Val Leu Pro Glu Val Glu Pro Gly Leu Thr Ala Arg
1               5                   10                  15

Glu Gln Glu Ala
            20

<210> SEQ ID NO 450
<211> LENGTH: 310
<212> TYPE: PRT
<213> ORGANISM: Homo sapiens

<400> SEQUENCE: 450

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
```

```
            100                 105                 110
Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 451
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Ala Ala Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr
    130                 135                 140
```

```
Ala Gln Glu Pro Ala Thr Ser His Pro His Arg Asp Met Gln Pro Gly
145                 150                 155                 160

His His Glu Thr Ser Thr Pro Ala Gly Pro Ser Gln Glu Gly Glu Ala
                165                 170                 175

Val Val Leu Pro Glu Val Glu Pro Gly Leu Thr Ala Arg Glu Gln Glu
            180                 185                 190

Ala Asp Leu His Thr Pro His Thr Glu Asp Gly Gly Pro Ser Ala Thr
        195                 200                 205

Glu Arg Ala Ala Glu Asp Gly Ala Ser Ser Gln Leu Pro Ala Ala Glu
    210                 215                 220

Gly Ser Gly Glu Gln Asp Phe Thr Phe Glu Thr Ser Gly Glu Asn Thr
225                 230                 235                 240

Ala Val Val Ala Val Glu Pro Asp Arg Arg Asn Gln Ser Pro Val Asp
                245                 250                 255

Gln Gly Ala Thr Gly Ala Ser Gln Gly Leu Leu Asp Arg Lys Glu Val
            260                 265                 270

Leu Gly Gly Val Ile Ala Gly Leu Val Gly Leu Ile Phe Ala Val
        275                 280                 285

Cys Leu Val Gly Phe Met Leu Tyr Arg Met Lys Lys Lys Asp Glu Gly
290                 295                 300

Ser Tyr Ser Leu Glu Glu Pro Lys Gln Ala Asn Gly Gly Ala Tyr Gln
305                 310                 315                 320

Lys Pro Thr Lys Gln Glu Phe Tyr Ala
                325                 330

<210> SEQ ID NO 452
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Ala Ala Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175
```

```
Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Glu Ser Gly Glu
            195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Glu Gly Glu Ala
225                 230                 235                 240

Val Val Leu Pro Glu Val Pro Gly Leu Thr Ala Arg Glu Gln Glu
            245                 250                 255

Gln Gly Ala Thr Gly Ala Ser Gln Gly Leu Leu Asp Arg Lys Glu Val
            260                 265                 270

Leu Gly Gly Val Ile Ala Gly Gly Leu Val Gly Leu Ile Phe Ala Val
            275                 280                 285

Cys Leu Val Gly Phe Met Leu Tyr Arg Met Lys Lys Lys Asp Glu Gly
            290                 295                 300

Ser Tyr Ser Leu Glu Glu Pro Lys Gln Ala Asn Gly Gly Ala Tyr Gln
305                 310                 315                 320

Lys Pro Thr Lys Gln Glu Glu Phe Tyr Ala
                325                 330

<210> SEQ ID NO 453
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
        50                  55                  60

Trp Lys Asp Thr Gln Leu Leu Thr Ala Ile Pro Thr Ser Pro Glu Pro
65              70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Ala Ala Ala Val Glu Pro
            100                 105                 110

Gly Leu Thr Ala Arg Glu Gln Glu Ala Thr Pro Arg Pro Arg Glu Thr
            115                 120                 125

Thr Gln Leu Pro Thr Thr His Leu Ala Ser Thr Thr Thr Ala Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Glu Ala Val
```

```
                195                 200                 205
Val Leu Pro Glu Val Glu Pro Gly Leu Thr Ala Arg Glu Gln Glu Gly
210                 215                 220

Ser Gly Glu Gln Asp Phe Thr Phe Glu Thr Ser Gly Glu Asn Thr Ala
225                 230                 235                 240

Val Val Ala Val Glu Pro Asp Arg Arg Asn Gln Ser Pro Val Asp Gln
                245                 250                 255

Gly Ala Thr Gly Ala Ser Gln Gly Leu Leu Asp Arg Lys Glu Val Leu
            260                 265                 270

Gly Gly Val Ile Ala Gly Gly Leu Val Gly Leu Ile Phe Ala Val Cys
            275                 280                 285

Leu Val Gly Phe Met Leu Tyr Arg Met Lys Lys Asp Glu Gly Ser
            290                 295                 300

Tyr Ser Leu Glu Glu Pro Lys Gln Ala Asn Gly Gly Ala Tyr Gln Lys
305                 310                 315                 320

Pro Thr Lys Gln Glu Glu Phe Tyr Ala
                325

<210> SEQ ID NO 454
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Ala Ala Val Glu Pro
            100                 105                 110

Gly Leu Thr Ala Arg Glu Gln Glu Ala Thr Pro Arg Pro Arg Glu Thr
            115                 120                 125

Thr Gln Leu Pro Thr Thr His Leu Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
210                 215                 220
```

Val Leu Pro Glu Val Glu Asn Gln Ser Pro Val Asp Gln Gly Ala Thr
225                 230                 235                 240

Gly Ala Ser Gln Gly Leu Leu Asp Arg Lys Glu Val Leu Gly Gly Val
            245                 250                 255

Ile Ala Gly Gly Leu Val Gly Leu Ile Phe Ala Val Cys Leu Val Gly
        260                 265                 270

Phe Met Leu Tyr Arg Met Lys Lys Lys Asp Glu Gly Ser Tyr Ser Leu
    275                 280                 285

Glu Glu Pro Lys Gln Ala Asn Gly Gly Ala Tyr Gln Lys Pro Thr Lys
290                 295                 300

Gln Glu Glu Phe Tyr Ala
305                 310

<210> SEQ ID NO 455
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
            85                  90                  95

Glu Gly Pro Lys Glu Gly Glu Ala Val Val Ala Ala Val Glu Pro
        100                 105                 110

Gly Leu Thr Ala Arg Glu Gln Glu Ala Thr Pro Arg Pro Arg Glu Thr
    115                 120                 125

Thr Gln Leu Pro Thr Thr His Leu Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
            165                 170                 175

Thr Pro His Thr Glu Asp Gly Gly Pro Ser Ala Thr Glu Arg Ala Ala
        180                 185                 190

Glu Asp Gly Ala Ser Ser Gln Leu Pro Ala Ala Glu Gly Ser Gly Glu
    195                 200                 205

Gln Asp Phe Thr Phe Glu Thr Ser Gly Glu Asn Thr Ala Val Val Ala
210                 215                 220

Val Glu Pro Asp Arg Arg Asn Gln Leu Pro Glu Val Glu Gly Ala Thr
225                 230                 235                 240

Gly Ala Ser Gln Gly Leu Leu Asp Arg Lys Glu Val Leu Gly Gly Val
            245                 250                 255

Ile Ala Gly Gly Leu Val Gly Leu Ile Phe Ala Val Cys Leu Val Gly
        260                 265                 270

```
Phe Met Leu Tyr Arg Met Lys Lys Asp Glu Gly Ser Tyr Ser Leu
            275                 280                 285

Glu Glu Pro Lys Gln Ala Asn Gly Gly Ala Tyr Gln Lys Pro Thr Lys
        290                 295                 300

Gln Glu Glu Phe Tyr Ala
305                 310

<210> SEQ ID NO 456
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Ser Pro Glu Pro Thr Gly Leu Glu Ala Thr Ala Ala Ser Thr Ser Thr
1               5                   10                  15

Leu Pro Ala Gly Glu Gly Pro Lys Glu Gly Glu Ala Val Val Leu Pro
            20                  25                  30

Glu Val Glu Pro Gly Leu Thr Ala Arg Glu Gln Glu Ala Thr Pro Arg
        35                  40                  45

Pro Arg Glu Thr Thr Gln
    50

<210> SEQ ID NO 457
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Gly Ser Gly Glu Gln Asp Phe Thr Phe Glu Thr Ser Gly Glu Asn Thr
1               5                   10                  15

Ala Val Val Ala Val Glu Pro Asp Arg Arg Asn Gln Ser Pro Val Asp
            20                  25                  30

Gln Gly Ala Thr Gly Ala Ser Gln Gly Leu Leu Asp Arg Lys Glu Val
        35                  40                  45

Leu Gly
    50
```

ANTIBODY MOLECULES TO CD138 AND USES THEREOF

CROSS REFERENCE TO RELATED APPLICATIONS

This application claims the benefit of U.S. Provisional Application No. 62/566,936, filed Oct. 2, 2017, and U.S. Provisional Application No. 62/725,880, filed Aug. 31, 2018. The contents of the aforesaid applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 26, 2018, is named P2029-7017WO-_SL.txt and is 171,304 bytes in size.

BACKGROUND

Multiple myeloma (MM) is a cancer formed by malignant plasma cells. These tumors generally develop in bone, but occasionally are found in other tissues. Disease with a single plasma cell tumor is known as an isolated (or solitary) plasmacytoma. When more than one plasmacytoma is present, it is known as multiple myeloma. In the United States, the estimated new cases are about 30,000 in 2017 and more than 10,000 deaths are expected to occur. Despite treatment advances in multiple myeloma therapy, multiple myeloma remains an incurable disease in most patients.

There is a need for developing new approaches for treating, preventing and diagnosing multiple myeloma and other disorders that share similar disease mechanisms.

SUMMARY

This disclosure provides, at least in part, antibody molecules that bind to CD138, e.g., human CD138, and that comprise one or more functional and structural properties disclosed herein. In an embodiment, the antibody molecule is capable of causing an effector function (e.g., an antibody-dependent cellular cytotoxicity (ADCC) activity) on a cell expressing CD138. In an embodiment, the antibody molecule preferentially binds to a membrane-bound CD138 versus a soluble CD138. In an embodiment, the antibody molecule binds to an epitope in an extracellular region of CD138 that is proximal to the transmembrane domain. In an embodiment, the antibody molecule does not bind to the integrin binding domain (IBD) of CD138. In an embodiment, the antibody molecule does not bind exclusively to the IBD of CD138. While not wishing to be bound by theory, it is believed that in an embodiment, improved or optimal cytotoxicity can be achieved, by targeting certain extracellular region(s) on membrane-bound CD138 that is proximal to the cell membrane.

In an embodiment, the antibody molecule is selected from Table 1, or competes for binding to CD138 with an anti-CD138 monoclonal antibody selected from Table 1. In an embodiment, the antibody molecule binds to the same or overlapping epitope as the epitope recognized by an anti-CD138 monoclonal antibody selected from Table 1. In an embodiment, the antibody molecule comprises one or more heavy chain variable regions and/or one or more light chain variable regions described in Table 1. In an embodiment, the antibody molecule comprises one or more heavy chain CDRs and/or one or more light chain CDRs described in Table 1.

In an embodiment, antibody molecule-drug conjugates (ADCs), nucleic acid molecules encoding the antibody molecules, expression vectors, host cells, compositions (e.g., pharmaceutical compositions), kits, containers, and methods for making the antibody molecules, are also provided. The antibody molecules disclosed herein can be used (alone or in combination with other agents or therapeutic modalities) to treat, prevent and/or diagnose disorders associated with CD138, e.g., cancer or precancerous conditions (e.g., multiple myeloma or smoldering myeloma).

Accordingly, in certain aspects, this disclosure provides an antibody molecule, e.g., an antibody molecule described herein, having one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or all) of the following properties a)-dd):

a) Binds to CD138 (e.g., human CD138) with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM, b) Binds to a membrane-bound CD138 with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM, c) Binds to a soluble CD138 i) with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM; or ii) with low affinity, e.g., with a dissociation constant ($K_D$) of greater than about 100 nM, e.g., greater than about 200, 300, 400, or 500 nM, d) Binds to a membrane-bound CD138, or an intact ectodomain of CD138, i) preferably over a soluble CD138, e.g., the binding affinity to a membrane-bound CD138, or an intact ectodomain of CD138, is at least 2, 3, 4, 5, 6, 7, 8, 9, or 10-fold higher than the binding affinity to a soluble CD138; or ii) with a binding affinity similar to the binding affinity to a soluble CD138, e.g., the binding affinity to a membrane-bound CD138, or an intact ectodomain of CD138, is less than about 10%, 20%, 30%, 40%, 50%, 60%, 70%, 80%, 90%, or 100% higher than the binding affinity to a soluble CD138, e) Binds to one or more (e.g., 2, 3, 4, 5, 6, 7, 8, 9, 10, 11, 12, 13, 14, 15, 20, 25, 30, 35, 40, 45, 50, 55, 60, 65, 70, 75, or more) amino acid residues of CD138 in an extracellular region proximal to the transmembrane domain of CD138, e.g., within 75, 70, 65, 60, 55, 50, 45, 40, 35, 30, 25, 20, 15, 10, or 5 amino acids from the N-terminus of the transmembrane domain, f) i) Binds to an extracellular region of CD138 distant from the transmembrane domain, e.g., the C-terminus of the region is at least 100, 110, 120, 130, 140, 150, 160, 170, 180, 190, or 200 amino acids from the N-terminus of the transmembrane domain; or ii) does not bind, or binds with low affinity, to an extracellular region of CD138 distant from the transmembrane domain, e.g., the C-terminus of the region is at least 100, 110, 120, 130, 140, 150, 160, 170, 180, 190, or 200 amino acids from the N-terminus of the transmembrane domain, g) Binds to the integrin binding domain (IBD) of CD138 or a region N-terminal to the IDB; or ii) does not bind, or binds with low affinity, to the IBD of CD138 or a region N-terminal to the IDB, h) Binds to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region proximal to the transmembrane domain, e.g., a region comprising amino acids 176-250 (e.g., 176-214 or 210-250) of any of SEQ ID NOS: 1-3 or 450, optionally, wherein the epitope further comprises four or more (e.g., 5, 6, 7, 8, 9, 10, 11, 12, 13, 14, 15, 20, 25, 30, 35, or more) consecutive amino acid residues in an extracellular region distant from the transmembrane domain, e.g., a region comprising amino acids 23-50, 51-95, 88-121, 88-102, or 111-150 of any of SEQ ID NOS: 1-3 or 450, i) Binds to two or more different regions in CD138, e.g., a multivalent (e.g., bivalent, trivalent, or tetravalent) antibody molecule comprising two sets of identical, or substantially identical, VH-VL pairs that each bind to the same two or more regions, or comprising different sets of VH-VL pairs that each independently bind to different regions, j) Does not bind to an epitope on CD138 comprising four or more (e.g., 5, 6, 7, 8, 9, 10, 11, 12, 13, 14, 15, 20, 25, 30, 35, or more) consecutive amino acid residues in an extracellular region distant from the transmembrane domain, e.g., a region comprising amino acids 23-50, 51-95, 88-121, 88-101, or 111-150 of any of SEQ ID NOS: 1-3 or 450, k) Binds to a cancer or precancerous cell (e.g., a myeloma cell) expressing CD138 with high affinity, l) Binds to an Fc receptor (FcR) (e.g., one or more of FcγRI, FcγRIIa, FcγRIIb, FcγRIIe, FcγRIIIa, or FcγRIIIb) on the surface of an immune cell (e.g., a natural killer (NK) cell, a macrophage, a monocyte, or an eosinophil), m) Causes an effector function (e.g., an ADCC activity) on a target cell expressing CD138, n) Binds to C1q and causes complement-dependent cytotoxicity (CDC) on a target cell expressing CD138, o) Mediates homotypic adhesion of one or more CD138-expressing cells, p) Inhibits the action of a protease on a membrane-bound CD138, e.g., to reduce shedding of CD138;

q) Reduces (e.g., inhibits) one or more biological activities of a cell expressing CD138, in vitro, ex vivo, or in vivo, r) Reduces (e.g., inhibits) one or more functions of CD138 (e.g., binding of CD138 to a ligand), in vitro, ex vivo, or in vivo, s) Reduces (e.g., inhibits) proliferation of a cancer or precancerous cell expressing CD138, t) Binds to the same, similar, or overlapping epitope on CD138 as the epitope recognized by an anti-CD138 monoclonal antibody described herein, u) Shows the same or similar binding affinity or specificity, or both, as an anti-CD138 monoclonal antibody described herein, v) Shows the same or similar binding affinity or specificity, or both, as an antibody molecule comprising a heavy chain variable region and/or light chain variable region described herein, e.g., a heavy chain variable region and/or light chain variable region of any of the anti-CD138 monoclonal antibodies described herein, w) Shows the same or similar binding affinity or specificity, or both, as an antibody molecule comprising one or more (e.g., two or three) heavy chain CDRs and/or one or more (e.g., two or three) light chain CDRs described herein, e.g., one or more (e.g., two or three) heavy chain CDRs and/or one or more (two or three) light chain CDRs of any of the anti-CD138 monoclonal antibodies described herein, x) Shows the same or similar binding affinity or specificity, or both, as an antibody molecule comprising an amino acid sequence described herein, y) Shows the same or similar binding affinity or specificity, or both, as an antibody molecule comprising an amino acid sequence encoded by a nucleotide sequence described herein, z) Inhibits, e.g., competitively inhibits, the binding of a second antibody molecule to CD138, wherein the second antibody molecule is an antibody molecule described herein, e.g., any of the anti-CD138 monoclonal antibodies described herein, aa) Competes for binding with a second antibody molecule to CD138, wherein the second antibody molecule is an anti-CD138 monoclonal antibody described herein, bb) Has one or more biological properties of an anti-CD138 monoclonal antibody described herein, cc) Has one or more structural properties of an anti-CD138 monoclonal antibody described herein, or dd) Has one or more pharmacokinetic properties of an anti-CD138 monoclonal antibody described herein.

In an aspect, this disclosure features an anti-CD138 antibody molecule, which: (i) binds, or substantially binds, to CD138 in an extracellular region proximal to the transmembrane domain of CD138; and (ii) causes an antibody-dependent cellular cytotoxicity (ADCC) activity on a cell expressing CD138.

In an embodiment, the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain. In an embodiment, the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain.

In an embodiment, the antibody molecule binds to an epitope on CD138 comprising five or more (e.g., 6, 7, 8, 9, 10, 11, 12, 13, 14, 15, 20, 25, 30, 35, 40, 45, 50, 55, 60, 65, 70, 75, or more) consecutive amino acid residues in the extracellular region.

In an embodiment, the extracellular region proximal to the transmembrane domain comprises, or consists of, amino acids 210-250 or 220-245 of any of SEQ ID NOS: 1-3 or 450.

In an embodiment, the antibody molecule binds to an Fc receptor (FcR) (e.g., one or more of FcγRI, FcγRIIa, FcγRIIb, FcγRIIc, FcγRIIIa, or FcγRIIIb) on the surface of an immune cell (e.g., a natural killer (NK) cell, a macrophage, a monocyte, or an eosinophil).

In an embodiment, the cell expressing CD138 is a cancer cell or precancerous cell. In an embodiment, the cancer or precancerous cell is a myeloma cell.

In an embodiment, the antibody molecule further binds, or binds with higher affinity, to an extracellular region of CD138 distant from the transmembrane domain. In an embodiment, the antibody molecule binds to an epitope on CD138 comprising five or more (e.g., 6, 7, 8, 9, 10, 11, 12, 13, 14, 15, 20, 25, 30, 35, or more) consecutive amino acid residues in an extracellular region distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain. In an embodiment, the extracellular region distant from the transmembrane domain comprises amino acids 23-50, 51-95, 88-121, or 111-150 of any of SEQ ID NOS: 1-3 or 450. In some embodiments, the extracellular region distant from the transmembrane domain comprises amino acids 88-121 or 101-121 of any of SEQ ID NOS: 1-3 or 450.

In an embodiment, the antibody molecule further binds, or binds with higher affinity, to the integrin binding domain (IBD) of CD138. In an embodiment, the antibody molecule further binds, or binds with high affinity, to a region N-terminal to the IBD of CD138.

In an embodiment, the antibody molecule does not bind, or binds with low affinity, to an extracellular region of CD138 distant from the transmembrane domain. In an embodiment, the antibody molecule does not bind to an epitope on CD138 comprising five or more (e.g., 6, 7, 8, 9, 10, 11, 12, 13, 14, 15, 20, 25, 30, 35, or more) consecutive amino acid residues in an extracellular region distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain. In an embodiment, the extracellular region distant from the transmembrane domain comprises amino acids 23-50, 51-95, 88-121, or 111-150 of any of SEQ ID NOS: 1-3 or 450.

In an embodiment, the antibody molecule does not bind, or binds with low affinity, to the integrin binding domain (IBD) of CD138. In an embodiment, the antibody molecule does not bind, or binds with low affinity, to a region N-terminal to the IBD of CD138.

In an embodiment, the antibody molecule binds to CD138 with a disassociation constant ($K_D$) of less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.

In an embodiment, the binding affinity of the antibody molecule to a membrane-bound CD138 is at least 2, 3, 4, 5, 6, 7, 8, 9, 10, 20, 50, 100, 200, or 500-fold higher than the binding affinity to a soluble CD138. In an embodiment, the antibody molecule binds to a membrane-bound CD138 with a $K_D$ less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.

In an embodiment, the binding affinity of the antibody molecule to a membrane-bound CD138 is similar its binding affinity to a soluble CD138, e.g., the binding affinity to a membrane-bound CD138 is within about ±10%, ±20%, ±30%, ±40%, ±50%, ±60%, ±70%, ±80%, ±90%, ±100% of, e.g., less than about 10%, 20%, 30%, 40%, 50%, 60%, 70%, 80%, 90%, or 100% higher than, the binding affinity to a soluble CD138. In an embodiment, the antibody molecule binds to a soluble CD138 with a $K_D$ of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM. In an embodiment, the antibody molecule binds to a soluble CD138 with a $K_D$ of greater than about 100, 200, 300, 400, or 500 nM.

In an embodiment, the antibody molecule binds to a membrane-bound CD138 preferably over a soluble CD138, e.g., the binding affinity to a membrane-bound CD138 is at least 2, 3, 4, 5, 6, 7, 8, 9, or 10-fold higher than the binding affinity to a soluble CD138. In an embodiment, the antibody molecule binds to a soluble CD138 preferably over a membrane-bound CD138, e.g., the binding affinity to a soluble CD138 is at least 2, 3, 4, 5, 6, 7, 8, 9, or 10-fold higher than the binding affinity to a membrane-bound CD138. In an embodiment, the antibody molecule binds to both soluble CD138 and to membrane-bound CD138.

In an embodiment, the antibody molecule binds to C1q and causes a complement-dependent cytotoxicity (CDC) activity on a cell expressing CD138. In an embodiment, the antibody molecule reduces (e.g., inhibits, blocks, or neutralizes) one or more biological activities of a cell expressing CD138 in vitro, ex vivo, or in vivo. In an embodiment, the antibody molecule mediates homotypic adhesion of one or more CD138-expressing cells. In an embodiment, the antibody molecule inhibits the action of a protease on a membrane-bound CD138, e.g., to reduce shedding of CD138. In an embodiment, the antibody molecule reduces (e.g., inhibits) proliferation of a cancer or precancerous cell expressing CD138.

In an embodiment, the antibody molecule comprises one or more (e.g., two or three) heavy chain CDRs and/or one or more (e.g., two or three) light chain CDRs of an anti-CD138 monoclonal antibody described herein. In an embodiment, the antibody molecule comprises a heavy chain variable region (VH) and/or light chain variable region (VL) of an anti-CD138 monoclonal antibody described herein. In an embodiment, the antibody molecule comprises an Fc region.

In an aspect, the disclosure features an anti-CD138 antibody molecule, which binds, or substantially binds, to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region proximal to the transmembrane domain of CD138.

In an embodiment, the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain. In an embodiment, the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain. In an embodiment, the extracellular region proximal to the transmembrane domain comprises, or consists of, amino acids 176-250 of any of SEQ ID NOS: 1-3 or 450.

In an embodiment, the antibody molecule binds to an Fc receptor (FcR) (e.g., one or more of FcγRI, FcγRIIa, FcγRIIb, FcγRIIc, FcγRIIIa, or FcγRIIIb) on the surface of an immune cell (e.g., a natural killer (NK) cell, a macrophage, a monocyte, or an eosinophil). In an embodiment, the antibody molecule is capable of causing (e.g., promoting or inducing) an ADCC activity on a cell expressing CD138. In an embodiment, the antibody molecule is capable of causing (e.g., promoting or inducing) antibody dependent cellular phagocytosis (ADCP) activity on a cell expressing CD138. In an embodiment, the cell expressing CD138 is a cancer cell or precancerous cell. In an embodiment, the cancer or precancerous cell is a myeloma cell.

In an embodiment, the antibody molecule further binds, or binds with higher affinity, to an extracellular region of CD138 distant from the transmembrane domain. In an embodiment, the antibody molecule binds to an epitope on CD138 comprising five or more (e.g., 6, 7, 8, 9, 10, 11, 12, 13, 14, 15, 20, 25, 30, 35, or more) consecutive amino acid residues in an extracellular region distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain. In an embodiment, the extracellular region distant from the transmembrane domain comprises amino acids 23-50, 51-95, 88-121, or 111-150 of any of SEQ ID NOS: 1-3 or 450.

In an embodiment, the antibody molecule further binds, or binds with higher affinity, to the integrin binding domain (IBD) of CD138. In an embodiment, the antibody molecule further binds, or binds with high affinity, to a region N-terminal to the IBD of CD138.

In an embodiment, the antibody molecule does not bind, or binds with low affinity, to an extracellular region of CD138 distant from the transmembrane domain.

In an embodiment, the epitope does not comprise five or more (e.g., 6, 7, 8, 9, 10, 11, 12, 13, 14, 15, 20, 25, 30, 35, or more) consecutive amino acid residues in an extracellular region distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain. In an embodiment, the extracellular region distant from the transmembrane domain comprises amino acids 23-50, 51-95, 88-121, or 111-150 of any of SEQ ID NOS: 1-3 or 450.

In an embodiment, the antibody molecule does not bind, or binds with low affinity, to the integrin binding domain (IBD) of CD138. In an embodiment, the antibody molecule does not bind, or binds with low affinity, to a region N-terminal to the IBD of CD138.

In an embodiment, the antibody molecule binds to CD138 with a disassociation constant ($K_D$) of less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.

In an embodiment, the binding affinity of the antibody molecule to a membrane-bound CD138 is at least 2, 3, 4, 5, 6, 7, 8, 9, 10, 20, 50, 100, 200, or 500-fold higher than the binding affinity to a soluble CD138. In an embodiment, the antibody molecule binds to a membrane-bound CD138 with a $K_D$ less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM. In an embodiment, the antibody molecule binds to a soluble CD138 with a $K_D$ of greater than about 100, 200, 300, 400, or 500 nM.

In an embodiment, the binding affinity of the antibody molecule to a membrane-bound CD138 is similar its binding affinity to a soluble CD138, e.g., the binding affinity to a membrane-bound CD138 is within about ±10%, ±20%, ±30%, ±40%, ±50%, ±60%, ±70%, ±80%, ±90%, ±100% of, e.g., less than about 10%, 20%, 30%, 40%, 50%, 60%, 70%, 80%, 90%, or 100% higher than, the binding affinity to a soluble CD138. In an embodiment, the antibody molecule binds to a soluble CD138 with a $K_D$ of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM. In an embodiment, the antibody molecule binds to a soluble CD138 with a $K_D$ of greater than about 100, 200, 300, 400, or 500 nM.

In an embodiment, the antibody molecule binds to a membrane-bound CD138 preferably over a soluble CD138, e.g., the binding affinity to a membrane-bound CD138 is at least 2, 3, 4, 5, 6, 7, 8, 9, or 10-fold higher than the binding affinity to a soluble CD138. In an embodiment, the antibody molecule binds to a soluble CD138 preferably over a membrane-bound CD138, e.g., the binding affinity to a soluble CD138 is at least 2, 3, 4, 5, 6, 7, 8, 9, or 10-fold higher than the binding affinity to a membrane-bound CD138. In an embodiment, the antibody molecule binds to both soluble CD138 and to membrane-bound CD138.

In an embodiment, the antibody molecule binds to C1q and causes a complement-dependent cytotoxicity (CDC) activity on a cell expressing CD138. In an embodiment, the antibody molecule reduces (e.g., inhibits, blocks, or neutralizes) one or more biological activities of a cell expressing CD138 in vitro, ex vivo, or in vivo. In an embodiment, the antibody molecule mediates homotypic adhesion of one or more CD138-expressing cells. In an embodiment, the antibody molecule inhibits the action of a protease on a membrane-bound CD138, e.g., to reduce shedding of CD138. In an embodiment, the antibody molecule reduces (e.g., inhibits) proliferation of a cancer or precancerous cell expressing CD138.

In an embodiment, the antibody molecule comprises one or more (e.g., two or three) heavy chain CDRs and/or one or more (e.g., two or three) light chain CDRs of an anti-CD138 monoclonal antibody described herein. In an embodiment, the antibody molecule comprises a heavy chain variable region (VH) and/or light chain variable region (VL) of an anti-CD138 monoclonal antibody described herein. In an embodiment, the antibody molecule comprises an Fc region.

In an aspect, the disclosure features an anti-CD138 antibody molecule comprising one or both of:

(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of an anti-CD138 monoclonal antibody described herein (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody; or (b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; or (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody.

In an embodiment, the VH comprises: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

In an embodiment, the VL comprises: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

In an embodiment, the antibody molecule comprises: (a) a VH comprising: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody. In an embodiment, the antibody molecule the VH comprises the amino acid sequence of the VH of the anti-CD138 antibody.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL of the anti-CD138 antibody. In an embodiment, the VL comprises the amino acid sequence of the VL of the anti-CD138 antibody.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody.

In an embodiment, the VH comprises the amino acid sequence of the VH of the anti-CD138 antibody and the VL comprises the amino acid sequence of the VL of the anti-CD138 antibody.

In an embodiment, the antibody molecule comprises an Fc region.

In an aspect, the disclosure features an antibody molecule, which competes for binding to CD138 with an anti-CD138 monoclonal antibody described herein (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409).

In an aspect, the disclosure features an antibody molecule, which binds, or substantially binds, to an epitope that completely or partially overlaps with the epitope of an anti-CD138 monoclonal antibody described herein (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409).

In an aspect, the disclosure features an antibody-molecule drug conjugate (ADC) comprising an antibody molecule described herein, optionally comprising a cytotoxic agent, further optionally comprising a linker.

In an aspect, the disclosure features a composition comprising an antibody molecule described herein, or an ADC described herein, optionally, wherein the composition is a pharmaceutical composition.

In an embodiment, the composition further comprises a pharmaceutically acceptable carrier.

In an aspect, the disclosure features a nucleic acid molecule encoding a heavy chain variable region (VH), a light chain variable region (VL), or both, of an antibody molecule described herein.

In an aspect, the disclosure features a vector comprising a nucleic acid molecule described herein.

In an aspect, the disclosure features a cell comprising a nucleic acid molecule described herein or a vector described herein, optionally, wherein the cell is an isolated cell.

In an aspect, the disclosure features a kit comprising an antibody molecule described herein, an ADC described herein, or a composition described herein, and instructions to use of the antibody molecule or composition.

In an aspect, the disclosure features a container comprising an antibody molecule described herein, an ADC described herein, or a composition described herein.

In an aspect, the disclosure features a method of producing an anti-CD138 antibody molecule, the method comprising culturing a cell described herein under conditions that allow production of an antibody molecule, thereby producing the antibody molecule.

In an embodiment, the method further comprises isolating or purifying the antibody molecule.

In an aspect, the disclosure features an antibody molecule of described herein, an ADC described herein, or a composition described herein, for use in a method of treating a cancer in a subject.

In an embodiment, the cancer is a hematological cancer. In an embodiment, the cancer is a multiple myeloma. In an embodiment, the cancer is a solid tumor, e.g., a solid tumor described herein.

In an embodiment, the antibody molecule, ADC, or composition is administered to the subject intravenously.

In an embodiment, the antibody molecule, ADC, or composition is administered to the subject at a dose between 0.1 mg/kg and 50 mg/kg, between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg.

In an embodiment, the antibody molecule, ADC, or composition is administered to the subject at a fixed dose between 10 mg and 1000 mg, between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg, between 100 mg and 200 mg, or between 150 mg and 250 mg.

In an embodiment, the antibody molecule, ADC, or composition is administered once a week, twice a week, once every two weeks, once every three weeks, or once every four weeks.

In an embodiment, the use further comprises determining the level of CD138 in a sample from the subject. In an embodiment, the use further comprises administering to the subject a second therapy for cancer.

In an aspect, the disclosure features an antibody molecule described herein, an ADC described herein, or a composition described herein, for use in a method of treating a precancerous condition or preventing a cancer.

In an embodiment, the precancerous condition is smoldering myeloma or monoclonal gammopathy of undetermined significance (MGUS). In an embodiment, the cancer is multiple myeloma.

In an aspect, the disclosure features a method of causing an ADCC activity, the method comprising contacting a cell or subject an antibody molecule described herein, an ADC described herein, or a composition described herein, thereby causing the ADCC activity.

In an aspect, the disclosure features a method of treating a cancer, the method comprising administering to a subject in need thereof an effective amount of an antibody molecule described herein, an ADC described herein, or a composition described herein, thereby treating the cancer.

In an aspect, the disclosure features a method of treating a precancerous condition or preventing a cancer, the method comprising administering to a subject in need thereof an effective amount of an antibody molecule described herein, an ADC described herein, or a composition described herein, thereby treating the precancerous condition or preventing the cancer.

In an aspect, the disclosure features, a method of detecting an anti-CD138 molecule, the method comprising contacting a cell or a subject with an antibody molecule described herein, thereby detecting the CD138 molecule.

In an embodiment, the antibody molecule is coupled with a detectable label. In an embodiment, the CD138 molecule is detected in vitro, ex vivo, or in vivo.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depict an exemplary amino acid sequence of human CD138 (UniProt ID: P18827). The signal peptide includes residues 1-22 (shown in italics); the extracellular domain includes residues 23-254; the transmembrane domain includes residues 255-275; and the cytoplasmic domain includes residues 276-310. The integrin binding domain (IBD) includes residues 88-122. Known O-linked heparin sulfate chains are located at residues 37, 45 and 47 (underlined); and known O-linked chondroitin sulfate chains are located at residues 206 and 216 (underlined). A possible N-linked glycan is located at residue 43. The inferred B-B4 antibody hot spot epitope residues are Leu107, Pro108, Glu109 and Val110 (shown in bold). Exemplary peptide region that can be targeted by an anti-CD138 antibody molecules described herein includes residues Gly217 to Glu251 (shown in bold and italics). FIG. 1 discloses SEQ ID NO: 450.

FIG. 5 depicts the ability of rabbit polyclonal anti-CD138 antibody to induce ADCC in human multiple myeloma U266 cells.

FIG. 6A depicts the constructs which include the transposition of B-B4 epitope at different positions.

FIG. 6B depicts the amino acid sequences of mutated CD138 in Clones 1-3. FIG. 6B discloses SEQ ID NOS 451-453, respectively, in order of appearance.

FIG. 6C depicts the amino acid sequences of mutated CD138 in Clones 4 and 5. FIG. 6C discloses SEQ ID NOS 454-455, respectively, in order of appearance.

FIG. 7C depicts the further enhancement of ADCC potential by Fc engineering.

FIGS. 9A-9C are a series of graphs showing binding of various anti-CD138 antibodies to peptide fragments of CD138 as measured by ELISA: (A) Peptide 2a, (B) Peptide 5, (C) Peptide 6.

FIG. 9D shows the structure of the CD138 polypeptide. The locations of Peptides 2a, 5, and 6 are indicated.

FIGS. 14A-14B are a series of diagrams showing comparative binding kinetics for anti-CD138 antibody 1610 (A) and B-B4 (B) to CD138 peptide fragments (Peptides 2A and 6B) as measured by bio-layer interferometry. The ability of mAb 1610 (but not B-B4) to bind to both peptides 2A and 6B with differential kinetics is noted.

FIGS. 15A-15C are a series of graphs showing competition for binding to cell surface CD138 between biotinylated test antibodies (anti-CD138 antibodies 1610, 624, and B-B4) and varying concentrations of corresponding, unlabeled antibodies. Differentiated profiles by epitope binning are indicated.

FIG. 16 is a graph showing induction of ADCC activity by afucosylated anti-CD138 antibodies 1610, 624, and B-B4 in U266 cells.

FIG. 17 is a table showing the mutations made in anti-CD138 antibody variants 2510, 2610, 2710, 2810, and 2910 relative to the parental antibody 1610. The protein titers produced for each of these antibodies from transiently-transfected HEK293 cells are also shown.

FIGS. 18A-18D are a series of diagrams showing binding of antibody 1610 and its variants, 2510, 2610, and 2810 to each of recombinant CD138 extracellular domain (A), Peptide 2a (B), and Peptide 6 (C) as measured by ELISA. EC50 values for each antibody variant are shown in FIG. 17D. Improvement of binding of mAb 1610 variants (relative to parental antibody 1610) to membrane proximal region (as represented by peptide 6) are noted.

FIGS. 22A-22C are a series of diagrams showing that the antibody variant 2810 (A) binds to different portions of CD138 compared to antibody B-B4 (B). Peptide sequences are described in C. FIG. 22C discloses SEQ ID NOS 456, 10, 449, 445, 457, 440, 444, 443, 443 and 449, respectively, in order of appearance.

DETAILED DESCRIPTION

Figure 2:
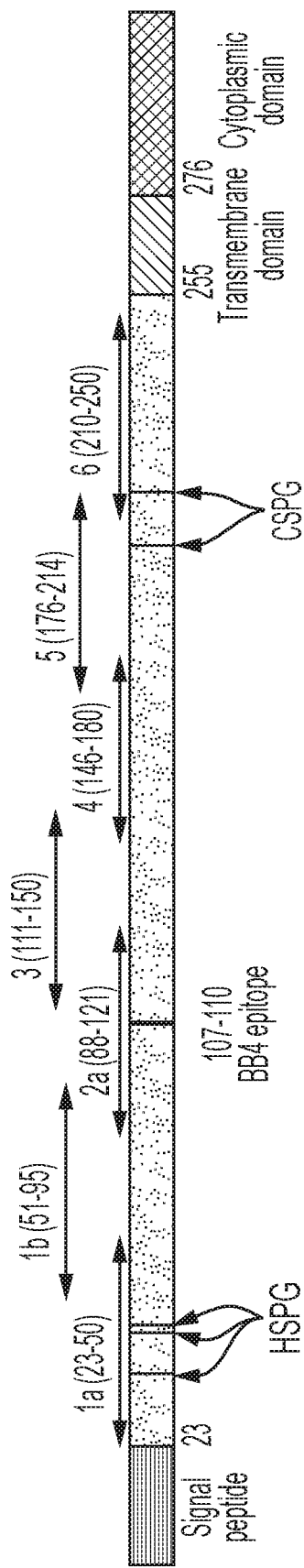
FIG. 2 depicts the peptides used to identify anti-CD138 antibodies that bind to a desired epitope.

Disclosed herein are antibody molecules that bind to CD138, e.g., human CD138. Advantageously, at least several of the antibody molecules describe herein have improved ability to inhibit cells expressing CD138, e.g., by eliciting an effector function. Without wishing to be bound by theory, it is believed that in an embodiment, anti-CD138 antibodies that bind to a desired epitope described herein have increased effector functions and preferential binding to the membrane-associated form of CD138. Targeting CD138 effectively can result in broad activity and favorable therapeutic index across myelomas and other cancers. Antibody-drug conjugates (ADCs), nucleic acid molecules encoding the antibody molecules, expression vectors, host cells, compositions (e.g., pharmaceutical compositions), kits, and methods for making the antibody molecules, are also provided. The antibody molecules and pharmaceutical compositions disclosed herein can be used (alone or in combination with other agents or therapeutic modalities) to treat, prevent and/or diagnose disorders and conditions, e.g., disorders and conditions associated with CD138, e.g., cancer or precancerous conditions.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values. When "about" or "approximately" is present before a series of numbers or a range, it is understood that "about" or "approximately" can modify each of the numbers in the series or range. Similarly, when "at least," "more than," "no more than," "less than," "no less than," or "within" is present before a series of numbers or a range, it is understood that "at least," "more than," "no more than," "less than," "no less than," or "within" can modify each of the numbers in the series or range. As used herein, ranges include both the upper and lower limit.

The compositions and methods disclosed herein encompass polypeptides and nucleic acids having the sequences specified, or sequences substantially identical or similar thereto, e.g., sequences at least 85%, 90%, 95% identical or higher to the sequence specified.

In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) *J. Mol. Biol.* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," a disorder, e.g., a myeloma, means that a subject (e.g., a human) who has a disorder, e.g., a myeloma, and/or experiences a symptom of a disorder, e.g., a myeloma, will, in an embodiment, suffer less a severe symptom and/or recover faster when an antibody molecule is administered than if the antibody molecule were never administered. In an embodiment, when a myeloma is treated, a bone marrow biopsy will show fewer clonal plasma cells, after effective treatment for myeloma. For example, a diagnostic assay will detect fewer clonal plasma cells in a biological sample of a subject after administration of an antibody molecule described herein for the effective treatment of a myeloma. Other assays, urine tests, or blood tests, can also be used to monitor treatment in a patient, or to detect the presence, e.g., decreased presence (or absence), of a symptom of a myeloma, after treatment of a myeloma in the subject. In an embodiment, when a myeloma is treated, the level of β2 microglobulin (β2M) in serum or urine will be decreased, after effective treatment for myeloma. Treatment can, e.g., partially or completely, alleviate, ameliorate, relieve, inhibit, or reduce the severity of, and/or reduce incidence, and optionally, delay onset of, one or more manifestations of the effects or symptoms, features, and/or causes of a disorder, e.g., a myeloma. In an embodiment, treatment is of a subject who does not exhibit certain signs of a disorder, e.g., a myeloma, and/or of a subject who exhibits only early signs of a disorder, e.g., nephropathy. In an embodiment, treatment is of a subject who exhibits one or more established signs of a disorder, e.g., a myeloma. In an embodiment, treatment is of a subject diagnosed as suffering from a disorder, e.g., a myeloma.

As used herein, the term "prevent," a disorder, e.g., a myeloma, means that a subject (e.g., a human) is less likely to have the disorder, e.g., a myeloma, if the subject receives the antibody molecule.

Various aspects of the compositions and methods herein are described in further detail below. Additional definitions are set out throughout the specification.

CD138

CD138 is a protein which in human is encoded by the SDC1 gene. CD138 is also known as Syndecan 1, Syndecan Proteoglycan 1, CD138 Antigen, SYND1, SDC, Syndecan-1, or Syndecan.

CD138 is a transmembrane (type I) heparan sulfate proteoglycan and is a member of the syndecan proteoglycan family. The syndecans mediate cell binding, cell signaling, and cytoskeletal organization, and syndecan receptors are required for internalization of the HIV-1 tat protein. CD138 functions as an integral membrane protein and participates in cell proliferation, cell migration and cell-matrix interactions via its receptor for extracellular matrix proteins. Altered CD138 expression has been detected in several different tumor types.

The core of CD138 includes three major domains: 1) short cytoplasmic domain; 2) plasma membrane-spanning hydrophobic domain; and 3) long extracellular domain. The functions of CD138 domains are described, e.g., in Stepp et al. *Adv Wound Care (New Rochelle)*. 2015; 4(4):235-249).

The cytoplasmic domains can transmit signals and also bind to anchoring molecules including PDZ family members. The heparan sulfate chains of CD138 also serve important biological functions. In mammals, CD138 is a major heparan sulfate proteoglycan (HSPG) on epithelial cells with high levels of expression (Fuki et al. *J Clin Invest.* 1997; 100(6):1611-1622). Without wishing to be bound by theory, it is believed that the HSPGs of CD138 allow the proteoglycan to bind to the heparin-binding sites present on a number of ECM proteins, growth factors, cytokines, and other proteins (Stepp et al. *Adv Wound Care (New Rochelle)*. 2015; 4(4):235-249).

For example, the signal peptide comprises residues 1-22; the extracellular domain comprises residues 23-254; the transmembrane domain comprises residues 255-275; the cytoplasmic domain comprises residues 276-310; or the integrin binding domain (IBD) comprises residues 88-122, of a human CD138 protein, e.g., any of SEQ ID NOS: 1-3 or 450.

In an embodiment, an anti-CD138 antibody molecule described herein can modulate (e.g., inhibit) the binding of CD138 to one or more proteins that interact (e.g., bind directly or indirectly) with the extracellular domain of CD138. In an embodiment, an anti-CD138 antibody molecule described herein can modulate (e.g., inhibit) a function associated with a protein that interacts (e.g., bind directly or indirectly) with the extracellular domain of CD138. In an embodiment, a CD138-interacting protein binds to the extracellular domain of CD138 directly. In an embodiment, a CD138-interacting protein binds to the extracellular domain of CD138 through a glycosaminoglycan (GAG) chain.

Exemplary of CD138-interacting proteins and their functions are described, e.g., in Stepp et al. *Adv Wound Care (New Rochelle)*. 2015; 4(4):235-249, the content of which is incorporated by reference in its entirety.

For example, proteins that are capable of interacting with the extracellular domain of CD138 directly or indirectly include, but are not limited to, a matrix protein (e.g., a laminin, a fibronectin, thrombospondin, collagen, fibrin, HB-GAM, tenascin, vitronectin, fibrillin, or tropoelastin), a protease (e.g., MMP7, MMP9, ADAMTS4, MT1-PPT, neutrophil elastase, cathepsin G, or carboxypeptidase), a receptor (e.g., an integrin, $\alpha_v\beta_3$, $\alpha_v\beta_5$, $\alpha_6\beta_4$, $\alpha_2\beta_1$, $\alpha_3\beta_1$, or $a_M\beta_2$), a cytokine or growth factor (e.g., a morphogen (e.g., activin, BMP-2, BMP-4, chordin, Sonic Hedgehog, a Frizzled related protein, a Sprouty peptide, any of Wnt1 to Wnt13, an antiangiogenic factor (e.g., angistatin or endostatin), a growth factor (e.g., amphiregulin, batacellulin, HB-EGF, neuregulin, any of FGF1 to FGF23, PDGF, GDNF, an VEGF, HGF, TGFβ1, TGFβ2, TPA, or PAI-1), or a cytokine (e.g., GM-CSF, IL-2, IL-3, IL-4, IL-5, IL-7, IL-12, interferon, TNF-α, a CC chemokine, or a CXC chemokine), a protein associated with energy balance (e.g., ApoB, ApoE, or lipoprotein lipase), a complement or coagulation protein (e.g., antithrombin II, tissue factor (TF), pathway inhibitor, Factor IX, Factor X, Factor XI, or Factor XII), or a viral or parasite coat protein (e.g., HIV-1-tat, HIV-1 gp41, HIV-1 gp120, HSV gB, HSV gC, HSV gD, a coat protein of HHV-6 or HHV-8, or G-protein of RSV).

CD138 expressed on the cell surface can be cleaved by specific proteases and the shed CD138 is responsible for mediating paracrine and autocrine functions. Shed CD138 is soluble and secreted ectodomain (ECD) in blood and matrix. Shed CD138 is an indicator of poor prognosis in multiple myeloma patients and enhanced tumor progression in myeloma mouse models. Typically, shed CD138 is not considered to be primarily responsible for the disease manifestation. Translocation of CD138 to the cell nucleus can correlate to the differentiation and proliferation of certain tumor cells. In an embodiment, the anti-CD138 antibody molecules described herein preferentially target membrane-associated CD138 over soluble CD138.

CD138 is generally not present on B lymphocytes and it is expressed after the onset of plasma cell differentiation. CD138 is highly expressed on malignant plasma cells (myeloma) and has a causal role in disease progression. CD138 is implicated in various biological functions. For example, it can bind to extracellular proteins, growth factors, and chemokines; engage and activate the αVβ3 and αVβ5 integrin when clustered; regulate the biogenesis of exosomes; and regulate bone marrow microenvironment that supports myeloma growth and metastasis. Multiple signals can be attenuated by targeting CD138.

CD138 is upregulated in multiple myeloma (Tassone et al. *Blood.* 104(12): 3688-3696). It is overexpressed on malignant plasma cells. Multiple myeloma cells typically express between 50-200 fold higher levels of CD138. Soluble CD138 (sCD138) levels are generally from less than 60 ng/mL in normal serum to 200-1500 ng/mL in sera of multiple myeloma patients. CD138 is overexpressed in about 80% multiple myeloma patients.

CD138 can be used as a primary diagnostic marker for multiple myeloma. Increased levels of shed CD138 in serum correlated to increased tumor burden and poorer outcomes. CD138+ myeloma cells show higher proliferation and CD138+ myeloma patients have lower overall survival rates. CD138+ myeloma cells aberrantly express angiogenic factors, e.g., HGF, IL-15, ANG, APRIL, CTGF, or TGFA (Hose et al. *Blood.* 2009; 114(1): 128-143). Expression levels of CD138 and its released extracellular domain correlate with tumor malignancy, phenotype, and metastatic potential for both solid and hematological tumors. CD138 expression varies among cancer types, but the differential expression signatures between normal and cancer cells in epithelial and stromal compartments are directly associated with aggressiveness of tumors and patient's clinical outcome and survival.

Exemplary amino acid and nucleotide sequences of human CD138 are described, e.g., in Mali et al. *J Biol Chem.* 1990; 265(12): 6884-6889; Lories et al. *J Biol Chem.* 1992; 267(2): 1116-1122; and in FIG. 1.

The amino acid sequence of an exemplary human CD138 precursor (SEQ ID NO: 1) is provided as follows.

MRRAALWLWLCALALSLQPALPQIVATNLPPEDQDGSGDDSDNFSGSGAG

ALQDITLSQQTPSTWKDTQLLTAIPTSPEPTGLEATAASTSTLPAGEGPK

EGEAVVLPEVEPGLTAREQEATPRPRETTQLPTTHQASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA

The amino acid sequence of an exemplary human CD138 precursor variant (Q136L) (SEQ ID NO: 2) is provided as follows.

MRRAALWLWLCALALSLQPALPQIVATNLPPEDQDGSGDDSDNFSGSGAG

ALQDITLSQQTPSTWKDTQLLTAIPTSPEPTGLEATAASTSTLPAGEGPK

EGEAVVLPEVEPGLTAREQEATPRPRETTQLPTTHLASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA

The amino acid sequence of an exemplary human CD138 precursor variant (T76M) (SEQ ID NO: 3) is provided as follows.

MRRAALWLWLCALALSLQPALPQIVATNLPPEDQDGSGDDSDNFSGSGAG

ALQDITLSQQTPSTWKDTQLLTAIPMSPEPTGLEATAASTSTLPAGEGPK

EGEAVVLPEVEPGLTAREQEATPRPRETTQLPTTHQASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA

The signal peptide includes amino acids 1-22 of any of SEQ ID NOs: 1-3. The mature peptide includes amino acids 23-310 of any of SEQ ID NOs: 1-3. The extracellular domain includes amino acids 23-254 of any of SEQ ID NOs: 1-3. The transmembrane domain includes amino acids 255-275 of any of SEQ ID NOs: 1-3. The cytoplasmic domain includes amino acids 276-310 of any of SEQ ID NOs: 1-3.

An exemplary coding nucleotide sequence of human CD138 (SEQ ID NO: 4) is provided as follows. This nucleotide sequence encodes the amino acid sequence of SEQ ID NO: 1.

ATGAGGCGCGCGGCGCTCTGGCTCTGGCTGTGCGCGCTGGCGCTGAGCCT

GCAGCCGGCCCTGCCGCAAATTGTGGCTACTAATTTGCCCCCTGAAGATC

AAGATGGCTCTGGGGATGACTCTGACAACTTCTCCGGCTCAGGTGCAGGT

GCTTTGCAAGATATCACCTTGTCACAGCAGACCCCCTCCACTTGGAAGGA

CACGCAGCTCCTGACGGCTATTCCCACGTCTCCAGAACCCACCGGCCTGG

AGGCTACAGCTGCCTCCACCTCCACCCTGCCGGCTGGAGAGGGGCCCAAG

GAGGGAGAGGCTGTAGTCCTGCCAGAAGTGGAGCCTGGCCTCACCGCCCG

GGAGCAGGAGGCCACCCCCCGACCCAGGGAGACCACACAGCTCCCGACCA

CTCATCAGGCCTCAACGACCACAGCCACCACGGCCCAGGAGCCCGCCACC

TCCCACCCCCACAGGGACATGCAGCCTGGCCACCATGAGACCTCAACCCC

TGCAGGACCCAGCCAAGCTGACCTTCACACTCCCCACACAGAGGATGGAG

GTCCTTCTGCCACCGAGAGGGCTGCTGAGGATGGAGCCTCCAGTCAGCTC

CCAGCAGCAGAGGGCTCTGGGGAGCAGGACTTCACCTTTGAAACCTCGGG

GGAGAATACGGCTGTAGTGGCCGTGGAGCCTGACCGCCGGAACCAGTCCC

CAGTGGATCAGGGGGCCACGGGGGCCTCACAGGGCCTCCTGGACAGGAAA

GAGGTGCTGGGAGGGGTCATTGCCGGAGGCCTCGTGGGGCTCATCTTTGC

TGTGTGCCTGGTGGGTTTCATGCTGTACCGCATGAAGAAGAAGGACGAAG

GCAGCTACTCCTTGGAGGAGCCGAAACAAGCCAACGGCGGGGCCTACCAG

AAGCCCACCAAACAGGAGGAATTCTATGCCTGA

Another exemplary coding nucleotide sequence of human CD138 (SEQ ID NO: 5) is provided as follows. This nucleotide sequence also encodes the amino acid sequence of SEQ ID NO: 1.

ATGAGGCGCGCGGCGCTCTGGCTCTGGCTGTGCGCGCTGGCGCTGAGCCT

GCAGCCGGCCCTGCCGCAAATTGTGGCTACTAATTTGCCCCCTGAAGATC

AAGATGGCTCTGGGGATGACTCTGACAACTTCTCCGGCTCAGGTGCAGGT

GCTTTGCAAGATATCACCTTGTCACAGCAGACCCCCTCCACTTGGAAGGA

CACGCAGCTCCTGACGGCTATTCCCACGTCTCCAGAACCCACCGGCCTGG

AGGCTACAGCTGCCTCCACCTCCACCCTGCCGGCTGGAGAGGGGCCCAAG

GAGGGAGAGGCTGTAGTCCTGCCAGAAGTGGAGCCTGGCCTCACCGCCCG

GGAGCAGGAGGCCACCCCCCGACCCAGGGAGACCACACAGCTCCCGACCA

CTCATCAGGCCTCAACGACCACAGCCACCACGGCCCAGGAGCCCGCCACC

TCCCACCCCCACAGGGACATGCAGCCTGGCCACCATGAGACCTCAACCCC

TGCAGGACCCAGCCAAGCTGACCTTCACACTCCCCACACAGAGGATGGAG

GTCCTTCTGCCACCGAGAGGGCTGCTGAGGATGGAGCCTCCAGTCAGCTC

CCAGCAGCAGAGGGCTCTGGGGAGCAGGACTTCACCTTTGAAACCTCGGG

GGAGAATACGGCTGTAGTGGCCGTGGAGCCTGACCGCCGGAACCAGTCCC

CAGTGGATCAGGGGGCCACGGGGGCCTCACAGGGCCTCCTGGACAGGAAA

GAGGTGCTGGGAGGGGTCATTGCCGGAGGCCTCGTGGGGCTCATCTTTGC

TGTGTGCCTGGTGGGTTTCATGCTGTACCGCATGAAGAAGAAGGACGAAG

GCAGCTACTCCTTGGAGGAGCCGAAACAAGCCAACGGCGGGGCCTACCAG

AAGCCCACCAAACAGGAGGAATTCTATGCCTGA

As used herein, when an anti-CD138 antibody molecule binds, or substantially binds, to human CD138, it binds, or substantially binds, to one or more isoforms of human CD138. In an embodiment, the antibody molecule binds or substantially binds to human CD138 having an amino acid sequence described herein, or encoded by a nucleotide sequence described herein. In an embodiment, the antibody molecule binds or substantially binds to human CD138 comprising amino acids 23-254 of any of SEQ ID NOs: 1-3.

Exemplary amino acid and nucleotide sequences of mouse CD138 are described, e.g., in Saunders et al. *J Cell Biol.* 1989; 108(4): 1547-1556; and Vihinen et al. *J Biol Chem.* 1993; 268(23): 17261-17269.

The amino acid sequence of an exemplary mouse CD138 precursor (SEQ ID NO: 6) is provided as follows.

MRRAALWLWLCALALRLQPALPQIVAVNVPPEDQDGSGDDSDNFSGSGTG

ALPDTLSRQTPSTWKDVWLLTATPTAPEPTSSNTETAFTSVLPAGEKPEE

GEPVLHVEAEPGFTARDKEKEVTTRPRETVQLPITQRASTVRVTTAQAAV

TSHPHGGMQPGLHETSAPTAPGQPDHQPPRVEGGGTSVIKEVVEDGTANQ

LPAGEGSGEQDFTFETSGENTAVAAVEPGLRNQPPVDEGATGASQSLLDR

KEVLGGVIAGGLVGLIFAVCLVAFMLYRMKKKDEGSYSLEEPKQANGGAY

QKPTKQEEFYA

The signal peptide includes amino acids 1-22 of SEQ ID NO: 6. The mature peptide includes amino acids 23-311 of SEQ ID NO: 6. The extracellular domain includes amino acids 23-255 of SEQ ID NO: 6. The transmembrane domain includes amino acids 256-276 of SEQ ID NO: 4. The cytoplasmic domain includes amino acids 277-311 of SEQ ID NO: 6.

An exemplary coding nucleotide sequence of mouse CD138 (SEQ ID NO: 7) is provided as follows.

ATGAGACGCGGCGCTCTGGCTCTGGCTCTGCGCGCTGGCGCTGCGCCT

GCAGCCTGCCCTCCCGCAAATTGTGGCTGTAAATGTTCCTCCTGAAGATC

AGGATGGCTCTGGGGATGACTCTGACAACTTCTCTGGCTCTGGCACAGGT

GCTTTGCCAGATACTTTGTCACGGCAGACACCTTCCACTTGGAAGGACGT

GTGGCTGTTGACAGCCACGCCCACAGCTCCAGAGCCCACCAGCAGCAACA

CCGAGACTGCTTTTACCTCTGTCCTGCCAGCCGGAGAGAAGCCCGAGGAG

GGAGAGCCTGTGCTCCATGTAGAAGCAGAGCCTGGCTTCACTGCTCGGGA

CAAGGAAAAGGAGGTCACCACCAGGCCCAGGGAGACCGTGCAGCTCCCCA

TCACCCAACGGGCCTCAACAGTCAGAGTCACCACAGCCCAGGCAGCTGTC

ACATCTCATCCGCACGGGGCATGCAACCTGGCCTCCATGAGACCTCGGC

TCCCACAGCACCTGGTCAACCTGACCATCAGCCTCCACGTGTGGAGGGTG

GCGGCACTTCTGTCATCAAAGAGGTTGTCGAGGATGGAACTGCCAATCAG

CTTCCCGCAGGAGAGGGCTCTGGAGAACAAGACTTCACCTTTGAAACATC

TGGGGAGAACACAGCTGTGGCTGCCGTAGAGCCCGGCCTGCGGAATCAGC

CCCCGGTGGACGAAGGAGCCACAGGTGCTTCTCAGAGCCTTTTGGACAGG

AAGGAAGTGCTGGGAGGTGTCATTGCCGGAGGCCTAGTGGGCCTCATCTT

TGCTGTGTGCCTGGTGGCTTTCATGCTGTACCGGATGAAGAAGAAGGACG

AAGGCAGCTACTCCTTGGAGGAGCCCAAACAAGCCAATGGCGGTGCCTAC

CAGAAACCCACCAAGCAGGAGGAGTTCTACGCCTGA

As used herein, when an anti-CD138 antibody molecule binds, or substantially binds, to mouse CD138, it binds, or substantially binds, to one or more isoforms of mouse CD138. In an embodiment, the antibody molecule binds or substantially binds to human CD138 having an amino acid sequence described herein, or encoded by a nucleotide sequence described herein. In an embodiment, the antibody molecule binds or substantially binds to mouse CD138 comprising amino acids 23-255 of SEQ ID NO: 6.

Epitope

The antibody molecule described herein can bind to an epitope on CD138 (e.g., human CD138). For example, an epitope bound by an antibody molecule described herein can include one or more epitope contact points described herein.

Without wishing to be bound by theory, it is believed that in an embodiment, an antibody bound to the IBD (e.g., residues 88-122 of any of SEQ ID NOS: 1-3 or 450) or any region distant from the membrane of CD138 may not be effective in signaling transduction for NK cell activation and/or may not efficiently deliver molecules such as perforins and/or granzymes for cytotoxicity.

In some embodiments, the anti-CD138 antibody molecules described herein have one, two, or all of the following properties: optimal distance of epitope from the cell membrane (e.g., not on the N-terminal of IDB); appropriate orientation of the Fc region for CD16 engagement; or proper CD138 engagement that allows for CD16 clustering on NK cells (e.g., to overcome the effect of high amount of glycosylation on CD138 molecules that may restrict the access of NK cells).

Without wishing to be bound by theory, it is believed that in an embodiment altering the position of the antibody epitope can change certain effector mechanisms engaged. For example, antibody-dependent cellular cytotoxicity (ADCC) and complement-dependent cytotoxicity (CDC) may favor a membrane-proximal epitope versus a membrane-distal epitope (Cleary et al. *J Immunol.* 2017; 198(10): 3999-4011). In an embodiment, antibodies designed to delete target cells through specific effector mechanisms can be selected by altering the position of the antibody epitope (e.g., the distance of epitope from membrane).

In an embodiment, the mode of engagement can affect the ability of the antibody to mediate effector functions. For example, the angle of antibody binding to the extracellular loop with regard to the membrane surface may be different (e.g., parallel or perpendicular to the membrane surface) between antibodies that bind to the same peptide epitopes.

In an embodiment, the anti-CD138 antibody molecules described herein bind to an epitope that has one, two, or all of the following properties: proximal to the cell membrane; not restricted or occluded by the glycosaminoglycan (GAG) chains; or preferentially present on membrane-associated CD138. In an embodiment, the anti-CD138 antibody molecules described herein can bind to a desired epitope region and engage with the optimal pose relative to the membrane. In an embodiment, the epitope is a linear epitope. In an embodiment, the antibody molecule binds to an extracellular region of CD138 distant from the transmembrane region. In an embodiment, the epitope is a non-contiguous or conformational epitope.

FIG. 2 shows peptides for identification of desired epitopes for anti-CD138 antibodies. Without wishing to be bound by theory, it is believed that in an embodiment, the anti-CD138 antibody molecules described herein target a peptide region between residues Gly217 to Glu251 of human CD138, e.g., as shown in FIG. 1. This region is expected to have a linear random coil conformation. In an embodiment, the anti-CD138 antibody molecule binds to at least one linear tetrapeptide in the aforesaid region. In an embodiment, the anti-CD138 antibody molecule binds to a combination of linear tetrapeptides (e.g., two, three, four, or more adjacent tetrapeptides) in the aforesaid region.

The amino acid sequences of the aforesaid peptides are shown in Table 3.

TABLE 3

Peptides for Identification of CD138 Epitopes

| Peptide | Region | Amino Acid Sequence | SEQ ID NO | Length |
|---|---|---|---|---|
| Pep1a | 23-50 | QIVATNLPPEDQDGSGDDSDNFSGSGAGALQDTTLSQQT | 8 | 39 |
| Pep1b | 51-95 | ALQDTTLSQQTPSTWKDTQLLTAIPTSPEPTGLEATAASTSTLPA | 9 | 45 |
| Pep2a | 88-121 | ASTSTLPAGEGPKEGEAVV*LPEV*EPGLTAREQEA | 10 | 34 |
| Pep2b | 88-102 | ASTSTLPAGEGPKEG | 11 | 15 |
| Pep3 | 111-150 | EPGLTAREQEATPRPRETTQLPTTHQASTTTATTAQEPAT | 12 | 40 |
| Pep4 | 146-180 | QEPATSHPHRDMQPGHHETSTPAGPSQADLHTPHT | 13 | 35 |
| Pep5-6 | 176-250 | HTPHTEDG*GPSAT*ERAAE*DGASSQ*LPAAEGSGEQ*DFTFE*TSGENTAVVAVEPDRRNQSPVDQGATGASQGLLDRK | 14 | 75 |
| Pep5 | 176-214 | HTPHTEDG*GPSAT*ERAAE*DGASSQ*LPAAEGSGEQDFTFE | 15 | 39 |
| Pep6 | 210-250 | DFTFETSGENTAVVAVEPDRRNQSPVDQGATGASQGLLDRK | 16 | 41 |
| Pep6a | 220-245 | TAVVAVEPDRRNQSPVDQGATGASQG | 17 | 26 |

In Table 3, the overlapping amino acids among the peptides are shown in bold; the BB4 epitope residues are shown in italic; the glycosaminoglycan (heparan sulfate, chondroitin sulfate) chain carrying serine residues are underlined. The terms "Peptide" and "Pep" are used interchangeably herein. For peptide designations, the lower case and upper-case letters are intended to have the same meaning. For example, the terms "Peptide 1A," "Peptide 1a," "Pep1A," and "Pep1a" can be used to refer to the same peptide.

Figure 13:
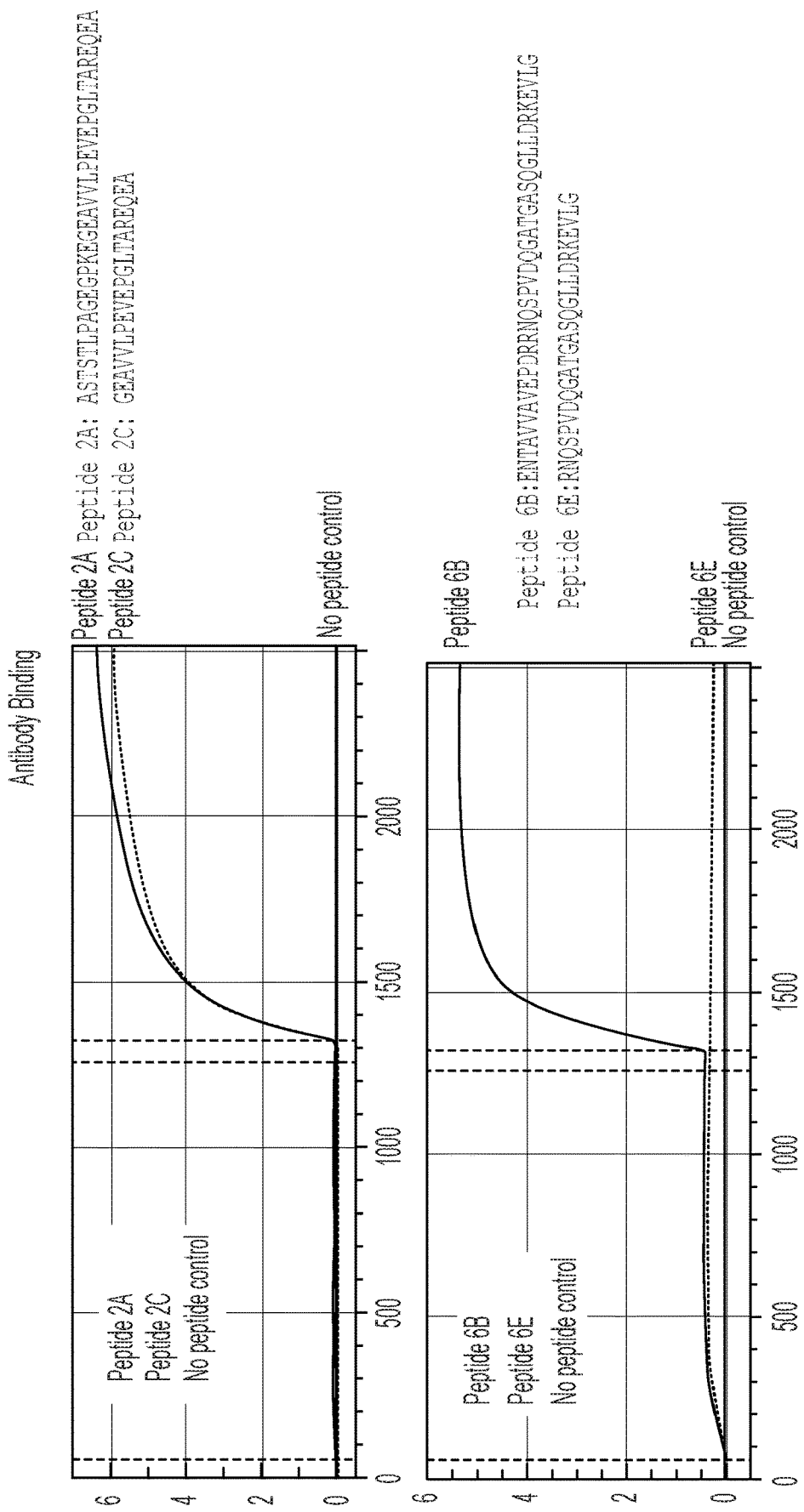
FIG. 13 is a series of graphs showing binding kinetics for anti-CD138 antibody 1610 to CD138 peptide fragments (top panel: Peptides 2A (SEQ ID NO: 10), 2C (SEQ ID NO: 449); bottom panel: Peptides 6B (SEQ ID NO: 440), 6E (SEQ ID NO: 444)) as measured by bio-layer interferometry using biotinylated peptides.

Other exemplary peptides used for identification of desired epitopes for anti-CD138 antibodies are described herein, e.g., in FIGS. 13 and 22C.

In an embodiment, the antibody molecule contacts (e.g., binds, or substantially binds, to) a region in CD138 corresponding to one or more peptides as described in Table 3, FIG. 13 or 22C. In an embodiment, the peptide is Pep6. In an embodiment, the peptide is Pep6a. In an embodiment, the peptide is Pep5. In an embodiment, the peptide is Pep4. In an embodiment, the antibody molecule contacts Pep6 or Pep6a and does not contact Pep4. In an embodiment, the antibody molecule does not contact any of Pep1a, Pep1b, Pep2a, Pep2b, Pep3, Pep4, or Pep5. In an embodiment, the antibody molecule does not contact Pep2a. In an embodiment, the antibody molecule contacts Pep2a but does not bind to the same epitope as BB4.

In an embodiment, the antibody molecule contacts Pep2a and Pep6. In an embodiment, the antibody molecule contacts Pep2a and Pep2c. In an embodiment, the antibody molecule contacts Pep6b. In an embodiment, the antibody molecule contacts Pep2a, Pep2c, and Pep6b. In an embodiment, the antibody molecule does not contact Pep6e. In an embodiment, the antibody molecule contacts Pep6b and does not contact Pep6e. In an embodiment, the antibody molecule contacts Pep2a and Pep2c and does not contact Pep6e. In an embodiment, the antibody molecule contacts Pep2a, Pep2c, and Pep6b and does not contact Pep6e.

In an embodiment, the antibody molecule contacts Pep2a and Pep2d. In an embodiment, the antibody molecule contacts Pep6b and Pep6f. In an embodiment, the antibody molecule contacts Pep2a, Pep2d, Pep6b, and Pep6f.

In an embodiment, the antibody molecule binds, or substantially binds, to CD138 in an extracellular region proximal to the transmembrane domain of CD138. In an embodiment, the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain. In an embodiment, the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain.

In an embodiment, the antibody molecule binds to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in the extracellular region proximal to the transmembrane domain.

In an embodiment, the antibody molecule binds to an epitope on CD138 comprising five or more consecutive amino acid residues in the extracellular region proximal to the transmembrane domain. In an embodiment, the antibody molecule binds to an epitope on CD138 comprising six or more consecutive amino acid residues in the extracellular region proximal to the transmembrane domain. In an embodiment, the antibody molecule binds to an epitope on CD138 comprising seven or more consecutive amino acid residues in the extracellular region proximal to the transmembrane domain. In an embodiment, the antibody molecule binds to an epitope on CD138 comprising eight or more consecutive amino acid residues in the extracellular region proximal to the transmembrane domain. In an embodiment, the antibody molecule binds to an epitope on CD138 comprising nine or more consecutive amino acid residues in the extracellular region proximal to the transmembrane domain. In an embodiment, the antibody molecule binds to an epitope on CD138 comprising ten or more consecutive amino acid residues in the extracellular region proximal to the transmembrane domain. In an embodiment, the antibody molecule binds to an epitope on CD138 comprising eleven or more consecutive amino acid residues in the extracellular region proximal to the transmembrane domain. In an embodiment, the antibody molecule binds to an epitope on CD138 comprising twelve or more consecutive amino acid residues in the extracellular region proximal to the transmembrane domain.

In an embodiment, the extracellular region proximal to the transmembrane domain corresponds to (e.g., comprises or consists of) Pep6. In an embodiment, the extracellular region proximal to the transmembrane domain corresponds to (e.g., comprises or consists of) Pep6a, 6b, 6e, and/or 6f. In an embodiment, the extracellular region proximal to the transmembrane domain corresponds to (e.g., comprises or consists of) Pep5.

In an embodiment, the antibody molecule contacts four or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) consecutive amino acid residues in Pep6. In an embodiment, the antibody molecule contacts four or more (e.g., 5, 6, 7, 8, 9, 10, 11, 12, 13, 14, 15, 16, 17, 18, 19, 20, 21, 22, 23, 24, 25, or 26) consecutive amino acid residues in Pep6a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38) of the following peptides (e.g., from Pep6a): DFTF (SEQ ID NO: 18); FTFE (SEQ ID NO: 19); TFET (SEQ ID NO: 20); FETS (SEQ ID NO: 21); ETSG (SEQ ID NO: 22); TSGE (SEQ ID NO: 23); SGEN (SEQ ID NO: 24); GENT (SEQ ID NO: 25); ENTA (SEQ ID NO: 26); NTAV (SEQ ID NO: 27); TAVV (SEQ ID NO: 28); AVVA (SEQ ID NO: 29); VVAV (SEQ ID NO: 30); VAVE (SEQ ID NO: 31); AVEP (SEQ ID NO: 32); VEPD (SEQ ID NO: 33); EPDR (SEQ ID NO: 34); PDRR (SEQ ID NO: 35); DRRN (SEQ ID NO: 36); RRNQ (SEQ ID NO: 37); RNQS (SEQ ID NO: 38); NQSP (SEQ ID NO: 39); QSPV (SEQ ID NO: 40); SPVD (SEQ ID NO: 41); PVDQ (SEQ ID NO: 42); VDQG (SEQ ID NO: 43); DQGA (SEQ ID NO: 44); QGAT (SEQ ID NO: 45); GATG (SEQ ID NO: 46); ATGA (SEQ ID NO: 47); TGAS (SEQ ID NO: 48); GASQ (SEQ ID NO: 49); ASQG (SEQ ID NO: 50); SQGL (SEQ ID NO: 51); QGLL (SEQ ID NO: 52); GLLD (SEQ ID NO: 53); LLDR (SEQ ID NO: 54); or LDRK (SEQ ID NO: 55).

In an embodiment, the antibody molecule contacts five or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) consecutive amino acid residues in Pep6a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following peptides (e.g., from Pep6a): DFTFE (SEQ ID NO: 56); FTFET (SEQ ID NO: 57); TFETS (SEQ ID NO: 58); FETSG (SEQ ID NO: 59); ETSGE (SEQ ID NO: 60); TSGEN (SEQ ID NO: 61); SGENT (SEQ ID NO: 62); GENTA (SEQ ID NO: 63); ENTAV (SEQ ID NO: 64); NTAVV (SEQ ID NO: 65); TAVVA (SEQ ID NO: 66); AVVAV (SEQ ID NO: 67); VVAVE (SEQ ID NO: 68); VAVEP (SEQ ID NO: 69); AVEPD (SEQ ID NO: 70); VEPDR (SEQ ID NO: 71); EPDRR (SEQ ID NO: 72); PDRRN (SEQ ID NO: 73); DRRNQ (SEQ ID NO: 74); RRNQS (SEQ ID NO: 75); RNQSP (SEQ ID NO: 76); NQSPV (SEQ ID NO: 77); QSPVD (SEQ ID NO: 78); SPVDQ (SEQ ID NO: 79); PVDQG (SEQ ID NO: 80); VDQGA (SEQ ID NO: 81); DQGAT (SEQ ID NO: 82); QGATG (SEQ ID NO: 83); GATGA (SEQ ID NO: 84); ATGAS (SEQ ID NO: 85); TGASQ (SEQ ID NO: 86); GASQG (SEQ ID NO: 87); ASQGL (SEQ ID NO: 88); SQGLL (SEQ ID NO: 89); QGLLD (SEQ ID NO: 90); GLLDR (SEQ ID NO: 91); or LLDRK (SEQ ID NO: 92).

In an embodiment, the antibody molecule contacts six or more (e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) consecutive amino acid residues in Pep6a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following peptides (e.g., from Pep6a): DFTFET (SEQ ID NO: 93); FTFETS (SEQ ID NO: 94); TFETSG (SEQ ID NO: 95); FETSGE (SEQ ID NO: 96); ETSGEN (SEQ ID NO: 97); TSGENT (SEQ ID NO: 98); SGENTA (SEQ ID NO: 99); GENTAV (SEQ ID NO: 100); ENTAVV (SEQ ID NO: 101); NTAVVA (SEQ ID NO: 102); TAVVAV (SEQ ID NO: 103); AVVAVE (SEQ ID NO: 104); VVAVEP (SEQ ID NO: 105); VAVEPD (SEQ ID NO: 106); AVEPDR (SEQ ID NO: 107); VEPDRR (SEQ ID NO: 108); EPDRRN (SEQ ID NO: 109); PDRRNQ (SEQ ID NO: 110); DRRNQS (SEQ ID NO: 111); RRNQSP (SEQ ID NO: 112); RNQSPV (SEQ ID NO: 113); NQSPVD (SEQ ID NO: 114); QSPVDQ (SEQ ID NO: 115); SPVDQG (SEQ ID NO: 116); PVDQGA (SEQ ID NO: 117); VDQGAT (SEQ ID NO: 118); DQGATG (SEQ ID NO: 119); QGATGA (SEQ ID NO: 120); GATGAS (SEQ ID NO: 121); ATGASQ (SEQ ID NO: 122); TGASQG (SEQ ID NO: 123); GASQGL (SEQ ID NO: 124); ASQGLL (SEQ ID NO: 125); SQGLLD (SEQ ID NO: 126); QGLLDR (SEQ ID NO: 127); or GLLDRK (SEQ ID NO: 128).

In an embodiment, the antibody molecule contacts four or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) consecutive amino acid residues in Pep5.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following peptides (e.g., from Pep5): HTPH (SEQ ID NO: 129), TPHT (SEQ ID NO: 130), PHTE (SEQ ID NO: 131), HTED (SEQ ID NO: 132), TEDG (SEQ ID NO: 133), EDGG (SEQ ID NO: 134), DGGP (SEQ ID NO: 135), GGPS (SEQ ID NO: 136), GPSA (SEQ ID NO: 137), PSAT (SEQ ID NO: 138), SATE (SEQ ID NO: 139), ATER (SEQ ID NO: 140), TERA (SEQ ID NO: 141), ERAA (SEQ ID NO: 142), RAAE (SEQ ID NO: 143), AAED (SEQ ID NO: 144), AEDG (SEQ ID NO: 145), EDGA (SEQ ID NO: 146), DGAS (SEQ ID NO: 147), GASS (SEQ ID NO: 148), ASSQ (SEQ ID NO: 149), SSQL (SEQ ID NO: 150), SQLP (SEQ ID NO: 151), QLPA (SEQ ID NO: 152), LPAA (SEQ ID NO: 153), PAAE (SEQ ID NO: 154), AAEG (SEQ ID NO: 155), AEGS (SEQ ID NO: 156), EGSG (SEQ ID NO: 157), GSGE (SEQ ID NO: 158), SGEQ (SEQ ID NO: 159), GEQD (SEQ ID NO: 160), EQDF (SEQ ID NO: 161), QDFT (SEQ ID NO: 162), DFTF (SEQ ID NO: 18), or FTFE (SEQ ID NO: 19).

In an embodiment, the antibody molecule contacts five or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) consecutive amino acid residues in Pep5.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) of the following peptides (e.g., from Pep5): HTPHT (SEQ ID NO: 163), TPHTE (SEQ ID NO: 164), PHTED (SEQ ID NO: 165), HTEDG (SEQ ID NO: 166), TEDGG (SEQ ID NO: 167), EDGGP (SEQ ID NO: 168), DGGPS (SEQ ID NO: 169), GGPSA (SEQ ID NO: 170), GPSAT (SEQ ID NO: 171), PSATE (SEQ ID NO: 172), SATER (SEQ ID NO: 173), ATERA (SEQ ID NO: 174), TERAA (SEQ ID NO: 175), ERAAE (SEQ ID NO: 176), RAAED (SEQ ID NO: 177), AAEDG (SEQ ID NO: 178), AEDGA (SEQ ID NO: 179), EDGAS (SEQ ID NO: 180), DGASS (SEQ ID NO: 181), GASSQ (SEQ ID NO: 182), ASSQL (SEQ ID NO: 183), SSQLP (SEQ ID NO: 184), SQLPA (SEQ ID NO: 185), QLPAA (SEQ ID NO: 186), LPAAE (SEQ ID NO: 187), PAAEG (SEQ ID NO: 188), AAEGS (SEQ ID NO: 189), AEGSG (SEQ ID NO: 190), EGSGE (SEQ ID NO: 191), GSGEQ (SEQ ID NO: 192), SGEQD (SEQ ID NO: 193), GEQDF (SEQ ID NO: 194), EQDFT (SEQ ID NO: 195), QDFTF (SEQ ID NO: 196), or DFTFE (SEQ ID NO: 56).

In an embodiment, the antibody molecule contacts six or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) consecutive amino acid residues in Pep5.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) of the following peptides (e.g., from Pep5): HTPHTE (SEQ ID NO: 197), TPHTED (SEQ ID NO: 198), PHTEDG (SEQ ID NO: 199), HTEDGG (SEQ ID NO: 200), TEDGGP (SEQ ID NO: 201), EDGGPS (SEQ ID NO: 202), DGGPSA (SEQ ID NO: 203), GGPSAT (SEQ ID NO: 204), GPSATE (SEQ ID NO: 205), PSATER (SEQ ID NO: 206), SATERA (SEQ ID NO: 207), ATERAA (SEQ ID NO: 208), TERAAE (SEQ ID NO: 209), ERAAED (SEQ ID NO: 210), RAAEDG (SEQ ID NO: 211), AAEDGA (SEQ ID NO: 212), AEDGAS (SEQ ID NO: 213), EDGASS (SEQ ID NO: 214), DGASSQ (SEQ ID NO: 215), GASSQL (SEQ ID NO: 216), ASSQLP (SEQ ID NO: 217), SSQLPA (SEQ ID NO: 218), SQLPAA (SEQ ID NO: 219), QLPAAE (SEQ ID NO: 220), LPAAEG (SEQ ID NO: 221), PAAEGS (SEQ ID NO: 222), AAEGSG (SEQ ID NO: 223), AEGSGE (SEQ ID NO: 224), EGSGEQ (SEQ ID NO: 225), GSGEQD (SEQ ID NO: 226), SGEQDF (SEQ ID NO: 227), GEQDFT (SEQ ID NO: 228), EQDFTF (SEQ ID NO: 229), or QDFTFE (SEQ ID NO: 230).

In an embodiment, the antibody molecule does not bind, or binds with low affinity, to an extracellular region of CD138 distant from the transmembrane domain. In an embodiment, the antibody molecule does not bind to an epitope on CD138 comprising four or more (e.g., 5, 6, 7, 8, 9, 10, 11, 12, 13, 14, 15, 20, 25, 30, 35, or more) consecutive amino acid residues in an extracellular region distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain. In an embodiment, the extracellular region distant from the transmembrane domain corresponds to Pep1a, Pep1b, Pep2a, Pep2b, Pep2c, Pep2d, Pep3, Pep4, or a combination thereof. In an embodiment, the antibody molecule does not bind, or binds with low affinity, to the integrin binding domain (IBD) of CD138. In an embodiment, the antibody molecule does not bind, or binds with low affinity, to a region N-terminal to the IBD of CD138.

In an embodiment, the antibody molecule binds, or substantially binds, to an extracellular region of CD138 distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain. In an embodiment, the extracellular region distant from the transmembrane domain corresponds to Pep1a, Pep1b, Pep2a, Pep2b, Pep2c, Pep2d, Pep3, Pep4, or a combination thereof. In an embodiment, the antibody molecule binds, or substantially binds, to the integrin binding domain (IBD) of CD138. In an embodiment, the antibody molecule binds, or substantially binds, to a region N-terminal to the IBD of CD138. In an embodiment, the antibody molecule does not bind, or binds with low affinity, to the epitope of BB4.

In an embodiment, the antibody molecule binds to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in the extracellular region distant from the transmembrane domain.

In an embodiment, the antibody molecule binds to an epitope on CD138 comprising five or more consecutive amino acid residues in the extracellular region distant to the transmembrane domain. In an embodiment, the antibody molecule binds to an epitope on CD138 comprising six or more consecutive amino acid residues in the extracellular region distant to the transmembrane domain. In an embodiment, the antibody molecule binds to an epitope on CD138 comprising seven or more consecutive amino acid residues in the extracellular region distant to the transmembrane domain. In an embodiment, the antibody molecule binds to an epitope on CD138 comprising eight or more consecutive amino acid residues in the extracellular region distant to the transmembrane domain. In an embodiment, the antibody molecule binds to an epitope on CD138 comprising nine or more consecutive amino acid residues in the extracellular region distant to the transmembrane domain. In an embodiment, the antibody molecule binds to an epitope on CD138 comprising ten or more consecutive amino acid residues in the extracellular region distant to the transmembrane domain. In an embodiment, the antibody molecule binds to an epitope on CD138 comprising eleven or more consecutive amino acid residues in the extracellular region distant to the transmembrane domain. In an embodiment, the antibody molecule binds to an epitope on CD138 comprising twelve or more consecutive amino acid residues in the extracellular region distant to the transmembrane domain.

In an embodiment, the extracellular region distant to the transmembrane domain corresponds to (e.g., comprises or consists of) Pep2a.

In an embodiment, the antibody molecule contacts four or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) consecutive amino acid residues in Pep2a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31) of the following peptides (e.g., from Pep2a): ASTS (SEQ ID NO: 231), STST (SEQ ID NO: 232), TSTL (SEQ ID NO: 233), STLP (SEQ ID NO: 234), TLPA (SEQ ID NO: 235), LPAG (SEQ ID NO: 236), PAGE (SEQ ID NO: 237), AGEG (SEQ ID NO: 238), GEGP (SEQ ID NO: 239), EGPK (SEQ ID NO: 240), GPKE (SEQ ID NO: 241), PKEG (SEQ ID NO: 242), KEGE (SEQ ID NO: 243), EGEA (SEQ ID NO: 244), GEAV (SEQ ID NO: 245), EAVV (SEQ ID NO: 246), AVVL (SEQ ID NO: 247), VVLP (SEQ ID NO: 248), VLPE (SEQ ID NO: 249), LPEV (SEQ ID NO: 250), PEVE (SEQ ID NO: 251), EVEP (SEQ ID NO: 252), VEPG (SEQ ID NO: 253), EPGL (SEQ ID NO: 254), PGLT (SEQ ID NO: 255), GLTA (SEQ ID NO: 256), LTAR (SEQ ID NO: 257), TARE (SEQ ID NO: 258), AREQ (SEQ ID NO: 259), REQE (SEQ ID NO: 260), or EQEA (SEQ ID NO: 261). In an embodiment, the antibody molecule does not contact LPEV (SEQ ID NO: 250).

In an embodiment, the antibody molecule contacts five or more (e.g., 6, 7, 8, 9, 10, 11, 12, 13, 14, 15, 16, 17, 18, 19, 20, 21, 22, 23, 24, 25, 26, 27, 28, 29, or 30) consecutive amino acid residues in Pep2a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33) of the following peptides (e.g., from Pep2a): ASTS (SEQ ID NO: 231), STST (SEQ ID NO: 232), TSTL (SEQ ID NO: 233), STLP (SEQ ID NO: 234), TLPA (SEQ ID NO: 235), LPAG (SEQ ID NO: 236), PAGE (SEQ ID NO: 237), AGEG (SEQ ID NO: 238), GEGP (SEQ ID NO: 239), EGPK (SEQ ID NO: 240), GPKE (SEQ ID NO: 241), PKEG (SEQ ID NO: 242), KEGE (SEQ ID NO: 243), EGEA (SEQ ID NO: 244), GEAV (SEQ ID NO: 245), EAVV (SEQ ID NO: 246), AVVL (SEQ ID NO: 247), VVLP (SEQ ID NO: 248), VLPE (SEQ ID NO: 249), LPEV (SEQ ID NO: 250), PEVE (SEQ ID NO: 251), EVEP (SEQ ID NO: 252), VEPG (SEQ ID NO: 253), EPGL (SEQ ID NO: 254), PGLT (SEQ ID NO: 255), GLTA (SEQ ID NO: 256), LTAR (SEQ ID NO: 257), TARE (SEQ ID NO: 258), AREQ (SEQ ID NO: 259), REQE (SEQ ID NO: 260), or EQEA (SEQ ID NO: 261). In an embodiment, the antibody molecule does not contact a peptide comprising LPEV (SEQ ID NO: 250).

In an embodiment, the antibody molecule contacts six or more (e.g., 7, 8, 9, 10, 11, 12, 13, 14, 15, 16, 17, 18, 19, 20, 21, 22, 23, 24, 25, 26, 27, 28, or 29) consecutive amino acid residues in Pep2a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) of the following peptides (e.g., from Pep2a): ASTS (SEQ ID NO: 231), STST (SEQ ID NO: 232), TSTL (SEQ ID NO: 233), STLP (SEQ ID NO: 234), TLPA (SEQ ID NO: 235), LPAG (SEQ ID NO: 236), PAGE (SEQ ID NO: 237), AGEG (SEQ ID NO: 238), GEGP (SEQ ID NO: 239), EGPK (SEQ ID NO: 240), GPKE (SEQ ID NO: 241), PKEG (SEQ ID NO: 242), KEGE (SEQ ID NO: 243), EGEA (SEQ ID NO: 244), GEAV (SEQ ID NO: 245), EAVV (SEQ ID NO: 246), AVVL (SEQ ID NO: 247), VVLP (SEQ ID NO: 248), VLPE (SEQ ID NO: 249), LPEV (SEQ ID NO: 250), PEVE (SEQ ID NO: 251), EVEP (SEQ ID NO: 252), VEPG (SEQ ID NO: 253), EPGL (SEQ ID NO: 254), PGLT (SEQ ID NO: 255), GLTA (SEQ ID NO: 256), LTAR (SEQ ID NO: 257), TARE (SEQ ID NO: 258), AREQ (SEQ ID NO: 259), REQE (SEQ ID NO: 260), EQEA (SEQ ID NO: 261). In an embodiment, the antibody molecule does not contact a peptide comprising LPEV (SEQ ID NO: 250).

In an embodiment, the antibody molecule binds, or substantially binds, to an extracellular region of CD138 proximal to the transmembrane domain (e.g., an extracellular region described herein) and an extracellular region of CD138 distant from the transmembrane domain (e.g., an extracellular region described herein). In an embodiment, the antibody molecule binds to the extracellular region of CD138 proximal to the transmembrane domain with a binding affinity that is higher (e.g., at least 2, 3, 4, 5, 6, 7, 8, 9, 10, 20, 30, 40, 50, 100, 200, 300, 400, or 500-fold higher) than the binding affinity to the extracellular region of CD138 distant from the transmembrane domain. In an embodiment, the antibody molecule binds to the extracellular region of CD138 distant from the transmembrane domain with a binding affinity that is higher (e.g., at least 2, 3, 4, 5, 6, 7, 8, 9, 10, 20, 30, 40, 50, 100, 200, 300, 400, or 500-fold higher) than the binding affinity to the extracellular region of CD138 proximal to the transmembrane domain.

Antibody Molecules

Disclosed herein are antibody molecules that bind to CD138, e.g., a CD138 molecule described herein.

As used herein, the term "antibody molecule" refers to a protein, e.g., an immunoglobulin chain or a fragment thereof, comprising at least one immunoglobulin variable domain sequence. The term "antibody molecule" includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody molecule can also be a human, humanized, CDR-grafted, or in vitro generated antibody. The antibody molecule can have a heavy chain constant region chosen from, e.g., IgG1, IgG2, IgG3, or IgG4. The antibody molecule can also have a light chain chosen from, e.g., kappa or lambda. The term "immunoglobulin" (Ig) is used interchangeably with the term "antibody" herein.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibody molecule can be a single chain antibody. A single-chain antibody (scFv) may be engineered (see e.g., Colcher et al. (1999) *Ann N Y Acad Sci* 880: 263-280; and Reiter & Pastan (1996) *Clin Cancer Res* 2: 245-252). The single chain antibody can be dimerized or multimerized to generate multivalent antibodies having specificities for different epitopes of the same target protein.

The antibody molecules disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco. Other species besides *Camelidae* may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In an embodiment, the following definitions are used: AbM definition of CDR1 of the heavy chain variable domain and Kabat definitions for the other CDRs. In an embodiment, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, and FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an antigen, e.g., CD138, or an epitope thereof. With respect to proteins (or protein mimetics), the antigen-binding region typically includes one or more loops (of at least, e.g., four amino acids or amino acid mimics) that form an interface that binds to the antigen, e.g., CD138. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-CD138 antibody molecule, e.g., an anti-CD138 antibody molecule provided herein, to a target, e.g., CD138. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In an embodiment, a competition binding assay is a quantitative competition assay. In an embodiment, a first anti-CD138 antibody molecule is said to compete for binding to the target with a second anti-CD138 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see e.g., Saleh et al., *Cancer Immunol. Immunother.*, 32:180-190 (1990)) and also because of potential allergic reactions (see e.g., LoBuglio et al., *Hybridoma*, 5:5117-5123 (1986)).

The antibody molecule can be a polyclonal or a monoclonal antibody. In some embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In an embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Application Publication No. WO1987/002671; Akira, et al., European Patent Application Publication No. 184,187; Taniguchi, M., European Patent Application Publication No. 171,496; Morrison et al., European Patent Application Publication No. 173,494; Neuberger et al., International Patent Application Publication No. WO 86/01533; Cabilly et al. U.S. Pat. No. 4,816,567; Cabilly et al., European Patent Application Publication No. 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to lipopolysaccharide. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2 (e.g., IgG2a), IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In certain embodiments, the antibody molecule has reduced or no ability to bind an Fc receptor. For example, it may be an isotype or subtype, fragment or other mutant, which does not support binding to an Fc receptor, e.g., it has a mutagenized or deleted Fc receptor binding region.

In an embodiment, a constant region of the antibody molecule is altered. Methods for altering an antibody constant region are known in the art. Antibody molecules s with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference) Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the Fc region is altered to extend half-life. For example, the Fc region can contain one or more of: FcMut183 (T256D-Q311V-A378V), FcMut197 (H285N-T307Q-N315D), FcMut213 (H285D-T307Q-A378V), FcMut215 (T307Q-Q311V-A378V), or FcMut228 (T256D-N286D-T307R-Q311V-A378V).

In an embodiment, the Fc region is altered to enhance ADCC. For example, the Fc region can contain one or more of: A330L-I332E-5239D, F243L-R292P-Y300L-V305I-P396L, or S298A-E333A-K334A. In an embodiment, afucosylation can be aachieved by expression in a cell line such as CHO in which fucosyltransferase (FucT8) is knocked out.

In an embodiment, the Fc region is altered to enhance CDC. For example, the Fc region contains 5267E-H268F-S324T.

In an embodiment, the Fc region is altered to enhance antibody-dependent cellular phagocytosis (ADCP). For example, the Fc region contains 5239D-I332E-A330L.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the anti-CD138 antibody can be coupled to a radioactive isotope such as an α-, β-, or γ-emitter, or a β- and γ-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-CD138 antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., antimicrobial (e.g., antibacterial or bactericidal), immunomodulatory, immunostimularoty, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac) praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In) technetium ($^{99m}$Tc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

In some aspects, this disclosure provides a method of making an antibody molecule disclosed herein. The method includes: providing an antigen, e.g., CD138 or a fragment thereof; obtaining an antibody molecule that specifically binds to the antigen; evaluating efficacy of the antibody molecule in modulating activity of the antigen and/or organism expressing the antigen, e.g., CD138. The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes, but is not limited to, RNA, genomic DNA and cDNA.

Amino acid and nucleotide sequences of exemplary antibody molecules are described in Tables 1 and 2, respectively.

TABLE 1

The amino acid sequences of the heavy chain variable region (VH) and light chain region (VL) of the exemplary anti-CD138 antibodies are provided as follows. CDRs, defined according to the Kabat or Chothia system, are indicated.

| Antibody | Chain | Amino Acid Sequence | SEQ ID NO | | | SEQ ID NO | | | SEQ ID NO |
|---|---|---|---|---|---|---|---|---|---|
| CD001 | VH | EVQLQQSGPELVKPGASVKISCETSGFSFT AHHMHWVKQSPEKSLEWIGEIDPNTGSTTY NQKFRAKATLTVDKSSNTTYMQLKSLTFED SAVYYCYSNWFPYWGQGTLVTVSA | 262 | HCDR1 HCDR2 HCDR3 | GFSFTAH DPNTGS NWFPY | 300 301 302 | HCDR1 HCDR2 HCDR3 | AHHMH EIDPNTGSTTYNQK FRA NWFPY | 362 363 302 |
| | VL | DVVMTQTPLTLSATIGQPASIYCKSSQSLL DGDGKTYLNWLLQRPGQSPKRLIYLVSKLD SGVPDRFTGSGSGTDFTLKISRVEAEDLGV YYCWQGTHFPRTFGGGTKLEIK | 263 | LCDR1 LCDR2 LCDR3 | KSSQSLLSGDGKTYLN LVSKLDS WQGTHFPRT | 303 304 305 | LCDR1 LCDR2 LCDR3 | KSSQSLLDGDGKTY LN LVDKSLD WQGTHFPRT | 303 304 305 |
| CD002 | VH | QVQLQQPGAELVKPGASVKLSCKASGFSI TYWMNWIKQRPGRGLEWIGRIHPSDSATQY NQKFKTKATLTVDKSSSTAYIQLSSLTSED SAVYYCARSTEGAHWGQGTLVTVSA | 264 | HCDR1 HCDR2 HCDR3 | GFSFITY HPSDSA STEGAH | 306 307 308 | HCDR1 HCDR2 HCDR3 | TYWMN RIHPSDSATQYNQK FKT STEGAH | 364 365 308 |
| | VL | DVVMTQTPLTLSVTIGQPASISCKSSQSLL HSDGKTYLNWLLQRPGQSPKRLIYLVSKLD SGVPDRFTGSGSGTDFTLKISRVEAEDLGV YYCWQGTHFPQTFGGGTKLEIK | 265 | LCDR1 LCDR2 LCDR3 | KSSQSLLHSDGKTYLN LVSKLDS WQGTHFPQT | 309 304 3100 | LCDR1 LCDR2 LCDR3 | KSSQSLLHSDGKTY LN LVSKLDS WQGTHFPQT | 309 304 310 |
| CD003 | VH | QVQLQQPGAELVKPGASVKLSCKASGYTFT SFWMHWVKQRPGQGLEWIGEIYPSSGVTNY NERFKNKATLTVDKSSRTAYMQLSSLTSED SAVYFCTPNYYYDGLYWGQGTLVTVSA | 266 | HCDR1 HCDR2 HCDR3 | GYTFTSY YPSSGV NYYYDGLY | 311 312 313 | HCDR1 HCDR2 HCDR3 | SFWMH EIYPSSGVTNYNER FKN NYYYDGLY | 366 367 313 |
| | VL | DVVMTQTPLTLSVTIGQPASISCKSSHSLL YTNGETYLNWLLQRPGQSPKRLIYLVSNLD SGVPDRFSGSGSGTDFTLKISRVEAEDLGI YYCLQSTHFPRTFGGGTKLEIK | 267 | LCDR1 LCDR2 LCDR3 | KSSHSLLYTNGETYLN LVSNLDS LQSTHFPRT | 314 315 316 | LCDR1 LCDR2 LCDR3 | KSSHSLLYTNGETY LN LVSNLDS LQSTHFPRT | 314 315 316 |
| CD004 | VH | QVQLQQPGAELVKPGASVKLSCKASGFSFT RYWMNWVKQRPGRGLEWIGRIHPSDSASQY NQKFKSKATLTVDKSSSTAYIQLSSLTSED SAVYYCGRSTEGAYWGQGTLVTVSA | 268 | HCDR1 HCDR2 HCDR3 | GFSFTRY HPSDSA STEGAY | 317 307 318 | HCDR1 HCDR2 HCDR3 | RYWMN RIHPSDSASQYNQK FKS STEGAY | 368 369 318 |
| | VL | DVVMTQTPLTLSVTIGQPASISCKSSQSLL HSDGKTYLNWLLQRPGQSPKRLIYLVSKLD SGVPDRFTGSGSGTDFTLKISRVEAEDLGV YYCWQGTHFPQTFGGGTKLEIK | 265 | LCDR1 LCDR2 LCDR3 | KSSQSLLHSDGKTYLN LVSKLDS WQGTHFPQT | 309 304 310 | LCDR1 LCDR2 LCDR3 | KSSQSLLHSDGKTY LN LVSKLDS WQGTHFPQT | 309 304 310- |
| CD005 | VH | QVQLQQPGAELVKPGASVKLSCKASGFSI TYWMNWIKQRPGRGLEWIGRIHPSDSATQY DQKFKTKATLTVDKSSSTAYIQLSSLTSED SAVYYCARSTEGAHWGPGTLVTVSA | 269 | HCDR1 HCDR2 HCDR3 | GFSFITY HPSDSA STEGAH | 306 307 308 | HCDR1 HCDR2 HCDR3 | TYWMN RIHPSDSATQYDQK FKT STEGAH | 364 370 308 |
| | VL | DVVMTQTPLTLSVTIGQPASICKSSHSLL YTNGETYLNWLLQRPGQSPKRLIYLVSNLD SGVPDRFSGSGSGTDFTLKISRVEAEDLGI YYCLQSTHFPRTFGGGTKLEIK | 267 | LCDR1 LCDR2 LCDR3 | KSSHSLLYTNGETYLN LVSNLDS LQSTHFPRT | 314 315 316 | LCDR1 LCDR2 LCDR3 | KSSHSLLYTNGETY LN LVSNLDS LQSTHFPRT | 314 315 316 |
| CD006 | VH | EIQLQQSGTELVKPGASVKISCKTSGYSFT DYNMNWVKQSHGKSLEWIGNINPYYGSTGY TQNFEGKATLTVDKSSSTAYMQLNSLTSED SALYYCAREGHDYYAMDYWGQGTSVTVSA | 270 | HCDR1 HCDR2 HCDR3 | GYSFTDY NPYYGS EGHDYYAMDY | 319 320 321 | HCDR1 HCDR2 HCDR3 | DYNMN NINPYYGSTGYTQN FEG EGHDYYAMDY | 371 372 321 |

TABLE 1-continued

The amino acid sequences of the heavy chain variable region (VH) and light chain region (VL) of the exemplary anti-CD138 antibodies are provided as follows. CDRs, defined according to the Kabat or Chothia system, are indicated.

| Antibody | Chain | Amino Acid Sequence | SEQ ID NO | | SEQ ID NO | | SEQ ID NO |
|---|---|---|---|---|---|---|---|
|  | VL | DVVMTQTPLTLSVTIGQPASISCKSSQSLLHSDGKTYLNWLLQRPGQSPKRLIYLVSKLDSGVPDRFTGSGSGTDFTLKISRVEAEDLGVYYCWQGTHFPQTFGGGTKLEIK | 265 | LCDR1 KSSQSLLHSDGKTYLN<br>LCDR2 LVSKLDS<br>LCDR3 WQGTHFPQT | 309<br>304<br>310 | LCDR1 KSSQSLLHSDGKTYLN<br>LCDR2 LVSKLDS<br>LCDR3 WQGTHFPQT | 309<br>304<br>310 |
| 602 | VH | QVQLQLPGAELVKPGASVKVSCKASGYTFTSYWMHWVKQRPGQGLEWIGRIHPSDSDTNYNQNFKGKATLIVDKSSSTAYMQLSSLTSEDSAVYYCATGFSFWGQGTLVTVSA | 271 | HCDR1 GYFTFSY<br>HCDR2 HPSDSD<br>HCDR3 GFSF | 322<br>323<br>324 | HCDR1 SYWMN<br>HCDR2 RIHPSDSDTNYNQNFKG<br>HCDR3 GFSF | 373<br>374<br>324 |
| 603 | VH | QVQVQVPGAELVKPGASVKVSCKASGYTFTSYWMHWMKKRPGQGLEWIGRIHPSDSDTNYNQNFKGKATLTVDKSSSTAYMQLSSLTSEDSAVYFCATGFSFWGQGTLVTVSA | 272 | HCDR1 GYFTFSY<br>HCDR2 NPSDSD<br>HCDR3 GFSF | 322<br>323<br>324 | HCDR1 SYWMH<br>HCDR2 RIHSDSDTNYNQNFKG<br>HCDR3 GFSF | 373<br>374<br>324 |
|  | VL | DVVMTQTPLTLSVTIGQPASISCKSSQSLLYSDGKTYLNWLLQRPGESPKLLIYLVSKLDSGVPDRFTGSGSGTDFTLKISRVEAEDLGVYYCLQTTSFPYTFGGGTKLDIK | 273 | LCDR1 KSSQSLLYSDGKTYLN<br>LCDR2 LVSKLDS<br>LCDR3 LQTTSFPYT | 325<br>304<br>326 | LCDR1 KSSQSLLYSDGKTYLN<br>LCDR2 LVSKLDS<br>LCDR3 LQTTSFPYT | 325<br>304<br>326 |
| 604 | VH | QVQLQQPGAELVKPGASVKVSCKASGYNFINYWMHWVKQRPGQGLEWIGRIHPSDSYTNYNQKFKGKATLTVDKSSSTAYMQLSSLTSEDSAVYYCASPISTLYWGQGTTLTVSS | 274 | HCDR1 FYNFINY<br>HCDR2 HPSDSY<br>HCDR3 PISTLY | 327<br>328<br>329 | HCDR1 NYWMH<br>HCDR2 RIHPSDSYTNYNQKFKG<br>HCDR3 PISTLY | 375<br>376<br>329 |
|  | VL | DVVMTQTPLTLSVTIGQPASISCKSSQSLLDSDGKTYLNWLLQRPGESPKLLIYLVSKLDSGVPDRFTGSGSGTDFTLKISRVEAEDLGVYYCLQATHFPQTFGGGTKLEIK | 275 | LCDR1 KSSQSLLDSDGKTYLN<br>LCDR2 LVSKLDS<br>LCDR3 LQATHFPQT | 330<br>304<br>331 | LCDR1 KSSQSLLDSDGKTYLN<br>LCDR2 LVSKLDS<br>LCDR3 LQATHFPQT | 330<br>304<br>331 |
| 607 | VH | QVQLQLPGAELVRPGTSVKVSCKASDYTFTTYWMHWVKQRPGQGLDWIGRIHPSDSDTNYNQNFKGKATLTVDKSSSTAYMHLSSLTSEDSAVYYCATGFSFWGQGTLVTVSA | 276 | HCDR1 DYTFTTY<br>HCDR2 HPSDSD<br>HCDR3 GFSF | 332<br>323<br>324 | HCDR1 TYWMN<br>HCDR2 RIHPSDSDTNYNQNFKG<br>HCDR3 GFSF | 377<br>374<br>324 |
| 613 | VH | QVQVQLPGAELVKPGASVKVSCKASGYTFTSYWMHWVKKRPGQGLEWIGRIHPSDSDTNYNQNFKGKATLTVDKSSSTAYMLLSSLTSEDSAVYYCATGFSFWGQGTLI | 277 | HCDR1 GYTFTSY<br>HCDR2 HPSDSD<br>HCDR3 GFSF | 322<br>323<br>324 | HCDR1 SYWMN<br>HCDR2 RIHPSDSDTNYNQNFKG<br>HCDR3 GFSF | 373<br>374<br>324 |
|  | VL | DVVMTQTPLTLSVTIGQPASISCKSSQSLLYSDGKTYLNWLLQRPGESPELLIYLVSKMDSGVPDRFHGHGSGTAFTMKISRMGGGGLGNYYCLPRTSFPYTFGGGTKLEIK | 278 | LCDR1 KSSQSLLYSDGKTYLN<br>LCDR2 LVSKMDS<br>LCDR3 LPRTSFPYT | 325<br>333<br>334 | LCDR1 KSSQSLLYSDGKTYLN<br>LCDR2 LVSKMDS<br>LCDR3 LPRTSFPYT | 325<br>333<br>334 |
| 614 | VH | QVQLQLPGAELVKPGASVKVSCKASGYTFTSYWMHWVKQRPGQGLEWIGRIHPSDSDTNYNQNFKGKATLTVDKSSNTAYMQLSSLTSEDSAVYYCATGFSFWGQGTLVTVSA | 279 | HCDR1 GYTFTSY<br>HCDR2 HPSDSD<br>HCDR3 GFSF | 322<br>323<br>324 | HCDR1 SYWMH<br>HCDR2 RIHPSDSDTNYNQNFKG<br>HCDR3 GFSF | 373<br>374<br>324 |
|  | VL | DVVMTPTSLHLLVTIGQPGFLFCKSSQNLLYNEGKTYLKWLLPEPGAFSKVLIYLVFKMGFGVPDRFHGHGSGTDFPMKISRMGGGGLGGYLCLPSTPFPYTFGGGTKLEIK | 280 | LCDR1 KSSQNLLYNEGKTYLK<br>LCDR2 LVFKMGF<br>LCDR3 LPSTPFPYT | 335<br>336<br>337 | LCDR1 KSSQNLLYNEGKTYLK<br>LCDR2 LVFKMGF<br>LCDR3 LPSTPFPYT | 335<br>336<br>337 |
| 616 | VH | QIHLVQSGPELKKPGETVRISCKASGYTFTTYGMSWVKQAPGKALKWMGWINTYSGVPTYADDFKGRFAFSLETSASTAYLQINNLKEDTATYFCTREGSTMVTRYYFDYWGQGTTLTVSS | 281 | HCDR1 GYTFTTY<br>HCDR2 NTYSGV<br>HCDR3 EGSTMVTRYYFDY | 338<br>339<br>340 | HCDR1 TYGMS<br>HCDR2 WINTYSGVPTYADDFKG<br>HCDR3 EGSTMVTRYYFDY | 378<br>379<br>340 |
|  | VL | DIVMTQAAPSVPVTPGESVSISCRSSKSLLHSNGNTYLYWFLQRPGQSPQLLIYRMSNLASGVPDRFSGSGSGTAFTLRISRVEAEDVGVYHCMQHLESPYTFGGGTTLEIK | 282 | LCDR1 RSSKSLLHSNGNTYLY<br>LCDR2 RMSNLAS<br>LCDR3 MQHLESPYT | 341<br>342<br>343 | LCDR1 RSSKSLLHSNGNTYLY<br>LCDR2 RMSNLAS<br>LCDR3 MQHLESPYT | 341<br>342<br>343 |
| 617 | VH | QVQLQLPGAELVKPGASVKVSCKASAYTFTSYWMHWVKQRPGQGLEWIGRIHPSDSDTNYNQNFKGKATLTVDKSSNTAYMQLSSLTSEDSAVYYCATGFSFWGQGTLVTVSA | 283 | HCDR1 AYTFTSY<br>HCDR2 HPSDSD<br>HCDR3 GFSF | 344<br>323<br>324 | HCDR1 SYWMH<br>HCDR2 RIHPSDSDTNYNQNFKG<br>HCDR3 GFSF | 373<br>374<br>324 |
|  | VL | DIVMTQSHKFMSTSVGDRVSITCKASQDVSTTVAWYQQKPGQSPKLLIYSASYRYTGVPDRFTGSGSGTDFTFTISSVQAEDLAVYYCQQHYSTRPTFGGGTKLEIK | 284 | LCDR1 KASQDVSTTVA<br>LCDR2 SASYRYT<br>LCDR3 QQHYSTRPT | 345<br>346<br>347 | LCDR1 KASQDVSTTVA<br>LCDR2 SASYRYT<br>LCDR3 QQHYSTRPT | 345<br>346<br>347 |

TABLE 1-continued

The amino acid sequences of the heavy chain variable region (VH) and light chain region (VL) of the exemplary anti-CD138 antibodies are provided as follows. CDRs, defined according to the Kabat or Chothia system, are indicated.

| Antibody | Chain | Amino Acid Sequence | SEQ ID NO | | | SEQ ID NO | | | SEQ ID NO |
|---|---|---|---|---|---|---|---|---|---|
| 619 | VH | QIQLVQSGPELKKPGETVKISCKASGYTFT TYGMSWVKQAPGKGLKWMGWINTYSGVPTY ADDFKGRFAFSLETSASTAYLQINNLKNED TATYFCAREGSTMVTRYYFDYWGQGTTLTV SS | 285 | HCDR1 HCDR2 HCDR3 | GYTFTTY NTYSGV EGSTMVTRYYFDY | 338 339 340 | HCDR1 HCDR2 HCDR3 | TYGMS WINTYSGVPTYADD FKG EGSTMVTRYYFDY | 378 379 340 |
| | VL | DIVMTQAAPSVPVTPGESVSISCRSSKSLL HSNGNTYLYWFLQRPGQSPQVLIYRMSNLA SGVPDRFSGSGSGTAFTLRISRVEAEDVGV YYCMQHLESPYTFGGGTKLEIK | 286 | LCDR1 LCDR2 LCDR3 | RSSKSLLHSNGNTYLY RMSNLAS MQHSESPYT | 341 342 343 | LCDR1 LCDR2 LCDR3 | RSSKSLLHSNGNTY LY RMSNALS MQHLESPYT | 341 342 343 |
| 623 | VH | QIQLVQSGPELKKPGETVKISCKASGYTFT TYGMSWVKQAPGKGLKWMGWINTYSGVPTY ADDFKGRFAFSLETSASTAYLQINNLKNED TATFFCAREGSTMVTRYYFDYWGQGTTLTV SS | 287 | HCDR1 HCDR2 HCDR3 | GYTFTTY NTYSGV EGSTMVTRYYFDY | 338 339 340 | HCDR1 HCDR2 HCDR3 | TYGMS WINTYSGVPTYADD FKG EGSTMVTRYYFDY | 378 379 340 |
| | VL | DIVMTQAAPSVPVTPGESVSISCRSSKSLL HSNGNTYLYWFLQRPGQSPQLLIYRMSNLA SGVPDRFSGSGSGTAFTLRISRVEAEDVGV YYCMQHLEYPSTFGGGTKLEIK | 288 | LCDR1 LCDR2 LCDR3 | RSSKSLLHSNGNTYLY RMSNLAS MQHLEPYST | 341 342 348 | LCDR1 LCDR2 LCDR3 | RSSKSLLHSNGNTY LY RMSNLAS MQHLEYPST | 341 342 348 |
| 624 | VH | QVQVQLPGAELVKPGASVKVSCKASGYTFT SYWMHWVKKRPGQGLEWIGRIHPSDSDTNY NQNFKGKATLTVDKSSSTAYMQLTSLTSED FAVYYCSTGFSFWGQGTLVTSA | 289 | HCDR1 HCDR2 HCDR3 | GYTFTSY HPSDSD GFSF | 322 323 324 | HCDR1 HCDR2 HCDR3 | SYWMH RIHPSDSDTNYNQN FKG GFSF | 373 374 324 |
| | VL | DVVMTQTPLTLSVTIGQPASISCKSSQSLL YSDGKTYLNWLLQRPGESPKLLIYLVSKLD SGVPDRFTGSGSGTDFTLKISRVEAEDLGV YYCLQTTYFPYTFGGGTKLEIK | 290 | LCDR1 LCDR2 LCDR3 | KSSQSLLYSDGKTYLN KVSKLDS LQTTYFPYT | 325 304 349 | LCDR1 LCDR2 LCDR3 | KSSQSLLYSDGKTY LN LVSKLDS LQTTYFPYT | 325 304 349 |
| 1610 | VH | QVQLHQPGTSLVKPGASVKLSCKASGYNFS SYYMHWVKQRPGQGLEWIGTIHPSDSTTNC NQKFKGKATLTVDKSSRTAYMQLNSLTFED SAVYYCANFVYWGQGTSVTVSS | 291 | HCDR1 HCDR2 HCDR3 | GYNFSSY HPSDST FVY | 350 351 | HCDR1 HCDR2 HCDR3 | SYYMH TIHPSDSTTNCNQK FKG FVY | 380 381 |
| | VL | DIVITQDELSNPVTSGDSVSISCRSSKSLL YKDGKTYLNWFLQRPGQSPQLLIYVVSTRA SGVSDRFSGSGSGTDFTLEISRVKAEDVGV YYCQQLVEYPYTFGGGTKLEIK | 292 | LCDR1 LCDR2 LCDR3 | RSSKSLLYKDGKTYLN VVSTRAS QQLVEYPYT | 352 353 354 | LCDR1 LCDR2 LCDR3 | RSSKSLLYKDGKTY LN VVSTRAS QQLVEYPYT | 352 353 354 |
| 2510 | VH | QVQLHQPGTSLVKPGASVKLSCKASGYNFS SYYMHWVKQRPGQGLEWIGTIHPSDSTTNY NQKFKGKATLTVDKSSRTAYMQLNSLTFED SAVYYCANFVYWGQGTSVTVSS | 293 | HCDR1 HCDR2 HCDR3 | GYNFSSY HPSDST FVY | 350 351 | HCDR1 HCDR2 HCDR3 | SYYMH TIHPSDSTTNYNQK FKG FVY | 380 382 |
| | VL | DIVITQDELSNPVTSGDSVSISCRSSKSLL YKDGKTYLNWFLQRPGQSPQLLIYVVSTRA SGVSDRFSGSGSGTDFTLEISRVKAEDVGV YYCQQLVEYPYTFGGGTKLEIK | 292 | LCDR1 LCDR2 LCDR3 | RSSKSLLYKDGKTYLN VVSTRAS QQLVEYPYT | 352 353 354 | LCDR1 LCDR2 LCDR3 | RSSKSLLYKDGKTY YN VVSTRAS QQLVEYPYT | 352 353 354 |
| 2610 | VH | QVQLHQPGTSLVKPGASVKLSCKASGYSFS SYYMHWVKQRPGQGLEWIGTIHPSDSTTNC NQKFKGKATLTVDKSSRTAYMQLNSLTFED SAVYYCANFVYWGQGTSVTVSS | 294 | HCDR1 HCDR2 HCDR3 | GYSFSSY HPSDST FVY | 355 351 | HCDR1 HCDR2 HCDR3 | SYYMH TIHPSDSTTNCNQK FKG FVY | 380 381 |
| | VL | DIVITQDELSNPVTSGDSVSISCRSSKSLL YKDGKTYLNWFLQRPGQSPQLLIYVVSTRA SGVSDRFSGSGSGTDFTLEISRVKAEDVGV YYCQQLVEYPYTFGGGTKLEIK | 292 | LCDR1 LCDR2 LCDR3 | RSSKSLLYKDGKTYLN VVSTRAS QQLVEYPYT | 352 353 354 | LCDR1 LCDR2 LCDR3 | RSSKSLLYKDGKTY LN VVSTRAS QQLVEYPYT | 352 353 354 |
| 2710 | VH | QVQLHQPGTSLVKPGASVKLSCKASGYTFS SYYMHWVKQRPGQGLEWIGTIHPSDSTTNC NQKFKGKATLTVDKSSRTAYMQLNSLTFED SAVYYCANFVYWGQGTSVTVSS | 295 | HCDR1 HCDR2 HCDR3 | GYTFSSY HPSDST FVY | 356 351 | HCDR1 HCDR2 HCDR3 | SYYMH TIHPSDSTTNCNQK FKG FVY | 380 381 |
| | VL | DIVITQDELSNPVTSGDSVSISCRSSKSLL YKDGKTYLNWFLQRPGQSPQLLIYVVSTRA SGVSDRFSGSGSGTDFTLEISRVKAEDVGV YYCQQLVEYPYTFGGGTKLEIK | 292 | LCDR1 LCDR2 LCDR3 | RSSKSLLYKDGKTYLN VVSTRAS QQLVEYPYT | 352 353 354 | LCDR1 LCDR2 LCDR3 | RSSKSLLYKDGKTY LN VVSTRAS QQLVEYPYT | 352 353 354 |
| 2810 | VH | QVQLHQPGTSLVKPGASVKLSCKASGYSFS SYYMHWVKQRPGQGLEWIGTIHPSDSTTNY NQKFKGKATLTVDKSSRTAYMQLNSLTFED SAVYYCANFVYWGQGTSVTVSS | 296 | HCDR1 HCDR2 HCDR3 | GYSFSSY HPSDST FVY | 355 351 | HCDR1 HCDR2 HCDR3 | SYYMH TIHPSDSTTNYNQK FKG FVY | 380 382 |

TABLE 1-continued

The amino acid sequences of the heavy chain variable region (VH) and light chain region (VL) of the exemplary anti-CD138 antibodies are provided as follows. CDRs, defined according to the Kabat or Chothia system, are indicated.

| Antibody | Chain | Amino Acid Sequence | | SEQ ID NO | | SEQ ID NO |
|---|---|---|---|---|---|---|
| | VL | DIVITQDELSNPVTSGDSVSISCRSSKSLL YKDGKTYLNWFLQRPGQSPQLLIYVVSTRA SGVSDRFSGSGSGTDFTLEISRVKAEDVGV YYCQQLVEYPYTFGGGTKLEIK | 292 | LCDR1 RSSKSLLYKDGKTYLN | 352 | LCDR1 RSSKSLLYKDGKTYLN | 352 |
| | | | | LCDR2 VVSTRAS | 353 | LCDR2 VVSTRAS | 353 |
| | | | | LCDR3 QQLVEYPYT | 354 | LCDR3 QQLVEYPYT | 354 |
| 2910 | VH | QVQLHQPGTSLVKPGASVKLSCKASGYTFS SYYMHWVKQRPGQGLEWIGTIHPSDSTTNY NQKFKGKATLTVDKSSRTAYMQLNSLTFED SAVYYCANFVYWGQGTSVTVSS | 297 | HCDR1 CYTFSSY | 356 | HCDR1 SYYMH | 380 |
| | | | | HCDR2 HPSDST | 351 | HCDR2 TIHPSDSTTNYNQKFKG | 382 |
| | | | | HCDR3 FVY | | HCDR3 FVY | |
| | VL | DIVITQDELSNPVTSGDSVSISCRSSKSLL YKDGKTYLNWFLQRPGQSPQLLIYVVSTRA SGVSDRFSGSGSGTDFTLEISRVKAEDVGV YYCQQLVEYPYTFGGGTKLEIK | 292 | LCDR1 RSSKSLLYKDGKTYLN | 352 | LCDR1 RSSKSLLYKDGKTYLN | 352 |
| | | | | LCDR2 VVSTRAS | 353 | LCDR2 VVSTRAS | 353 |
| | | | | LCDR3 QQLVEYPYT | 354 | LCDR3 QQLVEYPYT | 354 |
| 1409 | VH | EVQLVESGGGLVQPKGSLKLSCAASGFTFN TYAMHWVRQAPGKGLEWVARIRSKSSNYAT YYADSVKDRFTISRDDSQSMLYLQMNNLKT EDTAMYCVRELRLRYAMDYWGQGTSVTVS S | 298 | HCDR1 GFTFNTY | 357 | HCDR1 TYAMH | 383 |
| | | | | HCDR2 RSKSSNYA | 358 | HCDR2 RIRSKSSNYATYYADSVKD | 384 |
| | | | | HCDR3 ELRLRAMDY | 359 | HCDR3 KSSQSLLYTNGKTYLN | 359 |
| | VL | DILMTQTPLTLSVTIGQPASISCKSSQSLL YTNGKTYLNWLLQRPGQSPKRLIYLVSKLD SGVPDRFSGSGSGTDFTLKISRVEAEDLGV YYCLQSTHFPLTFGAGTKLELK | 299 | LCDR1 KSSQSLLYTNGKTYLN | 360 | LCDR1 KSSQSLLYTNGKTYLN | 360 |
| | | | | LCDR2 LVSKLDS | 304 | LCDR2 LVSKLDS | 304 |
| | | | | LCDR3 LQSTHFPLT | 361 | LCDR3 LQSTHFPLT | 361 |

TABLE 2

Nucleotide sequences of heavy chain variable regions (VHs) and light chain variable regions (VLs) of exemplary anti-CD138 antibodies

| Antibody | Chain | Nucleotide Sequence | SEQ ID NO |
|---|---|---|---|
| CD001 | VH | GAAGTACAGTTGCAGCAATCTGGGCCTGAGCTGGTGAAGCCCGGTGCTTCCGTGAAAATTTCCTGCAAAC TTCAGGATTCTCATTTACTGCACATCATATGCACTGGGTAAAACAATCTCCAGAGAAATCACTCGAATGGA TAGGCGAGATTGATCCAAATACCGGGTCCACCACATACAATCAGAAATTTCGCGCTAAGGCCACCCTGACT GTCGATAAAAGTTCTAACACTACATACATGCAGCTTAAATCCCTTACATTCGAAGACAGTGCAGTGTACTA CTGTTACTCTAACTGGTTTCCATATTGGGGACAGGGAACACTGGTAACCGTTTCCGCT | 385 |
| | VL | GACGTAGTTATGACTCAGACACCACTTACACTCTCTGCTACTATCGGACAACCAGCCTCAATCTATTGCAA GTCCTCACAATCTTTGCTTGATGGCGACGGGAAGACCTATCTCAATTGGCTTCTCCAACGACCTGGGCAAA GCCCCAAGGACTCATATATCTCGTTTCCAAGCTGGACAGTGGGGTGCCAGATAGATTTACTGGGTCAGGT AGTGGTACTGACTTTACTTTGAAAATATCAAGAGTAGAGGCTGAGGACCTCGGAGTCTATTACTGCTGGCA AGGAACCCATTTCCCCCGCACCTTCGGAGGAGGGACAAAATTGGAAATAAAA | 386 |
| CD002 | VH | CAAGTGCAACTTCAGCAACCCGGCGCCGAGCTTGTGAAGCCTGGTGCCTCCGTTAAACTTTCTTGCAAGGC ATCCGGTTTCTCATTCATTACCTACTGGATGAACTGGATCAAACAAAGACCTGGACGTGGTCTGGAGTGGA TTGGGCGGATTCACCCCTCAGACTCCGCAACCCAATACAATCAGAAATTCAAAACAAAGGCCACCTTGACC GTTGATAAAAGCAGTTCTACCGCTTATATTCAACTGTCCTCTCTGACCTCAGAAGACTCCGCAGTGTATTA CTGCGCTCGCTACTAGGGGTGCCCATTGGGTCAGGGAACATTGGTGACTGTTAGTGCT | 387 |
| | VL | GATGTTGTTATGACCCAAACTCCCCTGACACTTTTCTGTAACAATAGGTCAGCCTGCCTCTATCTCATGCAA GTCCTCACAGAGTCTGCTGCACTCTGATGGGAAGACTTATTTGAACTGGTTGCTCCAGCGCCCCGGACAGT CTCCTAAACGCCTGATTTATTTGGTGAGCAAGTTGGACAGTGGCGTACCAGACCGATTCACCGGATCTGGC TCCGGGACAGACTTTACTTTGAAAATAAGTCGTGTCGAGGCTGAGGATCTTGGCGTGTACTACTGCTGGCA GGGGACACACTTCCCCCAGACCTTTGGAGGTGGAACTAAGCTCGAAATCAAA | 388 |
| CD003 | VH | AAGTACAGCTTCAGCAGCCAGGAGCAGAACTTGTTAAGCCCGGTGCTTCTGTGAAGCTGTCCTGTAAAGCT AGTGGTTACACTTTCACTAGCTTTTGGATGCACTGGGTGAAACAGAGGCCAGGACAAGGCTTGGAGTGGAT TGGAGAGATATACCCTAGCAGCGGTGTGACCAACTACAATGAGAAGATTTAAGAATAAAGCCACCCTGACAG TTGATAAATCCTCACGGACAGCATACATGCAACTCTCATCTCTGACATCCGAGGACAGCGCCGTCTATTT TGTACCCCAAACTATTACTACGACGGCTTGTACTGGGGGCAGGGGACTTTGGTCACAGTGTCCGCT | 389 |
| | VL | GATGTGGTAATGACTCAAACACCACTTACACTCAGTGTAACTATCGGCCAACCTGCCAGCATCTCCTGCAA ATCCAGTCAGAGTCTTGTGTATACCAATGGCGAGACCTATCTCAACTGGCTTCTCCAGAGGCCAGGACAGT CTCCCAAAAGACTTATATATTTGGTGTCTAACTTGGACTCTGGTGTGCCCGATAGATTTTCAGGGTCTGGG TCTGGCACCGATTTTACATTGAAAATATCCAGGGTGGAAGCCGAAGACCTTGGAATATACTACTGTCTCCA ATCAACCCATTTTCCTCGCACATTCGGCGGCGGCACTAAACTCGAAATAAAG | 390 |
| CD004 | VH | CAGGTACAGCTCCAGCAACCAGGGGCAGAGTTGGTAAAGCCCGGAGCAGTGTCAAGCTCTCATGCAAGGC TTCCGGCTTCAGTTTCACCAGATACTGGATGAATTGGGTTAAACAGCGCCCAGGACGAGGGCTTGAATGGA TAGGTAGGATTCATCCCTCAGACTCAGCAAGTCAGTACAATCAGAAGTTTAAGTCCAAAGCAACACTGACA GTAGACAAAAGCAGCAGCACAGCTTACATTCAGTTGAGTAGCTTGACATCAGAGGATAGCGCAGTTTATTA TTGTGGCCGTAGTACAGAAGGGGCTTATTGGGGGCAAGGAACACTTGTCACAGTGAGTGCA | 391 |

TABLE 2-continued

Nucleotide sequences of heavy chain variable regions
(VHs) and light chain variable regions (VLs) of exemplary anti-CD138 antibodies

| Antibody | Chain | Nucleotide Sequence | SEQ ID NO |
|---|---|---|---|
| | VL | GATGTTGTTATGACCCAAACTCCCCTGACACTTTCTGTAACAATAGGTCAGCCTGCCTCTATCTCATGCAA<br>GTCCTCACAGAGTCTGCTGCACTCTGATGGGAAGACTTATTTGAACTGGTTGCTCCAGCGCCCCGGACAGT<br>CTCCTAAACGCCTGATTTATTTGGTGAGCAAGTTGGACAGTGGCGTACCAGACCGATTCACCGGATCTGGC<br>TCCGGGACAGACTTTACTTTGAAAATAAGTCGTGTCGAGGCTGAGGATCTTGGCGTGTACTACTGCTGGCA<br>GGGGACACACTTCCCCCAGACCTTTGGAGGTGGAACTAAGCTCGAAATCAAA | 388 |
| CD005 | VH | CAAGTTCAATTGCAGCAGCCTGGTGCTGAGCTGGTGAAGCCAGGTGCAAGTGTTAAACTTTCATGCAAGGC<br>AAGCGGATTCTCCTTCATCACTTATTGGATGAATTGGATCAAACAACGTCCTGGGCGGGGCCTGGAGTGGA<br>TTGGTCGCATACACCCATCTGACTCCGCTACCCAATATGACCAGAAATTCAAAACCAAAGCAACCCTCACT<br>GTGGATAAAAGCAGCAGCACCGCATACATACAACTCAGCTCCCTCACTTCCGAGGACTCTGCCGTTTACTA<br>TTGCGCACGAAGCACTGAAGGGGCTCATTGGGGTCCAGGAACATTGGTAACAGTCAGCGCA | 392 |
| | VL | GATGTGGTAATGACTCAAACACCACTTACACTCAGTGTAACTATCGGCCAACCTGCCAGCATCTCCTGCAA<br>ATCCAGTCATAGCTTGTTGTATACCAATGGCGAGACCTATCTCAACTGGCTTCTCCAGAGGCCAGGACAGT<br>CTCCCAAAGACTTATATATTTGGTGTCTAACTTGGACTCTGGTGTGCCCGATAGATTTTCAGGGTCTGGG<br>TCTGGCACCGATTTTACATTGAAAATATCCAGGGTGGAAGCCGAAGACCTTGGAATATACTACTGTCTCCA<br>ATCAACCCATTTTCCTCGCACATTCGGCGGCGGCACTAAACTCGAAATAAAG | 390 |
| CD006 | VH | GAAATACAGCTTCAGCAGTCAGGCACTGAACTGGTGAAACCCGGTGCTTCAGTGAAGATTTCCTGTAAGAC<br>CAGTGGTTACAGTTTCACTGATTACAACATGAACTGGGTGAAACAATCCCACGGAAAAAGTCTCGAATGGA<br>TAGGTAATATAAACCCTTATTACGAAGCACCGGCTACACTCAGAATTTTGAAGGTAAGGCTACTTTGACC<br>GTGGATAAATCTTCTAGTACAGCATATATGCAGCTTAACTCACTTACTTCTGAGGACAGCGCCTTGTACTA<br>CTGCGCTCGTGAAGGGCATGACTACTACGCTATGGACTACTGGGGTCAAGGCACATCTGTCACAGTCAGCT<br>CA | 393 |
| | VL | GATGTTGTTATGACCCAAACTCCCCTGACACTTTCTGTAACAATAGGTCAGCCTGCCTCTATCTCATGCAA<br>GTCCTCACAGAGTCTGCTGCACTCTGATGGGAAGACTTATTTGAACTGGTTGCTCCAGCGCCCCGGACAGT<br>CTCCTAAACGCCTGATTTATTTGGTGAGCAAGTTGGACAGTGGCGTACCAGACCGATTCACCGGATCTGGC<br>TCCGGGACAGACTTTACTTTGAAAATAAGTCGTGTCGAGGCTGAGGATCTTGGCGTGTACTACTGCTGGCA<br>GGGGACACACTTCCCCCAGACCTTTGGAGGTGGAACTAAGCTCGAAATCAAA | 388 |
| 602 | VH | CAGGTCCAACTTCAGCTGCCCGGAGCTGAACTGGTAAAACCCGGTGCTTCCGTTAAGGTGTCTTGCAAAGC<br>ATCAGGCTACACATTTACTAGCTACTGGATGCACTGGGTAAAGCAACGTCCAGGTCAGGGCCTTGAATGGA<br>TCGGTCGTATACATCCTCAGACTCAGATACCAATTACAATCAAAACTTTAAGGGTAAAGCTACTTTGATT<br>GTCGATAAGTCTTCTTCAACTGCATACATGCAGTTGTTCTTCTTACATCCGAGGACAGTGCAGTGTATTA<br>CTGCGCTACAGGTTTCTCTTTTTGGGGACAGGGAACCCTCGTAACCGTGAGTGCC | 394 |
| 603 | VH | CAGGTACAAGTGCAGGTGCCAGGAGCTGAGTTGGTCAAGCCAGGCGCTAGTGTGAAAGTCTCATGTAAGGC<br>CAGCGGCTATACTTTCACTAGTTACTGGATGCACTGGATGAAGAAGAACCCGGACAGGGCTCGAATGGA<br>TAGGGCGAATCCACCCATCTGACAGCGATACAAATTACAACCAGAACTTTAAAGGAAAGGCAACACTTACA<br>GTTGATAAGTCTAGCAGCACAGCATACATGCAGCTTAGTTCACTCACATCAGAAGATTCCGCTGTCTATTT<br>TTGTGCTACTGGTTTCAGCTTTTGGGGTCAGGGAACTCTCGTAACTGTGTCCGCA | 395 |
| | VL | GATGTCGTTATGACCCAGACTCCATTGACTCTGTCTGTCACCATAGGACAACCCGCATCTATCTCCTGCAA<br>ATCATCACAGAGCTTGCTGTATTCTGACGGAAAGACATATTTGAACTGGCTGCTCCAACGGCCTGGGGAGT<br>CCCCTAAACTCCTTATCTATCTCGTTTCTAAACTTGACAGTGGCGTCCCTGATCGTTTTACCGGCTCCGGG<br>TCTGGCACTGATTTTACACTCAAGATCAGCCGGGTGGAAGCAGAGGATTTGGGTGTCTACTATTGTCTTCA<br>GACCACTTCCTTCCCATATACCTTCGGCGGCGGAACTAAATTGGAAATCAAA | 396 |
| 604 | VH | CAAGTCCAGTTGCAGCAGCCCGGTGCTGAGCTTGTCAAACCCGGCGCCTCAGTTAAAGTCTCATGCAAGGC<br>TTCTGGCTATAACTTTATAAATTACTGGATGCACTGGGTCAAACAGCGACCAGGACAGGGCCTCGAATGGA<br>TTGGTAGAATACACCCATCAGATAGTTACACTAATTACAATCGAAGTTTAAAGGTAAGGCAACACTGACT<br>GTGGACAAAAGCAGCTCAACTGCCTACATGCAGCTCAGTTCTCTCACCTCCGAGGATAGTGCTGTGTACTA<br>TTGTGCCAGTCCCATATCCACTCTTTATTGGGGCAGGGCACCACCTTGACCGTATCCTCA | 397 |
| | VL | GATGTCGTGATGACTCAAACTCCATTGACTCTGAGCGTCACTATTGGGCAACCTGCTAGTATATCATGCAA<br>GTCCTCTCAGTCTCTGTTGGACTCCGACGGGAAGACTTATCTCAACTGGTTGCTGCAACGTCCTGGTGAGA<br>GCCCCAAGCTCCTTATATACCTGGTATCAAAACTGGATTCTGGGGTTCCAGACCGTTTCACTGGGAGCGGG<br>AGCGGCACAGACTTTACCCTCAAGATTTCACGGGTAGAAGCTGAAGACCTGGGAGTGTATTACTGCCTTCA<br>AGCCACACATTTTCCTCAAACATTTGGGGGTGGTACTAAGCTGGAAATTAAG | 398 |
| 607 | VH | CAAGTTCAGTTGCAGCTTCCTGGAGCTGAGTTGGTTCGGCCAGGTACATCAGTTAAAGTAAGCTGCAAAGC<br>AAGCGACTACACCTTCACCACATATTGGATGCACTGGGTCAAACAGCGGCCTGGACAGGGGCTGGACTGGA<br>TCGGGAGGATACATCCTAGCGATTCTGATACTAACTACAATCAGAATTTCAAAGGTAAAGCCACACTCACT<br>GTGGACAAATCCTCTTCAACCGCTTACATGCACTTGTCATCCTTGACATCCGAGGACTCAGCAGTTTATTA<br>CTGCGCTACCGGTTTCAGCTTTTGGGGACAGGGTACTTTGGTGACAGTGAGCGCC | 399 |
| 613 | VH | CAGGTTCAAGTGCAACTCCCTGGTGCCGAACTTGTGAAGCCCGGAGCCAGTGTGAAGGTTAGCTGTAAGGC<br>CTCTGGGTACACATTTACTTCCTACTGGATGCACTGGGTAAAAAAGCGGCCAGGACAGGGACTCGAATGGA<br>TAGGACGTATTCACCCTTCCGACTCTGACACAAACTACAACCAAAACTTCAAAGGTAAAGCCACTCTCACC<br>GTAGACAAATCATCATCAACCGCATACATGCTCCTCTCATCCCTGACATCAGAAGACAGTGCTGTTTATTA<br>TTGCGCTACAGGGTTTAGTTTTTGGGGCCAAGGAACCTTGGTGACTGTGTCCGCA | 400 |
| | VL | GACGTGGTGATGACTCAGACACCTCTGACCCTGTCTGTAACCATTGGCCAGCCAGCCAGTATTAGTTGTAA<br>ATCATCTCAAAGTCTCCTCTACTCAGACGGCAAGACCTATTTGAACTGGTTGCTCCAGCGGCCAGGCGAAT<br>CACCCGAGCTGCTCATTTACTTGGTCTCCAAGATGATTCCGGTGTGCCAGATAGATTTCATGGTCACGGA<br>AGTGGGACAGCCTTCACAATGAAGATTTCCCGGATGGGCGGCGGTGGATTGGGAAACTATTACTGTCTCCC<br>TCGTACCTCCTTCCCTTACACTTTCGGTGGTGGGACAAAACTCGAGATAAAA | 401 |

TABLE 2-continued

Nucleotide sequences of heavy chain variable regions
(VHs) and light chain variable regions (VLs) of exemplary anti-CD138 antibodies

| Antibody | Chain | Nucleotide Sequence | SEQ ID NO |
|---|---|---|---|
| 614 | VH | CAAGTGCAGTTGCAGCTCCCCGGTGCCGAACTCGTAAAACCCGGCGCAAGCGTGAAAGTTTCCTGTAAGGC ATCCGGCTATACATTCATATCATATTGGATGCATTGGGTCAAACAGCGTCCTGGGCAGGGTCTTGAATGGA TTGGGCGGATACATCCATCTGACAGTGATACCAACTACAATCAAAATTTTAAAGGGAAGGCCACCCTCACA GTTGACAAGTCTAGTAATACAGCCTACATGCAGCTTTCTAGCCTGACTAGCGAGGATTCTGCTGTTTACTA CTGTGCAACCGGATTCAGTTTTTGGGGACAAGGAACTTTGGTGACAGTATCCGCC | 402 |
| | VL | GACGTGGTGATGACCCCAACATCACTTCATTTGCTTGTTACTATAGGGCAACCCGGCTTTTTGTTCTGTAA AAGTTCACAGAATCTCCTCTACAATGAAGGAAAAACATACTTGAAGTGGCTTTTGCCTGAGCCAGGTGCTT TCTCCAAGGTACTTATATACCTTGTCTTCAAGATGGGATTTGGGGTTCCTGATCGCTTCCACGGCCACGGA TCTGGCACCGACTTCCCTATGAAAATAAGCCGAATGGGAGGGGGCGGCCTTGGGGGCTACCTTTGCCTTCC CTCTACCCCCTTTCCTTATACCTTCGGCGGGGGTACTAAACTTGAAATAAAA | 403 |
| 616 | VH | CAGATCCACTTGGTACAGTCTGGACCTGAGCTGAAGAAGCCTGGAGAGACAGTCAGGATCTCCTGCAAGGC TTCTGGGTATACCTTCACAACCTATGGAATGAGCTGGGTGAAGCAGGCTCCAGGAAAGGCTTTAAAGTGGA TGGGCTGGATAAACACCTACTCTGGAGTGCCAACATATGCTGATGACTTCAAGGGACGGTTTGCCTTCTCT TTGGAAACCTCTGCCAGCACTGCCTATTTGCAGATCAACAACCTCAAAAATGAGGACACGGCTACATATTT CTGTACAAGAGAGGGATCTACTATGGTTACGAGGTACTACTTTGACTACTGGGGCCAAGGCACCACTCTCA CAGTCTCCTCA | 404 |
| | VL | GACATTGTTATGACCCAAGCCGCCCCAAGCGTACCAGTTACTCCTGGCGAGAGTGTCTCCATTAGTTGTCG GTCTTCAAAAAGTTTGCTCCACTCCAATGGGAATACTTACCTTTATTGGTTCCTTCAGCGTCCTGGTCAAT CTCCACAGCTGCTGATTTATCGAATGAGTAACCTGGCCTCAGGAGTCCCTGATCGCTTCAGTGGTTCAGGG TCCGGTACTGCCTTTACACTTAGGATCTCCAGGGTAGAAGCCGAGGATGTAGGCGTCTACCATTGTATGCA ACATCTCGAATCACCCTATACTTTCGGTGGAGGTACAAAACTCGAAATAAAA | 405 |
| 617 | VH | CAAGTACAACTGCAACTCCCAGGCGCCGAGTTGGTTAAACCTGGCGCTTCAGTGAAGGTATCCTGCAAAGC ATCTGCCTACACTTTCACATCTTACTGGATGCACTGGGTAAAACAGCGACCAGGGCAGGGACTTGAATGGA TTGGACGCATTCATCCTTCCGATAGCGACACTAACTATAACCAAAATTTTAAGGGGAAGGCCACCTTGACT GTGGATAAATCTAGCAACACAGCCTACATGCAACTCAGTTCACTGACTTCTGAGGATTCTGCCGTTTATTA TTGTGCCACAGGCTTCTCCTTCTGGGGGCAAGGAACCTTGGTGACCGTGTCAGCT | 406 |
| | VL | GACATAGTAATGACTCAAAGCCACAAATTCATGTCCACCAGTGTTGGTGACCGCGTATCAATCACTTGCAA GGCCAGTCAGGACGTATCCACAACAGTTGCATGGTATCAGCAAAAGCCAGGACAATCACCCAAACTTCTGA TTTACAGTGCCAGTTATCGATACACTGGGGTTCCCGACAGATTCACAGGATCAGGCAGCGGAACTGATTTT ACCTTCACCATTAGCTCAGTGCAAGCCGAAGATCTGGCCGTGTATTATTGTCAACAGCACTATAGTACCAG GCCCACCTTCGGCGGGGGAACTAAATTGGAAATAAAG | 407 |
| 691 | VH | CAGATCCAGTTGGTACAGTCTGGACCTGAGCTGAAGAAGCCTGGAGAGACAGTCAAGATCTCCTGCAAGGC TTCTGGGTATACCTTCACAACCTATGGAATGAGCTGGGTGAAACAGGCTCCAGGAAAGGGTTTAAAGTGGA TGGGCTGGATAAACACCTACTCTGGAGTGCCAACATATGCTGATGACTTCAAGGGACGGTTTGCCTTCTCT TTGGAAACCTCTGCCAGCACTGCCTATTTGCAGATCAACAACCTCAAAAATGAGGACACGGCTACATATTT CTGTGCAAGAGAGGGATCTACTATGGTTACGAGGTACTACTTTGACTACTGGGGCCAAGGCACCACTCTCA CAGTCTCCTCA | 408 |
| | VL | GATATTGTGATGACCCAAGCTGCCCCCTCCGTCCCCGTCACACCCGGTGAGTCCGTGTCTATAAGCTGTCG TAGTTCCAAGAGCTTGCTTCACTCAAATGGCAATACATACCTTTATTGGTTCCTGCAACGCCCCGGCCAGA GCCCACAGGTGTTGATTTATCGTATGTCAAACCTGGCCTCCGGCGTTCCCGACAGGTTTTCCGGCAGTGGA AGCGGGACCGCATTTACACTGCGAATATCTCGTGTTGAGGCAGAAGACGTTGGAGTCTATTACTGTATGCA ACACCTCGAAAGCCCATACACTTTCGGCGGTGGGACTAAGCTGGAAATTAAA | 409 |
| 623 | VH | CAGATCCAGTTGGTTCAGTCTGGACCTGAGCTGAAGAAGCCTGGAGAGACAGTCAAGATCTCCTGCAAGGC TTCTGGGTATACCTTCACAACCTATGGAATGAGCTGGGTGAAACAGGCTCCAGGAAAGGGTTTAAAGTGGA TGGGCTGGATAAACACCTACTCTGGAGTGCCAACATATGCTGATGACTTCAAGGGACGGTTTGCCTTCTCT TTGGAAACCTCTGCCAGCACTGCCTATTTGCAGATCAACAACCTCAAAAATGAGGACACGGCTACGTTTTT CTGTGCAAGAGAGGGATCTACTATGGTTACGAGGTACTACTTTGACTACTGGGGCCAAGGCACCACTCTCA CAGTCTCCTCA | 410 |
| | VL | GATATTGTCATGACCCAGGCAGCCCCCAGTGTCCCCGTGACTCCTGGAGAAAGTGTTAGTATTAGCTGTCG ATCAAGTAAATCACTTCTTCATAGTAACGGAAATACTTACTTGTATTGGTTCCTCCAAAGGCCAGGCCAGT CTCCACAGTTGCTCATCTATCGCATGAGTAATCTTGCTTCAGGTGTGCCTGATCGCTTCAGTGGCAGTGGA TCAGGTACTGCTTTCACACTCCGTATAAGTAGGGTGGAAGCCGAGGATGTCGGTGTCTACTATTGTATGCA GCACCTGGAGTATCCCTCAACATTTGGTGGGGGACAAAACTGGAGATTAAG | 411 |
| 624 | VH | CAAGTCCAGGTGCAACTGCCTGGCGCCGAACTTGTGAAACCCGGAGCCTCCGTTAAGGTCTCCTGCAAGGC TAGTGGCTATACCTTTACATCTTATTGGATGCACTGGGTGAAAAAACGCCCAGGGCAGGGCCTCGAATGGA TCGGCCGCATCCACCCATCTGATAGCGACACTAACTATAACCAGAACTTTAAAGGCAAGGCTACTCTGACC GTTGACAAAAGCAGTTCCACTGCCTACATGCAACTGACATCCCTTACCAGTGAGGATTTCGCCGTGTACTA CTGCTCCACAGGGTTCTCCTTCTGGGGCCAGGGGACCCTTGTTACCGTGTCCGCA | 412 |
| | VL | GATGTCGTTATGACCCAGACTCCATTGACTCTGTCTGTCACCATAGGACAACCCGCATCTATCTCCTGCAA ATCATCACAGAGCTTGCTGTATTCTGACGGAAAGACATATTTGAACTGGCTGCTCCAACGGCCTGGGGAGT CCCCTAAACTCCTTATCTATCGTTTCTAAACTTGACAGTGGCGTCCCTGATCGTTTTACCGGCTCCGGG TCTGGCACTGATTTTACACTCAAGATCAGCCGGGTGGAAGCAGAGGATTGGGTGTCTACTATTGTCTTCA GACCACTTACTTCCCATATACCTTCGGCGGCGGAACTAAATTGGAAATCAAA | 413 |
| 1610 | VH | CAAGTTCAGTTGCACCAACCTGGTACAAGCCTCGTTAAGCCCGGTGCGAGTGTCAAACTTAGCTGCAAAGC ATCTGGTTACAATTTTTCCAGTTATTACATGCACTGGGTTAAACAGCGGCCCGGCCAAGGACTGGAGTGGA TCGGAACCATCCACCCCTCAGACTCAACTACGAACTGCAATCAGAAGTTCAAGGGGAAGGCCACGCTTACC GTGGACAAGTCAAGTAGGACTGCTTACATGCAACTCAATAGCTTGACATTCGAGGATTCCGCGGTCTATTA TTGTGCGAATTTCGTCTATTGGGGACAAGGTACCAGCGTGACGGTCTCCAGC | 414 |

TABLE 2-continued

Nucleotide sequences of heavy chain variable regions
(VHs) and light chain variable regions (VLs) of exemplary anti-CD138 antibodies

| Antibody | Chain | Nucleotide Sequence | SEQ ID NO |
|---|---|---|---|
|  | VL | GACATTGTTATTACGCAAGACGAGCTGTCAAACCCTGTTACGAGTGGTGATTCTGTATCCATATCCTGTCG<br>CTCCTCAAAAAGTCTGTTGTACAAGGATGGAAAAACTTATCTGAACTGGTTTCTGCAACGGCCAGGCCAAT<br>CTCCTCAATTGCTTATATACGTCGTTTCAACGAGAGCCTCAGGAGTGTCTGACAGATTTTCCGGCTCCGGC<br>TCTGGGACCGATTTTACTCTCGAAATCAGCCGGGTTAAGGCCGAAGACGTTGGTGTGTATTATTGCCAACA<br>GCTCGTAGAGTACCCATATACATTCGGCGGGGGCACAAAACTCGAAATAAAG | 415 |
| 2510 | VH | CAAGTTCAGTTGCACCAACCTGGTACAAGCCTCGTTAAGCCCGGTGCGAGTGTCAAACTTAGCTGCAAAGC<br>ATCTGGTTACAATTTTTCCAGTTATTACATGCACTGGGTTAAACAGCGGCCCGGCCAAGGACTGGAGTGGA<br>TCGGAACCATCCACCCCTCAGACTCAACTACGAACTACAATCAGAAGTTCAAGGGGAAGGCCACGCTTACC<br>GTGGACAAGTCAAGTAGGACTGCTTACATGCAACTCAATAGCTTGACATTCGAGGATTCCGGTCTATTA<br>TTGTGCGAATTTCGTCTATTGGGGACAAGGTACCAGCGTGACGGTCTCCAGC | 416 |
|  | VL | GACATTGTTATTACGCAAGACGAGCTGTCAAACCCTGTTACGAGTGGTGATTCTGTATCCATATCCTGTCG<br>CTCCTCAAAAAGTCTGTTGTACAAGGATGGAAAAACTTATCTGAACTGGTTTCTGCAACGGCCAGGCCAAT<br>CTCCTCAATTGCTTATATACGTCGTTTCAACGAGAGCCTCAGGAGTGTCTGACAGATTTTCCGGCTCCGGC<br>TCTGGGACCGATTTTACTCTCGAAATCAGCCGGGTTAAGGCCGAAGACGTTGGTGTGTATTATTGCCAACA<br>GCTCGTAGAGTACCCATATACATTCGGCGGGGGCACAAAACTCGAAATAAAG | 415 |
| 2610 | VH | CAAGTTCAGTTGCACCAACCTGGTACAAGCCTCGTTAAGCCCGGTGCGAGTGTCAAACTTAGCTGCAAAGC<br>ATCTGGTTACAGCTTTTCCAGTTATTACATGCACTGGGTTAAACAGCGGCCCGGCCAAGGACTGGAGTGGA<br>TCGGAACCATCCACCCCTCAGACTCAACTACGAACTGCAATCAGAAGTTCAAGGGGAAGGCCACGCTTACC<br>GTGGACAAGTCAAGTAGGACTGCTTACATGCAACTCAATAGCTTGACATTCGAGGATTCCGCGGTCTATTA<br>TTGTGCGAATTTCGTCTATTGGGGACAAGGTACCAGCGTGACGGTCTCCAGC | 417 |
|  | VL | GACATTGTTATTACGCAAGACGAGCTGTCAAACCCTGTTACGAGTGGTGATTCTGTATCCATATCCTGTCG<br>CTCCTCAAAAAGTCTGTTGTACAAGGATGGAAAAACTTATCTGAACTGGTTTCTGCAACGGCCAGGCCAAT<br>CTCCTCAATTGCTTATATACGTCGTTTCAACGAGAGCCTCAGGAGTGTCTGACAGATTTTCCGGCTCCGGC<br>TCTGGGACCGATTTTACTCTCGAAATCAGCCGGGTTAAGGCCGAAGACGTTGGTGTGTATTATTGCCAACA<br>GCTCGTAGAGTACCCATATACATTCGGCGGGGGCACAAAACTCGAAATAAAG | 415 |
| 2710 | VH | CAAGTTCAGTTGCACCAACCTGGTACAAGCCTCGTTAAGCCCGGTGCGAGTGTCAAACTTAGCTGCAAAGC<br>ATCTGGTTACACCTTTTCCAGTTATTACATGCACTGGGTTAAACAGCGGCCCGGCCAAGGACTGGAGTGGA<br>TCGGAACCATCCACCCCTCAGACTCAACTACGAACTGCAATCAGAAGTTCAAGGGGAAGGCCACGCTTACC<br>GTGGACAAGTCAAGTAGGACTGCTTACATGCAACTCAATAGCTTGACATTCGAGGATTCCGGTCTATTA<br>TTGTGCGAATTTCGTCTATTGGGGACAAGGTACCAGCGTGACGGTCTCCAGC | 418 |
|  | VL | GACATTGTTATTACGCAAGACGAGCTGTCAAACCCTGTTACGAGTGGTGATTCTGTATCCATATCCTGTCG<br>CTCCTCAAAAAGTCTGTTGTACAAGGATGGAAAAACTTATCTGAACTGGTTTCTGCAACGGCCAGGCCAAT<br>CTCCTCAATTGCTTATATACGTCGTTTCAACGAGAGCCTCAGGAGTGTCTGACAGATTTTCCGGCTCCGGC<br>TCTGGGACCGATTTTACTCTCGAAATCAGCCGGGTTAAGGCCGAAGACGTTGGTGTGTATTATTGCCAACA<br>GCTCGTAGAGTACCCATATACATTCGGCGGGGGCACAAAACTCGAAATAAAG | 415 |
| 2810 | VH | CAAGTTCAGTTGCACCAACCTGGTACAAGCCTCGTTAAGCCCGGTGCGAGTGTCAAACTTAGCTGCAAAGC<br>ATCTGGTTACAGCTTTTCCAGTTATTACATGCACTGGGTTAAACAGCGGCCCGGCCAAGGACTGGAGTGGA<br>TCGGAACCATCCACCCCTCAGACTCAACTACGAACTACAATCAGAAGTTCAAGGGGAAGGCCACGCTTACC<br>GTGGACAAGTCAAGTAGGACTGCTTACATGCAACTCAATAGCTTGACATTCGAGGATTCCGCGGTCTATTA<br>TTGTGCGAATTTCGTCTATTGGGGACAAGGTACCAGCGTGACGGTCTCCAGC | 419 |
|  | VL | GACATTGTTATTACGCAAGACGAGCTGTCAAACCCTGTTACGAGTGGTGATTCTGTATCCATATCCTGTCG<br>CTCCTCAAAAAGTCTGTTGTACAAGGATGGAAAAACTTATCTGAACTGGTTTCTGCAACGGCCAGGCCAAT<br>CTCCTCAATTGCTTATATACGTCGTTTCAACGAGAGCCTCAGGAGTGTCTGACAGATTTTCCGGCTCCGGC<br>TCTGGGACCGATTTTACTCTCGAAATCAGCCGGGTTAAGGCCGAAGACGTTGGTGTGTATTATTGCCAACA<br>GCTCGTAGAGTACCCATATACATTCGGCGGGGGCACAAAACTCGAAATAAAG | 415 |
| 2910 | VH | CAAGTTCAGTTGCACCAACCTGGTACAAGCCTCGTTAAGCCCGGTGCGAGTGTCAAACTTAGCTGCAAAGC<br>ATCTGGTTACACCTTTTCCAGTTATTACATGCACTGGGTTAAACAGCGGCCCGGCCAAGGACTGGAGTGGA<br>TCGGAACCATCCACCCCTCAGACTCAACTACGAACTACAATCAGAAGTTCAAGGGGAAGGCCACGCTTACC<br>GTGGACAAGTCAAGTAGGACTGCTTACATGCAACTCAATAGCTTGACATTCGAGGATTCCGGTCTATTA<br>TTGTGCGAATTTCGTCTATTGGGGACAAGGTACCAGCGTGACGGTCTCCAGC | 420 |
|  | VL | GACATTGTTATTACGCAAGACGAGCTGTCAAACCCTGTTACGAGTGGTGATTCTGTATCCATATCCTGTCG<br>CTCCTCAAAAAGTCTGTTGTACAAGGATGGAAAAACTTATCTGAACTGGTTTCTGCAACGGCCAGGCCAAT<br>CTCCTCAATTGCTTATATACGTCGTTTCAACGAGAGCCTCAGGAGTGTCTGACAGATTTTCCGGCTCCGGC<br>TCTGGGACCGATTTTACTCTCGAAATCAGCCGGGTTAAGGCCGAAGACGTTGGTGTGTATTATTGCCAACA<br>GCTCGTAGAGTACCCATATACATTCGGCGGGGGCACAAAACTCGAAATAAAG | 415 |
| 1409 | VH | GAAGTTCAATTGGTTGAGTCAGGGGGCGGTCTTGTTCAACCTAAAGGCTCCCTCAAGTTGTCCTGTGCAGC<br>CTCTGGATTTACGTTTAACACTTATGCTATGCACTGGGTTCGGCAAGCACCGGGAAAGGGCTCGAGTGGG<br>TGGCCCGCATTAGATCAAAATCATCCAACTATGCCACCTACTATGCCGATTCCGTGAAGGACAGATTCACA<br>ATATCACGCGATGATAGCCAAAGTATGCTCTATTTGCAAATGAATAATCTTAAAACCGAAGACACAGCTAT<br>GTATTATTGTGTCAGAGAGTTGAGACTTAGGTATGCTATGGATTACTGGGGCCAAGGTACTTCAGTGACCG<br>TTTCATCC | 421 |
|  | VL | GATATACTGATGACCCAAACTCCACTGACTCTGTCTGTCACCATCGGTCAGCCCGCATCAATCAGTTGTAA<br>ATCTAGTCAGTCCCTGCTGTATACTAACGGAAAGACTTATCTGAATTGGCTTTTGCAACGGCCCGGTCAAT<br>CACCCAAAAGGCTTATATACCTGGTAAGCAAGTTGGACAGTGGAGTTCCGGATCGCTTCAGTGGCTCTGGT<br>AGTGGGACAGATTTTACGCTCAAAATTAGTAGGGTGGAGGCCGAGGATCTTGGCGTCTATTATTGCCTCCA<br>ATCTACGCACTTTCCACTCACGTTTGGGGCCGGAACCAAACTCGAACTTAAA | 422 |

TABLE 4

The amino acid sequences of the heavy chain variable region (VH) and light chain variable region (VL) of antibody B-B4 are provided as follows. CDRs, defined according to the Kabat or Chothia system, are indicated.

| Antibody | Chain | Amino Acid Sequence | SEQ ID NO | Chothia CDR | SEQ ID NO | Kabat CDR | SEQ ID NO |
|---|---|---|---|---|---|---|---|
| BB4 | VH | QVQLQQSGSELMMPGASVKISCKATG YTFSNYWIEWVKQRPGHGLEWIGEIL PGTGRTIYNEKFKGKATFTADISSNT VQMQLSSLTSEDSAVYYCARRDYYGN FYYAMDYWGQGTSVTVSS | 423 | HCDR1<br>HCDR2<br>HCDR3 | GYTFSNY<br>LPGTGR<br>RDYYGNFYYAMDY | 425<br>426<br>427 | HCDR1 NYWIE<br>HCDR2 EILPGTGRTIYNEKFKG<br>HCDR3 RDYYGNFYYAMDY | 431<br>432<br>427 |
|  | VL | DIQMTQSTSSLSASLGDRVTISCSAS QGINNYLNWYQQKPDGTVELLIYYTS TLQSGVPSRFSGSGSGTDYSLTISNL EPEDIGTYYCQQYSKLPRTFGGGTKL EIK | 424 | LCDR1<br>LCDR2<br>LCDR3 | SASQGINNYLN<br>YTSTLQS<br>QQYSKLPRT | 428<br>429<br>430 | LCDR1 SASQGINNYLN<br>LCDR2 YTSTLQS<br>LCDR3 QQYSKLPRT | 428<br>429<br>430 |

TABLE 5

Nucleotide sequences of heavy chain variable regions (VHs) and light chain variable regions (VLs) of antibody B-B4

| Antibody | Chain | Nucleotide Sequence | SEQ ID NO |
|---|---|---|---|
| BB4 | VH | CAGGTTCAGTTGCAGCAGTCTGGTTCCGAATTGATGATGCCAGGAGCTTCCGTGAAGATAAGCTGTAAG GCCACAGGTTACACTTTCAGTAACTATTGGATAGAATGGGTAAAGCAAAGACCTGGTCACGGTTTGGAA TGGATCGGGGAGATACTGCCTGGTACCGGCAGAACTATCTACAACGAGAAATTTAAGGGTAAAGCCACT TTTACAGCAGACATATCCAGTAATACAGTTCAAATGCAGCTGTCATCACTCACCAGTGAAGATAGCGCC GTGTATTACTGCGCCAGGCGCGATTATTACGGCAACTTTTATTATGCTATGGATTACTGGGGCCAAGGT ACTTCTGTAACTGTAAGCTCC | 433 |
|  | VL | GATATACAGATGACGCAGTCTACTTCTTCCCTCTCTGCGTCCCTTGGCGACCGGGTCACAATAAGCTGT TCTGCTTCCCAGGGTATAAATAACTACCTGAATTGGTATCAGCAAAAACCGGATGGGACGGTCGAACTC CTGATATATTACACATCTACACTTCAGTCTGGTGTCCCCTCTCGCTTTTCAGGTTCCGGTTCCGGCACT GATTATAGCCTTACAATTAGCAACCTCGAACCGGAGGACATCGGAACATATTATTGCCAGCAATATAGT AAACTGCCCAGGACGTTTGGCGGTGGCACCAAGTTGGAAATCAAA | 434 |

In an embodiment, the antibody molecule comprises one, two, or three CDRs of the VH region of an antibody molecule described herein, e.g., in Table 1, using the Kabat or Chothia definitions of CDRs. In an embodiment, the antibody molecule comprises one, two, or three CDRs of the VL region of an antibody molecule described herein, e.g., in Table 1, using the Kabat or Chothia definitions of CDRs. In an embodiment, the antibody molecule comprises one or more (e.g., two or three) CDRs of the VH region and one or more (e.g., two or three) CDRs of the VL region of an antibody molecule described herein, e.g., in Table 1, using the Kabat or Chothia definitions of CDRs.

In an embodiment, the antibody molecule comprises one, two, or three HCDRs described in Table 1. In an embodiment, the antibody molecule comprises one, two, or three LCDRs described in Table 1. In an embodiment, the antibody molecule comprises one or more (e.g., two or three) HCDRs and one or more (e.g., two or three) LCDRs described in Table 1.

In an embodiment, the antibody molecule comprises one, two, three, or four frameworks of the VH region of an antibody molecule described in Table 1. In an embodiment, the antibody molecule comprises one, two, three, or four frameworks of the VL region of an antibody molecule described in Table 1. In an embodiment, the antibody molecule comprises one or more (e.g., two, three, or four) frameworks of the VH region and one or more (e.g., two, three, or four) frameworks of the VL region of an antibody molecule described in Table 1.

In an embodiment, the antibody molecule comprises a VH of an antibody molecule described herein, e.g., in Table 1. In an embodiment, the antibody molecule comprises a VL of an antibody molecule described herein, e.g., in Table 1. In an embodiment, the antibody molecule comprises a VH and a VL of an antibody molecule described herein, e.g., in Table 1.

In an embodiment, the antibody molecule comprises a VH having an amino acid sequence described in Table 1, or an amino acid sequence substantially identical thereof (e.g., differing by no more than 1, 2, 3, 4, 5, 6, 7, 8, 9, 10, 11, 12, 13, 14, or 15 amino acid residues therefrom, or at least 85, 90, 95, or 99% identical thereto). In an embodiment, the antibody molecule comprises a VL having an amino acid sequence described in Table 1, or an amino acid sequence substantially identical thereof (e.g., differing by no more than 1, 2, 3, 4, 5, 6, 7, 8, 9, 10, 11, 12, 13, 14, or 15 amino acid residues therefrom, or at least 85, 90, 95, or 99% identical thereto). In an embodiment, the antibody molecule comprises a VH having an amino acid sequence described in Table 1 (or an amino acid sequence substantially identical thereof) and a VL having an amino acid sequences described in Table 1 (or an amino acid sequence substantially identical thereof).

In an embodiment, the antibody molecule comprises a VH encoded by a nucleotide sequence described in Table 2, or a nucleotide sequence substantially identical thereof (e.g., differing by no more than 3, 6, 15, 30, or 45 nucleotides therefrom, or at least about 85%, 90%, 95%, or 99% identical thereto). In an embodiment, the antibody molecule comprises a VL encoded by a nucleotide sequence described in Table 2, or a nucleotide sequence substantially identical thereof (e.g., differing by no more than 3, 6, 15, 30, or 45 nucleotides therefrom, or at least about 85%, 90%, 95%, or 99% identical thereto). In an embodiment, the antibody molecule comprises a VH encoded by a nucleotide sequence described in Table 2 (or a nucleotide sequence substantially identical thereof) and a VL encoded by a nucleotide sequence described in Table 2 (or a nucleotide sequence substantially identical thereof).

In an embodiment, the VH comprises one, two, or all of: (i) an HCDR1 comprising an amino acid sequence of GYNFSSY (SEQ ID NO: 350); (ii) an HCDR2 comprising an amino acid sequence of HPSDST (SEQ ID NO: 351); or (iii) an HCDR3 comprising an amino acid sequence of FVY; and the VL comprises one, two, or all of: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYNFSSY (SEQ ID NO: 350); (ii) an HCDR2 comprising an amino acid sequence of HPSDST (SEQ ID NO: 351); and (iii) an HCDR3 comprising an amino acid sequence of FVY; and the VL comprises: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNCNQKFKG (SEQ ID NO: 381); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSD-STTNCNQKFKG (SEQ ID NO: 381); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 291. In an embodiment, the VL comprises the amino acid sequence of SEQ ID NO: 292. In an embodiment, the VH comprises the amino acid sequence of SEQ ID NO: 291 and the VL comprises the amino acid sequence of SEQ ID NO: 292.

In an embodiment, the VH comprises one, two, or all of: (i) an HCDR1 comprising an amino acid sequence of GYNFSSY (SEQ ID NO: 350); (ii) an HCDR2 comprising an amino acid sequence of HPSDST (SEQ ID NO: 351); or (iii) an HCDR3 comprising an amino acid sequence of FVY; and the VL comprises one, two, or all of: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYNFSSY (SEQ ID NO: 350); (ii) an HCDR2 comprising an amino acid sequence of HPSDST (SEQ ID NO: 351); and (iii) an HCDR3 comprising an amino acid sequence of FVY; and the VL comprises: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSD-STTNYNQKFKG (SEQ ID NO: 382); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 293. In an embodiment, the VL comprises the amino acid sequence of SEQ ID NO: 292. In an embodiment, the VH comprises the amino acid sequence of SEQ ID NO: 293 and the VL comprises the amino acid sequence of SEQ ID NO: 292.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY; and the VL comprises one, two, or all of: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY; and the VL comprises three light chain complementarity determining regions (LCDR1, LCDR2, and LCDR3), wherein the VL comprises: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, VH comprises one, two, or all of: (i) an HCDR1 comprising an amino acid sequence of SYYMH (SEQ ID NO: 380); (ii) an HCDR2 comprising an amino acid sequence of TIHPSDSTTNCNQKFKG (SEQ ID NO: 381); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, VH comprises: (i) an HCDR1 comprising an amino acid sequence of SYYMH (SEQ ID NO: 380); (ii) an HCDR2 comprising an amino acid sequence of TIHPSDSTTNCNQKFKG (SEQ ID NO: 381); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 294. In an embodiment, the VL comprises the amino acid sequence of SEQ ID NO: 292. In an embodiment, the VH comprises the amino acid sequence of SEQ ID NO: 294 and the VL comprises the amino acid sequence of SEQ ID NO: 292.

In an embodiment, the VH comprises one, two, or all of: (i) an HCDR1 comprising an amino acid sequence of GYTFSSY (SEQ ID NO: 356); (ii) an HCDR2 comprising an amino acid sequence of HPSDST (SEQ ID NO: 351); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYTFSSY (SEQ ID NO: 356); (ii) an HCDR2 comprising an amino acid sequence of HPSDST (SEQ ID NO: 351); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNCNQKFKG (SEQ ID NO: 381); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNCNQKFKG (SEQ ID NO: 381); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 295. In an embodiment, the VL comprises the amino acid sequence of SEQ ID NO: 292. In an embodiment, the VH comprises the amino acid sequence of SEQ ID NO: 295 and the VL comprises the amino acid sequence of SEQ ID NO: 292.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 296. In an embodiment, the VL comprises the amino acid sequence of SEQ ID NO: 292. In an embodiment, the VH comprises the amino acid sequence of SEQ ID NO: 296 and the VL comprises the amino acid sequence of SEQ ID NO: 292.

In an embodiment, the VH comprises one, two, or all of: (i) an HCDR1 comprising an amino acid sequence of GYTFSSY (SEQ ID NO: 356); (ii) an HCDR2 comprising an amino acid sequence of HPSDST (SEQ ID NO: 351); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO:

353); or (iii) an LCDR3 comprising an amino acid sequence of QQLVEYPYT (SEQ ID NO: 354). In an embodiment, the VH comprises: (i) an HCDR1 comprising an amino acid sequence of GYTFSSY (SEQ ID NO: 356); (ii) an HCDR2 comprising an amino acid sequence of HPSDST (SEQ ID NO: 351); and (iii) an HCDR3 comprising an amino acid sequence of FVY; and the VL comprises: (i) an LCDR1 comprising an amino acid sequence of RSSKSLLY-KDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY; and the VL comprises one, two, or all of: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSD-STTNYNQKFKG (SEQ ID NO: 382); and (iii) an HCDR3 comprising an amino acid sequence of FVY; and the VL comprises: (i) an LCDR1 comprising an amino acid sequence of RSSKSLLYKDGKTYLN (SEQ ID NO: 352); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 297. In an embodiment, the VL comprises the amino acid sequence of SEQ ID NO: 292. In an embodiment, the VH comprises the amino acid sequence of SEQ ID NO: 297 and the VL comprises the amino acid sequence of SEQ ID NO: 292.

In an embodiment, the VH comprises one, two, or all of: (i) an HCDR1 comprising an amino acid sequence of GFTFNTY (SEQ ID NO: 357); (ii) an HCDR2 comprising an amino acid sequence of RSKSSNYA (SEQ ID NO: 358); or (iii) an HCDR3 comprising an amino acid sequence of ELRLRYAMDY (SEQ ID NO: 359); and the VL comprises one, two, or all of: (i) an LCDR1 comprising an amino acid sequence of KSSQSLLYTNGKTYLN (SEQ ID NO: 360); (ii) an LCDR2 comprising an amino acid sequence of LVSKLDS (SEQ ID NO: 304); or (iii) an LCDR3 comprising an amino acid sequence of LQSTHFPLT (SEQ ID NO: 361). In an embodiment, the VH comprises: (i) an HCDR1 comprising an amino acid sequence of GFTFNTY (SEQ ID NO: 357); (ii) an HCDR2 comprising an amino acid sequence of RSKSSNYA (SEQ ID NO: 358); and (iii) an HCDR3 comprising an amino acid sequence of ELRL-RYAMDY (SEQ ID NO: 359); and the VL comprises: (i) an LCDR1 comprising an amino acid sequence of KSSQSL-LYTNGKTYLN (SEQ ID NO: 360); (ii) an LCDR2 comprising an amino acid sequence of LVSKLDS (SEQ ID NO: 304); and (iii) an LCDR3 comprising an amino acid sequence of LQSTHFPLT (SEQ ID NO: 361).

In an embodiment, the VH comprises one, two, or all of: (i) an HCDR1 comprising an amino acid sequence of TYAMH (SEQ ID NO: 383); (ii) an HCDR2 comprising an amino acid sequence of RIRSKSSNYATYYADSVKD (SEQ ID NO: 384); or (iii) an HCDR3 comprising an amino acid sequence of ELRLRYAMDY (SEQ ID NO: 359); and the VL comprises one, two, or all of: (i) an LCDR1 comprising an amino acid sequence of KSSQSLLYTNGKTYLN (SEQ ID NO: 360); (ii) an LCDR2 comprising an amino acid sequence of LVSKLDS (SEQ ID NO: 304); or (iii) an LCDR3 comprising an amino acid sequence of LQSTHFPLT (SEQ ID NO: 361). In an embodiment, the VH comprises: (i) an HCDR1 comprising an amino acid sequence of TYAMH (SEQ ID NO: 383); (ii) an HCDR2 comprising an amino acid sequence of RIRSKSSNYATYY-ADSVKD (SEQ ID NO: 384); and (iii) an HCDR3 comprising an amino acid sequence of ELRLRYAMDY (SEQ ID NO: 359); and the VL comprises: (i) an LCDR1 comprising an amino acid sequence of KSSQSLLYTNGKTYLN (SEQ ID NO: 360); (ii) an LCDR2 comprising an amino acid sequence of LVSKLDS (SEQ ID NO: 304); and (iii) an LCDR3 comprising an amino acid sequence of LQSTHFPLT (SEQ ID NO: 361).

In an embodiment, the VH comprises the amino acid sequence of SEQ ID NO: 291. In an embodiment, the VL comprises the amino acid sequence of SEQ ID NO: 298. In an embodiment, the VH comprises the amino acid sequence of SEQ ID NO: 298 and the VL comprises the amino acid sequence of SEQ ID NO: 292.

In an embodiment, the anti-CD138 antibody molecule comprises:
(a) a heavy chain variable region (VH), wherein the VH comprises three heavy chain complementarity determining regions (HCDR1, HCDR2, and HCDR3), wherein the VH comprises one, two, or all of: (i) an HCDR1 comprising an amino acid sequence of G-F/Y-S/T-F-T/I-A/T/S/R/T/D-H/Y/F; (ii) an HCDR2 comprising an amino acid sequence of D/H/Y/N-P-N/S/Y-T/D/S/Y-G/S-S/A/V; or (iii) an HCDR3 comprising an amino acid sequence of N/S/E-W/Y/G-H/X-D/X-Y/X-T/Y/X-D/E/A/X-G/F/M/X-P/A/L/D-Y/H (X=absent); and
(b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K-S-S-Q/H-S-L-L-D/H/Y-G/S/T-D/N-G-K/E-T-Y-L-N(SEQ ID NO: 435); (ii) an LCDR2 comprising an amino acid sequence of L-V-S-K/N-L-D-S(SEQ ID NO: 436); or (iii) an LCDR3 comprising an amino acid sequence of W/L-Q-G/S-T-H-F-P-R/Q-T (SEQ ID NO: 437).

In an embodiment, the anti-CD138 antibody molecule comprises:
(a) a heavy chain variable region (VH), wherein the VH comprises three heavy chain complementarity determining regions (HCDR1, HCDR2, and HCDR3), wherein the VH comprises one, two, or all of: (i) an HCDR1 comprising an amino acid sequence of A/T/S/R/D/N-H/Y/F-H/W/N/G-M-H/N/S; (ii) an HCDR2 comprising an amino acid sequence of E/R/N/W-I-D/H/Y/N-P/T-N/S/Y-T/D/S/Y-G/S-S/A/V/D/Y-T/S/P-T/Q/N/G-Y-N/D/T/A-Q/E/D-K/R/N/D-F-R/K/E-A/T/N/S/G; or (iii) an HCDR3 comprising an amino acid sequence of N/S/E-W/Y/G-H/X-D/X-Y/X-T/Y/X-D/E/A/X-G/F/M/X-P/A/L/D-Y/H (X=absent); and
(b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K-S-S-Q/H-S-L-L-D/H/Y-G/S/T-D/N-G-K/E-T-Y-L-N(SEQ ID NO:

435); (ii) an LCDR2 comprising an amino acid sequence of L-V-S-KIN-L-D-S(SEQ ID NO: 436); or (iii) an LCDR3 comprising an amino acid sequence of W/L-Q-G/S-T-H-F-P-R/Q-T (SEQ ID NO: 437).

In an embodiment, the antibody molecule comprises: (a) a VH comprising: (i) an HCDR1 comprising the amino acid sequence of the HCDR1 of an anti-CD138 antibody described herein, e.g., chosen from antibodies CD001, CD002, CD003, CD004, CD005, CD006, 602, 603, 604, 607, 613, 614, 617, 624, 632, 616, 619, or 623; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment the anti-CD138 antibody molecule comprises:
- (a) a heavy chain variable region (VH), wherein the VH comprises three heavy chain complementarity determining regions (HCDR1, HCDR2, and HCDR3), wherein the VH comprises three heavy chain complementarity determining regions (HCDR1, HCDR2, and HCDR3), wherein the VH comprises one, two, or all of: (i) an HCDR1 comprising an amino acid sequence of G-Y-N/S/T-F-S-S-Y (SEQ ID NO: 438); (ii) an HCDR2 comprising an amino acid sequence of H-P-S-D-S-T (SEQ ID NO: 351); or (iii) an HCDR3 comprising an amino acid sequence of F-V-Y; and
- (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of R-S-S-K-S-L-L-Y-K-D-G-K-T-Y-L-N (SEQ ID NO: 352); (ii) an LCDR2 comprising an amino acid sequence of V-V-S-T-R-A-S(SEQ ID NO: 353); or (iii) an LCDR3 comprising an amino acid sequence of Q-Q-L-V-E-Y-P-Y-T (SEQ ID NO: 354).

In an embodiment, the HCDR1 comprises an amino acid sequence chosen from any of SEQ ID NOS: 350, 355, or 356, the HCDR2 comprises the amino acid sequence of SEQ ID NO: 351, and the HCDR3 comprises the amino acid sequence of F-V-Y. In an embodiment, the LCDR1 comprises the amino acid sequence of SEQ ID NO: 352; the LCDR2 comprises the amino acid sequence of SEQ ID NO: 353; and the LCDR3 comprises the amino acid sequence of SEQ ID NO: 354.

In an embodiment, the anti-CD138 antibody molecule comprises:
- (a) a heavy chain variable region (VH), wherein the VH comprises three heavy chain complementarity determining regions (HCDR1, HCDR2, and HCDR3), wherein the VH comprises three heavy chain complementarity determining regions (HCDR1, HCDR2, and HCDR3), wherein the VH comprises one, two, or all of: (i) an HCDR1 comprising an amino acid sequence of S—Y-Y-M-H (SEQ ID NO: 380); (ii) an HCDR2 comprising an amino acid sequence of T-I-H-P-S-D-S-T-T-N-C/Y-N-Q-K—F-K-G (SEQ ID NO: 439); or (iii) an HCDR3 comprising an amino acid sequence of F-V-Y; and
- (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of R-S-S-K-S-L-L-Y-K-D-G-K-T-Y-L-N (SEQ ID NO: 352); (ii) an LCDR2 comprising an amino acid sequence of V-V-S-T-R-A-S(SEQ ID NO: 353); or (iii) an LCDR3 comprising an amino acid sequence of Q-Q-L-V-E-Y-P-Y-T (SEQ ID NO: 354).

In an embodiment, the HCDR1 comprises an amino acid sequence chosen from any of SEQ ID NO: 380, the HCDR2 comprises the amino acid sequence of SEQ ID NO: 381 or 382, and the HCDR3 comprises the amino acid sequence of F-V-Y. In an embodiment, the LCDR1 comprises the amino acid sequence of SEQ ID NO: 352; the LCDR2 comprises the amino acid sequence of SEQ ID NO: 353; and the LCDR3 comprises the amino acid sequence of SEQ ID NO: 354.

In an embodiment, the antibody molecule comprises: (a) a VH comprising: (i) an HCDR1 comprising the amino acid sequence of the HCDR1 of an anti-CD138 antibody described herein, e.g., chosen from antibodies 1610, 2510, 2610, 2710, 2810, 2910, or 1409; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment, the VH comprises the amino acid sequence of the VH of the anti-CD138 antibody and the VL comprises the amino acid sequence of the VL of the anti-CD138 antibody.

In an embodiment, the antibody molecule comprises two VHs and two VLs.

In an embodiment, the antibody molecule is a synthetic antibody molecule. In an embodiment, the antibody molecule is an isolated antibody molecule. In an embodiment, the antibody molecule is a humanized antibody molecule. In an embodiment, the antibody molecule comprises one or more framework regions derived from human framework germline sequence.

In an embodiment, the antibody molecule comprises a VH region comprising one or more mutations relative to an anti-CD138 antibody described herein (e.g., antibody CD001, CD002, CD003, CD004, CD005, CD006, 602, 603, 604, 607, 613, 614, 617, 624, 632, 616, 619, 623, 1610, 2510, 2610, 2710, 2810, 2910, or 1409). In an embodiment, the mutations comprise one or more substitutions relative to the VH sequence of antibody 1610. In an embodiment, the substitution is C60Y. In an embodiment, the substitution is N28S. In an embodiment, the substitution is N28T. In an embodiment, the substitutions are N28S and C60Y. In an embodiment, the substitutions are N28T and C60Y. In an embodiment, the mutated antibody molecule is expressed in transiently transfected HEK293 cells at levels equal to or greater than antibody 1610.

In an embodiment, the antibody molecule binds to the extracellular domain of CD138. In an embodiment, the antibody molecule binds to an extracellular region of CD138 proximal to the transmembrane domain. In an embodiment, the antibody molecule is capable of binding to one or more (e.g., two, three, or all) of the following peptides: a peptide comprising the amino acid sequence of ENTAVVAVE-PDRRNQSPVDQGATGASQGLLDRKEVLG (SEQ ID NO: 440), a peptide comprising the amino acid sequence of TAVVAVEPDRRNQSPVDQGATGASQ (SEQ ID NO: 441), a peptide comprising the amino acid sequence of ENTAVVAVEPDRRNQSPVDQGATG (SEQ ID NO: 442), or a peptide comprising the amino acid sequence of ENTAVVAVEPDRRNQ (SEQ ID NO: 443). In an embodiment, the antibody molecule is capable of binding to one or more (e.g., two or all) of the following peptides: a peptide comprising the amino acid sequence of ENTAVVAVEPDRRNQSPVDQGATGASQGLLDRKEVLG (SEQ ID NO: 440), a peptide comprising the amino acid sequence of RNQSPVDQGATGASQGLLDRKEVLG (SEQ ID NO: 444), or a peptide comprising the amino acid sequence of ENTAVVAVEPDRRNQ (SEQ ID NO: 443).

In an embodiment, the antibody molecule further binds to an extracellular region of CD138 distal to the transmembrane domain, e.g., a region corresponding to or proximal to the integrin binding domain (IBD) of CD138. In an embodiment, the antibody molecule is capable of binding to one or both the following peptides: a peptide comprising the amino acid sequence of ASTSTLPAGEGPKEGEAVVLPEVEPGLTAREQEA (SEQ ID NO: 10) or a peptide comprising the amino acid sequence of GEAVVLPEVEPGLTA (SEQ ID NO: 445).

In an embodiment, the antibody molecule is a synthetic antibody molecule. In an embodiment, the antibody molecule is an isolated antibody molecule. In an embodiment, the antibody molecule is a humanized antibody molecule. In an embodiment, the antibody molecule comprises one or more framework regions derived from human framework germline sequence.

In an embodiment, the antibody molecule is an IgG antibody. In an embodiment, the antibody molecule comprises a heavy chain constant region of IgG chosen from IgG1, IgG2, IgG3, or IgG4. In an embodiment, the antibody molecule comprises a light chain constant region of kappa or lambda light chain.

In an embodiment, the antibody molecule comprises an Fc region comprising one or more mutations to increase the binding affinity to neonatal receptor FcRn and/or the half-life of the antibody molecule. In an embodiment, the antibody molecule comprises an Fc region comprising one or more mutations described herein, e.g., to increase one or more of half-life, ADCC, CDC, or ADCP.

In an embodiment, the antibody molecule is an IgG antibody. In an embodiment, the antibody molecule comprises a heavy chain constant region of IgG chosen from IgG1, IgG2, IgG3, or IgG4. In an embodiment, the antibody molecule comprises a light chain constant region of kappa or lambda light chain.

In an embodiment, the antibody molecule comprises an Fc region comprising one or more mutations to increase the binding affinity to neonatal receptor FcRn and/or the half-life of the antibody molecule. In an embodiment, the antibody molecule comprises an Fc region comprising one or more mutations described herein, e.g., to increase one or more of half-life, ADCC, CDC, or ADCP.

In an embodiment, the antibody molecule further comprises a heavy chain constant region. In an embodiment, the heavy chain constant region is an IgG1 constant region or a functional portion thereof. In another embodiment, the heavy chain constant region is an IgG2 constant region or a functional portion thereof. In an embodiment, the antibody molecule further comprises a light chain constant region. In an embodiment, the antibody molecule further comprises a heavy chain constant region and a light chain constant region. In an embodiment, the antibody molecule comprises a heavy chain constant region, a light chain constant region, and heavy and light chain variable regions of an antibody molecule described in Table 1. In certain embodiments, the antibody molecule comprises a heavy chain constant region, a light chain constant region, and variable regions that comprise one, two, three, four, five, or six CDRs of an antibody molecule described in Table 1.

Exemplary heavy chain constant regions are described below.

IgG1 HC constant region:
(SEQ ID NO: 446)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

IgG2 HC constant region:
(SEQ ID NO: 447)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

In an embodiment, the antibody molecule is a multivalent (e.g., bivalent, trivalent, or tetravalent) antibody molecule. In an embodiment, the antibody molecule binds to two or more (e.g., three or four) different regions in CD138. For example, the antibody molecule can comprise two or more sets of identical, or substantially identical, VH-VL pairs, wherein each VH-VL pair binds to two or more different regions in CD138. As another example, the antibody molecule can comprise two or more sets of different VH-VL pairs, wherein each VH-VL pair binds to a different region in CD138.

In an embodiment, the antibody molecule is a multispecific (e.g., bispecific, trispecific, or tetraspecific) antibody molecule. In an embodiment, the antibody molecule has a first binding specificity to CD138 and a second binding specificity other than CD138. For example, the antibody molecule can comprise two or more sets of identical, or substantially identical, VH-VL pairs, wherein each VH-VL pair has both the first binding specificity and the second binding specificity. As another example, the antibody molecule can comprise two or more sets of different VH-VL pairs, wherein each VH-VL pair has a different binding specificity.

Antibody Molecule-Drug Conjugates

As used herein, the term "antibody molecule-drug conjugate" or ADC refers to an antibody molecule that is coupled to a non-antibody moiety, e.g., a therapeutic agent or label, e.g., a cytotoxic agent. The antibody molecule can be coupled to the non-antibody moiety directly, or indirectly, e.g., through a linker.

In an embodiment, the antibody molecule is coupled to the non-antibody moiety by a covalent bond. In an embodiment, the antibody molecule is coupled to the non-antibody moiety by a peptide bond. In an embodiment, the antibody molecule is coupled to the non-antibody moiety by a non-peptide bond. In an embodiment, the antibody molecule is not coupled to the non-antibody moiety by a non-peptide bond. In an embodiment, a non-antibody moiety is also referred to as a "payload."

In an embodiment, the non-antibody moiety is coupled to the backbone of the antibody molecule. In another embodiment, the non-antibody moiety is coupled to a side chain of the antibody molecule. In an embodiment, two or more (e.g., three, four, five, six, seven, eight, or more) non-antibody moieties are coupled to the antibody molecule.

In an embodiment, the ADC comprises an antibody molecule that binds to CD138, e.g., an anti-CD138 antibody molecule described herein.

In an embodiment, the ADC comprises one, two, or three CDRs of the VH region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409), using the Kabat or Chothia definitions of CDRs. In an embodiment, the ADC comprises one, two, or three CDRs of the VL region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409), using the Kabat or Chothia definitions of CDRs. In an embodiment, the ADC comprises one or more (e.g., two or three) CDRs of the VH region and/or one or more (e.g., two or three) CDRs of the VL region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409), using the Kabat or Chothia definitions of CDRs.

In an embodiment, the ADC comprises one, two, or three VH CDRs described in Table 1. In an embodiment, the ADC comprises one, two, or three VL CDRs described in Table 1. In an embodiment, the ADC comprises one or more (e.g., two or three) VH CDRs and/or one or more (e.g., two or three) VL CDRs described in Table 1.

In an embodiment, the ADC comprises one, two, three, or four frameworks of the VH region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409). In an embodiment, the ADC comprises one, two, three, or four frameworks of the VL region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409). In an embodiment, the ADC comprises one or more (e.g., two, three, or four) frameworks of the VH region and/or one or more (e.g., two, three, or four) frameworks of the VL region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409).

In an embodiment, the ADC comprises a heavy chain variable region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409). In an embodiment, the ADC comprises a light chain variable region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409). In an embodiment, the ADC comprises a heavy chain variable region and a light chain variable region of an antibody molecule described in Table 1 (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409).

In an embodiment, the ADC comprises a heavy chain variable region having an amino acid sequence described in Table 1. In an embodiment, the ADC comprises a light chain variable region having an amino acid sequence described in Table 1. In an embodiment, the ADC comprises a heavy chain variable region having an amino acid sequence described in Table 2 and a light chain variable region having an amino acid sequence described in Table 1.

In an embodiment, the antibody molecule comprises a heavy chain variable region encoded by a nucleotide sequence described in Table 2. In an embodiment, the antibody molecule comprises a light chain variable region encoded by a nucleotide sequence described in Table 2. In an embodiment, the antibody molecule comprises a heavy chain variable region encoded by a nucleotide sequence described in Table 2 and a light chain variable region encoded by a nucleotide sequence described in Table 2.

In an embodiment, the ADC comprises a heavy chain constant region. In an embodiment, the ADC comprises a light chain constant region. In an embodiment, the ADC comprises a heavy chain constant region and a light chain constant region. In an embodiment, the ADC comprises a heavy chain constant region, a light chain constant region, and heavy and light chain variable regions of an antibody molecule described in Table 1. In certain embodiments, the ADC comprises a heavy chain constant region, a light chain constant region, and variable regions that comprise one, two, three, four, five, or six CDRs of antibody molecule described in Table 1.

In an embodiment, the non-antibody molecule comprises a cytotoxic agent (e.g., any cytotoxic agent that is active against a cancer). In an embodiment, the cytotoxic agent is chosen from a tubulin polymerase inhibitor (e.g., an auristatin), an agent associated with tubulin depolymerization (e.g., a maytansine), an agent associated with DNA cleavage (e.g., a calicheamicin), a DNA minor groove alkylating agent (e.g., a duocarymycin), a DNA minor groove cross-linker (e.g., a PBD dimers), or an RNA polymerase II inhibitor (e.g., α-amanitin).

In an embodiment, the cytotoxic agent is α-amanitin. α-amanitin is a bicyclic octapeptide which belongs to a large group of protoplasmic mushroom toxins known as amatoxins. α-Amanitin binds to the bridging helix of RNA polymerase II inhibiting the translocation of RNA and DNA needed to empty the site for the next round of synthesis, thereby reducing the rate of transcription. α-amanitin and its use in ADCs are described, e.g., in Moldenhauer et al. *J Natl Cancer Inst.* 2012; 104(8): 622-634. The structure of α-amanitin is as follows:

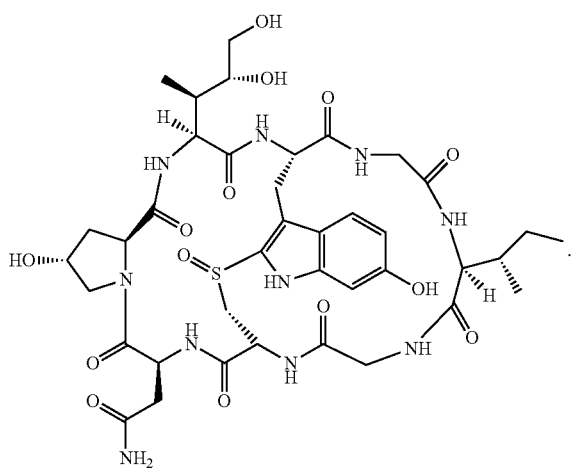

In an embodiment, the cytotoxic agent is a cryptophycin analog. The cryptophycins are a group of cyanobacterial depsipeptides with a remarkable biological activity against multi-drug-resistant (MDR) cancer cells. Cryptophycins deplete microtubules through interaction with tubulin, thereby preventing cell division. They are capable of inducing apoptosis, possibly through other mechanisms in addition to that mediated by microtubule inhibition. Cryptophycin, analogues, and their uses in ADCs are described, e.g., in Shih & Teicher. *Curr Pharm Des.* 2001; 7(13): 1259-1276; Eggen & Georg. *Med Res Rev.* 2002; 22(2): 85-101. The structure of a cryptophycin analog is as follows:

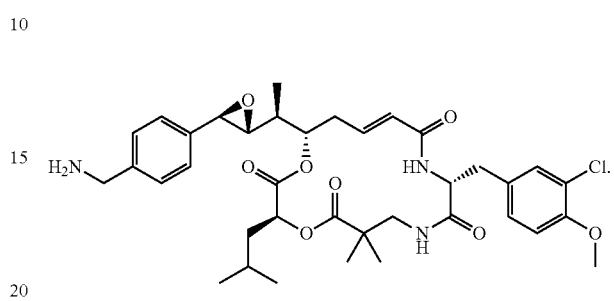

In an embodiment, the cytotoxic agent is calicheamicin (also known as LL-E33288).

Calicheamicin contacts DNA and causes the Bergman cyclization, which results in cleaving the DNA and thus destroying cells. Calicheamicin and its use in ADCs is described, e.g., in Maiese et al. *J Antibiot* (Tokyo). 1989; 42(4): 558-563; Watanabe et al. *Chem Biol.* 2002; 9(2): 245-251; Ricart & Tolcher. *Nat Clin Pract Oncol.* 2007; 4: 245-255. The structure of calicheamicin is as follows.

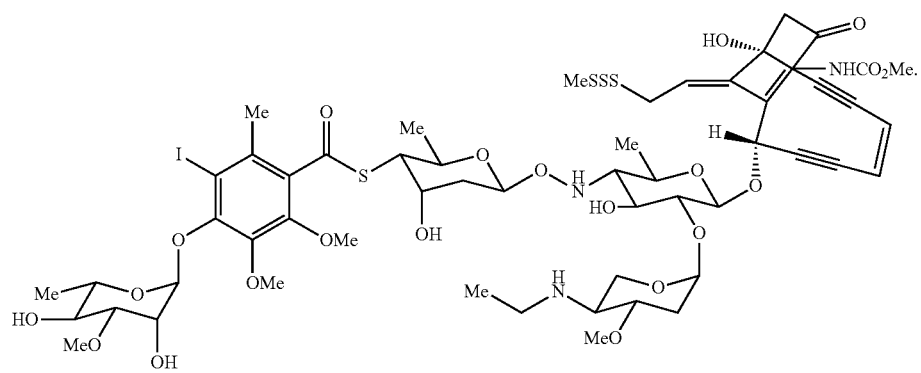

In an embodiment, the cytotoxic agent is centanamycin. Centanamycin is also known as ML-970, AS-I-145, NSC 716970, or N-[4-Amino-1-(2-chloroethyl)-2-naphthyl]-5,6,7-trimethoxy-1H-indole-2-carboxamide). Centanamycin binds the A-T-rich DNA minor groove and alkylates DNA. Centanamycin and its use in ADCs is described, e.g., in Rayburn et al. *Cancer Chemother Pharmacol.* 2012; 69(6): 1423-31.

In an embodiment, the cytotoxic agent is a dolastatin. In an embodiment, the dolastatin is dolastatin 10 or dolastatin 15. Dolastatins noncompetitively inhibit binding of vincristine to tubulin at the *vinca*/peptide region). Analogues of dolastatins include, e.g., symplostatin 1, symplostatin 3, and auristatin. Dolastatins, analogues, and their uses are described, e.g., in Amador et al. *Annals of Oncology.* 2003; 14: 1607-1615; Kijjoa & Sawangwong. *Mar Drugs.* 2004; 2(2): 73-82; Luesch et al. *J Nat Prod.* 2001; 64(7): 907-910; Luesch et al. *J Nat Prod.* 2002; 65(1): 16-20. The structure of dolastatin 10 is as follows:

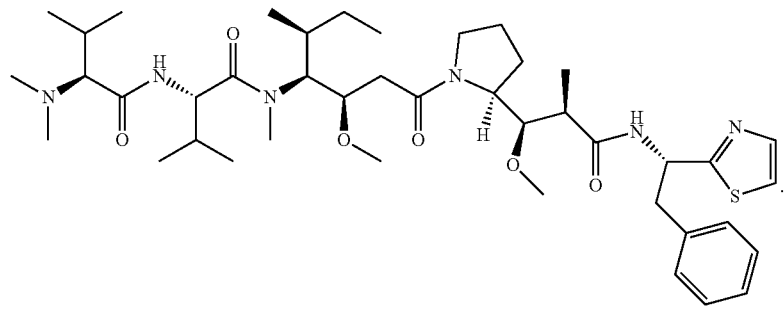 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C)C(C)C]

The structure of dolastatin 15 is as follows:

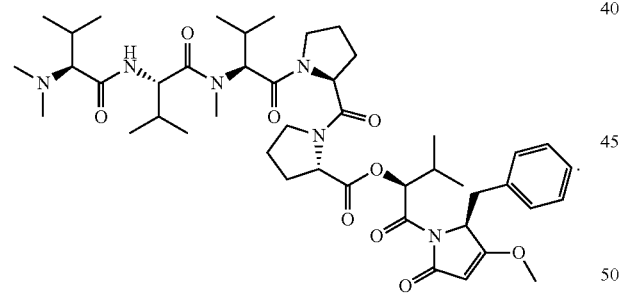

In an embodiment, the cytotoxic agent is a duocarmycin analogue. Duocarmycin analogues are DNA minor groove, AT-sequence selective, and adenine-N3 alkylating agents. Duocarmycin, analogues, and their uses in ADCs are described, e.g., in Tietze & Krewer. *Chem Biol Drug Des.* 2009; 74(3):205-211; Cacciari et al. *Expert Opinion on Therapeutic Patents.* 2000; 10 (12): 1853-1871; Tercel et al. *Angew Chem Int Ed Engl.* 2013; 52(21): 5442-5446. Exemplary duocarmycin and analogues include, e.g., duocarmycin A, duocarmycin B1, duocarmycin B2, duocarmycin C1, duocarmycin C2, duocarmycin D, duocarmycin SA, and CC-1065. The structure of duocarymycin A is as follows:

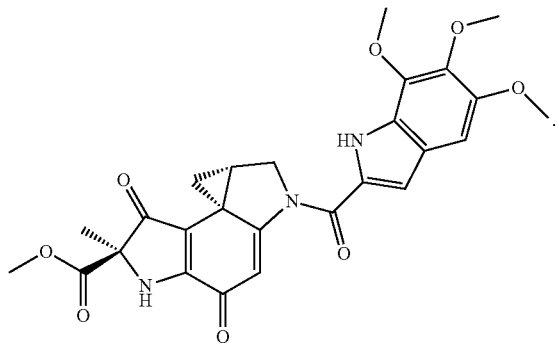

In an embodiment, the cytotoxic agent is maytansine. Maytansine, a benzoansamacrolide, is a highly potent microtubule-targeted compound that induces mitotic arrest and kills tumor cells at subnanomolar concentrations. Maytansine and its analogs (maytansinoids DM1 and DM4) are potent microtubule-targeted compounds that inhibit proliferation of cells at mitosis. Maytansine is described, e.g., in Lopus et al. *Mol Cancer Ther.* 2010; 9(10): 2689-2699; Widdison et al. *J Med Chem.* 2006; 49(14): 4392-4408; Liu et al. *J Mass Spectrom.* 2005; 40(3): 389-399; Tassone et al. *Cancer Res.* 2004; 64(13): 4629-4636; Sawada et al. *Bioconjug Chem.* 1993; 4(4):284-289. The structure of maytansine is as follows:

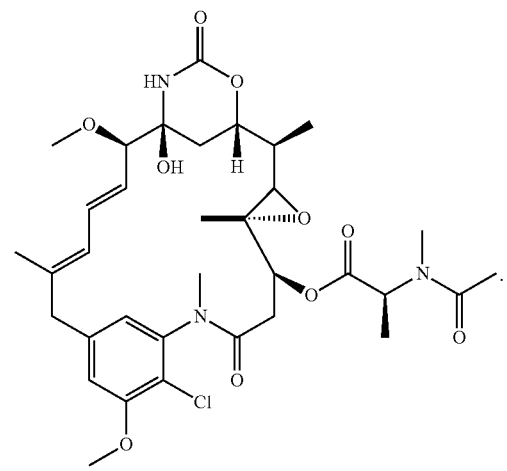

In an embodiment, the cytotoxic agent is monomethyl auristatin E (MMAE, vedotin). MMAE is a highly potent antimitotic agent that inhibits cell division by blocking the polymerization of tubulin. MMAE and its use in ADCs are described, e.g., in Francisco et al. *Blood.* 2003; 102(4):1458-1465; Junutula et al. *Nat Biotechnol.* 2008; 26(8):925-932; Asundi et al. *Clin Cancer Res.* 2011; 17(5): 965-975; Younes et al. *J Clin Oncol.* 2012; 30(18):2183-2189; Pettit et al. *Anticancer Drug Des.* 1995; 10(7): 529-544; Doronina et al. *Nat Biotechnol.* 2003; 21(7): 778-784. The structure of MMAE is as follows:

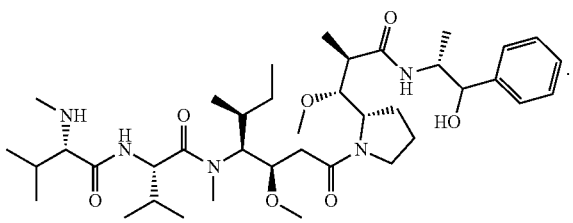 [SMILES: CC[C@H](C)[C@@H]([C@@H](CC(=O)N1CCC[C@H]1[C@H](OC)[C@@H](C)C(=O)N[C@H](C)C(O)c1ccccc1)OC)N(C)C(=O)[C@@H](NC(=O)[C@@H](NC)C(C)C)C(C)C]

In an embodiment, the cytotoxic agent is monomethyl auristatin F (MMAF). MMAF is an antitubulin agent that inhibits cell division by blocking the polymerization of tubulin. It is an auristatin derivative with a charged C-terminal phenylalanine that attenuates its cytotoxic activity compared to its uncharged counterpart, monomethyl auristatin E (MMAE). MMAF can induce potent antitumor effects when conjugated via protease cleavable linkers to a monoclonal antibody targeting internalizing, tumor-specific cell surface antigens. For example, the linker to the monoclonal antibody is stable in extracellular fluid, but can be cleaved by cathepsin once the conjugate has entered a tumor cell, thus activating the anti-mitotic mechanism. MMAF and its use in ADCs are described, e.g., in Smith et al. *Mol Cancer Ther.* 2006 5; 1474-1482; Doronina et al., *Bioconjug Chem.* 2006; 17(1):114-24; Oflazoglu et al. *Clin Cancer Res.* 2008; 14(19): 6171-6180; Nilsson et al. *Cancer.* 2010; 116(4 Suppl): 1033-1042. The structure of MMAF is as follows:

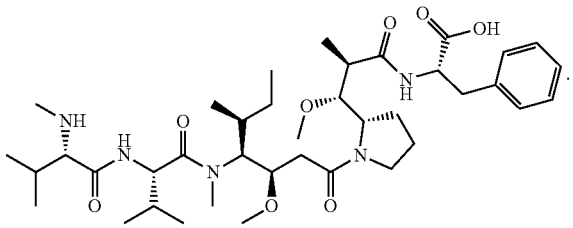 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

In an embodiment, the cytotoxic agent is a pyrrolobenzodiazepine (PBD). PBDs are a class of sequence-selective DNA minor-groove binding crosslinking agents. The mechanism of action of the PBDs is associated with their ability to form an adduct in the minor groove, thus interfering with DNA processing. Exemplary agents that belong to the pyrrolobenzodiazepine antibiotic group include, but are not limited to, anthramycin. abbeymycin, chicamycin, DC-81, mazethramycin, neothramycin A, neothramycin B, porothramycin, prothracarcin, sibanomicin (DC-102), sibiromycin, and tomamycin. PBDs and their use in ADCs are described, e.g., in Antonow & Thurston D E. *Chem Rev.* 2011; 111: 2815-2864; Cipolla et al. *Anticancer Agents Med Chem.* 2009; 9: 1-31; Gerratana. *Med Res Rev.* 2012; 32: 254-293; Li et al. *Appl Environ Microbiol.* 2009; 75(9): 2869-2878; Rahman et al. *Org. Biomol. Chem.* 2011; 9: 1632-1641; Saunders et al. *Sci Transl Med.* 2015; 7(302): 302ra136; Hu et al. *Chem Biol.* 2007; 14(6):691-701. The structure of PBD is as follows:

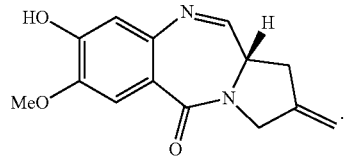 [SMILES: C=C1C[C@H]2C=Nc3cc(O)c(OC)cc3C(=O)N2C1]

In an embodiment, the ADC further comprises a linker, e.g., a linker that couples an antibody molecule to a non-antibody moiety. In an embodiment, the linker comprises a hydrazone, a disulfide bond, a peptide, or a thioether bond.

In an embodiment, the linker is a non-cleavable linker. Exemplary non-cleavable linkers include, e.g., a non-cleavable thioether linker (e.g., N-succinimidyl-4-(N-maleimidomethyl)cyclohexane-1-carboxylate (SMCC)) or a non-cleavable maleimidocaproyl linker.

In an embodiment, the liner is a cleavable linker. In an embodiment, the cleavable linker is a chemically labile linker, e.g., an acid-cleavable linker (e.g., an acid-cleavable hydrazone) or a reducible linker (e.g., a disulfide linker). In an embodiment, the cleavable linker is an enzyme cleavable linker, e.g., a peptide-based linker (e.g., a dipeptide linker (e.g., a valine-citrulline (Val-Cit) linker or a phenylalanine-lysine (Phe-Lys) dipeptide linker)) or a β-glucuronide linker. Other linkers and their use in ADCs are described, e.g., in Lu et al. *Int J Mol Sci.* 2016; 17(4): 561, the content of which is incorporated by reference in its entirety.

In an embodiment, the linker is a poly(ethylene glycol) (PEG) linker.

Animal Models

The antibody molecules described herein can be evaluated in vivo, e.g., using various animal models. For example, an animal model can be used to test the efficacy of an antibody molecule described herein in inhibiting CD138 and/or in treating or preventing a disorder described herein, e.g., a myeloma (e.g., multiple myeloma) Animal models can also be used, e.g., to investigate for side effects, measure concentrations of antibody molecules in situ, demonstrate correlations between a CD138 function and a disorder described herein, e.g., a myeloma (e.g., multiple myeloma). Exemplary types of animals that can be used to evaluate the antibody molecules described herein include, but are not limited to, mice, rats, rabbits, guinea pigs, and monkeys.

Exemplary animal models for myelomas (e.g., multiple myeloma) that can be used for evaluating an antibody molecule described herein include, but are not limited to, immunocompetent murine models, e.g., STMM (5T Radl), 5T2, 5T33, and STGMA models (Radl et al. *Am J Pathol.* 1988; 132: 593-597); immunocompromised murine models, e.g., RAG-2 model (Fowler et al. *Dis Model Mech.* 2009; 2: 604-611), xenograft murine myeloma models, e.g., SCID and NOD/SCID models (Huang et al. *Cancer Res.* 1993; 53: 1392-1396; Tsunenari et al. *Blood.* 1997; 90: 2437-2444; Torcia et al. *Exp Hematol.* 1996; 24: 868-874; Hjorth-Hansen et al. *J Bone Miner Res.* 1999; 14: 256-263); SCID-Hu and SCID-Rab models (Urashima et al. *Blood.* 1997; 90: 754-765; Yaccoby et al. *Blood.* 1998; 92: 2908-2913; Yata & Yaccoby. *Leukemia.* 2004; 18: 1891-1897); genetically engineered models, e.g., IL-6- and MYC-driven models (Kovalchuk et al. *Proc Natl Acad Sci USA.* 2002; 99: 1509-1514; Adams et al. *Nature.* 1985; 318: 533-538; Chesi et al. *Blood.* 2012; 120: 376-385); Eμ-xbp-1s model (Carrasco et al. *Cancer Cell.* 2007; 11(4):349-360); L-GP130 model (Dechow et al. *J Clin Invest.* 2014; 124(12): 5263-5274).

Various murine and human myeloma cell lines and primary human myeloma cells can be used in preclinical in vivo models. Exemplary murine and human myeloma cell lines that can be used for engraftment include, but are not limited to, 5T myeloma cells (Radl et al. *Am J Pathol.* 1988; 132: 593-597), human lymphoblastoid ARH-77 cells (Huang et al. *Cancer Res.* 1993; 53(6):1392-1396), the human JJN3 myeloma cell line (Hjorth-Hansen et al. *J Bone Miner Res.* 1999; 14(2): 256-263), and IL-6-dependent myeloma cell lines (Tsunenari et al. *Blood.* 1997; 90(6): 2437-2444). A desired cell line can be selected based on, e.g., the pace of tumor engraftment, characteristics of the particular tumor type (e.g., propensity to develop lytic bone lesions), or the type of monoclonal protein that is produced.

Other animal models for myelomas (e.g., multiple myeloma) are described, e.g., in Lwin et al. *Bonekey Rep.* 2016; 5: 772; Libouban et al. *Morphologic.* 2015; 99(325): 63-72; Campbell et al. *Curr Protoc Pharmacol.* 2008; Chapter 14: Unit 14.9.

Pharmaceutical Compositions and Kits

In some aspects, this disclosure provides compositions, e.g., pharmaceutically acceptable compositions, which include an anti-CD138 antibody molecule described herein (e.g., a humanized antibody molecule described herein), formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In certain embodiments, less than about 5%, e.g., less than about 4%, 3%, 2%, or 1% of the antibody molecules in the pharmaceutical composition are present as aggregates. In other embodiments, at least about 95%, e.g., at least about 96%, 97%, 98%, 98.5%, 99%, 99.5%, 99.8%, or more of the antibody molecules in the pharmaceutical composition are present as monomers. In some embodiments, the level of aggregates or monomers is determined by chromatography, e.g., high performance size exclusion chromatography (HP-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In some embodiments, the antibody molecule is administered by intravenous infusion or injection. In certain embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules described herein can be administered by a variety of methods. Several are known in the art, and for many therapeutic, prophylactic, or diagnostic applications, an appropriate route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic, prophylactic, or diagnostic effect to be achieved, and (b) the limitations inherent in the art of compounding such an antibody molecule for the treatment of sensitivity in individuals.

An exemplary, non-limiting range for a therapeutically, prophylactically, or diagnostically effective amount of an antibody molecule is about 0.1-50 mg/kg body weight of a subject, e.g., about 0.1-30 mg/kg, e.g., about 1-30, 1-15, 1-10, 1-5, 5-10, or 1-3 mg/kg, e.g., about 1, 2, 3, 4, 5, 6, 7, 8, 9, 10, 15, 20, 30, 40, or 50 mg/kg. The antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, e.g., about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of an antibody molecule described herein.

A "therapeutically effective amount" refers to an amount effective, at dosages and for periods of time necessary, to achieve the desired therapeutic result. A therapeutically effective amount of the antibody molecule may vary according to factors such as the disease state, age, sex, and weight of the individual, and the ability of the antibody or antibody portion to elicit a desired response in the individual. A therapeutically effective amount is also one in which any toxic or detrimental effect of the antibody molecule is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., hematuria, colored urine, foamy urine, pain, swelling (edema) in the hands and feet, or high blood pressure. The ability of an antibody molecule to inhibit a measurable parameter can be evaluated in an animal model system predictive of efficacy in treating or preventing a myeloma. Alternatively, this property of a composition can be evaluated by examining the ability of the antibody molecule to inhibit CD138, e.g., by an in vitro assay.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder, e.g., a disorder described herein, e.g., A myeloma, can be diagnosed in vitro, ex vivo, or in vivo.

Also within this disclosure is a kit that comprises an antibody molecule, described herein. The kit can include one or more other elements including: instructions for use; other reagents, e.g., a label, a therapeutic agent, or an agent useful for chelating, or otherwise coupling, an antibody molecule to a label or therapeutic agent, or a radioprotective composition; devices or other materials for preparing the antibody molecule for administration; pharmaceutically acceptable carriers; and devices or other materials for administration to a subject.

Nucleic Acids

The present disclosure also features nucleic acids comprising nucleotide sequences that encode the anti-CD138 antibody molecules (e.g., heavy and light chain variable regions and CDRs of the antibody molecules), as described herein.

For example, the present disclosure features a first and second nucleic acid encoding heavy and light chain variable regions, respectively, of an antibody molecule chosen from one or more of the antibody molecules disclosed herein, e.g., an antibody molecule of Table 2, or a portion of an antibody molecule, e.g., the variable regions of Table 2. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein).

In certain embodiments, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in Table 2, a sequence substantially homologous thereto (e.g., a sequence at least about 85%, 90%, 95%, 99% or more identical thereto, and/or capable of hybridizing under the stringency conditions described herein). In some embodiments, the nucleic acid can comprise a nucleotide sequence encoding at least one, two, or three CDRs from a light chain variable region having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein). In certain embodiments, the nucleic acid can comprise a nucleotide sequence encoding at least one, two, three, four, five, or six CDRs from heavy and light chain variable regions having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein).

In certain embodiments, the nucleic acid comprises a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). In some embodiments, the nucleic acid comprises a portion of a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). The portion may encode, for example, a variable region (e.g., VH or VL); one, two, or three or more CDRs; or one, two, three, or four or more framework regions.

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In some aspects, the application features host cells and vectors containing the nucleic acids described herein. The nucleic acids may be present in a single vector or separate vectors present in the same host cell or separate host cell, as described in more detail below.

Vectors

Further provided herein are vectors that comprise nucleotide sequences encoding an anti-CD138 antibody molecule described herein.

In an embodiment, the vector comprises a nucleotide encoding an antibody molecule described herein, e.g., as described in Table 1. In another embodiment, the vector comprises a nucleotide sequence described herein, e.g., in Table 2. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The present disclosure also provides cells (e.g., host cells) comprising a nucleic acid encoding an anti-CD138 antibody molecule as described herein. For example, the host cells may comprise a nucleic acid molecule having a nucleotide sequence described in Table 2, a sequence substantially homologous thereto (e.g., a sequence at least about 85%, 90%, 95%, 99% or more identical thereto, and/or capable of hybridizing under the stringency conditions described herein), or a portion of one of said nucleic acids. Additionally, the host cells may comprise a nucleic acid molecule encoding an amino acid sequence of Table 1, a sequence substantially homologous thereto (e.g., a sequence at least about 80%, 85%, 90%, 95%, 99% or more identical thereto), or a portion of one of said sequences.

In some embodiments, the host cells are genetically engineered to comprise nucleic acids encoding the antibody molecule described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells. In an embodiment, the cell (e.g., host cell) is an isolated cell.

Uses of Antibody Molecules

The anti-CD138 antibody molecules disclosed herein, as well as the pharmaceutical compositions disclosed herein, have in vitro, ex vivo, and in vivo therapeutic, prophylactic, and/or diagnostic utilities.

In an embodiment, the antibody molecule causes (e.g., induces or increases) an effector function on a cell expressing CD138. For example, the antibody molecules can be administered to a subject, e.g., a human subject, to cause an antibody-dependent cellular cytotoxicity activity on a diseased cell (e.g., a cancer cell or a precancerous cell) that it binds to. In an embodiment, the antibody molecule causes a complement-dependent cytotoxicity activity on a cell expressing CD138. In an embodiment, the antibody molecule reduces (e.g., inhibits, blocks, or neutralizes) one or more biological activities of a cell expressing CD138. In an embodiment, the antibody molecule inhibits the action of a protease on a membrane-bound CD138, e.g., to reduce shedding of CD138. For example, these antibodies molecules can be administered to cells in culture, in vitro or ex vivo, or to a subject, e.g., a human subject, e.g., in vivo, to reduce (e.g., inhibits, blocks, or neutralizes) one or more biological activities of the cell.

Accordingly, in an aspect, the disclosure provides a method of treating, preventing, or diagnosing a disorder, e.g., a disorder described herein (e.g., multiple myeloma), in a subject, comprising administering to the subject an anti-CD138 antibody molecule described herein, such that the disorder is treated, prevented, or diagnosed. For example, the disclosure provides a method comprising contacting the antibody molecule described herein with cells in culture, e.g. in vitro or ex vivo, or administering the antibody molecule described herein to a subject, e.g., in vivo, to treat, prevent, or diagnose a disorder, e.g., a disorder associated with CD138 (e.g., multiple myeloma).

As used herein, the term "subject" is intended to include human and non-human animals. In some embodiments, the subject is a human subject, e.g., a human patient having a disorder described herein (e.g., multiple myeloma), or at risk of having a disorder described herein (e.g., multiple myeloma). The term "non-human animals" includes mammals and non-mammals, such as non-human primates. In some embodiments, the subject is a human. The methods and compositions described herein are suitable for treating human patients a disorder described herein (e.g., multiple myeloma). Patients having a disorder described herein include, e.g., those who have developed a disorder described herein but are (at least temporarily) asymptomatic, patients who have exhibited a symptom of a disorder described herein, and patients having a disorder related to or associated with a disorder described herein.

Methods of Treating or Preventing Disorders

The antibody molecules described herein can be used to treat or prevent disorders associated with CD138 or symptoms thereof.

Exemplary disorders or conditions that can be associated with CD138 include, but are not limited to cancer (e.g., hematological cancer (e.g., a myeloma, e.g., multiple myeloma) or solid tumors, and precancerous conditions (e.g., smoldering myeloma or monoclonal gammopathy of undetermined significance (MGUS)). In an embodiment, the disorder is associated with aberrant expression of CD138. In an embodiment, the antibody molecule is used to treat a subject having a disorder described herein, or is at risk of developing a disorder described herein. In an embodiment, the antibody molecule is used to reduce progression of the disorder, e.g., to reduce progression of a precancerous condition to cancer.

The antibody molecules described herein are typically administered at a frequency that keeps a therapeutically effective level of antibody molecules in the patient's system until the patient recovers. For example, the antibody molecules may be administered at a frequency that achieves a serum concentration sufficient for at least about 1, 2, 5, 10, 20, 30, or 40 antibody molecules to bind each CD138 molecule. In an embodiment, the antibody molecules are administered every 1, 2, 3, 4, 5, 6, or 7 days, every 1, 2, 3, 4, 5, or 6 weeks, or every 1, 2, 3, 4, 5, or 6 months.

Methods of administering various antibody molecules are known in the art and are described below. Suitable dosages of the antibody molecules used will depend on the age and weight of the subject and the particular drug used.

In an embodiment, the antibody molecule is administered to the subject (e.g., a human subject) intravenously. In an embodiment, the antibody molecule is administered to the subject at a dose between 0.1 mg/kg and 50 mg/kg, e.g., between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg. In an embodiment, the antibody molecule is administered to the subject at a fixed dose between 10 mg and 1000 mg, e.g., between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg. In an embodiment, the antibody molecule is administered once a week, twice a week, once every two weeks, once every three weeks, once every four weeks, once every eight weeks, once a month, once every two months, or once every three months. In an embodiment, the antibody molecule is administered between 0.5 mg/kg and 3 mg/kg or between 50 mg and 150 mg, once a week, twice a week, once every two weeks, or once every four weeks.

The antibody molecules can be used by themselves or conjugated to a second agent, e.g., a bacterial agent, toxin, or protein, e.g., a second anti-CD138 antibody molecule. This method includes: administering the antibody molecule, alone or conjugated to a second agent, to a subject requiring such treatment. The antibody molecules can be used to deliver a variety of therapeutic agents, e.g., a toxin, or mixtures thereof.

Cancer

The anti-CD138 antibody molecules described herein can be used to treat or prevent a cancer or a precancerous condition.

CD138 expression is dysregulated in many cancers, e.g., prostate cancer, breast cancer, pancreatic cancer, ovarian cancer, colon cancer, lung cancer, and myeloma (Kiviniemi et al. *APMIS.* 2004; 112(2): 89-97; Lendorf et al. *J Histochem Cytochem.* 2011; 59(6): 615-629; Juuti et al. *Oncology.* 2005; 68(2-3): 97-106; Kusumoto et al. *Oncol Rep.* 2010; 23(4): 917-25; Hashimoto et al. *BMC Cancer.* 2008; 8: 185; Joensuu et al. *Cancer Res.* 2002; 62(18):5210-5217;

Seidel et al. *Blood.* 2000; 95(2): 388-392). CD138 can modulate several key processes of tumorigenesis, e.g., cancer cell proliferation, apoptosis, and angiogenesis (Teng et al. *Matrix Biol.* 2012; 31(1): 3-16). The molecular and clinical profiles of CD138 in solid and hematological cancers are described, e.g., in Akl et al. *Oncotarget.* 2015; 6(30):28693-28715.

CD138 can affect tumorigenesis by regulating mediators of tumor cell survival and proliferation (e.g., oncogenes or growth factors). For example, Sdc1-/- mice were protected against Wnt-1 induced mammary tumorigenesis (Alexander et al. *Nat Genet.* 2000; 25(3): 329-32). Hepatocyte growth factor (HGF) binds to CD138 on myeloma cells (Derksen et al. *Blood.* 2002; 99(4): 1405-1410). The interaction of HGF with CD138 potentiated Met signaling, which is involved in the growth, survival, and spread of a number of cancers (Birchmeier et al. *Nat Rev Mol Cell Biol.* 2003; 4(12): 915-925; Derksen et al. *Blood.* 2002; 99(4):1405-1410). CD138 expression is elevated in the reactive stroma of breast carcinoma tissue (Stanley et al. *Am J Clin Pathol.* 1999; 112(3): 377-383). MEFs expressing CD138 enhanced the growth of breast cancer cell lines in co-culture and promoted breast carcinoma progression in vivo (Maeda et al. *Cancer Res.* 2004; 64(2):612-621).

CD138 can regulate tumor cell apoptosis. Knock-down of CD138 in myeloma cells induced growth arrest and apoptosis (Khotskaya et al. *J Biol Chem.* 2009; 284(38): 26085-26095). Recombinant CD138 ectodomains induced apoptosis in MCF-7 breast cancer cells and cultured human prostate cancer cells (Sun et al. *Cancer Res.* 2008; 68(8): 2912-2919; Hu et al. *Neoplasia.* 2010; 12(10): 826-836).

CD138 can bind to pro-angiogenic factors (e.g., FGF-2 and VEGF) and present these factors to their respective receptors on endothelial cells to initiate endothelial invasion and budding (Teng et al. *Matrix Biol.* 2012; 31(1): 3-16). Increased CD138 expression in stromal fibroblasts was observed in several carcinomas, such as those of the breast, stomach, and thyroid (Stanley et al. *Am J Clin Pathol.* 1999; 112(3): 377-383; Wiksten et al. *Int J Cancer.* 2001; 95(1): 1-6; Barbareschi et al. *Cancer.* 2003; 98(3): 474-483). In a xenograft model of human breast carcinoma cells and CD138-transfected fibroblasts implantation into mice, stromal CD138 expression was associated with significantly elevated microvessel density and larger vessel area (Maeda et al. *Oncogene.* 2006; 25(9): 1408-1412).

Exemplary cancers that can be treated or prevented by the antibody molecules described herein include, but are not limited to, acute lymphoblastic leukemia (ALL), acute myeloid leukemia (AML), adrenocortical carcinoma, Kaposi sarcoma, an AIDS-related lymphoma, primary central nervous system (CNS) lymphoma, anal cancer, appendix cancer, astrocytoma, atypical teratoid/rhabdoid tumor, basal cell carcinoma, bile duct cancer, bladder cancer, bone cancer (e.g., Ewing sarcoma or osteosarcoma and malignant fibrous histiocytoma), brain tumor (e.g., astrocytomas, brain stem glioma, central nervous system atypical teratoid/rhabdoid tumor, central nervous system embryonal tumor, central nervous system germ cell tumor, craniopharyngioma, or ependymoma), breast cancer, bronchial tumor, Burkitt lymphoma, carcinoid tumor (e.g., gastrointestinal carcinoid tumor), cardiac (heart) tumor, embryonal tumor, germ cell tumor, lymphoma, cervical cancer, cholangiocarcinoma, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma in situ (DCIS), endometrial cancer, ependymoma, esophageal cancer, esthesioneuroblastoma, Ewing sarcoma, extracranial germ cell tumor, extragonadal germ cell tumor, eye cancer (e.g., intraocular melanoma or retinoblastoma), fallopian tube cancer, fibrous histiocytoma of bone, osteosarcoma, gallbladder cancer, gastric (stomach) cancer, gastrointestinal carcinoid tumor, gastrointestinal stromal tumors (GIST), germ cell tumor (e.g., central nervous system tumor, extracranial tumor, extragonadal tumor, ovarian cancer, or testicular cancer), gestational trophoblastic disease, glioma, hairy cell leukemia, head and neck cancer, hepatocellular (liver) cancer, Hodgkin lymphoma, hypopharyngeal cancer, intraocular melanoma, islet cell tumor, pancreatic neuroendocrine tumor, Kaposi sarcoma, kidney cancer (e.g., renal cell cancer or Wilms tumor), Langerhans cell histiocytosis (LCH), laryngeal cancer, leukemia (e.g., acute lymphoblastic leukemia (ALL), acute myeloid leukemia (AML), chronic lymphocytic leukemia (CLL), chronic myelogenous leukemia (CML), or hairy cell leukemia), lip and oral cavity cancer, liver cancer, lung cancer (e.g., non-small cell lung cancer (NSCLC) or small cell lung cancer), lymphoma (e.g., aids-related, Burkitt lymphoma, cutaneous T-cell lymphoma, Hodgkin lymphoma, non-Hodgkin lymphoma, or primary central nervous system (CNS) lymphoma), Waldenström macroglobulinemia, male breast cancer, malignant fibrous histiocytoma of bone and osteosarcoma, melanoma (e.g., intraocular (eye) melanoma), Merkel cell carcinoma, mesothelioma, metastatic squamous neck cancer, midline tract carcinoma, mouth cancer, multiple endocrine neoplasia syndrome, multiple myeloma/plasma cell neoplasm, mycosis fungoides, myelodysplastic syndrome, myelodysplastic/myeloproliferative neoplasm, chronic myeloproliferative neoplasm, nasal cavity and paranasal sinus cancer, nasopharyngeal cancer, neuroblastoma, oral cancer, lip and oral cavity cancer, oropharyngeal cancer, osteosarcoma and malignant fibrous histiocytoma of bone, ovarian cancer (e.g., epithelial ovarian cancer or germ cell ovarian tumor), pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, pleuropulmonary blastoma, peritoneal cancer, prostate cancer, rectal cancer, retinoblastoma, rhabdomyosarcoma, salivary gland cancer, sarcoma (e.g., Ewing sarcoma, Kaposi sarcoma, osteosarcoma, rhabdomyosarcoma, soft tissue sarcoma, or uterine sarcoma), Sezary syndrome, skin cancer (e.g., melanoma, Merkel cell carcinoma, or nonmelanoma skin cancer), small intestine cancer, squamous cell carcinoma, testicular cancer, throat cancer, thymoma and thymic carcinoma, thyroid cancer, transitional cell cancer of the renal pelvis and ureter, urethral cancer, endometrial uterine cancer, vaginal cancer, vulvar cancer, or a metastatic lesion thereof.

In an embodiment, the cancer is a hematological cancer, e.g., a myeloma, lymphoma, or leukemia. In an embodiment, the cancer is a myeloma. In an embodiment, the cancer is a multiple myeloma.

In another embodiment, the cancer is a solid tumor. In an embodiment, the cancer is a cervical cancer (e.g., a cervical squamous cell carcinoma or an endocervical adenocarcinoma), a uterine cancer (e.g., a uterine corpus endometrioid carcinoma), a brain cancer (e.g., a glioblastoma), a lung cancer (e.g., a lung squamous cell carcinoma), or a breast cancer (e.g., a breast invasive carcinoma).

In an embodiment, the cancer is chosen from a bladder cancer, a breast cancer, a cervical cancer, a colorectal cancer, an endometrial cancer, a gallbladder cancer, a gastric cancer, a glioma, a head and neck cancer, a laryngeal cancer, a liver cancer, a lung cancer, a mesothelioma, a nasopharyngeal cancer, an oral cancer, an ovarian cancer, a pancreatic cancer, a prostate cancer, or a thyroid cancer.

In an embodiment, the cancer is a bladder cancer. CD138 is expressed in bladder cancer (Kim & Park. *Hum Pathol.* 2014; 45: 1830-1838). In an embodiment, the bladder cancer is a urothelial carcinoma, a squamous cell carcinoma, or an adenocarcinoma. In an embodiment, the bladder cancer is a noninvasive, non-muscle-invasive, or muscle-invasive. The anti-CD138 antibody molecules described herein can be used alone or in combination with a second therapeutic agent, procedure, or modality to treat a bladder cancer. In an embodiment, the anti-CD138 antibody molecule is used in combination with a surgery (e.g., transurethral resection of bladder tumor (TURBT) or cystectomy), an intravesical therapy (e.g., an intravesical immunotherapy (e.g., *Bacillus* Calmette-Guerin (BCG) therapy) or an intravesical chemotherapy (e.g., mitomycin, valrubicin, docetaxel, thiotepa, or gemcitabine)), a chemotherapy (e.g., an intravesical chemotherapy or a systemic chemotherapy (e.g., cisplatin, fluorouracil (5-FU), mitomycin, gemcitabine, methotrexate, vinblastine, doxorubicin, carboplatin, paclitaxel, docetaxel, ifosfamide, or pemetrexed), a radiation therapy, or an immunotherapy (e.g., intravesical BCG, an immune checkpoint inhibitor (e.g., a PD-L1 inhibitor (e.g., atezolizumab, durvalumab, or avelumab) or a PD-1 inhibitor (e.g., nivolumab or pembrolizumab)).

In an embodiment, the cancer is a breast cancer. CD138 is expressed in breast cancer (Akl et al. *Oncotarget.* 2015; 6(30):28693-28715; Barbareschi et al. *Cancer.* 2003; 98: 474-483; Lim et al. *Singapore Med J.* 2014; 55: 468-472; Nguyen et al. *Am J Clin Pathol.* 2013; 140: 468-474; Lendorf et al. *J Histochem Cytochem.* 2011; 59: 615-629; Gotte et al. *Breast Cancer Res.* 2007; 9(1):R8; Tsanou et al. *J Exp Clin Cancer Res.* 2004; 23(4):641-650). In an embodiment, the breast cancer is a ductal carcinoma (e.g., ductal carcinoma in situ (DCIS), or invasive ductal carcinoma (IDC) (e.g., a tubular carcinoma, a medullary carcinoma, a mucinous carcinoma, a papillary carcinoma, or a cribriform carcinoma), a lobular carcinoma (e.g., a lobular carcinoma in situ (LCIS) or an invasive lobular carcinoma (ILC)), or an inflammatory breast cancer. In an embodiment, the breast cancer is ER-positive, PR-positive, HER2-positive, or triple-negative (ER-, PR- and HER2-). The anti-CD138 antibody molecules described herein can be used alone or in combination with a second therapeutic agent, procedure, or modality to treat a bladder cancer. In an embodiment, the anti-CD138 antibody molecule is used in combination with a surgery (e.g., a breast-conserving surgery or a mastectomy), a radiation therapy, a chemotherapy (e.g., an anthracycline (e.g., doxorubicin, liposomal doxorubicin, epirubicin), a taxane (e.g., paclitaxel, albumin-bound paclitaxel (e.g., nab-paclitaxel) or docetaxel), 5-fluorouracil (5-FU), cyclophosphamide, a platinum agent (e.g., cisplatin or carboplatin), vinorelbine, capecitabine, gemcitabine, mitoxantrone, ixabepilone, or eribulin), a hormone therapy (e.g., tamoxifen, toremifene, fulvestrant, an aromatase inhibitor (e.g., letrozole, anastrozole, or exemestane), ovarian ablation (e.g., oophorectomy, a luteinizing hormone-releasing hormone (LHRH) analog, or a chemotherapy drug)), a targeted therapy (e.g., trastuzumab, pertuzumab, ado-trastuzumab emtansine, lapatinib, neratinib, a CDK4/6 inhibitor (e.g., palbociclib or ribociclib), an mTOR inhibitor (e.g., everolimus), or a combination thereof.

In an embodiment, the cancer is a cervical cancer. CD138 is expressed in cervical cancer (Akl et al. *Oncotarget.* 2015; 6(30):28693-28715). In an embodiment, the cervical cancer is a microinvasive cervical cancer or invasive cervical cancer, In an embodiment, the cervical cancer is a squamous cell carcinoma or an adenocarcinoma. The anti-CD138 antibody molecules described herein can be used alone or in combination with a second therapeutic agent, procedure, or modality to treat a cervical cancer. In an embodiment, the anti-CD138 antibody molecule is used in combination with a surgery (e.g., a cryosurgery, a laser surgery, a conization, a simple hysterectomy, a radical hysterectomy, a trachelectomy, or a pelvic exenteration), a radiation therapy, a chemotherapy (e.g., cisplatin, carboplatin, paclitaxel, topotecan, gemcitabine, docetaxel, ifosfamide, 5-fluorouracil (5-FU), irinotecan, or mitomycin), a targeted therapy (e.g., an angiogenesis inhibitor (e.g., bevacizumab)), or a combination thereof.

In an embodiment, the cancer is an endometrial cancer. CD138 is expressed in endometrial cancer (Hasengaowa et al. *Ann Oncol.* 2005; 16:1109-1115). In an embodiment, the endometrial cancer is an endometrioid carcinoma, a serous carcinoma, a clear cell carcinoma, a mucinous carcinoma, a mixed or undifferentiated carcinoma, a squamous cell carcinoma, a transitional cell carcinoma, or an endometrial stromal sarcoma. The anti-CD138 antibody molecules described herein can be used alone or in combination with a second therapeutic agent, procedure, or modality to treat an endometrial cancer. In an embodiment, the anti-CD138 antibody molecule is used in combination with a surgery, a radiation therapy, a hormone therapy (e.g., a progestin (e.g., medroxyprogesterone acetate) or megestrol acetate), tamoxifen, a luteinizing hormone-releasing hormone (LHRH) agonist (e.g., goserelin or leuprolide), an aromatase inhibitor (e.g., letrozole, anastrozole, or exemestane), a chemotherapy (e.g., paclitaxel, carboplatin, doxorubicin, liposomal doxorubicin, or cisplatin), or a combination thereof.

In an embodiment, the cancer is a gallbladder cancer. CD138 is overexpressed in gallbladder cancer (Roh et al. *Eur Surg Res.* 2008; 41(2): 245-250). In an embodiment, the gallbladder cancer is an adenocarcinoma or a papillary adenocarcinoma. The anti-CD138 antibody molecules described herein can be used alone or in combination with a second therapeutic agent, procedure, or modality to treat a gallbladder cancer. In an embodiment, the anti-CD138 antibody molecule is used in combination with a surgery, a radiation therapy, a chemotherapy (e.g., gemcitabine, cisplatin, 5-fluorouracil (5-FU), capecitabine, or oxaliplatin), or a palliative therapy (e.g., a biliary stent, a biliary catheter, a biliary bypass, an alcohol injection, a pain medicine, or a combination thereof.

In an embodiment, the cancer is a gastric cancer. Strong stromal CD138 expression is associated with gastric cancer (Wiksten et al. *Int J Cancer.* 2001; 95(1):1-6). In an embodiment, the gastric cancer is an adenocarcinoma (ACA). The anti-CD138 antibody molecules described herein can be used alone or in combination with a second therapeutic agent, procedure, or modality to treat a gastric cancer. In an embodiment, the anti-CD138 antibody molecule is used in combination with a surgery, a chemotherapy (e.g., 5-FU (fluorouracil), capecitabine, carboplatin, cisplatin, docetaxel, epirubicin, irinotecan, oxaliplatin, or paclitaxel), or a combination thereof.

In an embodiment, the cancer is a brain cancer (e.g., a glioma). CD138 is expressed in glioma (Xu et al. *Mol Biol Rep.* 2012; 39(9): 8979-8985). In an embodiment, the glioma is an astrocytoma, an en ependymoma, or an oligodendroglioma. The anti-CD138 antibody molecules described herein can be used alone or in combination with a second therapeutic agent, procedure, or modality to treat a glioma. In an embodiment, the anti-CD138 antibody molecule is used in combination with a surgery, a radiation therapy, a chemotherapy (e.g., carboplatin, carmustine (BCNU), cisplatin, cyclophosphamide, etoposide, irinotecan, lomustine (CCNU), methotrexate, procarbazine, temozolomide, or vincristine), a targeted therapy (e.g., bevacizumab or everolimus), a corticosteroid (e.g., dexamethasone), an anti-seizure drug, or a hormone, or a combination thereof.

In an embodiment, the cancer is a laryngeal cancer. CD138 expression is in laryngeal cancer (Klatka et al. *Otolaryngol Pol.* 2004; 58: 933-940). In an embodiment, the laryngeal cancer is a squamous cell carcinoma or an adenocarcinoma. The anti-CD138 antibody molecules described herein can be used alone or in combination with a second therapeutic agent, procedure, or modality to treat a laryngeal cancer. In an embodiment, the anti-CD138 antibody molecule is used in combination with a surgery, a radiation therapy, a chemotherapy (e.g., cisplatin, carboplatin, 5-fluorouracil (5-FU), docetaxel, paclitaxel, bleomycin, methotrexate, or ifosfamide), a targeted therapy (e.g., an EGFR inhibitor (e.g., cetuximab)), or a combination thereof. In an embodiment, the cancer is a liver cancer. In an embodiment, the liver cancer is a hepatocellular carcinoma (HCC), a cholangiocarcinoma, an angiosarcoma, or a secondary liver cancer. The anti-CD138 antibody molecules described herein can be used alone or in combination with a second therapeutic agent, procedure, or modality to treat a liver cancer. In an embodiment, the anti-CD138 antibody molecule is used in combination with a surgery, tumor ablation, tumor embolization, a radiation therapy, a targeted therapy (e.g., sorafenib or regorafenib), a chemotherapy (e.g., doxorubicin, 5-fluorouracil (5-FU), or cisplatin), or a combination thereof.

In an embodiment, the cancer is a lung cancer. CD138 is expressed in lung cancer (Anttonen et al. *Lung Cancer.* 2001; 32:297-305). In an embodiment, the lung cancer is a non-small cell lung cancer (NSCLC) (e.g., an adenocarcinoma, a squamous cell carcinoma, a large cell carcinoma, or a large cell neuroendocrine tumor) or a small cell lung cancer (SCLC). The anti-CD138 antibody molecules described herein can be used alone or in combination with a second therapeutic agent, procedure, or modality to treat a lung cancer. In an embodiment, the anti-CD138 antibody molecule is used in combination with a surgery, radiofrequency ablation (RFA), a radiation therapy, a chemotherapy (cisplatin, carboplatin, paclitaxel, albumin-bound paclitaxel (nab-paclitaxel), docetaxel, gemcitabine, vinorelbine, irinotecan, etoposide, vinblastine, or pemetrexed), a targeted therapy (an angiogenesis inhibitor (e.g., bevacizumab or ramucirumab), an EGFR inhibitor (e.g., erlotinib, afatinib, gefitinib, osimertinib, or necitumumab), an ALK inhibitor (e.g., crizotinib, ceritinib, alectinib, or brigatinib), a BRAF inhibitor (e.g., dabrafenib or trametinib), an immunotherapy (e.g., a PD-1 inhibitor (e.g., nivolumab or pembrolizumab) or a PD-L1 inhibitor (e.g., atezolizumab), or a combination thereof, e.g., to treat a non-small cell lung cancer. In an embodiment, the anti-CD138 antibody molecule is used in combination with a surgery, a radiation therapy, a chemotherapy (cisplatin, etoposide, carboplatin, or irinotecan), or a combination thereof, e.g., to treat a small cell lung cancer.

In an embodiment, the cancer is a mesothelioma. CD138 is expressed in mesothelioma (Kumar-singh et al. *J Pathol.* 1998; 186:300-305). In an embodiment, the mesothelioma is an epithelioid mesothelioma, a sarcomatoid mesothelioma, or a biphasic mesothelioma. In an embodiment, the mesothelioma is a pleural mesothelioma, a peritoneal mesothelioma, or a pericardial mesothelioma. The anti-CD138 antibody molecules described herein can be used alone or in combination with a second therapeutic agent, procedure, or modality to treat a mesothelioma. In an embodiment, the anti-CD138 antibody molecule is used in combination with a surgery, a radiation therapy, a chemotherapy (e.g., pemetrexed, cisplatin, carboplatin, gemcitabine, methotrexate, vinorelbine, mitomycin, or doxorubicin), or a combination thereof.

In an embodiment, the cancer is a nasopharyngeal cancer. CD138 is expressed in nasopharyngeal cancer (Kim et al. *Head Neck.* 2011; 33:1458-1466). In an embodiment, the nasopharyngeal cancer is a keratinizing squamous cell carcinoma, a non-keratinizing differentiated carcinoma, or an undifferentiated carcinoma. The anti-CD138 antibody molecules described herein can be used alone or in combination with a second therapeutic agent, procedure, or modality to treat a nasopharyngeal cancer. In an embodiment, the anti-CD138 antibody molecule is used in combination with a surgery, a radiation therapy, a chemotherapy (e.g., carboplatin, doxorubicin, epirubicin, paclitaxel, docetaxel, gemcitabine, bleomycin, or methotrexate), a targeted therapy (e.g., cetuximab), or a combination thereof.

In an embodiment, the cancer is a nasopharyngeal cancer. CD138 is expressed in oral cancer (Al-Otaibi et al. *J Oral Pathol Med.* 2013; 42: 186-193). In an embodiment, the oral cancer is a squamous cell carcinoma, a verrucous carcinoma, or a minor salivary gland carcinoma. The anti-CD138 antibody molecules described herein can be used alone or in combination with a second therapeutic agent, procedure, or modality to treat an oral cancer. In an embodiment, the anti-CD138 antibody molecule is used in combination with a surgery, a radiation therapy, a chemotherapy (e.g., cisplatin, carboplatin, 5-fluorouracil (5-FU), paclitaxel, docetaxel, methotrexate, ifosfamide, or bleomycin), a targeted therapy (e.g., cetuximab), or a combination thereof.

In an embodiment, the cancer is an ovarian cancer. CD138 is expressed in ovarian cancer (Kusumoto et al. *Oncol Rep.* 2010; 23: 917-925; Davies et al. *Clin Cancer Res.* 2004; 10: 5178-5186). In an embodiment, the ovarian cancer is an epithelial cancer, a germ cell carcinoma, a stromal carcinoma, or a small cell carcinoma. The anti-CD138 antibody molecules described herein can be used alone or in combination with a second therapeutic agent, procedure, or modality to treat an ovarian cancer. In an embodiment, the anti-CD138 antibody molecule is used in combination with a surgery, a chemotherapy (e.g., cisplatin, carboplatin, paclitaxel, albumin bound paclitaxel (nab-paclitaxel), docetaxel, altretamine, capecitabine, cyclophosphamide, etoposide, gemcitabine, ifosfamide, irinotecan, liposomal doxorubicin, melphalan, pemetrexed, topotecan, or vinorelbine), a hormone therapy (e.g., a luteinizing-hormone-releasing hormone (LHRH) agonist (e.g., goserelin or leuprolide), tamoxifen, or aromatase inhibitor (e.g., letrozole, anastrozole, or exemestane), a targeted therapy (e.g., an angiogenesis inhibitor (e.g., bevacizumab), a PARP inhibitor (e.g., olaparib, rucaparib, or niraparib), a radiation therapy, or a combination thereof.

In an embodiment, the cancer is a pancreatic cancer. CD138 is expressed in pancreatic cancer (Juuti et al. *Oncology.* 2005; 68: 97-106). In an embodiment, the pancreatic cancer is an exocrine tumor or an endocrine tumor. The anti-CD138 antibody molecules described herein can be used alone or in combination with a second therapeutic agent, procedure, or modality to treat a pancreatic cancer. In an embodiment, the anti-CD138 antibody molecule is used in combination with a surgery, ablation, embolization, a radiation therapy, or a chemotherapy (cemcitabine, 5-fluorouracil (5-FU), irinotecan, oxaliplatin, albumin-bound paclitaxel, capecitabine, cisplatin, paclitaxel, docetaxel, or irinotecan liposome.

In an embodiment, the cancer is a prostate cancer. CD138 is expressed in prostate cancer (Ledezma et al. *Asian J Androl.* 2011; 13: 476-480; Shariat et al. *BJU Int.* 2008; 101:232-237; Kiviniemi et al. *Apmis.* 2004; 112: 89-97; Zellweger et al. *Prostate.* 2003; 55: 20-29). In an embodiment, the prostate cancer is an adenocarcinoma, a transitional cell (or urothelial) cancer, a squamous cell cancer, or a small cell prostate cancer. The anti-CD138 antibody molecules described herein can be used alone or in combination with a second therapeutic agent, procedure, or modality to treat a prostate cancer. In an embodiment, the anti-CD138 antibody molecule is used in combination with a surgery, a radiation therapy, a cryotherapy, a hormone therapy (e.g., orchiectomy, an LHRH agonist (e.g., leuprolide, goserelin, triptorelin, or histrelin), an LHRH antagonist (e.g., degarelix), a CYP17 inhibitor (e.g., abiraterone), an anti-androgen (e.g., flutamide, bicalutamide, nilutamide, or enzalutamide), an estrogen, or ketoconazole), a chemotherapy (e.g., docetaxel, cabazitaxel, mitoxantrone, or estramustine), a vaccine treatment (e.g., Sipuleucel-T), or a bone-directed treatment (e.g., a bisphosphonate (e.g., zoledronic acid), denosumab, a corticosteroid (e.g., prednisone or dexamethasone), an external radiation therapy, a radiopharmaceutical (e.g., Strontium-89, Samarium-153, or Radium-223), or a combination thereof.

In an embodiment, the cancer is a head and neck cancer. CD138 is expressed in head and neck cancer (Anttonen et al. *Br J Cancer.* 1999; 79: 558-564; Inki et al. *Br J Cancer.* 1994; 70: 319-323). In an embodiment, the head and neck cancer is a squamous cell carcinoma. The anti-CD138 antibody molecules described herein can be used alone or in combination with a second therapeutic agent, procedure, or modality to treat a head and neck cancer. In an embodiment, the anti-CD138 antibody molecule is used in combination with a surgery, a radiation therapy, a chemotherapy (e.g., methotrexate, bleomycin, or docetaxel), a targeted therapy (e.g., cetuximab), an immunotherapy (e.g., a PD-1 inhibitor (e.g., nivolumab or pembrolizumab)), or a combination thereof.

In an embodiment, the cancer is a thyroid cancer. CD138 is expressed in thyroid cancer (Oh & Park. *J Korean Med Sci.* 2006; 21: 397-405). In an embodiment, the thyroid cancer is a papillary carcinoma, a follicular carcinoma, a Hürthle cell carcinoma, a medullary thyroid carcinoma, or an anaplastic carcinoma. The anti-CD138 antibody molecules described herein can be used alone or in combination with a second therapeutic agent, procedure, or modality to treat a thyroid cancer. In an embodiment, the anti-CD138 antibody molecule is used in combination with a surgery, a radioactive iodine treatment, a thyroid hormone therapy, a radiation therapy, a chemotherapy, a targeted therapy (e.g., a kinase inhibitor (e.g., sorafenib or lenvatinib), or a combination thereof.

In an embodiment, the cancer is a chronic lymphocytic leukemia (CLL). CD138 is expressed in chronic lymphocytic leukemia cancer (Jilani et al. *Int J Lab Hematol.* 2009; 31:97-105). The anti-CD138 antibody molecules described herein can be used alone or in combination with a second therapeutic agent, procedure, or modality to treat a thyroid cancer. In an embodiment, the anti-CD138 antibody molecule is used in combination with a chemotherapy (e.g., a purine analog (e.g., fludarabine, pentostatin, or cladribine), an alkylating agent (e.g., chlorambucil, cyclophosphamide, or bendamustine), a corticosteroid (e.g., prednisone, methylprednisolone, or dexamethasone), doxorubicin, methotrexate, oxaliplatin, vincristine, etoposide, and cytarabine), an anti-CD20 antibody (rituximab, obinutuzumab, or ofatumumab), an anti-CD52 antibody (e.g., alemtuzumab), a targeted therapy (e.g., ibrutinib, idelalisib, or venetoclax), a stem cell transplant (SCT), or a combination thereof.

In an embodiment, the cancer is a lymphoma (e.g., a diffuse large B-cell lymphoma (DLBCL)). CD138 is expressed in DLBCL (Oh & Park. *J Korean Med Sci.* 2006; 21: 397-405; Bodoor et al. *Asian Pac J Cancer Prev.* 2012; 13: 3037-3046). The anti-CD138 antibody molecules described herein can be used alone or in combination with a second therapeutic agent, procedure, or modality to treat a DLBCL. In an embodiment, the anti-CD138 antibody molecule is used in combination with a chemotherapy (e.g., an alkylating agent (e.g., cyclophosphamide, chlorambucil, bendamustine, or ifosfamide), a corticosteroid (e.g., prednisone or dexamethasone), a platinum drug (cisplatin, carboplatin, or oxaliplatin), a purine analog (e.g., fludarabine, pentostatin, or cladribine), an anti-metabolite (e.g., cytarabine, gemcitabine, methotrexate, or pralatrexate), vincristine, doxorubicin, mitoxantrone, etoposide, or bleomycin), an immunotherapy (e.g., an anti-CD20 antibody (rituximab, obinutuzumab, or ofatumumab), an anti-CD52 antibody (e.g., alemtuzumab), an anti-CD30 antibody (e.g., brentuximab vedotin), interferon, an immunomodulating drug (e.g., thalidomide or lenalidomide), a targeted therapy (e.g., a proteasome inhibitor (e.g., bortezomib), a histone deacetylase (HDAC) inhibitor (e.g., romidepsin or belinostat), or a kinase inhibitor (e.g., ibrutinib or idelalisib)), a radiation therapy, a stem cell transplant (SCT), or a combination thereof.

In an embodiment, the cancer is a Hodgkin's lymphoma. CD138 is expressed in Hodgkin's lymphoma (Gharbaran et al. *J Hematol Oncol.* 2013; 6:62; Vassilakopoulos et al. *Anticancer Res.* 2005; 25: 4743-4746). The anti-CD138 antibody molecules described herein can be used alone or in combination with a second therapeutic agent, procedure, or modality to treat a Hodgkin's lymphoma. In an embodiment, the anti-CD138 antibody molecule is used in combination with a chemotherapy (e.g., doxorubicin, bleomycin, vinblastine, dacarbazine, etoposide, cyclophosphamide, vincristine, procarbazine, prednisone, mechlorethamine, vincristine, or vinblastine), a radiation therapy, an immunotherapy (e.g., an anti-CD30 antibody (e.g., brentuximab vedotin)), a stem cell transplant, or a combination thereof.

In an embodiment, the antibody molecule is used to treat or prevent a precancerous condition. Precancerous condition, also known as premalignant condition, potentially precancerous condition, or potentially premalignant condition, refers to a state of disordered morphology of cells that is associated with an increased risk of cancer. If left untreated, precancerous conditions may lead to cancer. In an embodiment, the premalignant lesion is morphologically atypical tissue which appears abnormal under microscopic examination, and in which cancer is more likely to occur than in its apparently normal counterpart. In an embodiment, the precancerous condition is smoldering myeloma or asymptomatic myeloma. In an embodiment, the precancerous condition is monoclonal gammopathy of undetermined significance (MGUS). Other examples of precancerous conditions include, but are not limited to, actinic keratosis, Barrett's esophagus, atrophic gastritis, ductal carcinoma in situ, dyskeratosis congenital, sideropenic dysphagia, lichen planus, oral submucous fibrosis, solar elastosis, cervical dysplasia, leukoplakia, and erythroplakia.

Multiple Myeloma

The antibody molecule described herein can be used to treat or prevent multiple myeloma.

Multiple myeloma, also known as plasma cell myeloma, is a cancer of plasma cells, which are normally responsible for producing antibodies (Raab et al. *Lancet.* 2009; 374 (9686): 324-39).

Signs or symptoms of multiple myeloma include, e.g., bone pain, anemia (e.g., normocytic and/or normochromic anemia), kidney failure (e.g., acute or chronical kidney failure), infection (e.g., pneumonias or pyelonephritis), a neurological symptom (e.g., weakness, confusion, fatigue, headache, visual change, retinopathy, radicular pain, loss of bowel or bladder control, carpal tunnel syndrome, or paraplegia).

Risk factors for multiple myeloma include, e.g., smoldering myeloma (also known as asymptomatic myeloma), monoclonal gammopathy of undetermined significance (MGUS), obesity, or familial predisposition. In an embodiment, the anti-CD138 antibody molecules described herein can be used to reduce (e.g., prevent) the progression of smoldering myeloma or MGUS to multiple myeloma.

Diagnostic criteria for symptomatic myeloma, asymptomatic myeloma and MGUS are described, e.g., in Kyle & Rajkumar *Leukemia.* 2009; 23(1): 3-9.

Diagnostic criteria for symptomatic myeloma (all three criteria must be met) include, e.g., clonal plasma cells>10% on bone marrow biopsy or (in any quantity) in a biopsy from other tissues (plasmacytoma), a monoclonal protein (Myeloma protein) in either serum or urine (except in cases of true non-secretory myeloma), and evidence of end-organ damage felt related to the plasma cell disorder (related organ or tissue impairment, commonly referred to by the acronym "CRAB"): hypercalcemia (corrected calcium>2.75 mmol/l, >11 mg/dL), renal insufficiency attributable to myeloma, anemia (hemoglobin <10 g/dl), bone lesions (lytic lesions or osteoporosis with compression fractures). Diagnostic criteria for asymptomatic/smoldering myeloma include, e.g., serum M protein>30 g/l (3 g/dL) and/or clonal plasma cells>10% on bone marrow biopsy and no myeloma-related organ or tissue impairment). Diagnostic criteria for monoclonal gammopathy of undetermined significance (MGUS) include, e.g., serum paraprotein <30 g/l (3 g/dL) and clonal plasma cells <10% on bone marrow biopsy and no myeloma-related organ or tissue impairment or a related B-cell lymphoproliferative disorder Related conditions include, e.g., solitary plasmacytoma, plasma cell dyscrasia (e.g., AL amyloidosis), and peripheral neuropathy, organomegaly, endocrinopathy, monoclonal plasma cell disorder, and skin changes.

The International Staging System (ISS) for myeloma is described, e.g., in Greipp et al. *J Clin Oncol.* 2005; 23(15): 3412-20. For example, the ISS includes the following: Stage I: β2 microglobulin (β2M)<3.5 mg/L, albumin ≥3.5 g/dL; Stage II: β2M <3.5 mg/L and albumin <3.5 g/dL; or β2M 3.5-5.5 mg/L irrespective of the serum albumin; Stage III: β2M ≥5.5 mg/L.

The ISS can be used along with the Durie-Salmon Staging System. The Durie-Salmon Staging System is described, e.g., in Durie & Salmon *Cancer.* 1975; 36(3):842-54. For example, the Durie-Salmon Staging System include the following: Stage I (all of Hb>10 g/dL, normal calcium, skeletal survey: normal or single plasmacytoma or osteoporosis, serum paraprotein level <5 g/dL if IgG, <3 g/dL if IgA, urinary light chain excretion <4 g/24 h); Stage II (fulfilling the criteria of neither I nor III); Stage III (one or more of Hb<8.5 g/dL, high calcium >12 mg/dL, skeletal survey: three or more lytic bone lesions, serum paraprotein >7 g/dL if IgG, >5 g/dL if IgA, urinary light chain excretion >12 g/24 h). Stages I, II, and III of the Durie-Salmon Staging System can be divided into A or B depending on serum creatinine: A: serum creatinine <2 mg/dL (<177 μmol/L); B: serum creatinine >2 mg/dL (>177 μmol/L).

Other treatments for multiple myeloma that can be used in combination with an anti-CD138 antibody molecule described herein include, e.g., a protease inhibitor (e.g., bortezomib (VELCADE®), carfilzomib (KYPROLIS®), or ixazomib (NINLARO®)), an immunomodulating agent (e.g., thalidomide (THALOMID®), lenalidomide (REVLIMID®), or pomalidomide (POMALYST®)), a chemotherapy (e.g., melphalan, vincristine (ONCOVIN®), cyclophosphamide, etoposide, doxorubicin (ADRIAMYCIN®), liposomal doxorubicin (DOXIL®), or bendamustine (TREANDA®)), a corticosteroid (e.g., prednisone or dexamethasone), a histone deacetylase (HDAC) inhibitor (e.g., panobinostat (FARYDAK®), an anti-CD38 antibody (e.g., daratumumab (DARZALEX®)), an anti-SLAMF7 antibody (e.g., elotuzumab (EMPLICITI®)), an interferon, or a bone marrow transplantation (e.g., autologous stem cell transplantation (ASCT) or allogeneic stem cell transplantation), a bisphosphonate (e.g., pamidronate (AREDIA®) and zoledronic acid (ZOMETA®), a radiation therapy, a surgery, an intravenous immunoglobulin (IVIG), a treatment for low blood cell count (e.g., erythropoietin (PROCRIT®) or darbepoietin (ARANESP®), plasmapheresis, or a combination thereof.

Exemplary combination therapies that can be used in combination with an anti-CD138 antibody molecule described herein for treating multiple myeloma include, but are not limited to, melphalan and prednisone (MP), with or without thalidomide or bortezomib; vincristine, doxorubicin (ADRIAMYCIN®), and dexamethasone (VAD); thalidomide (or lenalidomide) and dexamethasone; bortezomib, doxorubicin, and dexamethasone; bortezomib, dexamethasone, and thalidomide (or lenalidomide); liposomal doxorubicin, vincristine, and dexamethasone; carfilzomib, lenalidomide, and dexamethasone; dexamethasone, cyclophosphamide, etoposide, and cisplatin (DCEP); dexamethasone, thalidomide, cisplatin, doxorubicin, cyclophosphamide, and etoposide (DT-PACE), with or without bortezomib; panobinostat, bortezomib, and dexamethasone; ixazomib, lenalidomide; and dexamethasone, and elotuzumab, lenalidomide, and dexamethasone.

Combination Therapies

The antibody molecules described herein can be used in combination with other therapies. For example, the combination therapy can include an antibody molecule co-formulated with, and/or co-administered with, one or more additional therapeutic agents, e.g., one or more additional therapeutic agents described herein. In other embodiments, the antibody molecules are administered in combination with other therapeutic treatment modalities, e.g., other therapeutic treatment modalities described herein. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with a disorder. In an embodiment, two or more treatments are delivered prophylactically, e.g., before the subject has the disorder or is diagnosed with the disorder. In another embodiment, the two or more treatments are delivered after the subject has developed or diagnosed with the disorder. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, the additional agent is a second antibody molecule, e.g., an antibody molecule different from a first antibody molecule. Exemplary antibody molecules that can be used in combination include, but are not limited to, any combination of the antibody molecules listed in Table 1.

In an embodiment, the antibody molecule is administered in combination with a second therapy to treat or prevent a myeloma, e.g., multiple myeloma.

In an embodiment, the antibody molecule is administered in combination with a protease inhibitor. Exemplary protease inhibitors include, e.g., bortezomib (VELCADE®), carfilzomib (KYPROLIS®), and ixazomib (NINLARO®).

In an embodiment, the antibody molecule is administered in combination with an immunomodulating agent. Exemplary immunomodulating agents include, e.g., thalidomide (THALOMID®), lenalidomide (REVLIMID®), and pomalidomide (POMALYST®).

In an embodiment, the antibody molecule is administered in combination with a chemotherapeutic agent. Exemplary chemotherapeutic agents include, e.g., melphalan, vincristine (ONCOVIN®), cyclophosphamide, etoposide, doxorubicin (ADRIAMYCIN®), liposomal doxorubicin (DOXIL®), and bendamustine (TREANDA®).

In an embodiment, the antibody molecule is administered in combination with a corticosteroid, e.g., prednisone and dexamethasone.

In an embodiment, the antibody molecule is administered in combination with a histone deacetylase (HDAC) inhibitor, e.g., panobinostat (FARYDAK®).

In an embodiment, the antibody molecule is administered in combination with an anti-CD38 antibody, e.g., daratumumab (DARZALEX®).

In an embodiment, the antibody molecule is administered in combination with an anti-SLAMF7 antibody, e.g., elotuzumab (EMPLICITI®).

In an embodiment, the antibody molecule is administered in combination with an interferon.

In an embodiment, the antibody molecule is administered in combination with bone marrow transplantation (e.g., autologous stem cell transplantation (ASCT) or allogeneic stem cell transplantation).

In an embodiment, the antibody molecule is administered in combination with a bisphosphonate, e.g., pamidronate (AREDIA®) or zoledronic acid (ZOMETA®).

In an embodiment, the antibody molecule is administered in combination with a radiation therapy.

In an embodiment, the antibody molecule is administered in combination with a surgery.

In an embodiment, the antibody molecule is administered in combination with an intravenous immunoglobulin (IVIG).

In an embodiment, the antibody molecule is administered in combination with a treatment for low blood cell count, e.g., erythropoietin (PROCRIT®) or darbepoietin (ARANESP®).

In an embodiment, the antibody molecule is administered in combination with plasmapheresis.

In an embodiment, the antibody molecule is administered in combination with melphalan and prednisone (MP), with or without thalidomide or bortezomib.

In an embodiment, the antibody molecule is administered in combination with vincristine, doxorubicin (ADRIAMYCIN®), and dexamethasone (VAD).

In an embodiment, the antibody molecule is administered in combination with thalidomide (or lenalidomide) and dexamethasone.

In an embodiment, the antibody molecule is administered in combination with bortezomib, doxorubicin, and dexamethasone.

In an embodiment, the antibody molecule is administered in combination with bortezomib, dexamethasone, and thalidomide (or lenalidomide).

In an embodiment, the antibody molecule is administered in combination with liposomal doxorubicin, vincristine, and dexamethasone;

In an embodiment, the antibody molecule is administered in combination with carfilzomib, lenalidomide, and dexamethasone.

In an embodiment, the antibody molecule is administered in combination with dexamethasone, cyclophosphamide, etoposide, and cisplatin (DCEP).

In an embodiment, the antibody molecule is administered in combination with dexamethasone, thalidomide, cisplatin, doxorubicin, cyclophosphamide, and etoposide (DT-PACE), with or without bortezomib.

In an embodiment, the antibody molecule is administered in combination with panobinostat, bortezomib, and dexamethasone.

In an embodiment, the antibody molecule is administered in combination with ixazomib, lenalidomide, and dexamethasone.

In an embodiment, the antibody molecule is administered in combination with elotuzumab, lenalidomide, and dexamethasone.

In an embodiment, the antibody molecule is administered in combination with a second agent that targets the CD138 pathway. Exemplary agents that target the CD138 pathway include, e.g., an agent that targets the extracellular domain of CD138 (e.g., synstatin, BT-062-DM4 (indatuximab ravtansine), B-B4 conjugated to $^{131}$I, OC-46F2, or GLVGLIFAV (SEQ ID NO: 448)), an agent that targets shed CD138 (e.g., NSC 405020, BB-94, PI-88, PG545, M402, SST00001, or Pentraxin-3), and an agent that targets genetic expression of CD138 (e.g., an all-trans retinoic acid, nimesulide, zoledronic acid, or imatinib) Other agents that target the CD138 pathway are described, e.g., Akl et al. *Oncotarget*. 2015; 6(30):28693-28715, the content of which in incorporated by reference in its entirety.

In an embodiment, the antibody molecule is administered in combination with lenalidomide and/or dexamethasone, e.g., to treat a multiple myeloma (e.g., a relapsed multiple myeloma).

In an embodiment, the antibody molecule is administered in combination with an FGFR2 antagonist (e.g., an anti-FGFR2 antibody, e.g., FPA144) to treat a solid tumor (e.g., an advanced solid tumor).

In an embodiment, the antibody molecule is administered in combination with a $\alpha_v\beta_3$ inhibitor (e.g., an ADC against integrin $\alpha_v\beta_3$, e.g., brentuximab vedotin), e.g., to treat Hodgkin lymphoma (e.g., relapsed or refractory Hodgkin lymphoma).

In an embodiment, the antibody molecule is administered in combination with a heparin or heparanase inhibitor (e.g., roneparstat (SST0001)), e.g., to treat a multiple myeloma (e.g., an advanced multiple myeloma).

In an embodiment, the antibody molecule is administered in combination with a VEGFR inhibitor (e.g., bevacizumab or cediranib), e.g., to treat a cancer (e.g., an advanced cancer).

In an embodiment, the antibody molecule is administered in combination with a Wnt signaling pathway inhibitor (e.g., ipafricept (OMP-54F28)), e.g., to treat a solid tumor.

In an embodiment, the antibody molecule is administered in combination with an FAK inhibitor (e.g., defactinib (VS-6063) or GSK2256098), e.g., to treat a solid tumor, e.g., a lung cancer (e.g., a non-small cell lung cancer, e.g., with a KRAS mutation).

In an embodiment, the antibody molecule is administered in combination with a glysoaminoglycan or heparanase inhibitor (e.g., necuparanib (M402)), optionally, further in combination with a chemotherapeutic agent (e.g., nab-paclitaxel or gemcitabine), e.g., to treat a pancreatic cancer (e.g., a metastatic pancreatic cancer).

In an embodiment, the antibody molecule is administered in combination with a mannose oligosaccharide, or a FGF, heparanase, and/or VEGF inhibitor (e.g., muparfostat (PI-88)), e.g., to treat a cancer (e.g., a melanoma).

In an embodiment, the antibody molecule is administered in combination with a chemically modified heparin sulfate/heparanase inhibitor (e.g., PG545), e.g., to treat a solid tumor (e.g., an advanced solid tumor).

In an embodiment, the antibody molecule is administered in combination with an amino acid or matrix metalloprotease inhibitor (e.g., intrapleural batimastat (BB-94)), e.g., to treat a malignant pleural effusion.

In an embodiment, the antibody molecule is administered in combination with a chimeric anti-CD138 antigen receptor-modified T cells, e.g., to treat a multiple myeloma (e.g., a relapsed and/or refractory multiple myeloma). Exemplary therapies that can be used in combination with an antibody molecule or composition described herein to treat or prevent other disorders are also described in the section of "Methods of Treating or Preventing Disorders" herein.

Methods of Diagnosis

In some aspects, the present disclosure provides a diagnostic method for detecting the presence of CD138 in vitro (e.g., in a biological sample, such as a biopsy or blood sample) or in vivo (e.g., in vivo imaging in a subject). The method includes: (i) contacting the sample with an anti-CD138 antibody molecule described herein, or administering to the subject, the antibody molecule; (optionally) (ii) contacting a reference sample, e.g., a control sample (e.g., a control biological sample, such as a biopsy or blood sample) or a control subject with an antibody molecule described herein; and (iii) detecting formation of a complex between the antibody molecule and CD138 in the sample or subject, or the control sample or subject, wherein a change, e.g., a statistically significant change, in the formation of the complex in the sample or subject relative to the control sample or subject is indicative of the presence of CD138 in the sample. The antibody molecule can be directly or indirectly labeled with a detectable substance to facilitate detection of the bound or unbound antibody molecule. Suitable detectable substances include various enzymes, prosthetic groups, fluorescent materials, luminescent materials and radioactive materials, as described above and described in more detail below.

The term "sample," as it refers to samples used for detecting a polypeptide (e.g., CD138) or a nucleic acid encoding the polypeptide includes, but is not limited to, cells, cell lysates, proteins or membrane extracts of cells, body fluids such as blood, or tissue samples such as biopsies.

Complex formation between the antibody molecule, and CD138, can be detected by measuring or visualizing either the antibody molecule bound to CD138 or unbound antibody molecule. Any suitable detection assays can be used, and conventional detection assays include an enzyme-linked immunosorbent assays (ELISA), a radioimmunoassay (RIA) or tissue immunohistochemistry. Alternative to labeling the antibody molecule, the presence of CD138 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of CD138 in the sample is inversely proportional to the amount of labeled standard bound to the antibody molecule.

The anti-CD138 antibody molecules described herein can be used to diagnose disorders that can be treated or prevented by the anti-CD138 antibody molecules described herein. The detection or diagnostic methods described herein can be used in combination with other methods described herein to treat or prevent a disorder described herein.

The present disclosure also includes any of the following numbered paragraphs:

1. An anti-CD138 antibody molecule, which:
   (i) binds, or substantially binds, to CD138 in an extracellular region proximal to the transmembrane domain of CD138; and
   (ii) causes an antibody-dependent cellular cytotoxicity (ADCC) activity on a cell expressing CD138.

2. The antibody molecule of paragraph 1, wherein the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain.

3. The antibody molecule of paragraph 1 or 2, wherein the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain.

4. The antibody molecule of any of paragraphs 1-3, which binds to an epitope on CD138 comprising five or more (e.g., 6, 7, 8, 9, 10, 11, 12, 13, 14, 15, 20, 25, 30, 35, 40, 45, 50, 55, 60, 65, 70, 75, or more) consecutive amino acid residues in the extracellular region.

5. The antibody molecule of any of paragraphs 1-4, wherein the extracellular region proximal to the transmembrane domain comprises, or consists of, amino acids 210-250 or 220-245 of any of SEQ ID NOS: 1-3 or 450.
6. The antibody molecule of any of paragraphs 1-5, which binds to an Fc receptor (FcR) (e.g., one or more of FcγRI, FcγRIIa, FcγRIIb, FcγRIIc, FcγRIIIa, or FcγRIIIb) on the surface of an immune cell (e.g., a natural killer (NK) cell, a macrophage, a monocyte, or an eosinophil).
7. The antibody molecule of any of paragraphs 1-5, wherein the cell expressing CD138 is a cancer cell or precancerous cell.
8. The antibody molecule of paragraph 7, wherein the cancer or precancerous cell is a myeloma cell.
9. The antibody molecule of any of paragraphs 1-8, which does not bind, or binds with low affinity, to an extracellular region of CD138 distant from the transmembrane domain.
10. The antibody molecule of any of paragraphs 1-9, which does not bind to an epitope on CD138 comprising five or more (e.g., 6, 7, 8, 9, 10, 11, 12, 13, 14, 15, 20, 25, 30, 35, or more) consecutive amino acid residues in an extracellular region distant from the transmembrane domain.
11. The antibody molecule of any of paragraphs 1-8, which binds, or substantially binds, an epitope on CD138 comprising five or more (e.g., 6, 7, 8, 9, 10, 11, 12, 13, 14, 15, 20, 25, 30, 35, or more) consecutive amino acid residues in an extracellular region distant from the transmembrane domain.
12. The antibody molecule of any of paragraphs 9-11, wherein the C-terminus of the extracellular region distant from the transmembrane domain is at least 100, 110, 120, 130, 140, 150, 160, 170, 180, 190, or 200 amino acids away from the N-terminus of the transmembrane domain.
13. The antibody molecule of any of paragraphs 9-12, wherein the extracellular region distant from the transmembrane domain comprises amino acids 23-50, 51-95, 88-121, or 111-150 of any of SEQ ID NOS: 1-3 or 450.
14. The antibody molecule of any of paragraphs 1-13, which does not bind, or binds with low affinity, to the integrin binding domain (IBD) of CD138, a region N-terminal to the IBD of CD138, or both.
15. The antibody molecule of any of paragraphs 1-13, which binds to the IBD of CD138, a region N-terminal to the IBD of CD138, or both.
16. The antibody molecule of any of paragraphs 1-15, which binds to CD138 with a disassociation constant ($K_D$) of less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.
17. The antibody molecule of any of paragraphs 1-16, wherein the binding affinity of the antibody molecule to a membrane-bound CD138 is at least 2, 3, 4, 5, 6, 7, 8, 9, 10, 20, 50, 100, 200, or 500-fold higher than the binding affinity to a soluble CD138.
18. The antibody molecule of any of paragraphs 1-17, which binds to a membrane-bound CD138 with a $K_D$ less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.
19. The antibody molecule of any of paragraphs 1-18, which binds to a soluble CD138 with a $K_D$ less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM, or with a $K_D$ of more than about 100, 200, 300, 400, or 500 nM.
20. The antibody molecule of any of paragraphs 1-19, which binds to a membrane-bound CD138 preferably over a soluble CD138, e.g., the binding affinity to a membrane-bound CD138 is at least 2, 3, 4, 5, 6, 7, 8, 9, or 10-fold higher than the binding affinity to a soluble CD138; or binds with similar affinity to a membrane-bound CD138 and a soluble CD138, e.g., the binding affinity to a membrane-bound CD138 is less than about 10%, 20%, 30%, 40%, 50%, 60%, 70%, 80%, 90%, or 100% higher than the binding affinity to a soluble CD138.
21. The antibody molecule of any of paragraphs 1-20, which binds to C1q and causes a complement-dependent cytotoxicity (CDC) activity on a cell expressing CD138.
22. The antibody molecule of any of paragraphs 1-21, which reduces (e.g., inhibits, blocks, or neutralizes) one or more biological activities of a cell expressing CD138 in vitro, ex vivo, or in vivo.
23. The antibody molecule of any of paragraphs 1-22, which mediates homotypic adhesion of one or more CD138-expressing cells. 24. The antibody molecule of any of paragraphs 1-23, which inhibits the action of a protease on a membrane-bound CD138, e.g., to reduce shedding of CD138.
25. The antibody molecule of any of paragraphs 1-24, which reduces (e.g., inhibits) proliferation of a cancer or precancerous cell expressing CD138.
26. The antibody molecule of any of paragraphs 1-25, comprising one or more (e.g., two or three) heavy chain CDRs and/or one or more (e.g., two or three) light chain CDRs of an anti-CD138 monoclonal antibody described herein.
27. The antibody molecule of any of paragraphs 1-26, comprising a heavy chain variable region (VH) and/or light chain variable region (VL) of an anti-CD138 monoclonal antibody described herein.
28. The antibody molecule of any of paragraphs 1-27, comprising an Fc region.
29. An anti-CD138 antibody molecule, which binds, or substantially binds, to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region proximal to the transmembrane domain of CD138.
30. The antibody molecule of paragraph 29, wherein the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain.
31. The antibody molecule of paragraph 29 or 30, wherein the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain.
32. The antibody molecule of any of paragraphs 29-31, wherein the extracellular region proximal to the transmembrane domain comprises, or consists of, amino acids 176-250 of any of SEQ ID NOS: 1-3 or 450.

33. The antibody molecule of any of paragraphs 29-32, which does not bind, or binds with low affinity, to an extracellular region of CD138 distant from the transmembrane domain.
34. The antibody molecule of any of paragraphs 29-33, wherein the epitope does not comprise five or more (e.g., 6, 7, 8, 9, 10, 11, 12, 13, 14, 15, 20, 25, 30, 35, or more) consecutive amino acid residues in an extracellular region distant from the transmembrane domain.
35. The antibody molecule of paragraph 33 or 34, wherein the C-terminus of the extracellular region distant from the transmembrane domain is at least 100, 110, 120, 130, 140, 150, 160, 170, 180, 190, or 200 amino acids away from the N-terminus of the transmembrane domain.
36. The antibody molecule of any of paragraphs 33-35, wherein the extracellular region distant from the transmembrane domain comprises amino acids 23-50, 51-95, 88-121, or 111-150 of any of SEQ ID NOS: 1-3 or 450.
37. The antibody molecule of any of paragraphs 33-36, which does not bind, or binds with low affinity, to the integrin binding domain (IBD) of CD138, a region N-terminal to the IBD of CD138, or both.
38. The antibody molecule of any of paragraphs 33-36, which binds to the IBD of CD138, a region N-terminal to the IBD of CD138, or both.
39. An anti-CD138 antibody molecule, which binds, or substantially binds, to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region distant to the transmembrane domain of CD138, wherein the epitope does not consist of amino acid residues 107-111 of any of SEQ ID NOS: 1-3 or 450.
40. The antibody molecule of paragraph 39, wherein the epitope does not comprise amino acids 107-111 of any of SEQ ID NOS: 1-3 or 450.
41. The antibody molecule of paragraph 39 or 40, wherein the C-terminus of the extracellular region distant from the transmembrane domain is at least 100, 110, 120, 130, 140, 150, 160, 170, 180, 190, or 200 amino acids away from the N-terminus of the transmembrane domain.
42. The antibody molecule of any of paragraphs 39-41, wherein the extracellular region distant to the transmembrane domain comprises, or consists of, amino acids 88-121 of any of SEQ ID NOS: 1-3 or 450.
43. An anti-CD138 antibody molecule, which binds, or substantially binds, to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region proximal to the transmembrane domain of CD138; and four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region distant to the transmembrane domain of CD138.
44. The antibody molecule of paragraph 43, wherein the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain.
45. The antibody molecule of paragraph 43 or 44, wherein the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain.
46. The antibody molecule of any of paragraphs 43-45, wherein the extracellular region proximal to the transmembrane domain comprises, or consists of, amino acids 176-250 or amino acids 210-250 of any of SEQ ID NOS: 1-3 or 450.
47. The antibody molecule of any of paragraphs 43-46, wherein the C-terminus of the extracellular region distant from the transmembrane domain is at least 100, 110, 120, 130, 140, 150, 160, 170, 180, 190, or 200 amino acids away from the N-terminus of the transmembrane domain.
48. The antibody molecule of any of paragraphs 43-47, wherein the extracellular region distant from the transmembrane domain comprises, or consists of, amino acids 23-50, 51-95, 88-121, or 111-150 of any of SEQ ID NOS: 1-3 or 450.
49. The antibody molecule of any of paragraphs 43-48, wherein the extracellular region distant to the transmembrane domain comprises, or consists of, amino acids 88-121 of any of SEQ ID NOS: 1-3 or 450.
50. The antibody molecule of any of paragraphs 43-49, which does not bind, or binds with low affinity, to the integrin binding domain (IBD) of CD138.
51. The antibody molecule of any of paragraphs 43-50, which does not bind, or binds with low affinity, to a region N-terminal to the IBD of CD138.
52. The antibody molecule of paragraph 51, wherein the epitope does not comprise amino acids 107-111 of any of SEQ ID NOS: 1-3 or 450.
53. The antibody molecule of any of paragraphs 43-49, which binds to the IBD of CD138.
54. The antibody molecule of any of paragraphs 43-50, which binds to a region N-terminal to the IBD of CD138.
55. The antibody molecule of paragraph 54, wherein the epitope comprises amino acids 107-111 of any of SEQ ID NOS: 1-3 or 450.
56. The antibody molecule of any of paragraphs 29-55, which binds to an Fc receptor (FcR) (e.g., one or more of FcγRI, FcγRIIa, FcγRIIb, FcγRIIc, FcγRIIIa, or FcγRIIIb) on the surface of an immune cell (e.g., a natural killer (NK) cell, a macrophage, a monocyte, or an eosinophil).
57. The antibody molecule of any of paragraphs 29-56, which is capable of causing an ADCC activity on a cell expressing CD138.
58. The antibody molecule of paragraph 57, wherein the cell expressing CD138 is a cancer cell or precancerous cell.
59. The antibody molecule of paragraph 58, wherein the cancer or precancerous cell is a myeloma cell.
60. The antibody molecule of any of paragraphs 29-59, which binds to CD138 with a disassociation constant ($K_D$) of less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.
61. The antibody molecule of any of paragraphs 29-60, wherein the binding affinity of the antibody molecule to a membrane-bound CD138 is at least 2, 3, 4, 5, 6, 7, 8, 9, 10, 20, 50, 100, 200, or 500-fold higher than the binding affinity to a soluble CD138; or binds with similar affinity to a membrane-bound CD138 and a soluble CD138, e.g., the binding affinity to a membrane-bound CD138 is less than about 10%, 20%, 30%, 40%, 50%, 60%, 70%, 80%, 90%, or 100% higher than the binding affinity to a soluble CD138.
62. The antibody molecule of any of paragraphs 29-61, which binds to a membrane-bound CD138 with a $K_D$ less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM.
63. The antibody molecule of any of paragraphs 29-62, which binds to a soluble CD138 with a $K_D$ of less than about 100, 90, 80, 70, 60, 50, 40, 30, 20, 10, 8, 6, 4, 3, 2, 1, 0.5, 0.2, 0.1, 0.05, 0.01, 0.005, or 0.001 nM, or about 10-0.001, 10-0.01, 5-0.01, 3-0.05, or 1-0.1 nM, or greater than about 100, 200, 300, 400, or 500 nM.
64. The antibody molecule of any of paragraphs 29-63, which binds to a membrane-bound CD138 preferably over a soluble CD138, e.g., the binding affinity to a membrane-bound CD138 is at least 2, 3, 4, 5, 6, 7, 8, 9, or 10-fold higher than the binding affinity to a soluble CD138.
65. The antibody molecule of any of paragraphs 29-63, which binds to C1q and causes a complement-dependent cytotoxicity (CDC) activity on a cell expressing CD138.
66. The antibody molecule of any of paragraphs 29-65, which reduces (e.g., inhibits, blocks, or neutralizes) one or more biological activities of a cell expressing CD138 in vitro, ex vivo, or in vivo.
67. The antibody molecule of any of paragraphs 29-66, which mediates homotypic adhesion of one or more CD138-expressing cells.
68. The antibody molecule of any of paragraphs 29-67, which inhibits the action of a protease on a membrane-bound CD138, e.g., to reduce shedding of CD138.
69. The antibody molecule of any of paragraphs 29-68, which reduces (e.g., inhibits) proliferation of a cancer or precancerous cell expressing CD138.
70. The antibody molecule of any of paragraphs 29-69, comprising one or more (e.g., two or three) heavy chain CDRs and/or one or more (e.g., two or three) light chain CDRs of an anti-CD138 monoclonal antibody described herein.
71. The antibody molecule of any of paragraphs 29-70, comprising a heavy chain variable region (VH) and/or light chain variable region (VL) of an anti-CD138 monoclonal antibody described herein. 72. The antibody molecule of any of paragraphs 29-71, comprising an Fc region.
73. An anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following:
  (i) an HCDR1 comprising an amino acid sequence that differs by no more than 1, 2, or 3 amino acid residues from, or has at least 85, 90, 95, 99 or 100% homology with, the amino acid sequence of the HCDR1 of an anti-CD138 monoclonal antibody described herein (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409);
  (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; or
  (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody; or
(b) a light chain variable region (VL), wherein the VL comprises three light chain complementarity determining regions (LCDR1, LCDR2, and LCDR3), wherein the VL comprises one, two, or all of the following:
  (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody;
  (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; or
  (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.
74. The antibody molecule of paragraph 73, wherein the VH comprises:
(i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody;
(ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and
(iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody.
75. The antibody molecule of paragraph 73 or 74, wherein the VH comprises: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody.
76. The antibody molecule of any of paragraphs 73-75, wherein the VL comprises:
(i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody;
(ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and
(iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

77. The antibody molecule of any of paragraphs 73-76, wherein the VL comprises: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

78. The antibody molecule of any of paragraphs 73-77, comprising:
(a) a VH comprising:
   (i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody;
   (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and
   (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody, and
(b) a VL comprising:
   (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody;
   (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and
   (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

79. The antibody molecule of any of paragraphs 73-78, comprising:
(a) a VH comprising: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody, and
(b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

80. The antibody molecule of any of paragraphs 73-79, wherein the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody.

81. The antibody molecule of any of paragraphs 73-80, wherein the VH comprises the amino acid sequence of the VH of the anti-CD138 antibody.

82. The antibody molecule of any of paragraphs 73-81, wherein the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL of the anti-CD138 antibody.

83. The antibody molecule of any of paragraphs 73-82, wherein the VL comprises the amino acid sequence of the VL of the anti-CD138 antibody.

84. The antibody molecule of any of paragraphs 73-83, wherein:
(a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody; and
(b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody.

85. The antibody molecule of any of paragraphs 73-84, wherein the VH comprises the amino acid sequence of the VH of the anti-CD138 antibody and the VL comprises the amino acid sequence of the VL of the anti-CD138 antibody.

86. The antibody molecule of any of paragraphs 73-85, comprising an Fc region. 87. An anti-CD138 antibody molecule comprises:
(I) (a) a heavy chain variable region (VH), wherein the VH comprises three heavy chain complementarity determining regions (HCDR1, HCDR2, and HCDR3), wherein the VH comprises three heavy chain complementarity determining regions (HCDR1, HCDR2, and HCDR3), wherein the VH comprises: (i) an HCDR1 comprising an amino acid sequence of G-Y-N/S/T-F-S-S-Y (SEQ ID NO: 438); (ii) an HCDR2 comprising an amino acid sequence of H-P-S-D-S-T (SEQ ID NO: 351); or (iii) an HCDR3 comprising an amino acid sequence of F-V-Y; and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of R-S-S-K-S-L-L-Y-K-D-G-K-T-Y-L-N (SEQ ID NO: 352); (ii) an LCDR2 comprising an amino acid sequence of V-V-S-T-R-A-S(SEQ ID NO: 353); or (iii) an LCDR3 comprising an amino acid sequence of Q-Q-L-V-E-Y-P-Y-T (SEQ ID NO: 354); or
(II) (a) a heavy chain variable region (VH), wherein the VH comprises three heavy chain complementarity determining regions (HCDR1, HCDR2, and HCDR3), wherein the VH comprises three heavy chain complementarity determining regions (HCDR1, HCDR2, and HCDR3), wherein the VH comprises: (i) an HCDR1 comprising an amino acid sequence of S—Y-Y-M-H (SEQ ID NO: 380); (ii) an HCDR2 comprising an amino acid sequence of T-I-H-P-S-D-S-T-T-N-C/Y-N-Q-K-F-K-G (SEQ ID NO: 439); or (iii) an HCDR3 comprising an amino acid sequence of F-V-Y; and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of R-S-S-K-S-L-L-Y-K-D-G-K-T-Y-L-N(SEQ ID NO: 352); (ii) an LCDR2 comprising an amino acid sequence of V-V-S-

T-R-A-S(SEQ ID NO: 353); or (iii) an LCDR3 comprising an amino acid sequence of Q-Q-L-V-E-Y-P-Y-T (SEQ ID NO: 354).

88. The antibody molecule of any of paragraphs 1-87, comprising two VHs and two VLs.
89. The antibody molecule of any of paragraphs 1-88, which is a synthetic antibody molecule or an isolated antibody molecule.
90. The antibody molecule of any of paragraphs 1-89, which is a monovalent antibody molecule, a multivalent (e.g., bivalent, trivalent, or tetravalent) antibody molecule, a monospecific molecule, or a multispecific (e.g., bispecific, trispecific, or tetraspecific) antibody molecule.
91. The antibody molecule of any of paragraphs 1-90, which is a humanized antibody molecule.
92. The antibody molecule of any of paragraphs 1-91, comprising one or more framework regions derived from human framework germline sequence.
93. The antibody molecule of any of paragraphs 1-92, which is an IgG antibody.
94. The antibody molecule of any of paragraphs 1-93, comprising a heavy chain constant region of IgG chosen from IgG1, IgG2, IgG3, or IgG4.
95. The antibody molecule of any of paragraphs 1-94, comprising a light chain constant region of kappa or lambda light chain.
96. The antibody molecule of any of paragraphs 1-95, comprising an Fc region comprising one or more mutations to increase the binding affinity to neonatal receptor FcRn and/or the half-life of the antibody molecule.
97. The antibody molecule of any of paragraphs 1-96, comprising an Fc region comprising one or more mutations described herein, e.g., to increase one or more of half-life, ADCC, CDC, or ADCP.
98. An antibody molecule, which competes for binding to CD138 with an anti-CD138 antibody molecule described herein, e.g., an anti-CD138 monoclonal antibody described herein (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409).
99. An antibody molecule, which binds, or substantially binds, to an epitope that completely or partially overlaps with the epitope of an anti-CD138 antibody molecule described herein, e.g., an anti-CD138 monoclonal antibody described herein (e.g., any of antibodies CD001, CD002, CD003, CD004, CD005, CD006, 602, 603, 604, 607, 613, 614, 617, 624, 632, 616, 619, 623, 1610, 2510, 2610, 2710, 2810, 2910, or 1409).
100. An antibody-molecule drug conjugate (ADC) comprising an antibody molecule of any of paragraphs 1-99, optionally comprising a cytotoxic agent, further optionally comprising a linker.
101. A composition comprising an antibody molecule of any of paragraphs 1-99, or an ADC of paragraph 100, optionally, wherein the composition is a pharmaceutical composition.
102. The composition of paragraph 101, further comprising a pharmaceutically acceptable carrier.
103. A nucleic acid molecule encoding a heavy chain variable region (VH), a light chain variable region (VL), or both, of an antibody molecule of any of paragraphs 1-99.
104. A vector comprising a nucleic acid molecule of paragraph 103.
105. A cell comprising a nucleic acid molecule of paragraph 103 or a vector of paragraph 104, optionally, wherein the cell is an isolated cell.
106. A kit comprising an antibody molecule of any of paragraphs 1-99, an ADC of paragraph 100, or a composition of paragraph 101 or 102, and instructions to use of the antibody molecule or composition.
107. A container comprising an antibody molecule of any of paragraphs 1-99, an ADC of paragraph 100, or a composition of paragraph 101 or 102.
108. A method of producing an anti-CD138 antibody molecule, the method comprising culturing a cell of paragraph 105 under conditions that allow production of an antibody molecule, thereby producing the antibody molecule.
109. The method of paragraph 108, further comprising isolating or purifying the antibody molecule.
110. An antibody molecule of any of paragraphs 1-99, an ADC of paragraph 100, or a composition of paragraph 101 or 102, for use in a method of treating a cancer in a subject.
111. The antibody molecule, ADC, or composition for use of paragraph 110, wherein the cancer is a hematological cancer.
112. The antibody molecule, ADC, or composition for use of paragraph 110 or 111, wherein the cancer is a multiple myeloma.
113. The antibody molecule, ADC, or composition for use of paragraph 110, wherein the cancer is a solid tumor, e.g., a solid tumor described herein.
114. The antibody molecule, ADC, or composition for use of any of paragraphs 110-113, wherein the antibody molecule, ADC, or composition is administered to the subject intravenously.
115. The antibody molecule, ADC, or composition for use of any of paragraphs 110-114, wherein the antibody molecule, ADC, or composition is administered to the subject at a dose between 0.1 mg/kg and 50 mg/kg, between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg.
116. The antibody molecule, ADC, or composition for use of any of paragraphs 110-115, wherein the antibody molecule, ADC, or composition is administered to the subject at a fixed dose between 10 mg and 1000 mg, between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg.
117. The antibody molecule, ADC, or composition for use of any of paragraphs 110-116, wherein the antibody molecule, ADC, or composition is administered once a week, twice a week, once every two weeks, once every three weeks, or once every four weeks.

118. The antibody molecule, ADC, or composition for use of any of paragraphs 110-117, further comprising determining the level of CD138 in a sample from the subject.

119. The antibody molecule, ADC, or composition for use of any of paragraphs 110-118, further comprising administering to the subject a second therapy for cancer.

120. An antibody molecule of any of paragraphs 1-99, an ADC of paragraph 100, or a composition of paragraph 101 or 102, for use in a method of treating a precancerous condition or preventing a cancer.

121. The antibody molecule, ADC, or composition for use of paragraph 120, wherein the precancerous condition is smoldering myeloma or monoclonal gammopathy of undetermined significance (MGUS).

122. The antibody molecule, ADC, or composition for use of paragraph 120, wherein the cancer is multiple myeloma.

123. A method of causing an ADCC activity, the method comprising contacting a cell or subject an antibody molecule of any of paragraphs 1-99, an ADC of paragraph 100, or a composition of paragraph 101 or 102, thereby causing the ADCC activity.

124. A method of treating a cancer, the method comprising administering to a subject in need thereof an effective amount of an antibody molecule of any of paragraphs 1-99, an ADC of paragraph 100, or a composition of paragraph 101 or 102, thereby treating the cancer.

125. A method of treating a precancerous condition or preventing a cancer, the method comprising administering to a subject in need thereof an effective amount of an antibody molecule of any of paragraphs 1-99, an ADC of paragraph 100, or a composition of paragraph 101 or 102, thereby treating the precancerous condition or preventing the cancer.

126. A method of detecting an anti-CD138 molecule, the method comprising contacting a cell or a subject with an antibody molecule of any of paragraphs 1-99, thereby detecting the CD138 molecule.

127. The method of paragraph 126, wherein the antibody molecule is coupled with a detectable label.

128. The method of paragraph 126 or 127, wherein the CD138 molecule is detected in vitro, ex vivo, or in vivo.

EXAMPLES

Example 1: Mouse Immunizations

CD-1 IGS (outbred stock) mice (Charles River Laboratories), female (20-25 g weight), 5-6 weeks old were immunized intravenously (i.v.) with 50 µg of plasmid encoding human CD138 (pCDNA3.1-hCD138) vector on day 0, 14 and 28. A second group of mice were immunized intraperitoneally with rCD138 (Sino Biological, Inc.)+Sigma adjuvant (1:1) or Peptide 6+Sigma adjuvant (1:1) on day 0 and boosted with the same on day 14 and day 30. Following 3 rounds of DNA or protein/peptide immunization, the serum titers of anti-CD138 antibodies were detected by indirect ELISA using recombinant CD138 (R&D Systems). The titer of peptide-6 binding antibody was also evaluated by ELISA using Peptide-6. In brief, 200 ng of rCD138 or Peptide-6 in PBS were coated on Maxisorp 96-well flat bottom plates (NUNC #439454), overnight at 4° C. Coated plates were blocked in 1×blocking buffer containing 5% BLOTTO™ in PBS and 0.05% Tween-20 (PBST) for 1 hour at room temperature. All subsequent incubation steps were followed out with an intervening 3× wash step in PBST. Anti-CD138 (or anti-peptide-6) antibody titers were determined from a fold-dilution of mouse sera (in PBS) initially starting at 1:50 and followed by incubation of a 1:5000-1:10000 HRP conjugated goat anti-mouse IgG secondary antibody (Jackson ImmunoResearch Laboratories) for 1 hour at room temperature. Anti-CD138 (or anti-peptide-6) immunoglobulin reactivity was visualized using 100 µl/well of freshly prepared TMB substrate (KPL). Colorimetric development was carried out for up to 10 minutes at room temperature before quenching enzymatic reaction by the addition of 100 µl of 1N sulfuric acid and quantification by absorbance at 450 nm. Mice with strong seropositive titers against primary immunogen (human CD138) were boosted with 5-10 ug of rCD138 or Peptide-6 by tail vein injection three days prior to sacrifice, removal of spleen and isolation of splenoctye fusions. Select mice received two additional intraperitoneal (i.p.) immunizations with peptide-6 mixed with Sigma adjuvant prior to the Peptide-6 tail vein boost. Mice with preferable species cross-reactivity from serum profiling were noted.

Example 2: Hybridoma Development

P3X63Ag8.653 plasmacytomas (ATCC #CRL-1580), herein referred to as P3X cells, were used as source of fusion partner myelomas. Splenically-derived B cell clones were immortalized using published methods with modification. In brief, P3X cells were cultured at least 1 week prior to use and maintained in log phase to achieve a target cell density of between $6\times10^5$ and $1.2\times10^6$ cells/mL and 95% viability the day prior to subsequently performing the splenic fusion. Spleen cells were isolated from 2-3 mice per immunization arm following euthanization and cardiac puncture and collected into DMEM+1% antibiotic (penicillin/streptomycin), followed by gently washing centrifugation (2×) to pellet tissue debris and clarify suspended splenocytes. Splenocytes were then pelleted by centrifugation for 10 min at 400×g at 4° C., and red blood cells lysed at room temperature for 5 minutes following gentle resuspension of cell pellet in 1× red blood cell lysis buffer. Splenocytes were collected by centrifugation (2×) following dilution with ice cold DMEM. P3X cells were also washed 3× in DMEM prior to fusion.

Mouse splenocytes were fused with P3X cells in fusion medium (50% PEG 1450, Sigma Aldrich) at a 3:1 ratio in accordance with established methods. In brief, pre-warmed PEG was added gradually to pelleted mixture of splenocytes and P3X cells (37° C., with gentle resuspension) followed by gradual addition of pre-warmed DMEM. Fused cells were collected by low speed centrifugation and resuspended in hybridoma selective media (hypoxanthine-aminopterin-thymidine, Sigma Aldrich) followed by incubation at 37° C. for 30 minutes. Fused cells sere plated in a 96 well plate at a density of approximately $2.0\times10^6$ spleen cells per plate (20,000 cells per well). Hybridoma supernatants were screened for CD138 binding by ELISA on day 10-14 post-fusion as described. In brief, supernatants from conditioned media were quantified for total IgG by bioinferometry using AMC anti mouse IgG quantification kit (Pall Biosciences). Supernatants from hybridoma conditioned media were normalized to 10 µg/mL when possible and assayed for binding to CD138 or Peptide-6 by ELISA. Positive hybridomas were selected for culture scale up, antibody purification and further characterization as described.

CD138 and Peptide-6 positive hybridomas were screened for receptor blocking activity by ELISA. In brief, Recombinant CD138 (10 ug/ml) or Peptide-6 (20 ug/ml) in 1×PBS (pH 7.4) were coated on to Maxisorp 96-well flat bottom plates overnight at 4° C. Plates were washed with PBS+ 0.05% Tween20 (PBST) and blocked with 5% BLOTT™. Mouse sera or anti-CD138 antibodies were diluted in PBST and incubated for 2 hr at room temperature. The unbound antibody/sera was washed away post incubation by 3× wash with PBST. Detection of CD138 or Peptide-6 antibody was quantified using goat anti-mouse HRP secondary antibody conjugated with HRP (Sigma Aldrich) used at 1:5000 dilution followed by colorimetric development using 100 μl/well of freshly prepared TMB substrate (KPL) carried out for up to 30 minutes at room temperature before quenching enzymatic reaction by the addition of 1N sulfuric acid. ELISA signal was quantified by absorbance at 450 nm. ELISA data was analyzed by non-linear regression. $IC_{50}$ values were calculated based on a 4-parameter fit of antibody titration curves.

Example 3: Determination and Molecular Cloning of Anti-CD138 Immunoglobulin Sequences VH and VL gene sequences of mouse antibodies derived from hybridoma screening were initially determined by reverse transcriptase PCR of B cell RNA using a pool of pre-defined set of mouse Ig sequence-specific primers of varying degeneracy. 5' Primer design for VH sequencing was based on a comprehensive analysis of the mouse immunoglobulin database with corresponding alignment to variable leader sequences. From this analysis, VH leader sequences were clustered (or binned based on sequence relatedness and representation of germline "families"); a unique set of primers, each predicted to anneal more specifically to these binned VH sequence families were designed and used as a cocktail in the RT-PCR reaction. 3' primers were designed to anneal in the constant region of the heavy chain and corresponded to unique sequences in CH1 that define the four known mouse IgG constant regions (IgG1, IgG2a, IgG2b and IgG3). IgM related VH sequences were amplified as above but with substitution of an IgM isotype 3' primer. Similarly, a so-called "pooled primer" RT-PCR approach was used to amplify the corresponding VL sequences from mouse hybridoma RNA. A systematic query of all known mouse VL leader sequences was likewise performed. As kappa and lambda light chains share neither the constant region nor variable region sequences, separate primer sets (kappa vs. lambda specific) were designed. 3' primers were designed based on isotype specific light chain constant region sequence (kappa vs. lambda) in a manner analogous to the one described above for heavy chain sequences.

RT-PCR amplification of hybridoma gene sequences from B cell RNA was completed using otherwise established methods. In brief, RNA was extracted from $0.5-2\times10^6$ cells using the RNeasy kit (Life Technologies) as per manufacturer's instructions. Cell lysis was facilitated using QIAshredder or related method for initial nucleic acid extraction. Purified RNA was quantified by UV absorbance. cDNA synthesis and subsequent PCR amplification (using Platinum Taq polymerase and primer mixes described above) were completed in tandem using Superscript III One Step RT-PCR kit (Life Technologies). PCR amplicons were purified using QIAquick PCR clean up kit (Life Technologies) and quantified by UV absorbance at 260 and 280 nm using a Nanodrop spectrophotometer. PCR products were also analyzed by agarose gel electrophoresis to confirm predicted size and gel purified as needed. VH and VL gene sequences were determined by directly sequencing of PCR products using nested primers. Ambiguous sequence data was followed by re-amplification of cell RNA by RT PCR as described above but with modification to protocol and using a subset of smaller pooled primer sets; if necessary PCR products were cloned by TA cloning into an intermediate vector) and transformed into chemically competent TOP10 (Life Technologies) or DH5a (New England Biolabs) as per the manufacturers protocols.

DNA sequence data was analyzed using publically available databases (e.g., International Immunogenetics Information system (IMGT), VBase, or NCBI Ig-Blast) to evaluate germline usage, identify CDR sequences and assign putative isotype when possible. gBlocks based on the identified VH and VL sequences were ordered (IDT DNA) and sub-cloned into pcDNA3.1 vectors containing osteonectin leader sequence and human IgGlk heavy chain or light chain constant regions.

Example 4: Purification of Anti-CD138 Antibodies

CD138 positive hybridoma clones were cultured at sequentially higher scale from 96 well plates to 24 well plates and subsequently to T150 flasks (20 mL culture volume). Prior to purification, cells were transferred out of HAT selective media into pre-defined, low Ig media. Supernatants were harvested 3-5 days after media transfer and clarified by centrifugation, followed by sterile filtration through a 0.22 μm PES membranes (Corning). IgG titers were confirmed by Bioinferometry as described. Supernatants were diluted 1:1 with 2× Protein G binding buffer (1M glycine, 2M NaCl, pH 9.0). Antibodies were purified by Protein G affinity chromatography using 1 mL Protein G HiTrap columns (GE Health Care) at a flow rate of 1 ml/min and as per the manufacturer's recommendations. IgG was eluted from the protein G column by lowering pH using 0.1M glycine buffer, pH 2.8 followed by immediate neutralization using 2M TRIS, pH 8.5. Purified antibodies were reformulated by dialysis in 1×PBS, pH 7.4 followed by concentration by ultrafiltration using an Ultra-30 AMICON 30 kD MWCO filtration unit. Final antibody concentration was determined spectrophotometrically by NanoDrop using a generalized extinction coefficient for murine antibodies (IgG1). Antibody purity and integrity was confirmed by SDS-PAGE under both reducing and non-reducing conditions.

Example 5: Recombinant Expression and Purification of Antibodies

Co-expression of the heavy and light chain vectors was performed by transient transfection in Expi293 cells using the Expi293 transfection kit (Thermo Fisher catalogue #A14524) following the manufacturer's protocol. The heavy and light chain vectors were co-transfected at a 1:2 ratio. Supernatant was harvested 5 to 7 days post transfection for protein A purification. Antibody titer was quantified by bioinferometry using Protein A-immobilized biosensors (Pall Biosensors). Recombinant antibodies were purified from culture supernatant following clarification by low speed centrifugation and sterile filtration through 0.22 μm PES membranes. Antibodies were purified from cell culture supernatant using 1 mL columns packed with mAb select sure protein A resin (GE catalogue #17543801) using the AKTA purifier 10 FPLC system. Briefly, sterile filtered cell culture supernatant was loaded onto the columns at a flow rate of 2 mL/minute. Columns were washed with 10 column volumes of PBSN (1×PBS with 0.05% sodium azide). Antibodies were eluted with 10 column volumes of elution buffer (100 mM glycine pH 2.5) and neutralized by addition 17.5% v/v of neutralization buffer (1M Tris, 1M NaCl, pH 8.0) and collated in 1 mL fractions. The chromatogram for absorbance at 280 nm was used to identify elution fractions containing the antibody. All antibodies were then dialyzed into 1×PBS using 10,000 dalton molecular weight cut-off cassette (Thermo Fisher catalogue #66380).

Example 6: Characterization of Anti-CD138 Antibodies

Binding of anti-CD138 antibodies to CD138 was tested by flow cytometry binding assay. Multiple myeloma cell lines RPMI 8226 (ATCC) and U266 (ATCC) were grown in RPMI1640 with 10% FBS. On the day of experiment, $0.25 \times 10^6$ cells were washed with FACS buffer (PBS+0.5% BSA) and incubated with dilution series of anti-CD138 antibodies (starting 10 ug/ml) or hybridoma supernatants (starting with undiluted supernatant) for 30 min at 4° C. followed by incubation with goat-anti-human/mouse conjugated APC antibodies (BioLegend) for 30 min at 4° C. Fluorescence was detected using flow cytometer.

Antibody dependent cellular cytotoxicity (ADCC) assays were performed using the ADCC Reporter Bioassay from Promega (catalogue #G7014) following the manufacturer's protocol. Purified anti-CD138 antibodies or hybridoma supernatants were assessed for their ADCC activity on U266 myeloma cells in low IgG growth media. Briefly, in a 96 well white bottom plate Anti-CD138 antibodies were mixed with U266 cells at different concentration followed by Jurkat T cells were added at a ratio of 10:1 effector to target ratio and incubated at 37° C. for 16 hr. The Jurkat T cell used the assays express human/mouse CD16 (Promega effector cells). Bio Glo (Luciferin from Promega) was added to all wells and luminescence was analyzed by spectrophotometer. The values of antibody concentration (x-axis) and fold induction of the luminescent reporter gene (y-axis) were fit to a 4-parameter logistic regression (4PL) curve. The curve fit was then used to determine the EC50 (the midpoint of the 4PL) and the maximum induction for each Fc variant.

Anti-CD138 antibodies were tested for growth inhibition properties using WST assay. U266 and RPMI8226 cells were seeded in a 96well tissue culture plates at a density of 5000 cells/well. Purified anti-CD138 antibodies were diluted in low serum media at different concentrations and incubated at 37° C. After 3-5 days cell Proliferation reagent WST-1 was added at 1:10 final volume and incubated up to 4 h at 37° C. Absorbance was read at 440 nm using spectrophotometer.

Example 7: Identification of Anti-CD138 Antibodies that Bind to Desired Epitopes Multiple antibodies that bind to desired epitope were identified. The peptides used to identify the antibodies are described in FIG. 2. Representative examples are shown in Table 6 below.

TABLE 6

Exemplary Anti-CD138 Antibodies and Their Binding to CD138

| mAb ID | rCD138 (ELISA O.D.) | RPMI 8226 (% cells Positive) | U266 (% cells Positive) | Pep1/Pep2 (ELISA O.D.) | Pep3 (ELISA O.D.) | Pep4 (ELISA O.D.) | Pep5 (ELISA O.D.) | Pep6 (ELISA O.D.) |
|---|---|---|---|---|---|---|---|---|
| #101 | 3.032 | 11.8 | 7.6 | 0.162 | 0.138 | 0.176 | 2.817 | 0.108 |
| #102 | 2.878 | 12.9 | 6.8 | 0.109 | 0.087 | 0.129 | 2.581 | 0.078 |
| #106 | 2.861 | 89.3 | 91.3 | 0.121 | 0.095 | 0.120 | 2.834 | 0.292 |
| #110 | 2.780 | 33.1 | 58.7 | 0.123 | 0.094 | 0.125 | 0.359 | 0.083 |
| #128 | 2.815 | 65.0 | 19.2 | 0.128 | 0.138 | 2.926 | 0.084 | 0.073 |
| #135 | 2.861 | 96.8 | 98.6 | 0.120 | 0.090 | 0.115 | 2.810 | 0.111 |
| #149 | 2.879 | 95.7 | 98.4 | 0.097 | 0.089 | 0.106 | 2.792 | 0.075 |
| #150 | 2.884 | 9.8 | 12.0 | 0.104 | 0.080 | 0.154 | 2.806 | 0.086 |
| 602 | 0.574 | 87.9 | 96.8 | 0.150 | 0.058 | 0.056 | 0.059 | 1.002 |
| 603 | 0.585 | 81.4 | 95.8 | 0.075 | 0.047 | 0.051 | 0.053 | 0.863 |
| 604 | 0.610 | 82.5 | 96.0 | 0.062 | 0.058 | 0.058 | 0.067 | 0.939 |
| 607 | 0.453 | 7.6 | 69.1 | 0.062 | 0.062 | 0.074 | 0.076 | 0.746 |
| 613 | 0.486 | 77.4 | 94.8 | 0.062 | 0.056 | 0.058 | 0.053 | 0.642 |
| 614 | 0.682 | 85.3 | 96.3 | 0.147 | 0.066 | 0.069 | 0.082 | 0.925 |
| 617 | 0.581 | 43.3 | 89.4 | 0.102 | 0.084 | 0.091 | 0.066 | 0.809 |
| 624 | 1.525 | 89.3 | 96.7 | 0.680 | 0.069 | 0.069 | 0.066 | 1.682 |
| 632 | 1.503 | 43.1 | 80.9 | 0.477 | 0.062 | 0.063 | 0.068 | 1.642 |
| 616 | 1.178 | 18.3 | 6.1 | 0.069 | 0.063 | 0.065 | 0.061 | 1.618 |
| 619 | 0.882 | 85.0 | 3.7 | 0.064 | 0.067 | 0.066 | 0.066 | 1.367 |
| 623 | 0.803 | 63.8 | 7.0 | 0.098 | 0.086 | 0.082 | 0.080 | 1.674 |

Example 8: Effect of Epitope Engagement on Effector Functions

Figure 3:
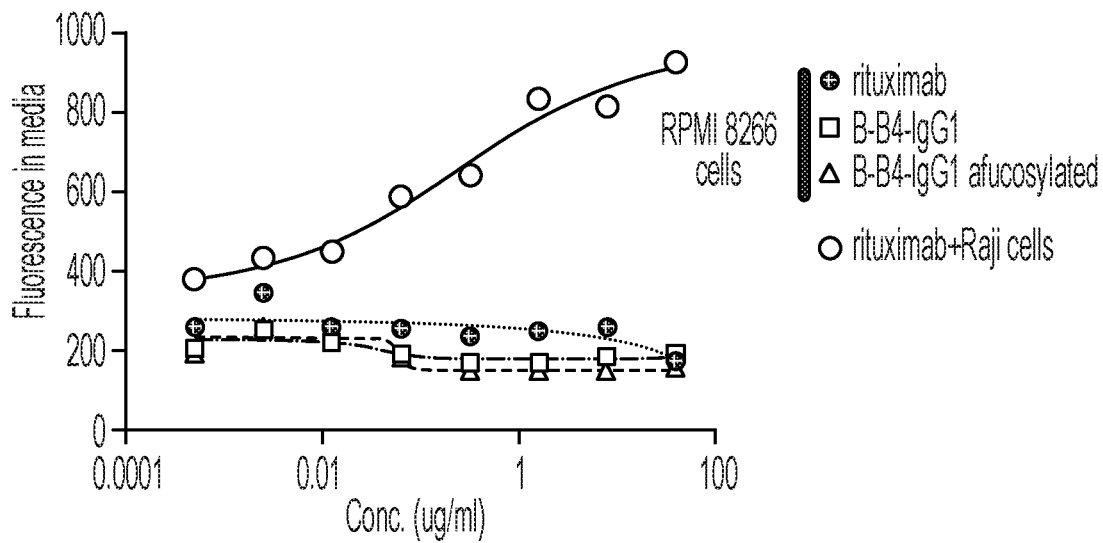
FIG. 3 depicts the characterization of anti-CD138 antibody B-B4 for complement-dependent cytotoxicity (CDC) in human myeloma RPMI 8226 cells.

B-B4 is an anti-CD138 antibody that binds to the integrin binding domain (IBD) of CD138. The ability of B-B4 to induce complement-dependent cytotoxicity (CDC) was examined. As shown in FIG. 3, both B-B4-IgG1 and afucosylated B-B4-IgG1 did not induce CDC in human myeloma RPMI 8226 cells. Rituximab, an antibody targeting B-lymphocyte antigen CD20, did not induce CDC in PRMI 8226 cells. Rituximab induced CDC in Raji cells, which are lymphoblastoid cells with B-cell characteristics derived from a Burkitt's lymphoma.

Figure 4:
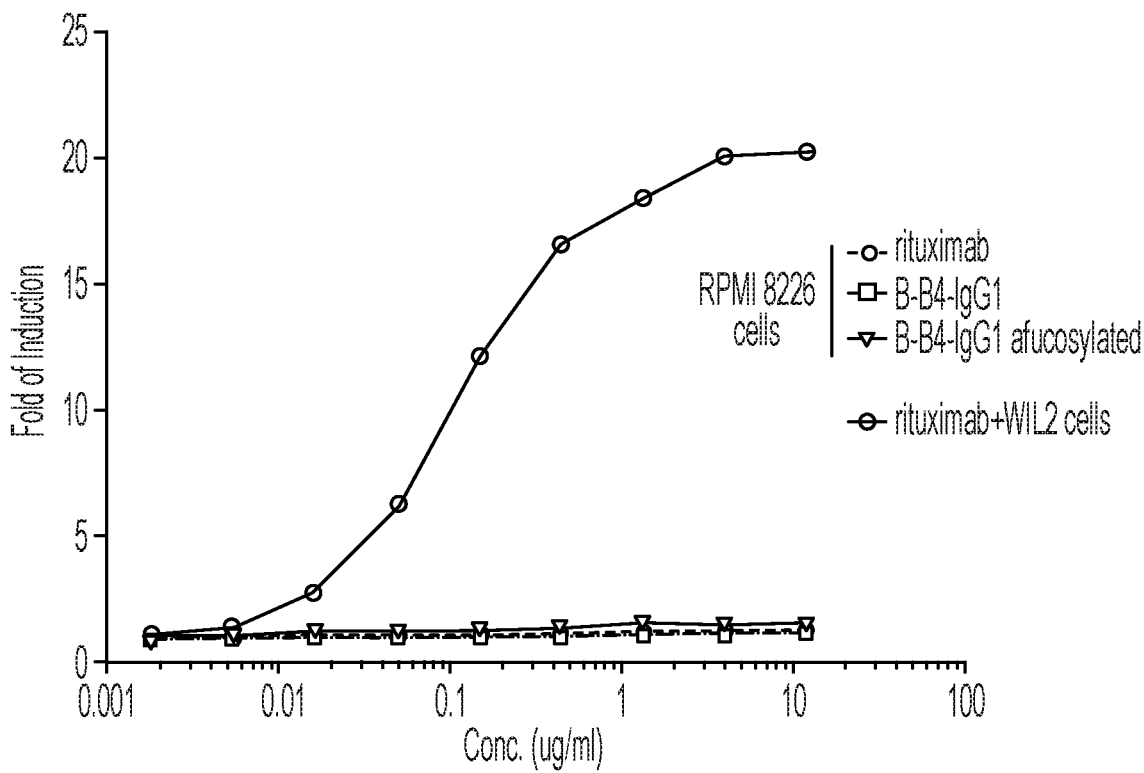
FIG. 4 depicts the characterization of anti-CD138 antibody B-B4 for antibody dependent cellular cytotoxicity (ADCC) in human myeloma RPMI 8226 cells.

The ability of B-B4 to induce antibody dependent cellular cytotoxicity (ADCC) was examined. As shown in FIG. 4, both B-B4-IgG1 and afucosylated B-B4-IgG1 did not induce ADCC in RPMI 8226 cells. Rituximab did not induce ADCC in PRMI 8226 cells. Rituximab induced CDC in WIL2 cells, which are human B lymphocytes.

The ability of rabbit anti-CD138 polyclonal antibody to induce ADCC was examined. As shown in FIG. 5, rabbit anti-CD138 polyclonal antibody induced ADCC in human multiple myeloma U266 cells. Compared to B-B4 IgG1, the induction of ADCC was increased by up to 5-fold.

Example 9: Role of Epitope Distance on ADCC Activity

The epitope of B-B4 has been mapped to a linear peptide toward the N-terminal of CD138 (FIG. 1). As shown in FIGS. 6A-6C, CD138 constructs were designed in which the native B-B4 epitope was mutated and B-B4 epitope was introduced at midway through the ectodomain or proximal to the membrane.

In clones 1, 2, and 3, a 20-amino acid peptide (residues 101-120) around the inferred B-B4 epitope (residues 107-110) is inserted at predetermined positions of the CD138 ectodomain while removing the original B-B4 binding site by mutating its hot spot residues Leu107, Pro108, and Glu109 to Ala. In clones 1, 2, and 3, the 20-amino acid B-B4 binding peptide is inserted between residues 172 and 173, residues 236 and 237, and residues 203 and 204, respectively.

Unlike the insertion of the 20-amino acid B-B4 binding peptide as in clone 1, 2 and 3, in clones 4 and 5 only the five amino acid B-B4 binding epitope is created by mutating the original CD138 residues, and in addition to these mutations, the original B-B4 hot spot residues Leu107, Pro108, and Glu109 are mutated to Ala. In clone 4, the mutations are E226L, D228E, R229V, and R230E, while in clone 5, the mutations are S233L, V235E, D236V, and Q237E.

Figure 7A:
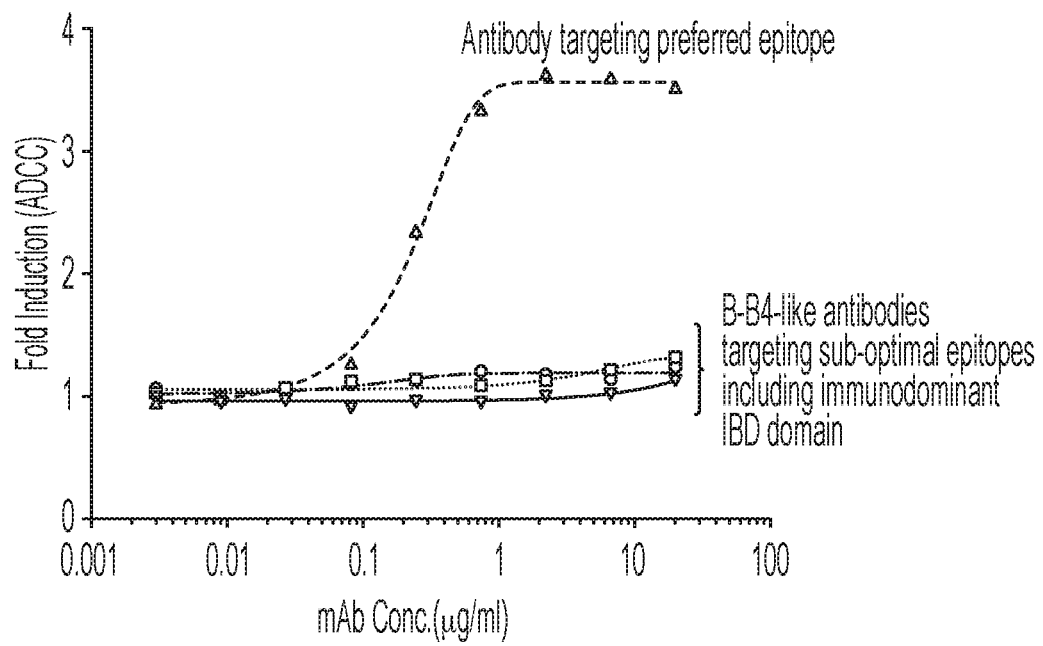
FIG. 7A is a line graph showing the ability of B-B4 to induce ADCC activity when the epitope is moved proximal to the cell membrane.
Figure 7B:
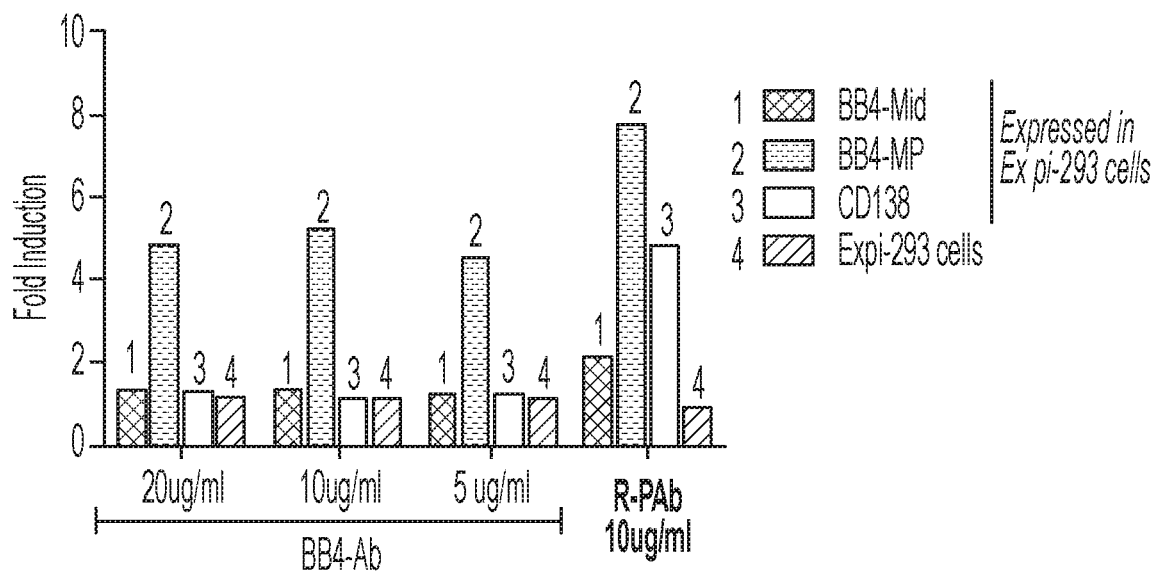
FIG. 7B is a bar graph showing the ability of B-B4 to induce ADCC activity when the epitope is moved proximal to the cell membrane. BB4-Mid: hCD138 with BB-4 epitope at midway through the ectodomain. BB4-MP: hCD138 with BB-4 epitope at membrane proximal region. CD138: human CD138 wild-type. R-PAb: rabbit polyclonal anti-CD138 antibody.

Wild-type CD138 and variants with the B-B4 epitope introduced at different sites of CD138 were recombinantly expressed on the surface of Expi293 cells. Expression was confirmed by staining with B-B4 and polyclonal anti-CD138 antibody. ADCC activity was assessed using ADCC reporter assay as described above. As shown in FIGS. 7A-7B, B-B4-like antibodies that target sub-optimal epitopes including immunodominant IBD do not elicit ADCC, and B-B4 is capable of inducing ADCC activity when the epitope is moved proximal to the cell membrane. As shown in FIG. 7C, Fc engineering further enhances ADCC.

Example 10: Binding of Additional Anti-CD138 Monoclonal Antibodies to Soluble Human CD138 Extracellular Domain Additional monoclonal anti-CD138 antibodies 1610 and 1409 were identified from screening of immunized mice. Briefly, total RNA from splenocytes of CD138/peptide6 immunized mice was extracted and cDNA was synthesized using SuperScript™ IV First-Strand Synthesis System. Variable regions i.e. VH and VL were amplified using mouse VH and VL specific primers. After a series of PCR reactions, VH and VL DNA with appropriate overhang sequences were amplified and VH and VL sequences were cloned into yeast expression vector pYDv6 by homologous recombination and as single chain Fragment variable (scFv) for yeast surface display. VH and VL DNA along with the linearized pYDv6 vector were transformed into EBY100 yeast cells by electroporation for surface scFv expression. Transformed yeast were grown in SDCAA media at 30° C., induced in SGCAA media at 20° C. and enriched for rCD138 binders magnetic bead capture using biotinylated CD138 and anti-biotin magnetic beads from Miltenyi Biotec. Yeast were then enriched for binding to recombinant CD138 (extracellular domain) by fluorescence-activated cell sorting (FACS) for at least 2-3 rounds to achieve >95% CD138 positive binders. Yeast were concurrently analyzed for surface scFv expression using anti-MYC antibody and binding to rCD138. Derivative yeast display libraries of CD138 positive binders were also further analyzed for binding to CD138 derived peptides, likewise biotinylated for detection by flow cytometry. After 3 rounds of enrichment by FACS, CD138 binders were plated on SDCAA plates and VH and VL genetic sequences of individual clones were genetically analyzed by direct DNA sequencing by the Sanger method. Antibody sequences were further analyzed using IMGT/V-quest. Based on this combined phenotype and genotype analyses, select VH and VL sequences were subsequently cloned and transiently expressed in HEK 293 cells as chimeric monoclonal antibodies with murine variable regions (Fab) and human IgG1 isotype IgG1. Recombinant antibodies were purified by affinity capture chromatography using protein A and characterized for binding to CD138, CD138 peptides and myeloma cell lines by methods described herein. Fc afucosylated variants of these antibodies were also produced in an engineered CHO M cell line in which fucosyltransferase 8 (FUT8) gene was ablated using Crisper-Cas based gene editing technologies commonly described in the literature.

Figure 8:
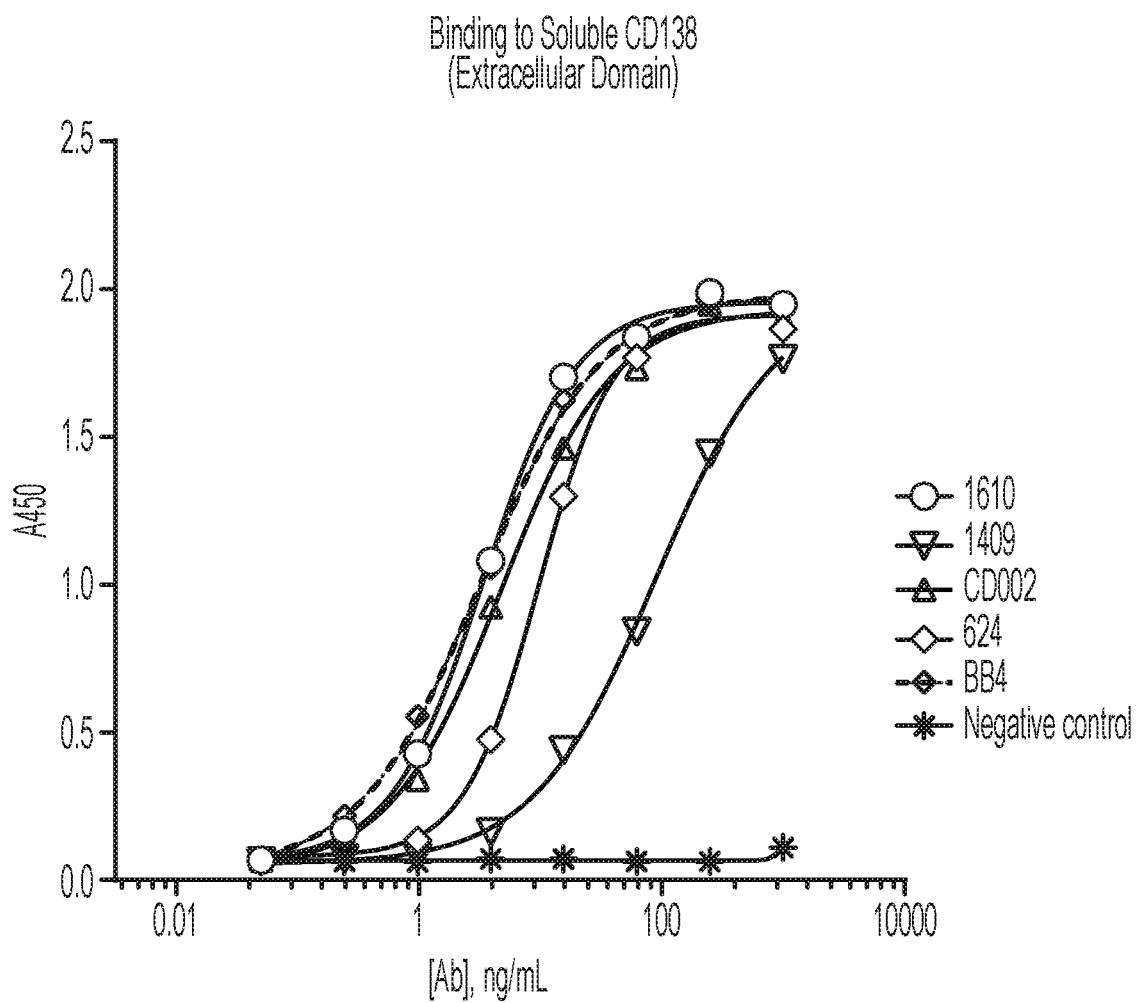
FIG. 8 is a graph showing binding of various anti-CD138 antibodies to a soluble form of the CD138 extracellular domain (amino acids 23-250, SEQ ID NO: 1) as measured by ELISA.

These antibodies were assessed for their capacity to bind to the soluble CD138 extracellular domain in an ELISA assay, alongside antibodies CD002 and 624 described above. Antibody B-B4 was included as a reference. Briefly, the monoclonal antibodies were tested for binding to recombinant CD138 extracellular domain consisting of amino acids 23-254 of human CD138, in four-fold serial dilutions starting at 1 µg/mL. HRP-conjugated anti-human IgG-Fc antibody (1:5000 dilution) was used for detection. As shown in FIG. 8, both antibodies 1610 and 1409 were able to bind to the CD138 extracellular domain Antibody 1610 exhibited comparable binding to antibody CD002 and the reference antibody B-B4.

Monoclonal anti-CD138 antibodies 1610, 1409, CD002, and 624 were then tested for their capacity to bind to different regions of CD138 using peptide binding ELISA. As above, the monoclonal antibodies were tested for binding to a series of CD138 peptides in four-fold serial dilutions starting at 1 µg/mL. A set of three CD138 peptides were tested: Peptide 2a (amino acids 88-121 of human CD138) Peptide 5 (amino acids 176-214 of human CD138), and Peptide 6 (amino acids 210-250 of human CD138) (FIG. 9D). HRP-conjugated anti-human IgG-Fc antibody (1:5000 dilution) was used for detection. Antibody B-B4 was also tested as a reference. As shown in FIGS. 9A-9C, antibodies 1610 and 1409 bound to Peptides 2a and Peptide 6, while antibody 1409 also bound to a lesser degree to Peptide 5. Antibody CD002 bound selectively to Peptide 5, and antibody 624 bound selectively to Peptide 6. Reference antibody B-B4 only bound to Peptide 2a.

Figure 10:
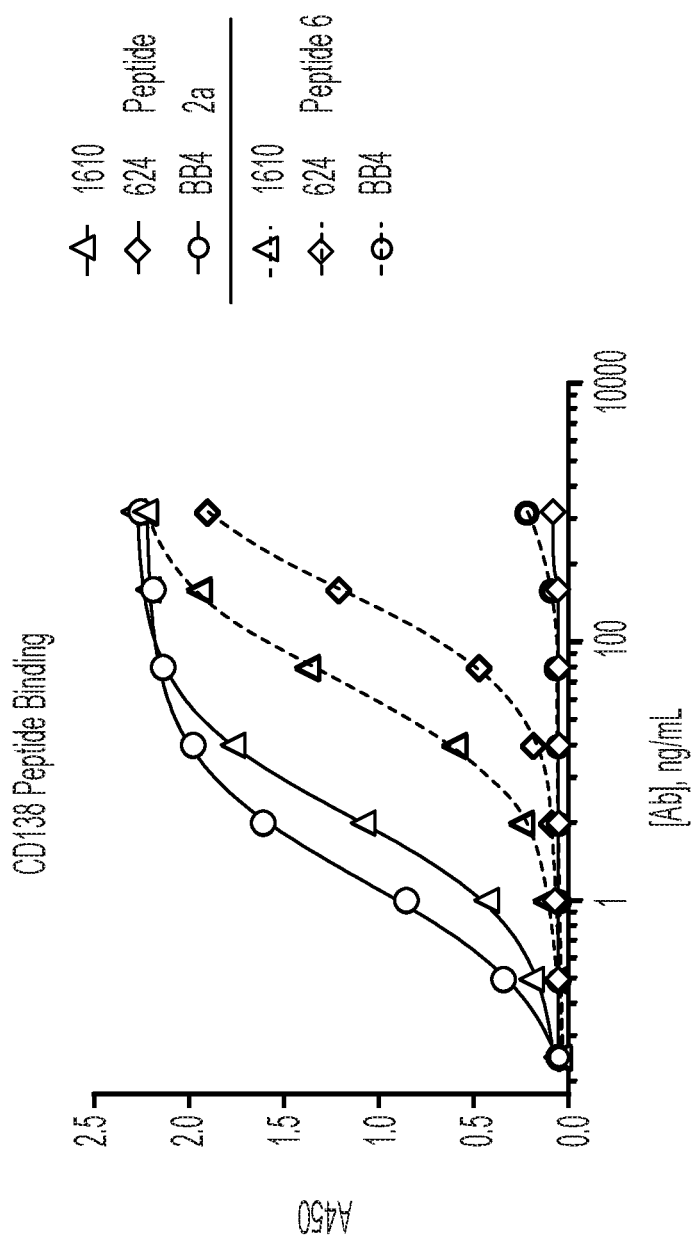
FIG. 10 is a graph showing binding of anti-CD138 antibodies 1610, 624, and B-B4 (also referred to as BB4 herein) to Peptides 2a and 6 of CD138 as measured by ELISA under higher stringency conditions of antibody-antigen binding.

Monoclonal antibodies 1610 and 624 were further evaluated for preferential binding to Peptide 2a or Peptide 6, using the peptide binding ELISA method described above. As shown in FIG. 10, antibody 1610 bound to both Peptide 2a and Peptide 6, and showed greater affinity for Peptide 2a than for Peptide 6. Antibody 624 bound preferentially to the membrane-proximal Peptide 6. The reference antibody B-B4 bound preferentially to Peptide 2a.

Figure 11:
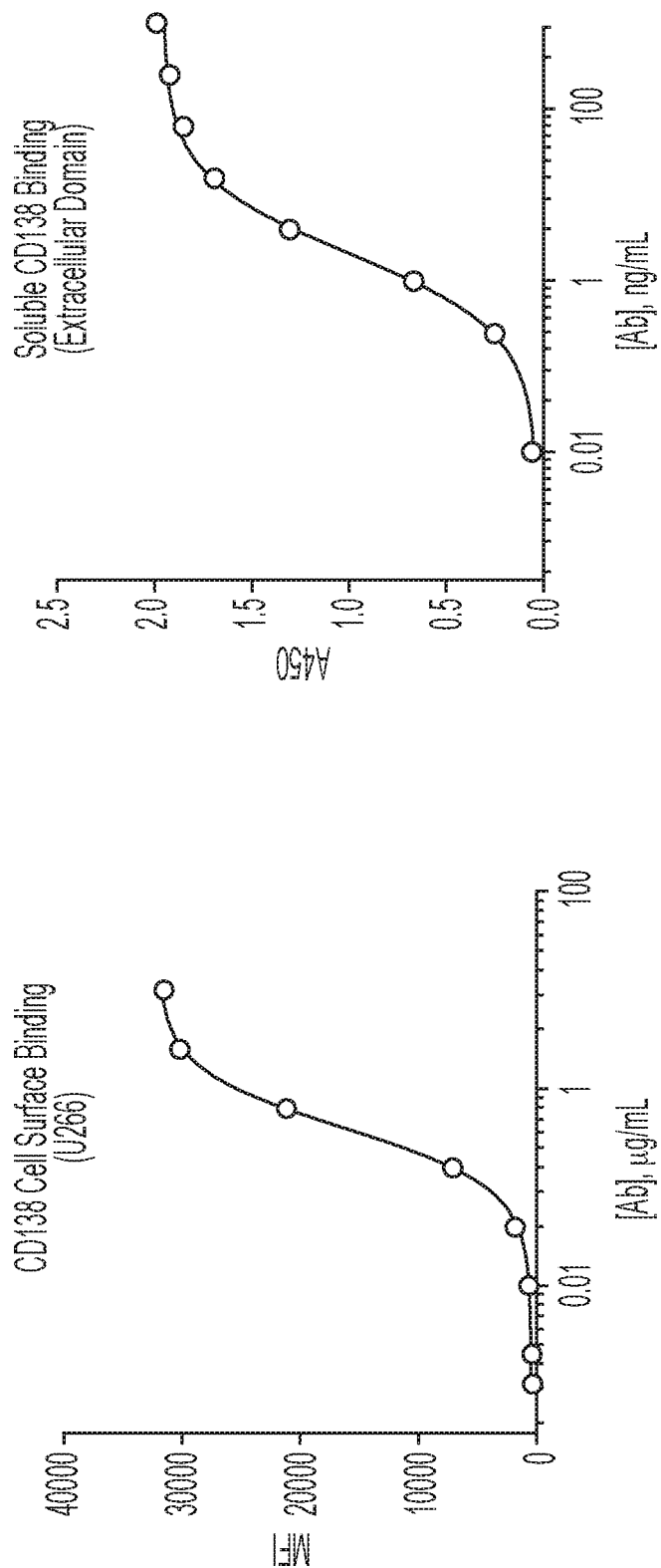
FIGS. 11A-11C are a series of diagrams showing binding of antibody 1610 to cell surface CD138 expressed on U266 multiple myeloma cells (A) or to soluble CD138 extracellular domain (B). (C) EC50 values for antibody 1610 binding to soluble or membrane-bound (cell surface) CD138.

In addition, monoclonal antibody 1610 was tested for binding to soluble and cell surface forms of CD138, using the ELISA method described above and the cell binding assay described in Example 6. As shown in FIG. 11A-11C, antibody 1610 was able to bind CD138 on the surface of U266 cells in a dose-dependent manner, with a binding EC50 of 1.9 ng/mL. Antibody 1610 was also able to bind soluble CD138 in a dose-dependent manner, with a binding EC50 of 394 ng/mL.

Example 11: Comparison of CD138 Binding Between Antibody 1610 and Reference Antibody B-B4

Figure 12:
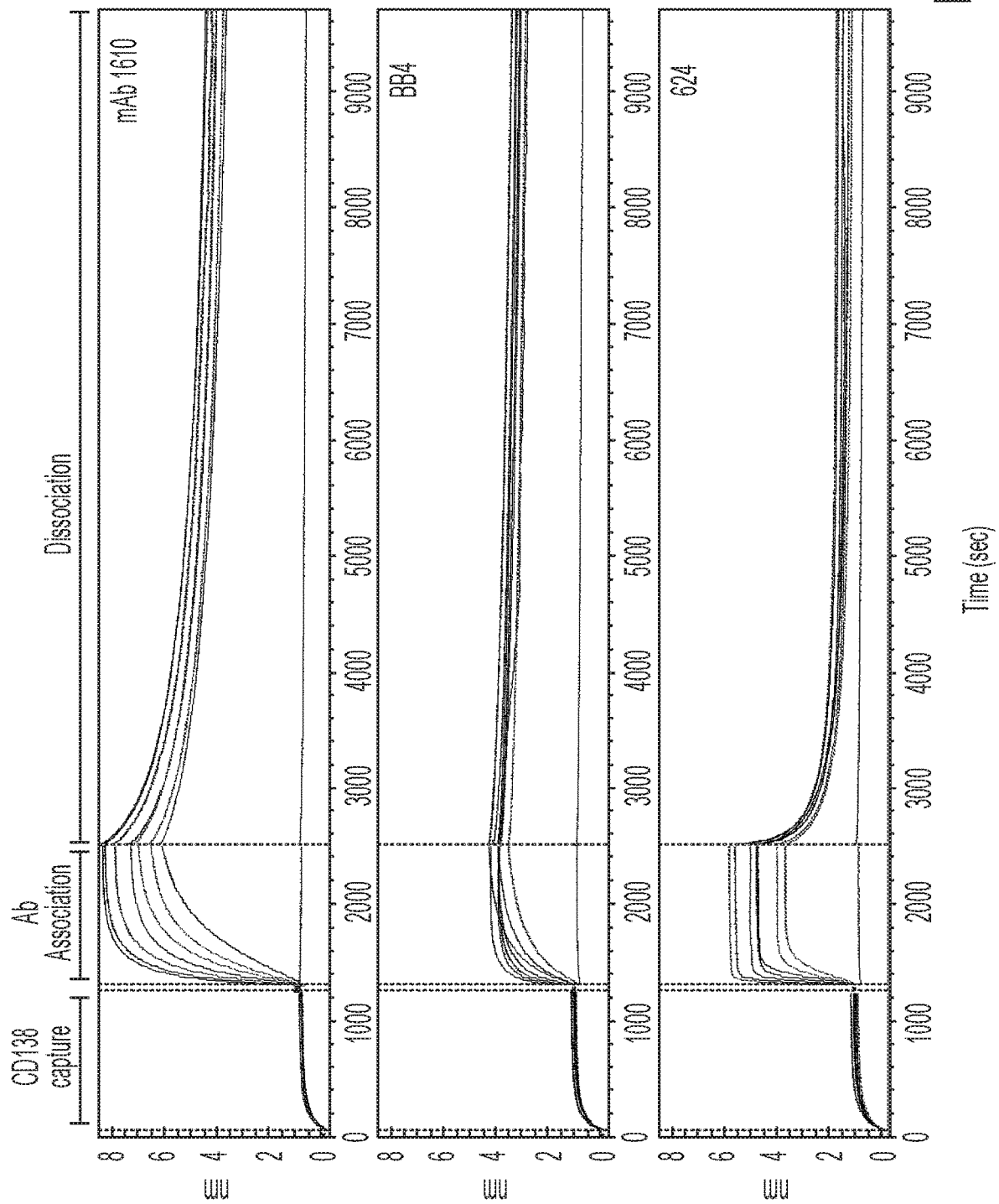
FIG. 12 is a series of graphs showing binding kinetics for anti-CD138 antibodies 1610, 624, and B-B4 to recombinant CD138 extracellular domain as measured by bio-layer interferometry.

The binding kinetics for antibody 1610 to CD138 was tested and compared to that of reference antibody B-B4. Briefly, binding to recombinant CD138 extracellular domain was evaluated by bio-layer interferometry (Octet). Biotinylated CD138 (150 nM) was immobilized on streptavidin biosensors, and then monoclonal antibodies 1610 and B-B4 were each tested for binding at 0-300 nM. As shown in FIG. 12, antibody 1610 was found to bind to CD138 with a substantially higher binding association in comparison to reference antibody B-B4. A faster dissociation rate for antibody 1610 was observed, which may be due to a second, lower-affinity binding site. These data suggest a potentially 2:1 binding stoichiometry of antibody 1610 to CD138.

The binding kinetics of antibody 1610 for several CD138 peptides, representing two distinct regions of CD138, was also tested by bio-layer interferometry according to the methodology described above but with the use of peptides modified with biotin at their respective amino termini. As shown in FIG. 13, the peptides tested had the following amino acid sequences:

```
                                            (SEQ ID NO: 10)
Peptide 2A:  ASTSTLPAGEGPKEGEAVVLPEVEPGLTAREQEA (SEQ ID NO: 449)
Peptide 2C:  GEAVVLPEVEPGLTAREQEA (SEQ ID NO: 440)
Peptide 6B:  ENTAVVAVEPDRRNQSPVDQGATGASQGLLDRKEVLG (SEQ ID NO: 444)
Peptide 6E:  RNQSPVDQGATGASQGLLDRKEVLG
```

FIG. 13 shows that antibody 1610 bound to Peptides 2A and 2C with similar binding association, but of the Peptide 6 variants, only bound to Peptide 6B, and not to Peptide 6E. Comparative binding kinetics for antibodies 1610 and B-B4 for CD138 peptide fragments were also measured by bio-layer interferometry. As shown in FIG. 14A, antibody 1610 was able to bind to both peptides 2A and 6B. In contrast, antibody B-B4 only bound to Peptide 2A, not to Peptide 6B (FIG. 14B).

Example 12: Competition for Binding to Cell Surface CD138

Competitive antibody binding to membrane CD138 expressed on human myeloma cell line U266 was assessed in an approach that is commonly referred to as "epitope binning" In this example, antibody competition for binding to the cell surface antigen (CD138 here) was set between a biotinylated test antibody at a fixed concentration and varying concentrations of unlabeled, competing antibody. Antibodies 1610, B-B4, and 624 were chemically biotinylated using EZ-Link™ Sulfo-NHS-LC-Biotinylation Kit (Thermal Fisher Scientific, catalog number 21435) according to the manufacturer's instruction. In brief, recombinant monoclonal antibodies (100 microgram) were incubated overnight at 4° C. in the presence of 5-fold molar excess of the biotin reagent. Excess, unconjugated biotin was removed by buffer exchange into PBS buffer, pH 7.4 using Amicon Ultra centrifugal filters (30 kDa MWCO). For the competition analysis, serially diluted unlabeled competing antibodies were pre-mixed with a fixed level of the biotinylated test antibody. Each of the mixtures contained 0.5 µg/mL of the biotinylated antibody and a varied amount (0-40 µg/mL) of the competing antibody. U266 cells were placed in a 96 well microtiter plate at 2-5E+4 cells/well, washed once with 1×PBS and then resuspended in 100 µl of the antibody pre-mixes. Competition between unlabeled and the biotinylated versions of the same antibody was used as a positive assay control ("self-competition"). The cells were incubated in the presence of the antibody for 30 minutes at 4° C., washed, and exposed to Alexa fluor 488-tagged streptavidin for additional 30 minutes at 4° C. The cells were washed again before being evaluated for biotin-antibody binding by flow cytometry as described in Example 6. MAb 1610 showed partial (~50%) inhibition by B-B4, no inhibition by 624, and was completely blocked by 1610 itself (FIG. 15A). MAb 624 showed no inhibition by B-B4 and was completely blocked by 1610 (FIG. 15B). MAb B-B4 showed no inhibition by 624, but was completely blocked by either 1610 or B-B4 itself (FIG. 15C).

Example 13: Antibody 1610 Demonstrates Potent ADCC Activity in a Reporter Based Cell Assay The ability of antibody 1610 to induce ADCC in its afucosylated form was tested and compared to that of antibody 624 and the reference antibody B-B4. Briefly, each of the anti-CD138 antibodies was produced in a CHO-based Fut8−/− cell line to reduce Fc fucosylation. ADCC activity induced by each antibody was measured using the ADCC Reporter Bioassay Kit (Promega), which utilizes, as effector cells, Jurkat T cells engineered to stably express the high-affinity human FcγRIIIa (V/V 158) variant and an NFAT response element driving the expression of firefly luciferase. A CD138-positive multiple myeloma cell line (U266) as the target cells. As shown in FIG. 16, afucosylation of antibody 1610 resulted in potent ADCC activity, which was not observed for antibody 624, which bound preferentially to a membrane proximal region, or for reference antibody B-B4, which bound to a region distal to the membrane proximal region. These data show that antibody 1610 binds differentially to CD138 in a manner that confers potent ADCC activity when afucosylated.

Example 14: Generation and Characterization of Variants of Antibody 1610

Monoclonal antibody 1610 was modified to produce a series of variants (FIG. 17). In one instance, an N-linked glycosylation site in HCDR1 of the heavy chain variable region of antibody 1610 was removed by mutating N28 to either S or T to produce antibodies 2610 and 2710, respectively. Antibodies 2610 and 2710 retained the CD138 binding and ADCC-inducing activities of the parental antibody 1610, as shown below, although the mutation resulted in lower expression levels in transiently-transfected HEK293 cells. A further mutation to antibodies 2610 and 2710, in which C60 was mutated to Y (antibodies 2810 and 2910, respectively), restored expression to levels comparable to that of antibody 1610. Without wishing to be bound by theory, it is contemplated that the C60Y mutation may also improve heavy and light chain pairing.

The binding properties of the antibody 1610 variants for CD138 was tested using assays as described above. In particular, antibodies 2510, 2610, and 2810 each showed similar dose-dependent binding to the extracellular domain of CD138 (FIG. 18A), Peptide 2a of CD138 (FIG. 18B), and Peptide 6 of CD138 (FIG. 18C), as shown in Table 3, when tested in ELISA assays. The EC50 values calculated for each antibody variant for CD138 extracellular domain, Peptide 2a, and Peptide 6 are shown in FIG. 18D.

Figure 19A:
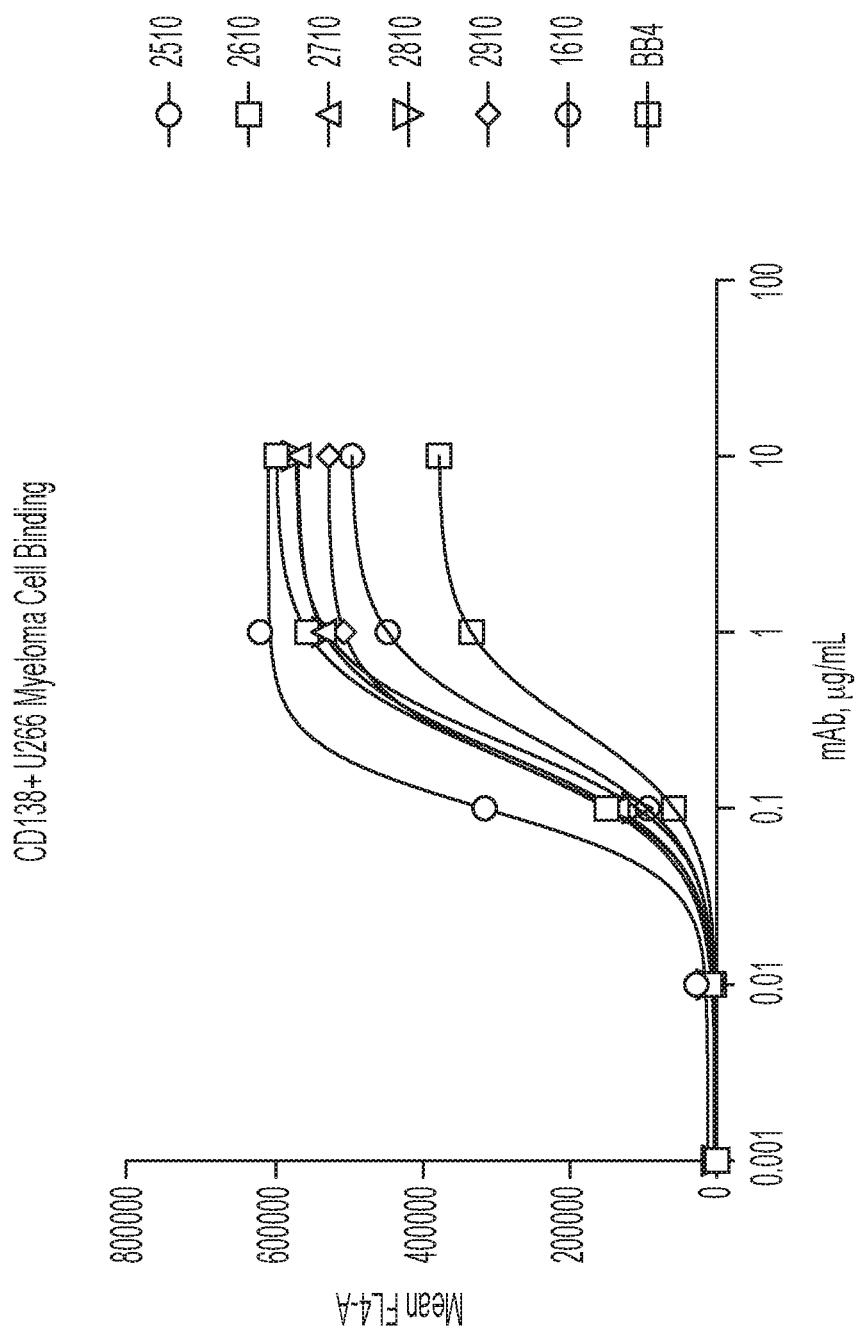
FIG. 19A is a graph showing that afucosylated versions of antibody 1610 and its variants bound to cell surface CD138 expressed by U266 cells.
Figure 19B:
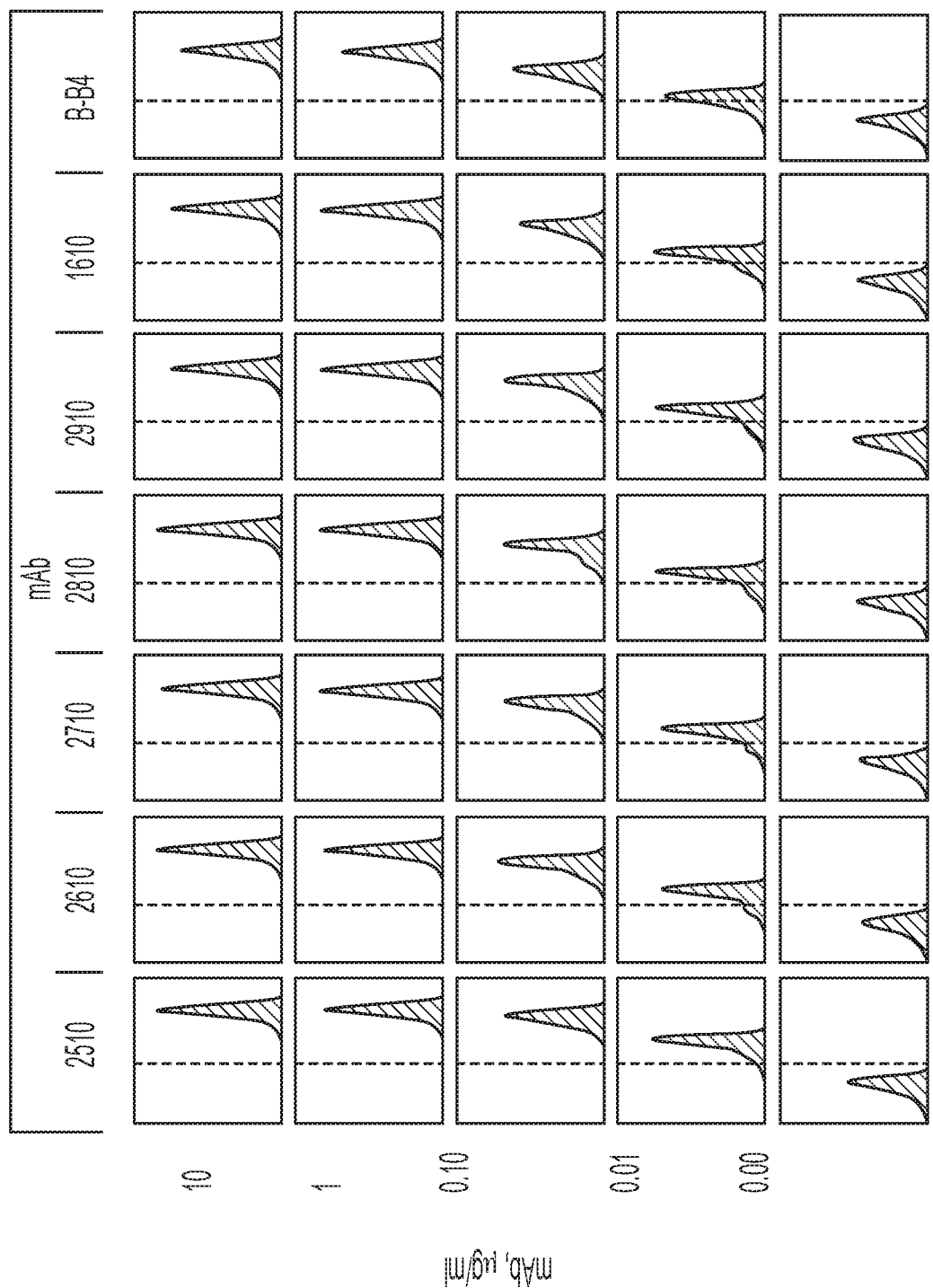
FIG. 19B is a series of graphs showing representative flow cytometry results for the cell binding assays summarized in FIG. 18A.
Figure 20:
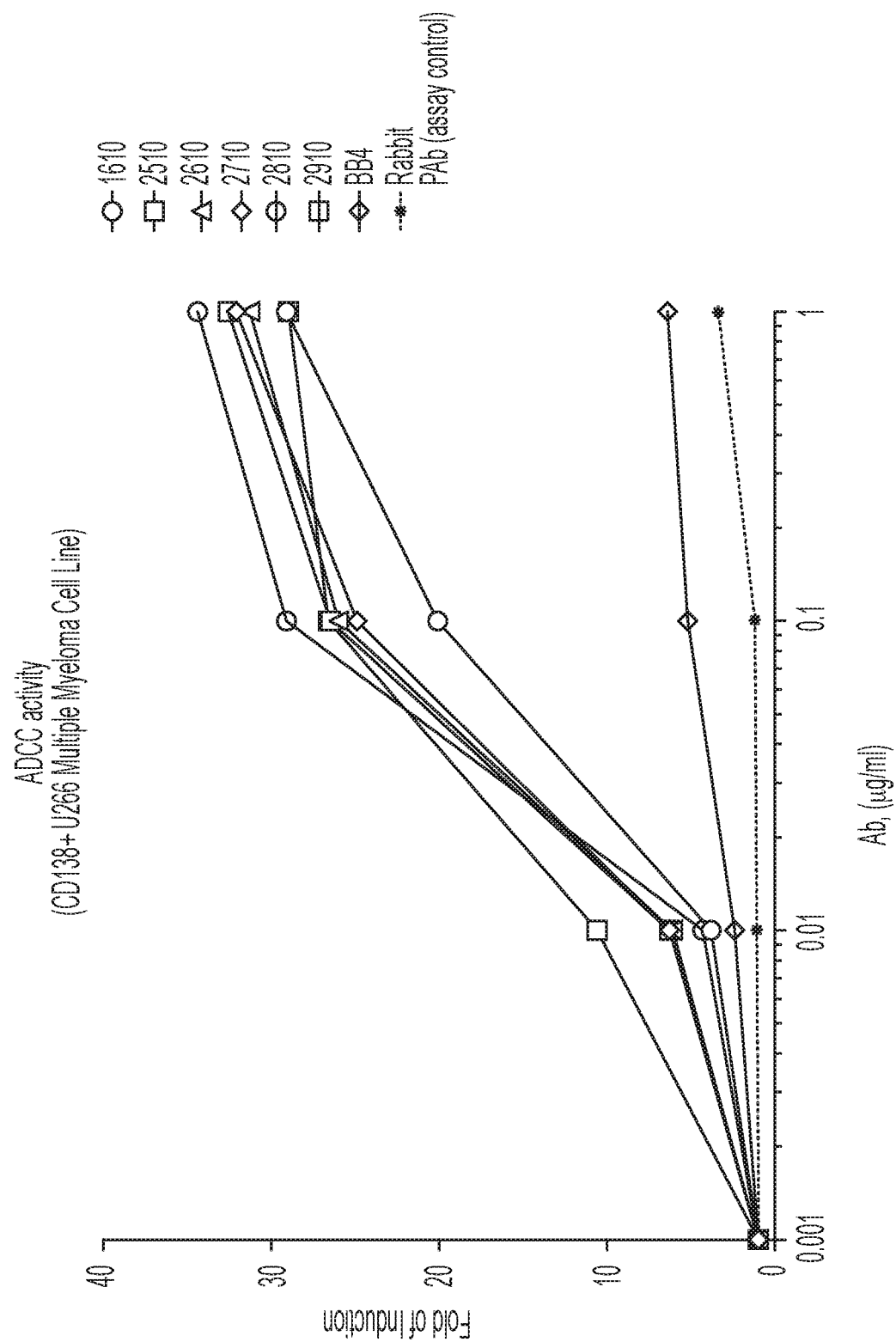
FIG. 20 is a graph showing that afucosylated versions of antibody 1610 and its variants induce ADCC activity in CD138+U266 cells. Rabbit polyclonal (PAb) anti-CD138 antibody used as an assay control.

Afucosylated versions of antibody 1610 variants 2510, 2610, 2710, 2810, and 2910 were generated as described above and then tested for binding to U266 cells expressing CD138 on their cell surfaces. As shown in FIG. 19A, antibody 1610 and its variants all exhibited stronger binding to cell surface CD138 than did reference antibody B-B4. Representative flow cytometry plots for each afucosylated antibody at varying antibody concentrations are shown in FIG. 19B. The afucosylated antibody variants were then tested for capacity to induce ADCC, as described above. As shown in FIG. 20, antibody 1610 and all of its variants were capable of inducing ADCC in CD138+U266 cells in a dose-dependent manner, whereas antibody B-B4 did not substantially induce ADCC in these cells.

Figure 21:
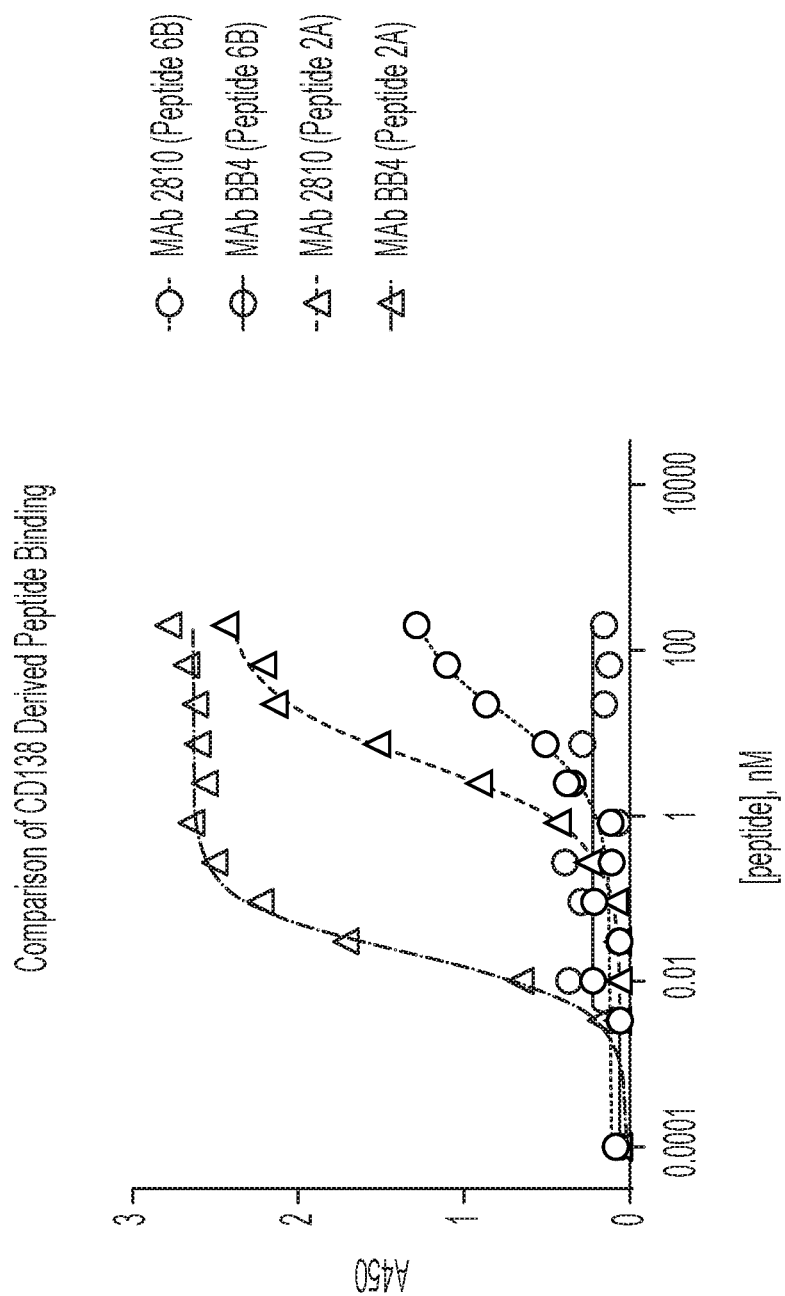
FIG. 21 is a graph showing the binding of CD138 peptide fragments (peptide 2A and peptide 6B) by antibody 2810 compared to BB4. Binding was measured by ELISA in a modified format in which antibody is captured directly on the ELISA plate and binding of CD138 peptides is measured at varying concentrations.
Figure 22A:
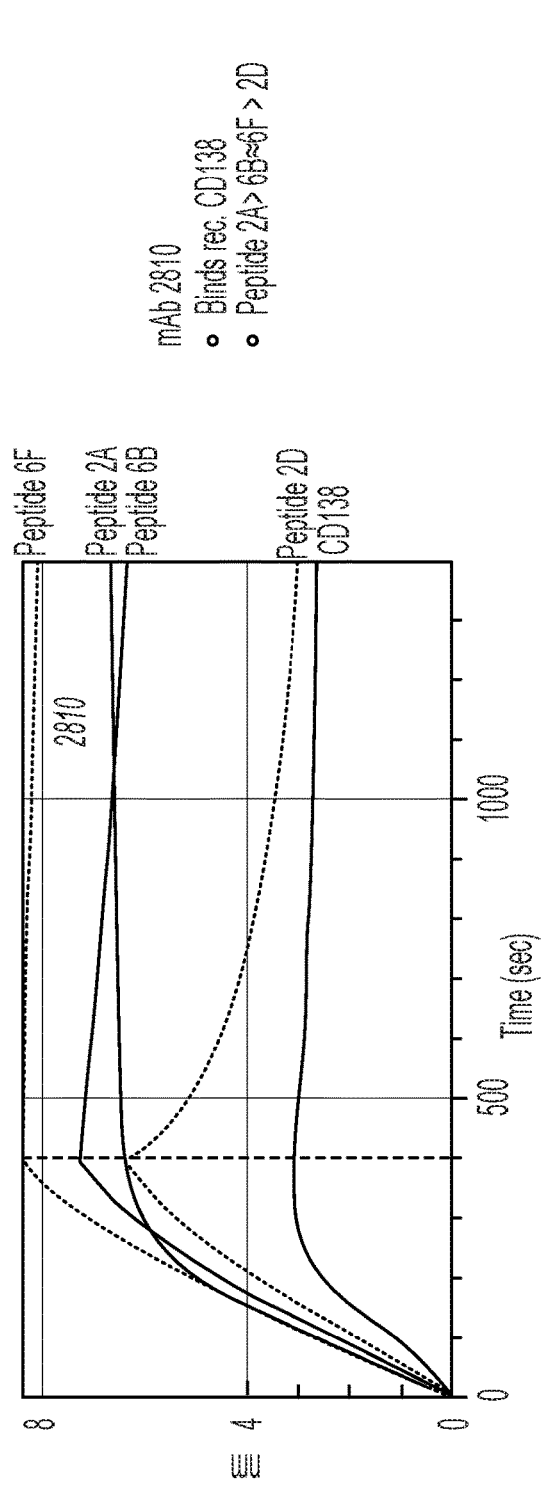
Figure 22B:
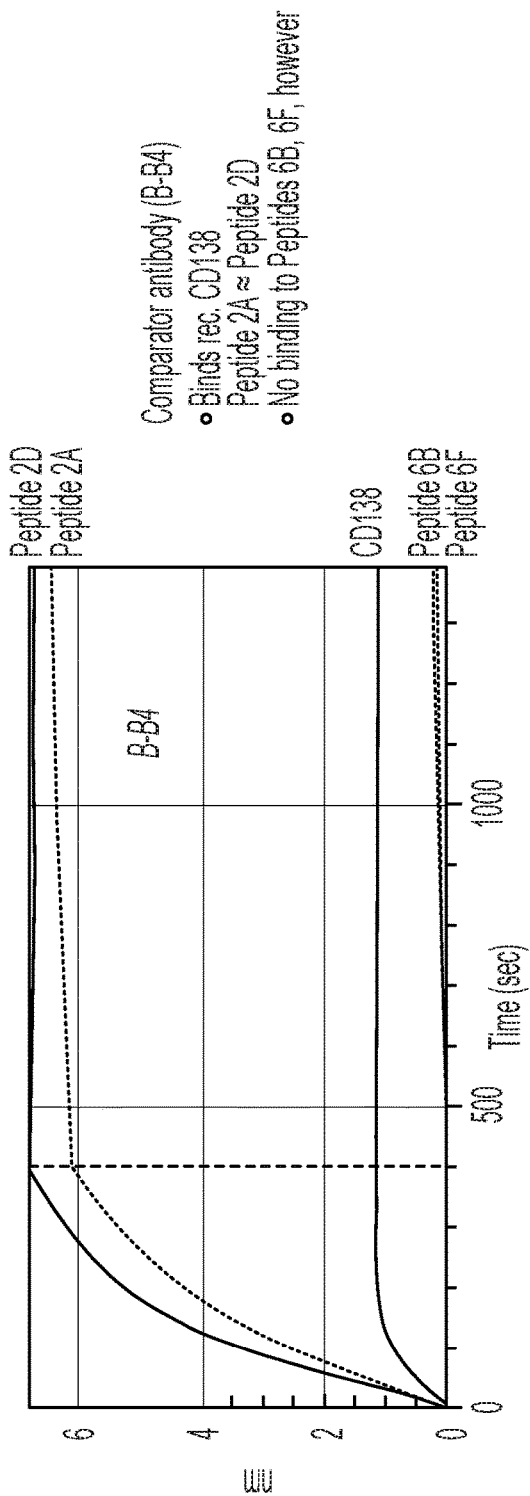

The capability of an antibody 1610 variant, antibody 2810, to bind to CD138 peptide fragments was also determined using ELISA. Briefly, antibodies 2810 or B-B4 were captured on an ELISA plate and the binding of CD138 peptides was measured at varying concentrations. As shown in FIG. 21, antibody 2810 exhibited stronger binding to Peptide 6B than did antibody B-B4, whereas antibody B-B4 bound to Peptide 2A more strongly than did antibody 2810 (although antibody 2810 did show binding to Peptide 2A). The binding kinetics of the antibody 1610 variant 2810 were compared to that of reference antibody B-B4. Briefly, biotinylated peptides (Peptides 2A, 2D, 6B, and 6F; sequences shown in FIG. 22C) were used at 50 nM and captured on streptavidin capture biosensors. Antibodies were then run over the captured peptides at concentrations of 25 nM to 6.25 nM. FIGS. 22A-22B show binding for antibodies 2810 and B-B4, respectively, at 12.5 nM. These data confirm that antibody 2810, like the parental antibody 1610, bound to two different regions of CD138, as represented by Peptides 2A and 2D (mid region) and Peptides 6B and 6F (membrane proximal region), respectively. As shown earlier, antibody B-B4 did not bind to the membrane proximal region.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An anti-CD138 antibody molecule comprising:
   (a) a heavy chain variable region (VH), wherein the VH comprises three heavy chain complementarity determining regions (HCDR1, HCDR2, and HCDR3), wherein the VH comprises:
      (i) an HCDR1 comprising the amino acid sequence of SEQ ID NO: 350, 355, or 356, an HCDR2 comprising the amino acid sequence of SEQ ID NO: 351, and an HCDR3 comprising the amino acid sequence of FVY; or
      (ii) an HCDR1 comprising the amino acid sequence of SEQ ID NO: 380, an HCDR2 comprising the amino acid sequence of SEQ ID NO: 381 or 382, and an HCDR3 comprising the amino acid sequence of FVY; and
   (b) a light chain variable region (VL), wherein the VL comprises three light chain complementarity determining regions (LCDR1, LCDR2, and LCDR3), wherein the VL comprises:
      an LCDR1 comprising the amino acid sequence of SEQ ID NO: 352 or an amino acid sequence that differs by 1 conservative amino acid substitution therefrom; an LCDR2 comprising the amino acid sequence of SEQ ID NO: 353; and an LCDR3 comprising the amino acid sequence of SEQ ID NO: 354.

2. The antibody molecule of claim 1, which is a synthetic antibody molecule, a humanized antibody molecule, or an isolated antibody molecule, and/or is a monovalent antibody molecule, a multivalent antibody molecule, a monospecific molecule, or a multispecific antibody molecule.

3. The antibody molecule of claim 1, comprising a heavy chain constant region of IgG chosen from IgG1, IgG2, IgG3, or IgG4, and/or a light chain constant region of kappa or lambda light chain.

4. The antibody molecule of claim 1, comprising an Fc region comprising one or more mutations that increases the binding affinity to neonatal receptor FcRn and/or the half-life of the antibody molecule.

5. An antibody-molecule drug conjugate (ADC) comprising an antibody molecule of claim 1.

6. A pharmaceutical composition comprising an antibody molecule of claim 1 and a pharmaceutically acceptable carrier.

7. A nucleic acid molecule encoding a heavy chain variable region (VH), a light chain variable region (VL), or both, of an antibody molecule of claim 1.

8. A vector comprising a nucleic acid molecule of claim 7.

9. A cell comprising a nucleic acid molecule of claim 7.

10. A kit comprising an antibody molecule of claim 1 and instructions to use of the antibody molecule or composition.

11. A container comprising an antibody molecule of claim 1.

12. A method of producing an anti-CD138 antibody molecule, the method comprising culturing a cell of claim 9 under conditions that allow production of an antibody molecule, thereby producing the antibody molecule.

13. A method of causing an ADCC activity, the method comprising contacting a CD138-expressing cell or a subject comprising said cell with an antibody molecule of claim 1, thereby causing the ADCC activity.

14. A method of treating a CD138-expressing cancer, the method comprising administering to a subject in need thereof an effective amount of an antibody molecule of claim 1, thereby treating the CD138-expressing cancer.

15. The method of claim 14, wherein the CD138-expressing cancer is a myeloma.

16. A method of treating a CD138-expressing precancerous condition, the method comprising administering to a subject in need thereof an effective amount of an antibody molecule of claim 1, thereby treating the CD138-expressing precancerous condition.

17. The method of claim 16, wherein the CD138-expressing precancerous condition is smoldering myeloma or monoclonal gammopathy of undetermined significance (MGUS).

18. A method of detecting a CD138 molecule, the method comprising contacting a cell or a subject with an antibody molecule of claim 1, thereby detecting the CD138 molecule.

19. The antibody molecule of claim 1, wherein the VH comprises an HCDR1 comprising the amino acid sequence of SEQ ID NO: 350, 355, or 356, an HCDR2 comprising the amino acid sequence of SEQ ID NO: 351, and an HCDR3 comprising the amino acid sequence of FVY.

20. The antibody molecule of claim 1, wherein the VH comprises an HCDR1 comprising the amino acid sequence of SEQ ID NO: 380, an HCDR2 comprising the amino acid sequence of SEQ ID NO: 381 or 382, and an HCDR3 comprising the amino acid sequence of FVY.

21. The antibody molecule of claim 1, wherein:
   (a) the VH comprises: an HCDR1 comprising the amino acid sequence of SEQ ID NO: 350, an HCDR2 comprising the amino acid sequence of SEQ ID NO: 351, and an HCDR3 comprising the amino acid sequence of FVY; and
   (b) the VL comprises: an LCDR1 comprising the amino acid sequence of SEQ ID NO: 352 or an amino acid sequence that differs by 1 conservative amino acid substitution therefrom, an LCDR2 comprising the amino acid sequence of SEQ ID NO: 353, and an LCDR3 comprising the amino acid sequence of SEQ ID NO: 354.

22. The antibody molecule of claim 1, wherein:
   (a) the VH comprises: an HCDR1 comprising the amino acid sequence of SEQ ID NO: 355, an HCDR2 comprising the amino acid sequence of SEQ ID NO: 351, and an HCDR3 comprising the amino acid sequence of FVY; and
   (b) the VL comprises: an LCDR1 comprising the amino acid sequence of SEQ ID NO: 352 or an amino acid sequence that differs by 1 conservative amino acid substitution therefrom, an LCDR2 comprising the amino acid sequence of SEQ ID NO: 353, and an LCDR3 comprising the amino acid sequence of SEQ ID NO: 354.

23. The antibody molecule of claim 1, wherein:
   (a) the VH comprises: an HCDR1 comprising an amino acid sequence comprising the amino acid sequence of SEQ ID NO: 356, an HCDR2 comprising an amino acid sequence comprising the amino acid sequence of SEQ ID NO: 351, and an HCDR3 comprising the amino acid sequence of FVY; and
   (b) the VL comprises: an LCDR1 comprising the amino acid sequence of SEQ ID NO: 352 or an amino acid sequence that differs by 1 conservative amino acid substitution therefrom, an LCDR2 comprising the amino acid sequence of SEQ ID NO: 353, and an LCDR3 comprising the amino acid sequence of SEQ ID NO: 354.

24. The antibody molecule of claim 1, wherein:
   (a) the VH comprises: an HCDR1 comprising an amino acid sequence comprising the amino acid sequence of SEQ ID NO: 380, an HCDR2 comprising an amino acid sequence comprising the amino acid sequence of SEQ ID NO: 381, and an HCDR3 comprising the amino acid sequence of FVY; and (b) the VL comprises: an LCDR1 comprising the amino acid sequence of SEQ ID NO: 352 or an amino acid sequence that differs by 1 conservative amino acid substitution therefrom, an LCDR2 comprising the amino acid sequence of SEQ ID NO: 353, and an LCDR3 comprising the amino acid sequence of SEQ ID NO: 354.

25. The antibody molecule of claim 1, wherein:

(a) the VH comprises: an HCDR1 comprising an amino acid sequence comprising the amino acid sequence of SEQ ID NO: 380, an HCDR2 comprising an amino acid sequence comprising the amino acid sequence of SEQ ID NO: 382, and an HCDR3 comprising the amino acid sequence of FVY; and (b) the VL comprises: an LCDR1 comprising the amino acid sequence of SEQ ID NO: 352 or an amino acid sequence that differs by 1 conservative amino acid substitution therefrom, an LCDR2 comprising the amino acid sequence of SEQ ID NO: 353, and an LCDR3 comprising the amino acid sequence of SEQ ID NO: 354.

26. The antibody molecule of claim 1, wherein the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of SEQ ID NO: 293, 294, 295, 296, or 297, and/or wherein the VL the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of 292.

27. The antibody molecule of claim 1, wherein the VH comprises the amino acid sequence of SEQ ID NO: 293, 294, 295, 296, or 297, or an amino acid sequence that differs by no more than 1, 2, 3, 4, 5, 6, 7, 8, 9, 10, 11, 12, 13, 14, or 15 amino acid residues therefrom, or has at least 85, 90, 95, 99 or 100% homology therewith.

28. The antibody molecule of claim 1, wherein the VH comprises the amino acid sequence of SEQ ID NO: 293, 294, 295, 296, or 297.

29. The antibody molecule of claim 1, wherein the VL comprises the amino acid sequence of SEQ ID NO: 292, or an amino acid sequence that differs by no more than 1, 2, 3, 4, 5, 6, 7, 8, 9, 10, 11, 12, 13, 14, or 15 amino acid residues therefrom, or has at least 85, 90, 95, 99 or 100% homology therewith.

30. The antibody molecule of claim 1, wherein the VL comprises the amino acid sequence of SEQ ID NO: 292.

31. The antibody molecule of claim 1, wherein the VH comprises the amino acid sequence of SEQ ID NO: 293, and wherein the VL comprises the amino acid sequence of 292.

32. The antibody molecule of claim 1, wherein the VH comprises the amino acid sequence of SEQ ID NO: 294, and wherein the VL comprises the amino acid sequence of 292.

33. The antibody molecule of claim 1, wherein the VH comprises the amino acid sequence of SEQ ID NO: 295, and wherein the VL comprises the amino acid sequence of 292.

34. The antibody molecule of claim 1, wherein the VH comprises the amino acid sequence of SEQ ID NO: 296, and wherein the VL comprises the amino acid sequence of 292.

35. The antibody molecule of claim 1, wherein the VH comprises the amino acid sequence of SEQ ID NO: 297, and wherein the VL comprises the amino acid sequence of 292.

36. The antibody molecule of claim 1, comprising a heavy chain constant region of IgG1 and/or a light chain constant region of kappa light chain.

37. The antibody molecule of claim 1, which is an afucosylated antibody molecule.

* * * * *